United States Patent
Zhang et al.

(10) Patent No.: US 11,505,819 B2
(45) Date of Patent: Nov. 22, 2022

(54) MOLECULAR HYBRIDIZATION PROBES FOR COMPLEX SEQUENCE CAPTURE AND ANALYSIS

(71) Applicant: WILLIAM MARSH RICE UNIVERSITY, Houston, TX (US)

(72) Inventors: David Zhang, Houston, TX (US); Juexiao Wang, Houston, TX (US); Yan Yan, Houston, TX (US)

(73) Assignee: William Marsh Rice University, Houston, TX (US)

( * ) Notice: Subject to any disclaimer, the term of this patent is extended or adjusted under 35 U.S.C. 154(b) by 307 days.

(21) Appl. No.: 16/335,505

(22) PCT Filed: Sep. 22, 2017

(86) PCT No.: PCT/US2017/053109
§ 371 (c)(1),
(2) Date: Mar. 21, 2019

(87) PCT Pub. No.: WO2018/057999
PCT Pub. Date: Mar. 29, 2018

(65) Prior Publication Data
US 2020/0080136 A1  Mar. 12, 2020

Related U.S. Application Data

(60) Provisional application No. 62/398,484, filed on Sep. 22, 2016.

(51) Int. Cl.
*C12Q 1/6818* (2018.01)
*C12Q 1/6811* (2018.01)
*C12Q 1/6883* (2018.01)

(52) U.S. Cl.
CPC .......... *C12Q 1/6818* (2013.01); *C12Q 1/6811* (2013.01); *C12Q 1/6883* (2013.01); *C12Q 2600/156* (2013.01)

(58) Field of Classification Search
CPC ......... C07H 21/00; C12Q 1/68; C12Q 1/6876
See application file for complete search history.

(56) References Cited

U.S. PATENT DOCUMENTS

| 5,451,503 A * | 9/1995 | Hogan ............... C12N 15/1068 435/6.1 |
| 5,627,032 A | 5/1997 | Ulanovsky | |
| 2001/0016327 A1 * | 8/2001 | Giulian ............... G01N 33/5091 435/7.2 |
| 2011/0171639 A1 * | 7/2011 | Kanashima .......... C12Q 1/6832 435/6.11 |
| 2011/0306758 A1 * | 12/2011 | Zhang .................. C12Q 1/6832 536/23.1 |
| 2013/0071839 A1 | 3/2013 | Seelig et al. | |
| 2013/0274135 A1 | 10/2013 | Zhang et al. | |
| 2014/0255924 A1 | 9/2014 | Sampas et al. | |
| 2016/0083783 A1 * | 3/2016 | Blainey ................. G01N 21/78 435/5 |
| 2016/0340727 A1 | 11/2016 | Zhang et al. | |

FOREIGN PATENT DOCUMENTS

| WO | WO 2015/094429 | 6/2015 |
| WO | WO 2018/057999 | 3/2018 |

OTHER PUBLICATIONS

Carvalho et al. J. of Genetics (Year: 2013).*
Mitas Nucleic Acids Research 25(12) :2245 (Year: 1997).*
Bonifazi et al., "Use of RNA fluorescence in situ hybridization in the prenatal molecular diagnosis of myotonic dystrophy type I." *Clinical Chemistry*, 52:319-322 (2006).
International HapMap Consortium. "A second generation human haplotype map of over 3.1 million SNPs." *Nature*, 449:851-861 (2007).
International Preliminary Report on Patentability issued in International Application No. PCT/US2017/053109, dated Mar. 4, 2019.
Kern & Seitz, "Template-directed ligation on repetitive DNA sequences: a chemical method to probe the length of Huntington DNA." *Chemical Science*, 6:724-728 (2015).
Khodakov et al., "Protected DNA strand displacement for enhanced single nucleotide discrimination in double-stranded DNA." *Scientific Reports*, 5:8721 (2015).
PCT International Search Report and Written Opinion, issued in International Application No. PCT/US17/53109, dated Feb. 13, 2018.
Wang et al. "Modular probes for enriching and detecting complex nucleic acid sequences." *Nature Chemistry*, 9:1222-1228, 2017.
Zhang & Winfree, "Control of DNA strand displacement kinetics using toehold exchange."*J Am Chem Soc*, 131:17303-17314 (2009).
Zhang et al., "Optimizing the specificity of nucleic acid hybridization." *Nature Chemistry*, 4:208-214 (2012).

* cited by examiner

*Primary Examiner* — Ethan C Whisenant
(74) *Attorney, Agent, or Firm* — Parker Highlander PLLC

(57) ABSTRACT

This present disclosure describes hybridization probes modularly constructed from several oligonucleotides with a pattern of designed complementary interactions, allowing the probes to sequence-specifically capture or analyze nucleic acid target sequences that are long and/or complex.

19 Claims, 84 Drawing Sheets

Specification includes a Sequence Listing.

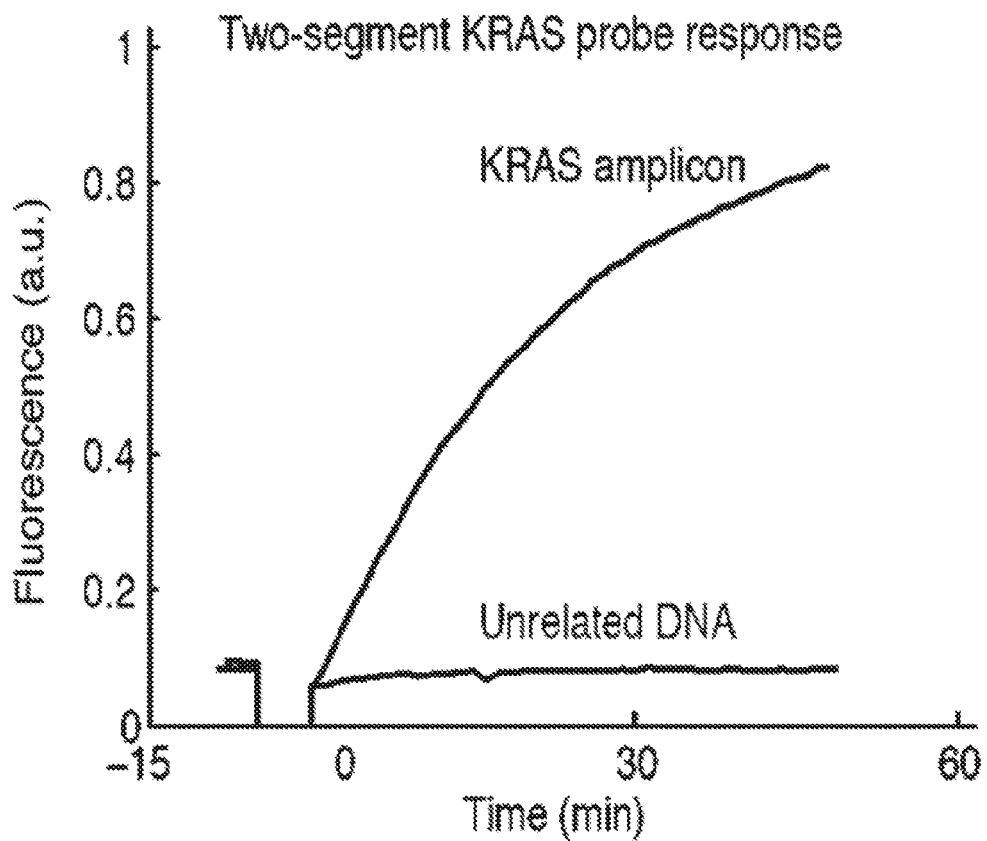

FIGURE 8A
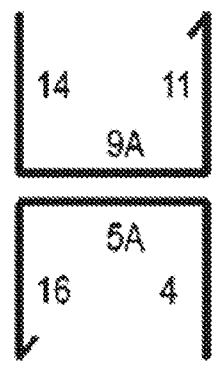
Segment 1A
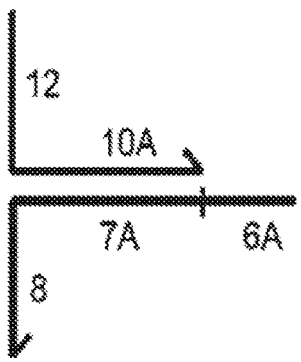
Segment 2A
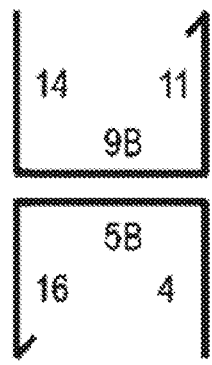
Segment 1B
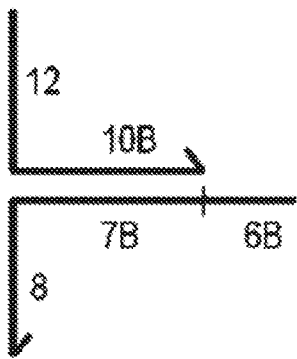
Segment 2B
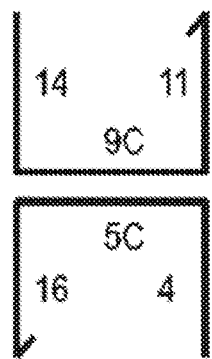
Segment 1C
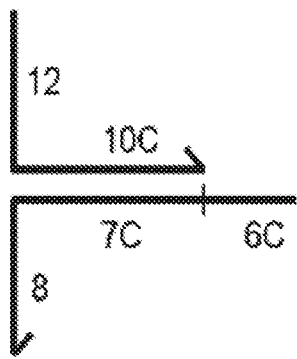
Segment 2C n-segment M-Probe

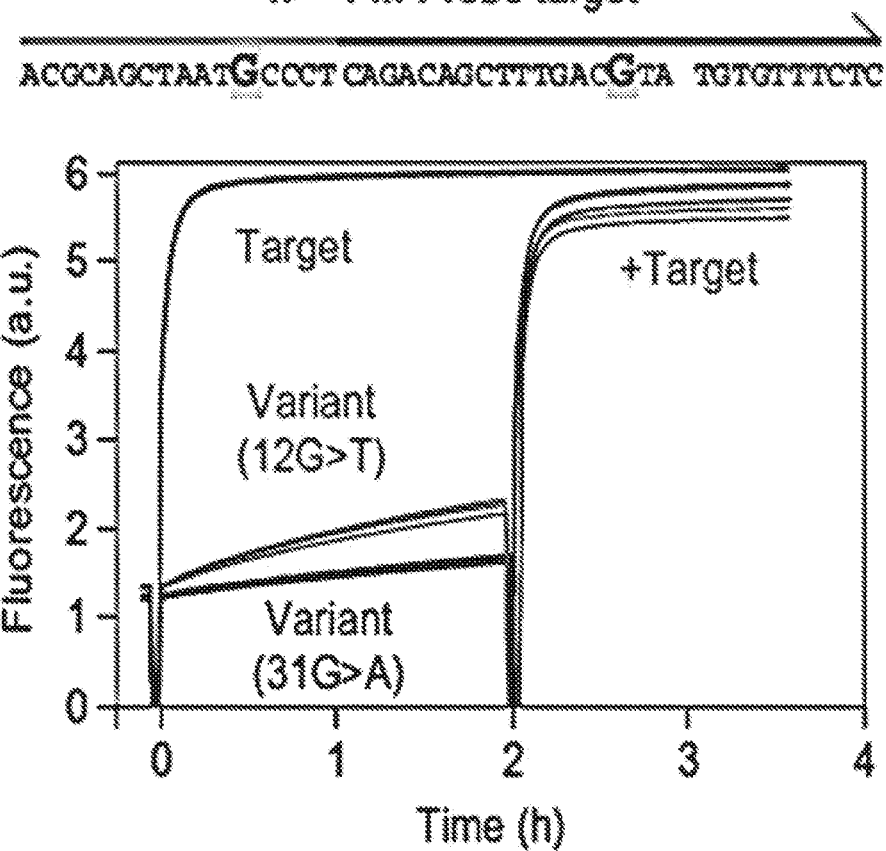

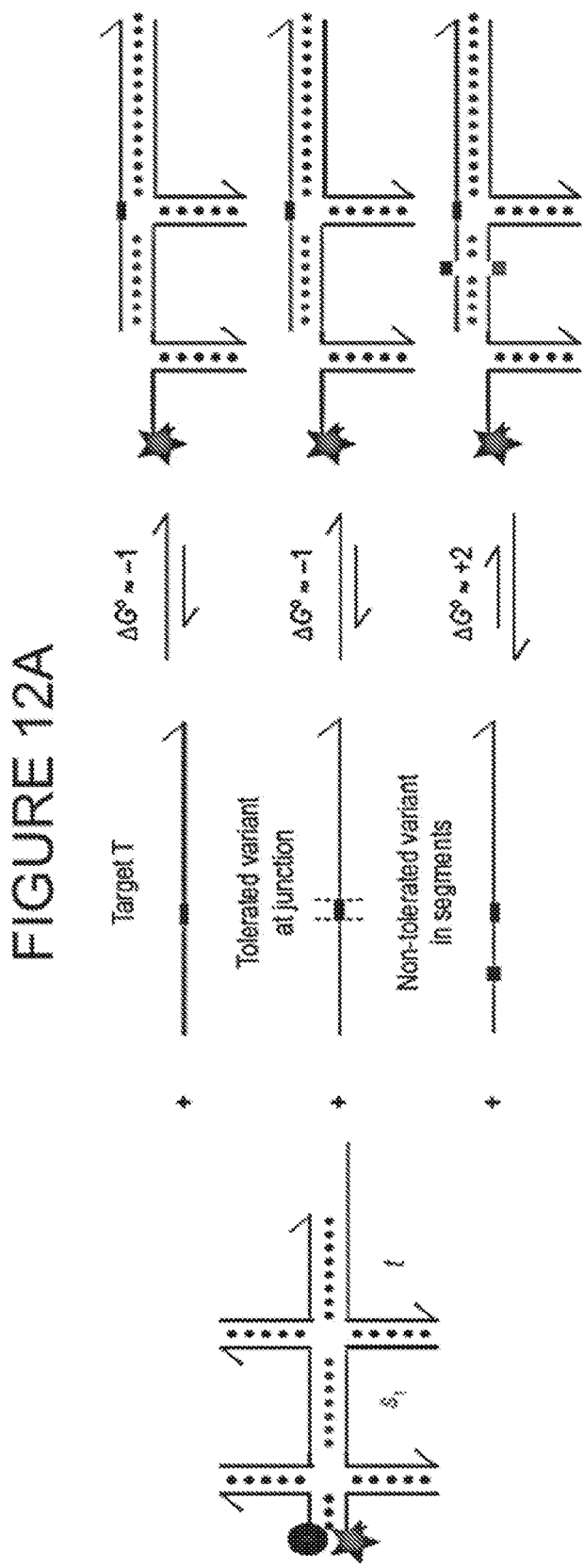

FIGURE 15G

| Sample | Probe9 Ct | Probe27 Ct | ΔCt | HTT repeats |
|---|---|---|---|---|
| NA20245 | 25.5 | 31.0 | 5.5 | 15/15 |
| NA20248 | 25.1 | 25.6 | 0.1 | 17/36 |
| NA20208 | 24.2 | 25.7 | 1.5 | 35/45 |
| NA20209 | 25.2 | 25.3 | 0.1 | 45/46 |
| NA20210 | 23.5 | 24.1 | 0.6 | 17/75 |
| NA18537 | 25.2 | 30.9 | 5.7 | N/A |
| NA18524 | 25.2 | 30.6 | 5.4 | N/A |

| | Ct | Average Ct | ΔCt |
|---|---|---|---|
| M-Probe33 | 26.5 | | |
| M-Probe35 | 26.3 | 26.4 | |
| M-Probe36 | 26.3 | | 5.3 |
| M-Probe37 | 31.6 | 31.7 | |
| M-Probe39 | 31.8 | | |

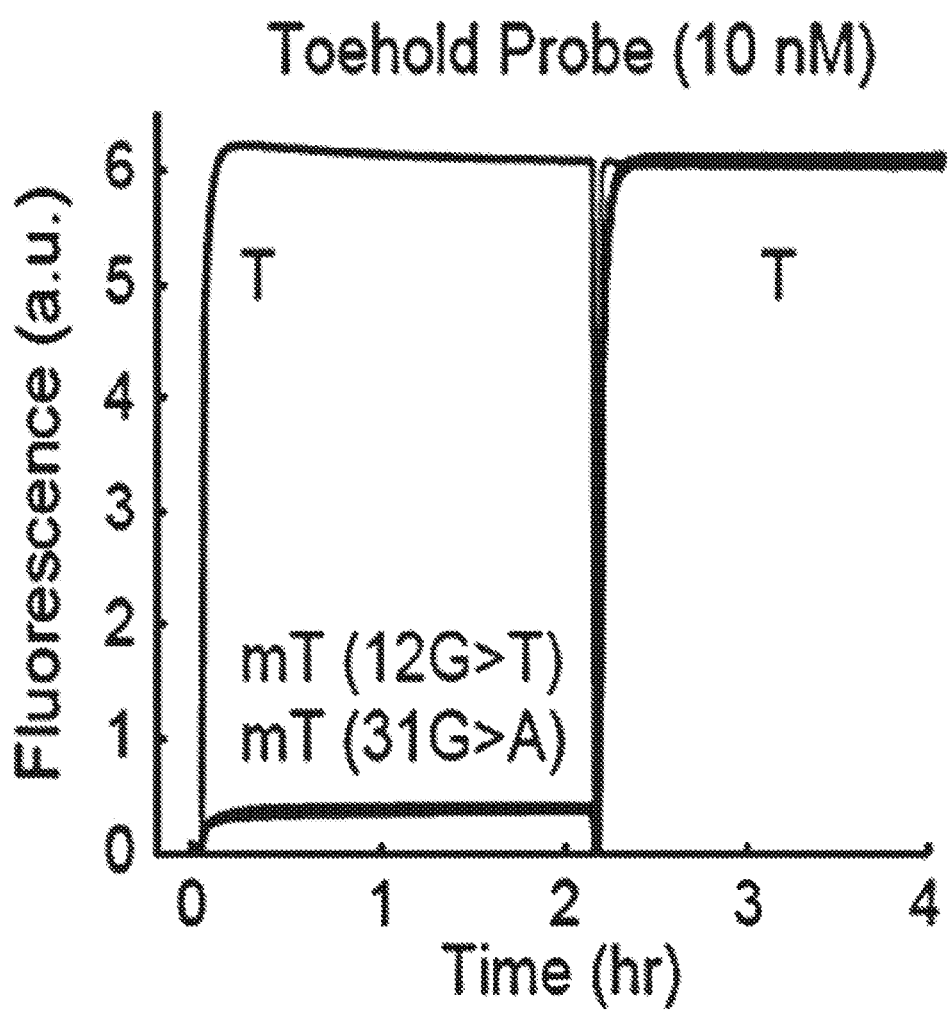

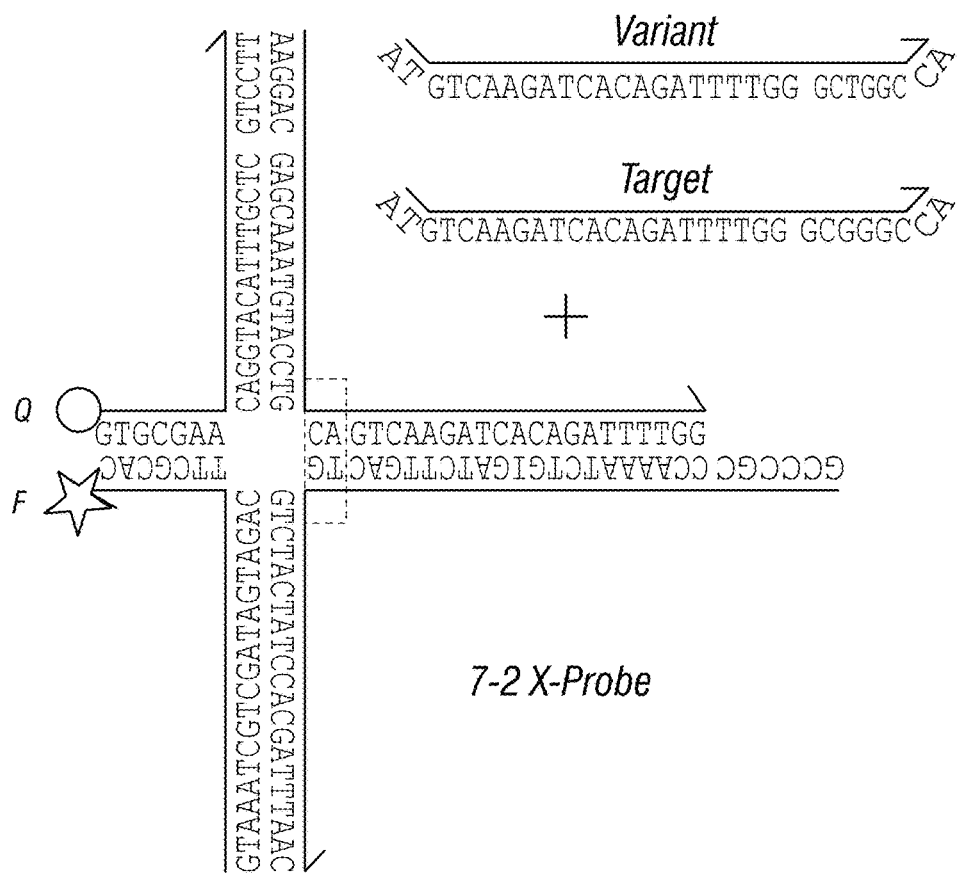
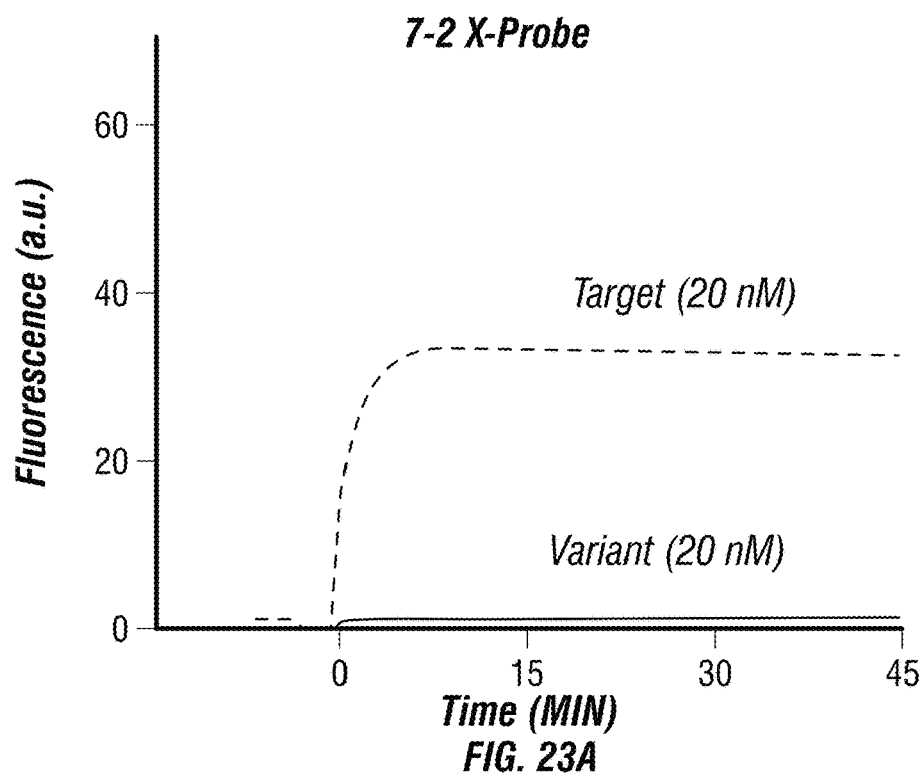
FIG. 23A

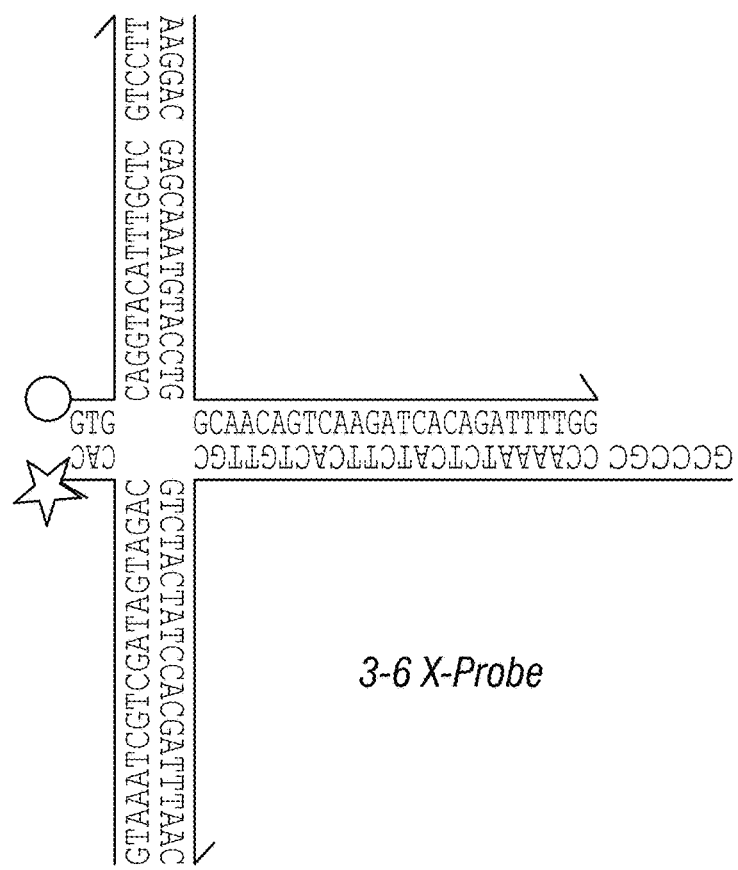
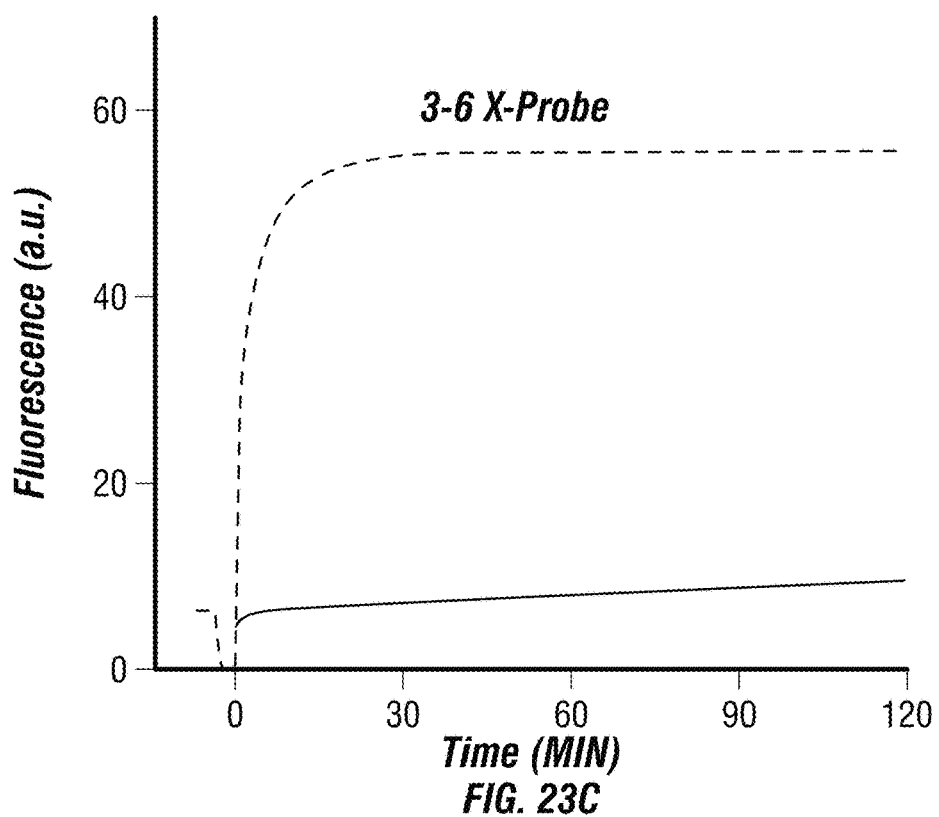
FIG. 23C

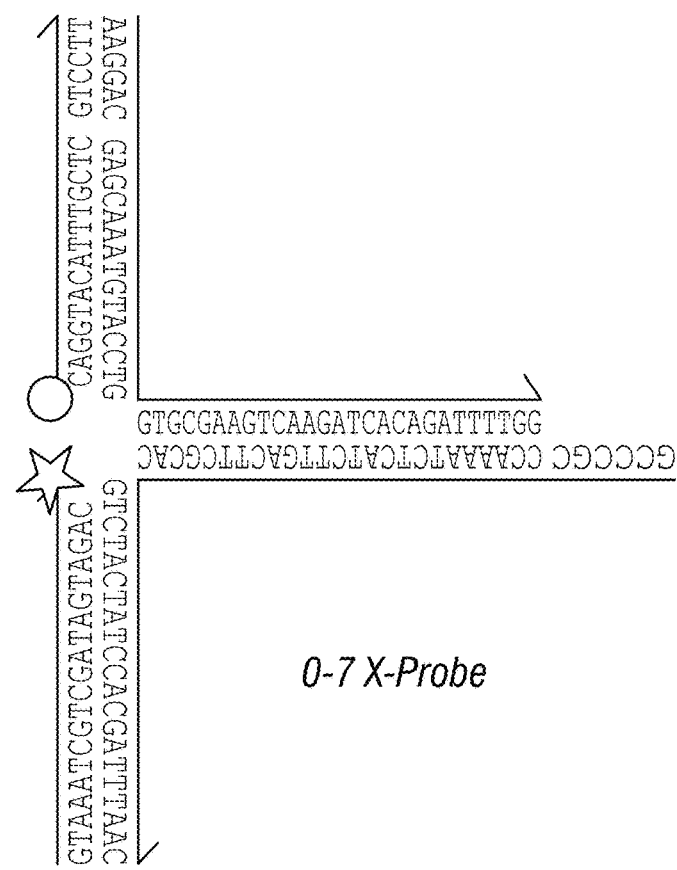
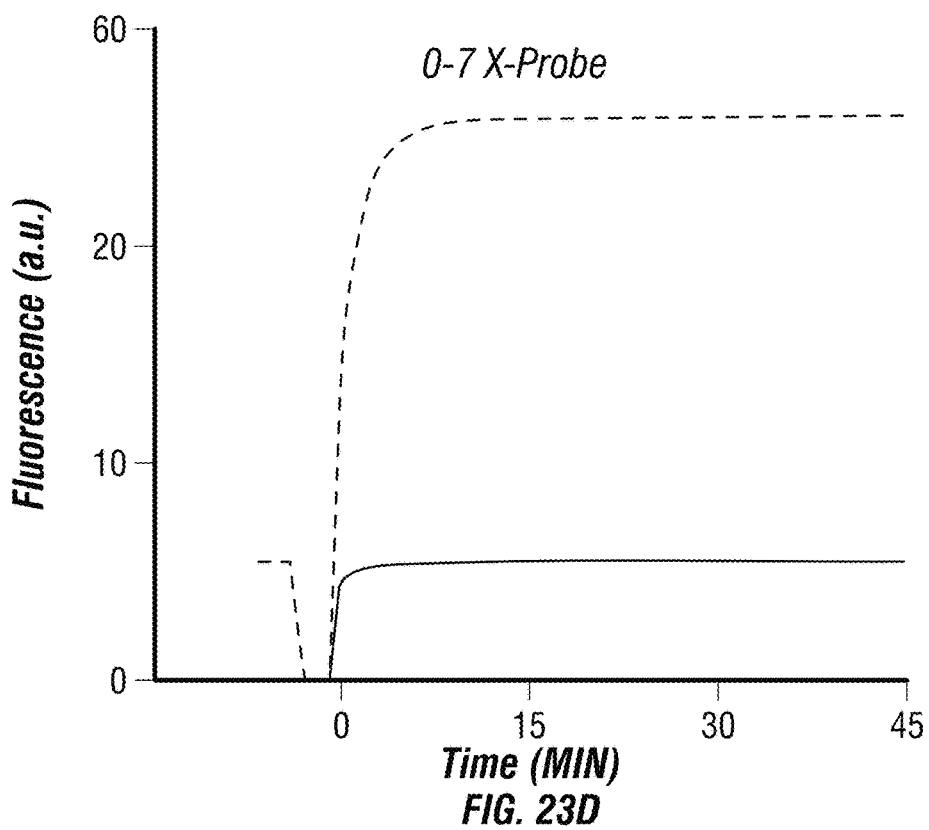
FIG. 23D

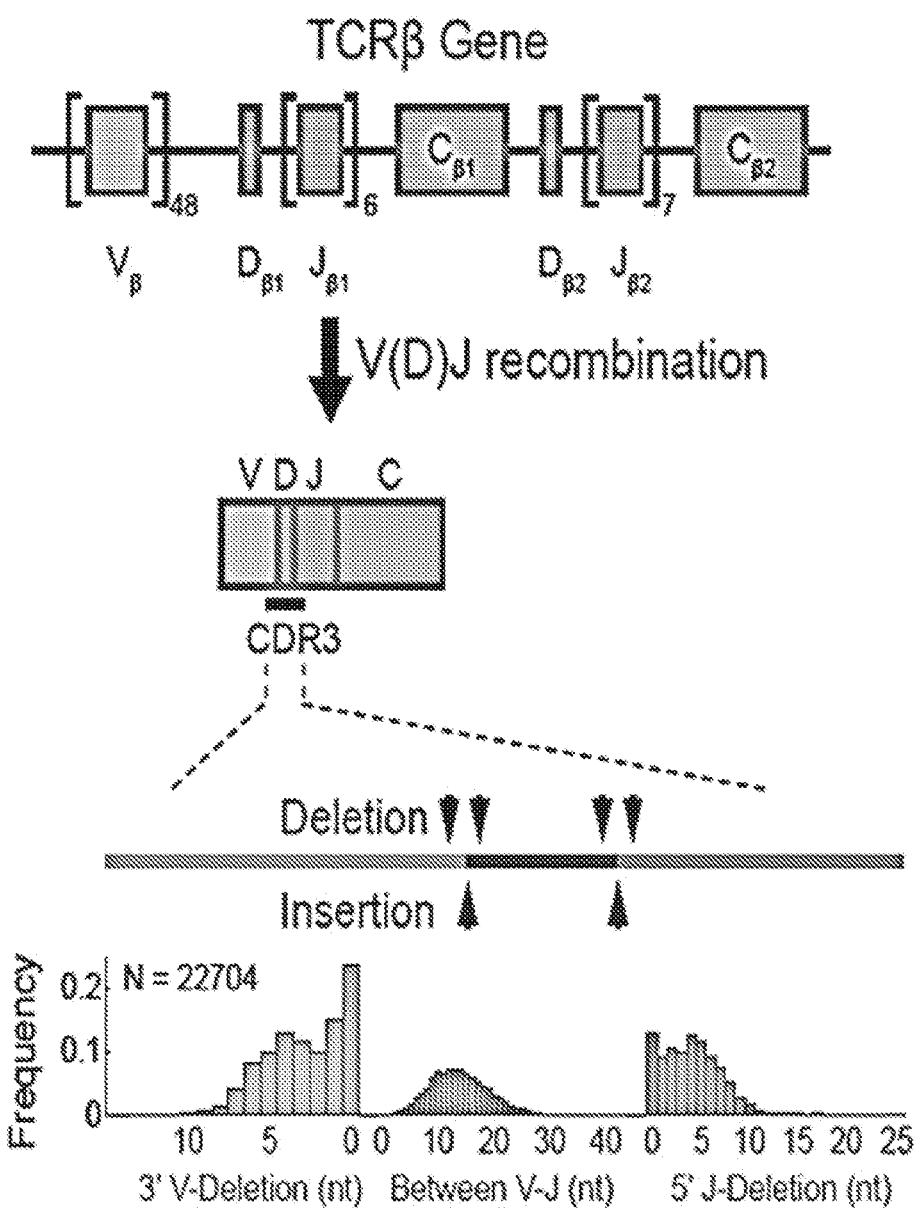

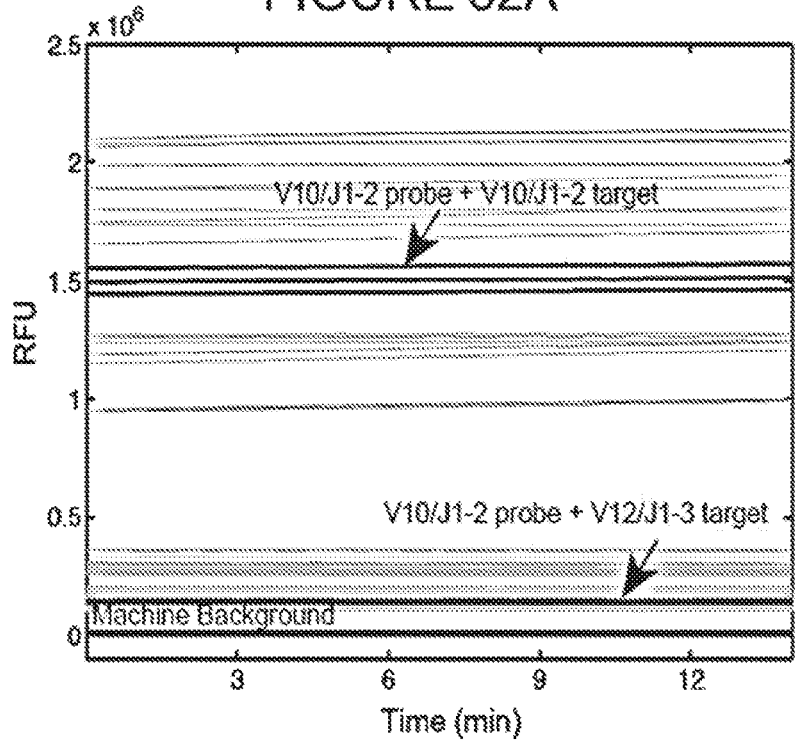
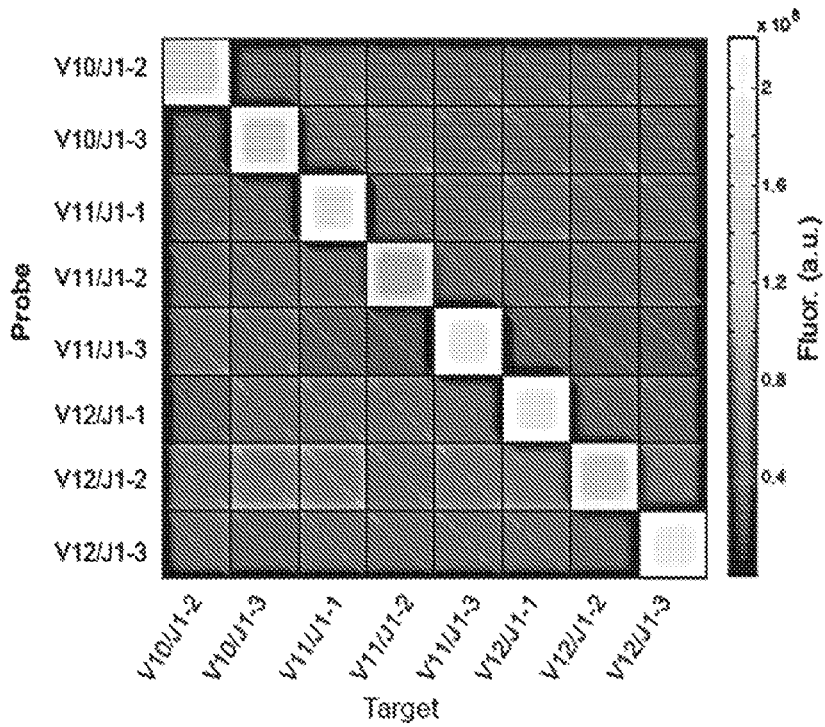

277nt KRAS Amplicon (Targeting c.210-427) MFE Structure
37 °C, 1xPBS (0.15 M Na+)

MP-218nt Targeting Region

Free energy of secondary structure: -10.74 kcal/mol

|  | Ct | NTC Ct | Melt Temp |
|---|---|---|---|
| T-correct | 17.1 ± 0.2 | NA | 77.5 |
| T-Δ3nt | 25.5 ± 0.4 | 37.0 ± 2.5 | 77 |
| T-Δ6nt | 22.0 ± 0.3 | 33.1 ± 0.3 | 76.5 |

459 nt MP-430nt Amplicon MFE Structure
45 °C, 1xPBS (0.15 M Na⁺)

Free energy of secondary structure: -4.88 kcal/mol 590 nt MP-1 nt Amplicon MFE Structure
45 °C, 1xPBS (0.15 M Na⁺)

Free energy of secondary structure: -11.35 kcal/mol

C 590 nt MP-2 nt Amplicon MFE Structure
45 °C, 1xPBS (0.15 M Na⁺)

Free energy of secondary structure: -5.97 kcal/mol

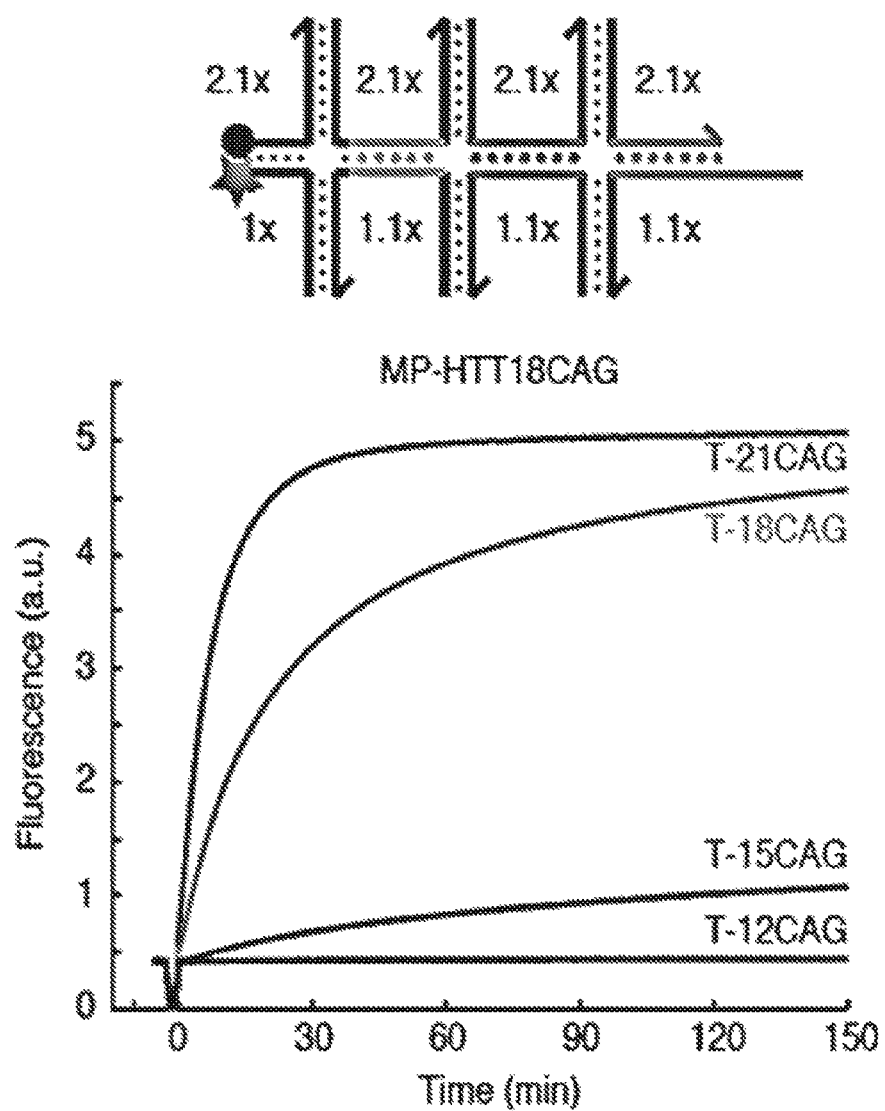

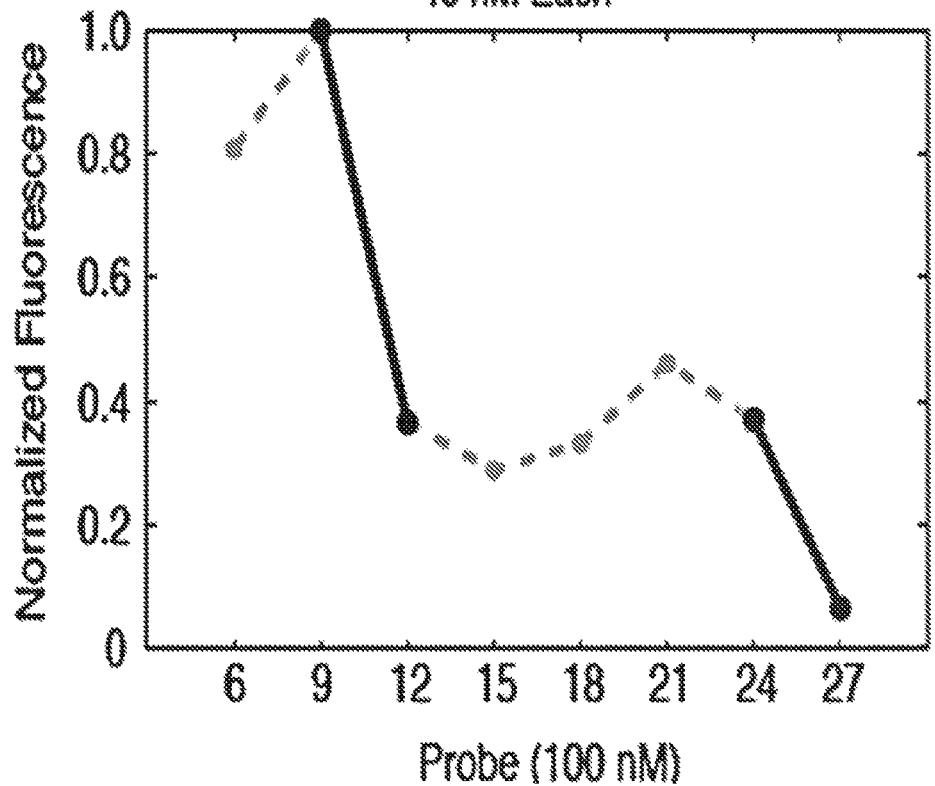

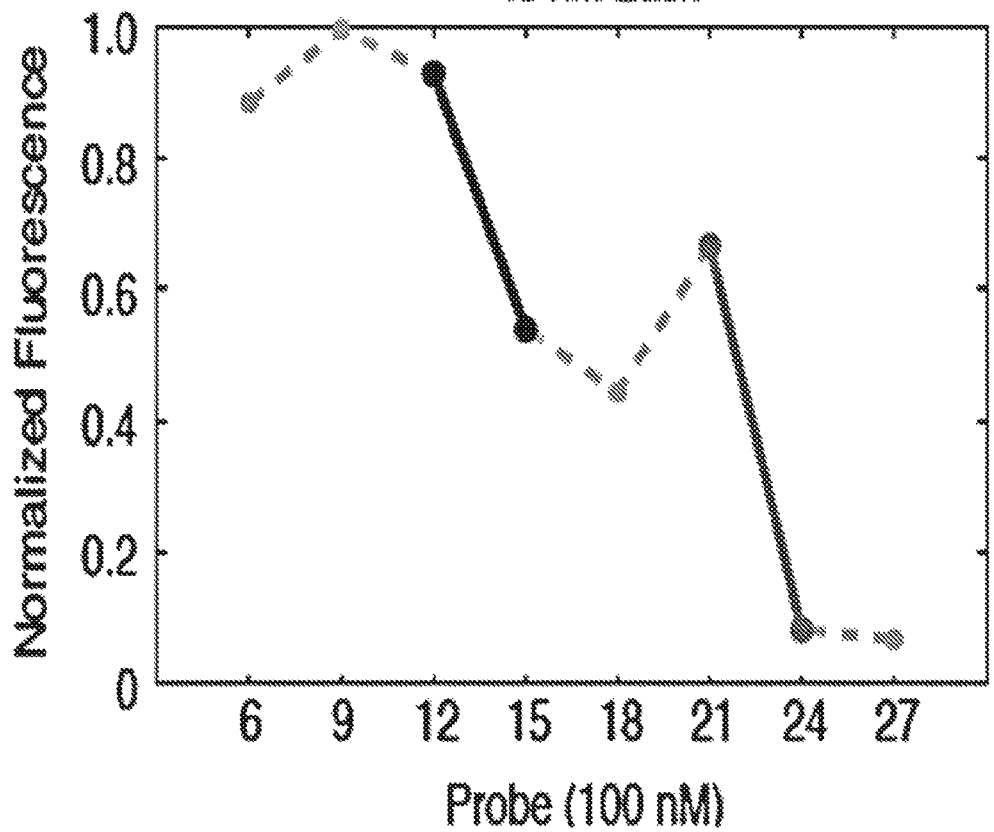

MOLECULAR HYBRIDIZATION PROBES FOR COMPLEX SEQUENCE CAPTURE AND ANALYSIS

CROSS-REFERENCE TO RELATED APPLICATIONS

The present application is a national phase application under 35 U.S.C. § 371 of International Application No. PCT/US2017/053109 filed on Sep. 22, 2017, and claims priority to U.S. Provisional Application No. 62/398,484, filed Sep. 22, 2016, the entirety of each of which is incorporated herein by reference.

SEQUENCE LISTING

The instant application contains a Sequence Listing which has been submitted electronically in ASCII format and is hereby incorporated by reference in its entirety. Said ASCII copy, created on Oct. 31, 2017, is named 16-21016-WO-_SL.txt and is 85,388 bytes in size.

BACKGROUND

Common techniques for analyzing nucleic acid sequences include the polymerase chain reaction (PCR) and next-generation sequencing (NGS), but these techniques fail in the analysis of long or complex sequences. Trinucleotide repeats, in particular, are difficult to analyze due to slipped strand mispairing, and the fact that pathogenic variants are frequently characterized by long strands (>200 nucleotides) that exceed the read length of NGS.

Standard hybridization probes are: (1) length-limited by synthesis capabilities and cannot query long target regions; (2) not economical for profiling of DNA samples with combinatorial diversity, such as T-cell receptors and antibody fragments; (3) incapable of accurate quantitation of trinucleotide repeats such as in Huntington's gene, Fragile X, and Federick's Ataxia, as well as microsatellite repeats.

U.S. Patent Application Publication No. 2014/0255924 discloses a modular probe design using different sections, each with a variable region that is complementary to a target, flanked by arms which are complementary to one another. However, this approach uses "or" logic where once any section binds to the target, it recruits the other sections. Thus, the approach lacks specifity across long target sequences.

Such prior art approaches have not demonstrated tolerance to multi-nucleotide variation at specified positions with single-nucleotide selectivity. Previous attempts have generally used degenerate nucleotide mixtures, for example N, or universal artificial nucleotides, for example inosine, in probes to confer sequence variation tolerance, but such approaches do not equally tolerate insertions, deletions and replacements. Furthermore, these approaches are generally not compatible with double-stranded probes that are designed to allow single-nucleotide selectivity across long target regions or to provide tolerance at segment junctions.

Hybridization probes which overcome these limitations would be useful in sequence capture and analysis.

SUMMARY

The present disclosure provides a nucleic acid probe approach for the capture and analysis of long and complex target nucleic acid sequences. The nucleic acid probe features a modular construction in which Complement Oligonucleotides collectively span and hybridize to a long target sequence. Simultaneously, the modular probe also includes molecular competitor species with sequence similar to the target, to ensure hybridization specificity through molecular competition.

Using this approach, the specific detection of target sequences 160 nucleotides (nt) long, and quantifying the number of repeats on triplet repeat sequences (e.g. CAG for Huntington's disease) have been demonstrated. This approach can permit combinatorial probe construction for immune profiling applications, where target sequences exhibit combinatorial diversity.

Compared to previous work on toehold probes and X-probes, which utilize a single oligonucleotide that is complementary to the target sequence, the modular probes presented here use multiple different oligonucleotides to bind different subsequences of the target. Because oligonucleotide synthesis capabilities are capped at roughly 200 nt for unfunctionalized DNA oligonucleotides and at roughly 90 nt for fluorophore-functionalized DNA oligonucleotides, prior art on hybridization probes could not effectively probe regions longer than roughly 100 nt. The current invention enables probes to query longer target regions through its modular construction. In addition, the probes of the present disclosure can combine the features of sequence variation tolerance with nucleotide selectivity.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the disclosure is not limited to the specific methods and instrumentalities disclosed herein.

FIG. 4 shows experimental results using a modular probe targeting a DNA sequence including the first 143 nucleotides of the KRAS cDNA on the sense strand and the 17 intron nucleotides directly to the 5' of the KRAS cDNA.

FIG. 8A illustrates different versions of each segment of a modular probe that can be synthesized and constructed to bind different target subsequences which are shown in FIG. 8B.

FIG. 11C shows the experimental fluorescence from the experiment depicted in FIG. 11B, measured in triplicate. Figure discloses SEQ ID NO: 47.

FIG. 12A depicts an M-probe design.

FIG. 15G shows the precise determination of triplet repeat number using a series of M-Probes.

FIG. 22B shows the performance of a toehold probe for comparison to that of the M-probe in FIG. 22A and an X-probe in FIG. 22C.

FIG. 23A-D shows the design and experimental results for 4×-Probes, respectively (M-Probe with n=0) with different length complementary sections in the u segment. FIG. 23A discloses the Variant and Target sequences as SEQ ID NOS 59 and 58, respectively, and the structure sequences as SEQ ID NOS 2, 66, 1, and 67, respectively, in order of appearance. FIG. 23B discloses the structure sequences as SEQ ID NOS 60, 68, 61, and 69, respectively, in order of appearance. FIG. 23C discloses the structure sequences as SEQ ID NOS 62, 264, 63, and 71, respectively, in order of appearance. FIG. 23D discloses the structure sequences as SEQ ID NOS 64, 72, 65, and 73, respectively, in order of appearance.

FIG. 24 depicts variation in the human TCR-β gene, VDJ recombination, and V-D and D-J junction regions. Regions between V-D, and D-J are subject to random deletions and non-templated insertions, resulting a hypervariable CDR3 region that is important for recognition of diverse antigens. The graph at the bottom of FIG. 24 depicts length distributions of V 3' deletions deletions, sequence between V and J, and J 5' deletions in T lymphocytes from peripheral blood, based on data from Freeman, J. D., Warren, R. L., Webb, J. R., Nelson, B. H., & Holt, R. A. Profiling the T-cell receptor beta-chain repertoire by massively parallel sequencing. *Genome Res.* 19, 1817-1824, (2009).

FIG. 31A shows the averaged raw Relative Fluorescence Units (RFU) value of ROX-labeled oligos in 1×PBS buffer with 0.1% Tween20. Each well contains a 10 μL solution at the indicated concentration. Shown here are the average values from 20 measurements collected once every 30 seconds at 37° C., after a 20 minute incubation at 37° C.

FIG. 31B shows example position correction for the A1 well. The RFU values at four concentrations are plotted against the corresponding reference RFU values (average over the entire plate). The least-squares linear fit was calculated and used to correct position biases for all subsequent experiments.

FIGS. 32A-32B show endpoint fluorescence signals for pairwise interactions between 8 M-Probes and 8 VDJ targets.

FIG. 32A: Matched probe/target fluorescence signals are shown in red or pink, mismatched probe/target pairs are shown in green or light green. All reaction experiments were done in triplicate. Each well contained 100 nM M-Probe and 300 nM Target. Data collection began after overnight incubation at 37° C. and 30 minutes incubation in the qPCR machine at 37° C. Then 30 data points are collected (30 seconds per data point).

FIG. 32B: Average position-corrected endpoint fluorescence for the 8 M-Probes and targets. Signals from matched probes and targets are displayed along the main diagonal.

FIG. 34A shows the amplicon used as target for FIGS. 33A-33B. Target sequences for the respective M-Probes are highlighted in gray (99 nt targeting region) and pink (160 nt targeting region).

FIG. 34B shows the amplicon used as target for FIGS. 33C-33D.

FIG. 35A shows qPCR data collected from 96-well plates using the Bio-Rad CFX96 Touch Real-Time PCR machine. Traces show that amplification of all three targets reach equilibrium within 50 cycles.

FIG. 35B shows a summary of observed cycle threshold (Ct) values.

FIG. 36A shows M-Probe (n=2) was designed to have the same genotype as sample NA18562. Amplicons generated from sample NA18537 create a single base mismatch when react with the M-Probe.

FIG. 36B shows fluorescence responses of M-Probe (10 nM) to amplicon targets generated from samples NA18562 and NA18537. Hybridization experiments were performed at 45° C. in 1×PBS.

FIG. 37A shows the amplicon used as target for 430 nt M-Probe (FIGS. 36A-36B).

FIGS. 37B-37C depict amplicons used as target for FIGS. 36A-36B.

FIGS. 40A-40B demonstrate the effect of different M-Probe strand stoichiometries on target hybridization reactions.

FIG. 40A shows stoichiometry with increasing concentrations to ensure lack of adversarial side products.

FIG. 40B shows simplified stoichiometry facilitates scalability to larger n. There does not appear to be a significant difference in performance for the two stoichiometries.

FIG. 41A: The target sequence is the antisense strand of the FMR1 gene because targets with CGG repeats adopts highly stable secondary structures that slow the hybridization reaction with M-Probes. This M-Probe, targeting 19 CCG repeats, clearly distinguishes 16 repeats from 19. Figure discloses T-CGG19 and T-CGG16 sequences as SEQ ID NOS 245 and 246, respectively, and structure sequences as SEQ ID NOS 2, 247, 249, 251, 1, 248, 250, and 252, respectively, in order of appearance.

FIG. 41B: M-Probe targeting 19 GAA repeats clearly distinguishes 16 from 19. Figure discloses T-GAA19 and T-GAA16 sequences as SEQ ID NOS 253 and 254, respectively, and structure sequences as SEQ ID NOS 2, 274, 275, 259, 1, 256, 258, and 260, respectively, in order of appearance.

FIGS. 43A-43E show M-Probe response curves for heterozygous samples. Final concentrations of M-Probes in these experiments are 100 nM.

FIG. 43A: Fluorescence observed by reacting a 1:1 mix of synthetic targets with 9 and 24 CAG repeats with the M-Probe.

FIG. 43B: Fluorescence observed by reacting a 1:1 mix of synthetic targets with 12 and 21 CAG repeats with the M-Probe.

FIG. 43C: Fluorescence observed by reacting a synthetic target with 27 CAG repeats with the M-Probe.

FIG. 43D: Normalized response curve to 1:1 mix of synthetic targets with 9 and 24 CAG repeats.

FIG. 43E: Normalized response curve to 1:1 mix of synthetic targets with 12 and 21 CAG repeats.

DETAILED DESCRIPTION

The present disclosure will provide description to the accompanying drawings, in which some, but not all embodiments of the subject matter of the disclosure are shown. Indeed, the subject matter may be embodied in many different forms and should not be construed as limited to the embodiments set forth herein, rather, these embodiments are provided so that this disclosure satisfies all the legal requirements.

Unless otherwise defined, all technical and scientific terms used herein have the same meaning as commonly understood by one of ordinary skill in the art.

The modular probe is designed based on detection or capture of a target nucleic acid sequence of at least partially known sequence. The target sequence is divided conceptually into several regions, a region being a number of continuous nucleotides that act as a unit in hybridization or dissociation. In most of the present disclosure we will consider the target as comprising three regions, labeled in 5' to 3' order as regions 1, 2, and 3. Note that the regions may or may not be directly adjoining one another; the dashed line between regions 1 and 2 in FIGS. 1A-1B denote possible existence of additional nucleotides not part of either region 1 or region 2.

Figure 1A:
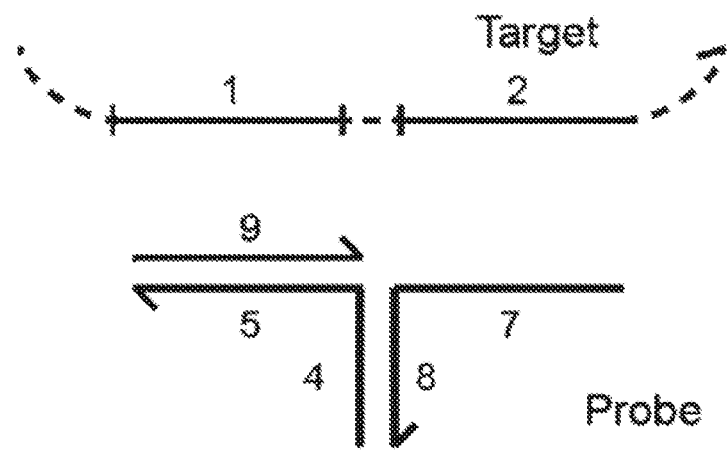
FIG. 1A depicts a general implementation of a modular probe. A First Complement Oligonucleotide comprising regions 4 and 5 can hybridize to a Second Complement Oligonucleotide comprising regions 7 and 8. The target comprises regions 1 and 2, that are respectively complementary to regions 5 and 7. A First Protector Oligonucleotide comprises region 9, which is complementary to region 5.
Figure 1B:
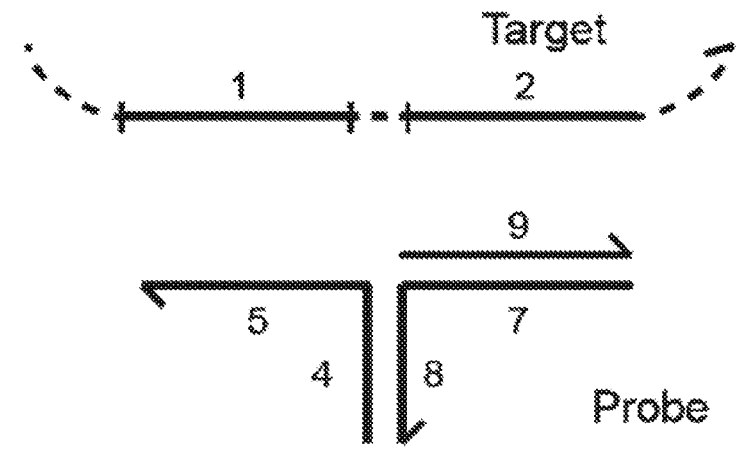
FIG. 1B depicts a general implementation of a modular probe. A First Complement Oligonucleotide comprising regions 4 and 5 can hybridize to a Second Complement Oligonucleotide comprising regions 7 and 8. The target comprises regions 1 and 2, that are respectively complementary to regions 5 and 7. A First Protector Oligonucleotide comprises region 9, which is complementary to region 7.

The most general instance of the modular probe comprises two Complement Oligonucleotides and a Protector Oligonucleotide (FIGS. 1A-1B). The two Complement Oligonucleotides each possess a region (5 and 7) that is complementary to a different region of a target sequence (1 and 2, respectively). Furthermore, the two Complement Oligonucleotides further possess regions 4 and 8, respectively, that are complementary to each other, and serve to colocalize the two Complement Oligonucleotides in solution. The Protector Oligonucleotide comprises region 9, which is complementary to either region 5 or 7, and hence homologous in sequence to target region 1 or target region 2. The Protector Oligonucleotide competes with the target in hybridizing to the two Complement Oligonucleotides, and thus improves the sequence specificity of the modular probe.

In some embodiments, Complement Oligonucleotides of the nucleic acid hybridization probes of the present disclosure can include from any one of 1, 2, 3, 4, 5, 6, 7, 8, 9, 10, 15, 20, 25, 30, 35, 40, 45, 50, 60, 70, 80, 90, 100, 105, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540 and 550 to any one of 560, 550, 540, 530, 520, 510, 500, 490, 480, 470, 460, 450, 440, 430, 420, 410, 400, 390, 380, 370, 360, 350, 340, 330, 320, 310, 300, 290, 280, 270, 260, 250, 240, 230, 220, 210, 200, 190, 180, 170, 160, 150, 140, 130, 120, 110, 100, 90, 80, 70, 60, 50, 45, 40, 35, 30, 25, 20, 15, 10, 9, 8, 7, 6, 5, 4, 3, 2 and 1 nucleotides. In some embodiments the Complement Oligonucleotides of the nucleic acid hybridization probes of the present disclosure can include more than 500 nucleotides. In some embodiments, the portion of the Complement Oligonucleotides complementary to a portion of the target nucleic acid sequence can include from any one of 1, 2, 3, 4, 5, 6, 7, 8, 9, 10, 15, 20, 25, 30, 35, 40, 45, 50, 60, 70, 80, 90, 100, 105, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540 and 550 to any one of 560, 550, 540, 530, 520, 510, 500, 490, 480, 470, 460, 450, 440, 430, 420, 410, 400, 390, 380, 370, 360, 350, 340, 330, 320, 310, 300, 290, 280, 270, 260, 250, 240, 230, 220, 210, 200, 190, 180, 170, 160, 150, 140, 130, 120, 110, 100, 90, 80, 70, 60, 50, 45, 40, 35, 30, 25, 20, 15, 10, 9, 8, 7, 6, 5, 4, 3, 2 and 1 nucleotides. In some embodiments, the portion of the Complement Oligonucleotides complementary to a portion of the target nucleic acid sequence can include more than 500 nucleotides. In some embodiments, any portion of a Complement Oligonucleotide that is complementary to a portion of another Complement Oligonucleotide can include from any one of 1, 2, 3, 4, 5, 6, 7, 8, 9, 10, 15, 20, 25, 30, 35, 40, 45, 50, 60, 70, 80, 90 to any one of 100, 90, 80, 70, 60, 50, 45, 40, 35, 30, 25, 20, 15, 10, 9, 8, 7, 6, 5, 4, 3, 2 and 1 nucleotides. In some embodiments, the portion of the target sequence that is complementary to a portion of the nucleic acid hybridization probe that does not correspond to a complementary Protector Oligonucleotide comprises from any one of 1, 2, 3, 4, 5, 6, 7, 8, 9, 10, 15, 20, 25, 30, 35, 40, and 45 to any one of 50, 45, 40, 35, 30, 25, 20, 15, 10, 9, 8, 7, 6, 5, 4, 3, 2 and 1 nucleotides. In some embodiments, the portion of the target sequence that is complementary to a portion of the nucleic acid hybridization probe that does not correspond to a complementary Protector Oligonucleotide comprises more than 50 nucleotides. For example, the toehold region of the nucleic acid hybridization probe, such as region 6 in FIGS. 2A-2B can include from any one of 1, 2, 3, 4, 5, 6, 7, 8, 9, 10, 15, 20, 25, 30, 35, 40, and 45 to any one of 50, 45, 40, 35, 30, 25, 20, 15, 10, 9, 8, 7, 6, 5, 4, 3, 2 and 1 nucleotides or can comprise more than 50 nucleotides.

Figure 2A:
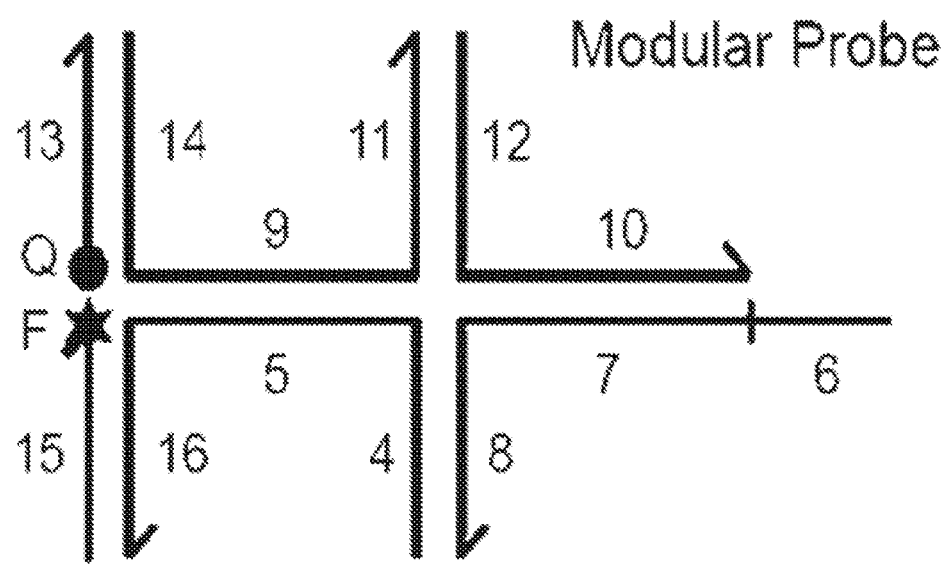
FIG. 2A depicts a schematic drawing of an embodiment of the modular probe with 2 Complement Oligonucleotides, 2 Protector Oligonucleotides, and 2 Universal Oligonucleotides. The probe is natively in a dark state because the fluorophore F is colocalized to a quencher Q.
Figure 2B:
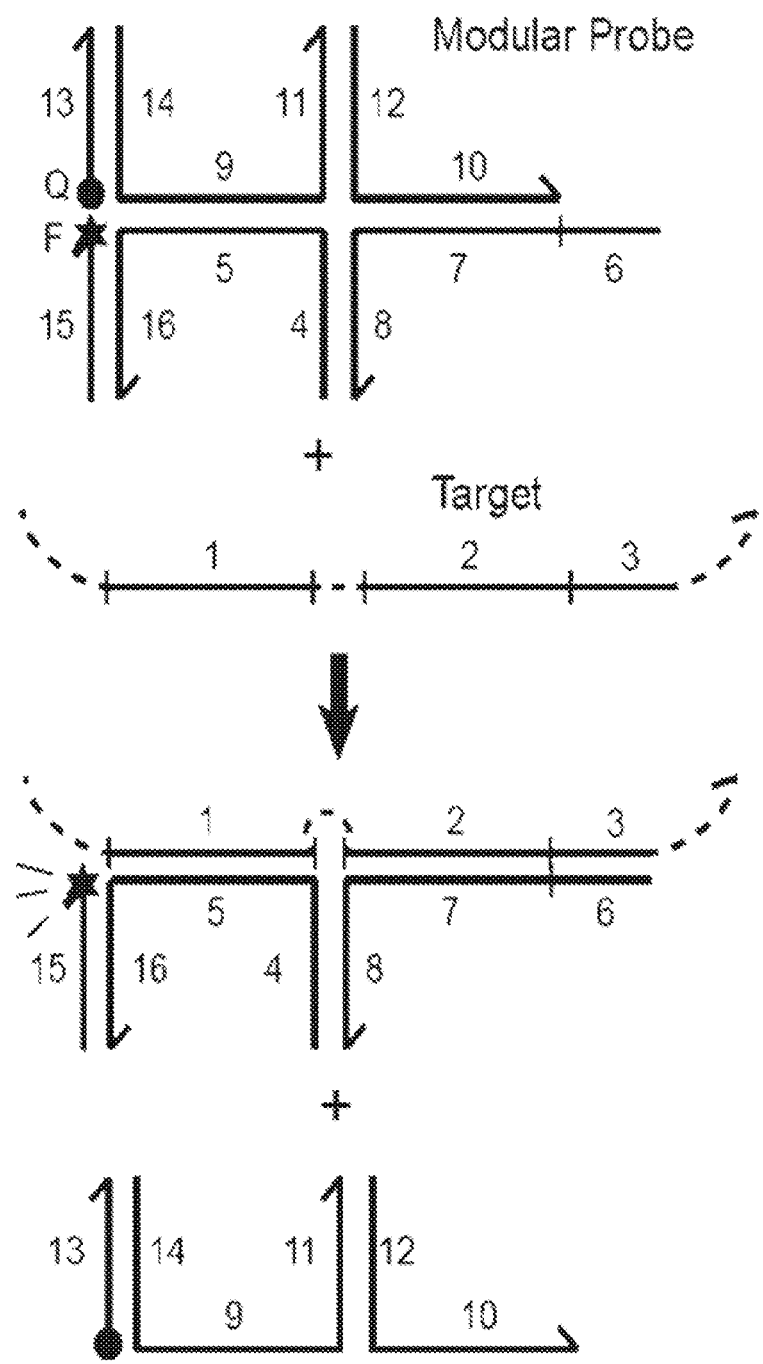
FIG. 2B shows a reaction of the modular probe of FIG. 2A with a target results in an increase in solution fluorescence because the fluorophore (represented by a star) is no longer quenched.

Conditionally Fluorescent Modular Probe. FIGS. 2A-2B show an embodiment of the modular probe with 2 Complement Oligonucleotides (one including regions 16, 5 and 4 and the other including regions 6, 7 and 8), 2 Protector Oligonucleotides (one including regions 14, 9 and 11 and the other including regions 12 and 10), and 2 Universal Oligonucleotides (13 and 15). One of the Universal Oligonucleotides (15) is functionalized with a fluorophore (F), and the other (13) is functionalized with a quencher (Q). As depicted, region 5 is complementary to region 9 and to region 1 while region 7 is complementary to region 10 and to region 2. Region 6 (toehold) is complementary to region 3 of the target. In addition, regions 13 and 14, 15 and 16, 11 and 12 and 4 and 8 are also complementary to one another, respectively. In the native configuration of the modular probe, the quencher is within the Forster radius of the fluorophore (5 nm), and probe fluorescence is low. Upon hybridization to the target sequence, the Protector Oligonucleotides and the Universal Oligonucleotide bearing the quencher are displaced and delocalized from the Complement Oligonucleotides, resulting in increased solution fluorescence. The background-subtracted fluorescence is, to first approximation, linear with the number of bound target molecules. Thus, the conditionally fluorescent modular probe serves as a method of assaying the hybridization yield of different targets, as well as the hybridization kinetics of the target-probe binding.

Figure 3A:
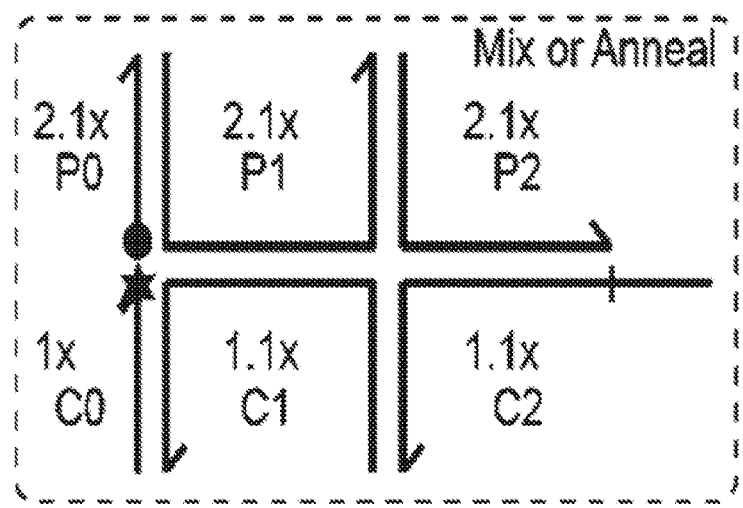
FIG. 3A depicts an exemplary probe formulation.
Figure 3B:
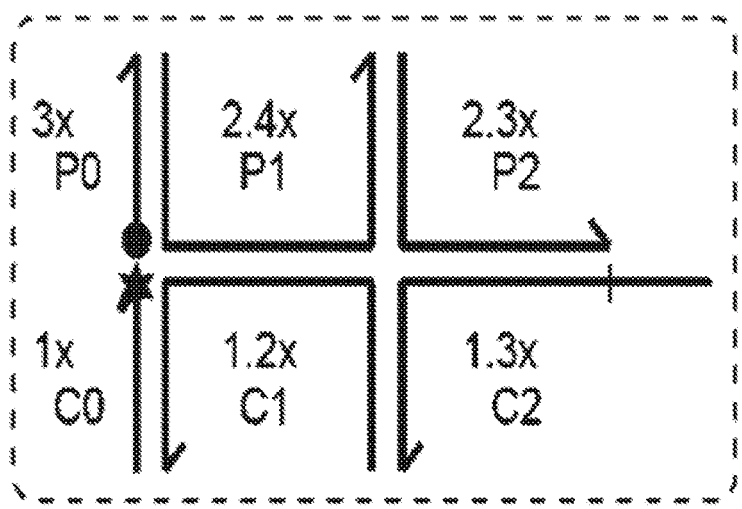
FIG. 3B depicts an exemplary probe formulation.
Figure 3C:
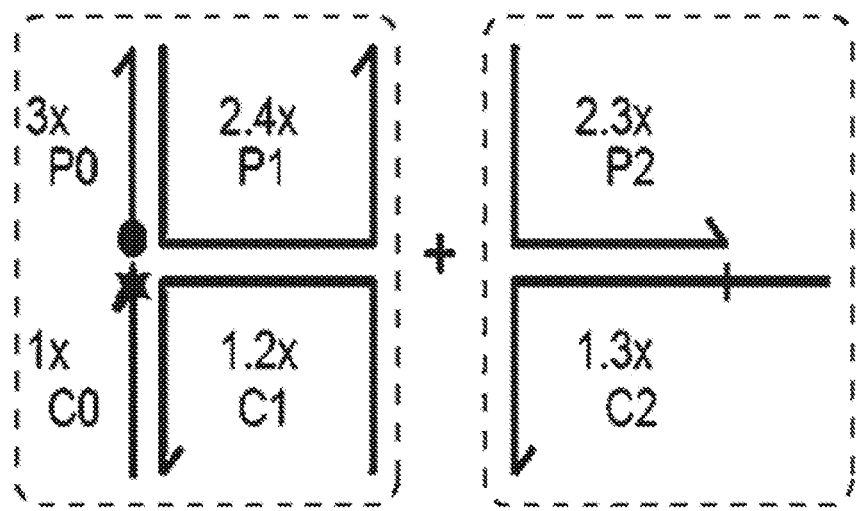
FIG. 3C depicts an exemplary probe formulation.
Figure 3D:
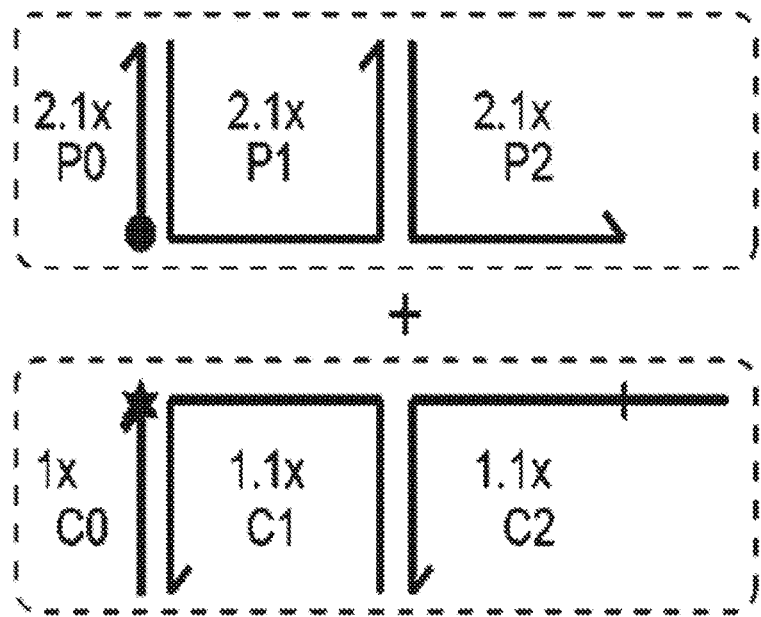
FIG. 3D depicts an exemplary probe formulation.

Many formulation protocols for preparing the modular probe from its component oligonucleotides (i.e. Complement Oligonucleotides, Protector Oligonucleotides, and Universal Oligonucleotides) are possible (examples are shown in FIGS. 3A-3D), and their relative effectiveness depends on the complexity of the target sequence, the purity of the component oligonucleotides, and the achievable accuracy of pipetting and aliquoting. FIG. 3A depicts a combination of the Complement Oligonucleotides (C1 and C2) and Protector Oligonucleotides (P1 and P2) along with Universal Oligonucleotides (C0 and P0) which have a fluorophore (F) and a quencher (Q) in solution in a buffer and at a temperature conducive to hybridization. The Universal Oligonucleotide C0 is present at a 1× stoichiometry while the Complement Oligonucleotides are present at 1.1× and the the Protector Oligonucleotides and P0 are present at 2.1×. Optionally, a thermal anneal process can by applied to improve hybridization yield. Protector Oligonucleotide and Complement Oligonucleotide stoichiometries shown here are examples and are not intended as limits or constraints on formulation. FIG. 3B shows another set of stoichiometries for the probe (C0 at 1×; C1 at 1.2×; C2 at 1.3×, P0 at 3×, P1 at 2.4×; and P2 at 2.3×). FIG. 3C shows another formulation through separating forming two sub-probes through mixing or annealing (dotted boxes) and subsequently combining the sub-probes to formulate the probe (C0 at 1×; C1 at 1.2×; C2 at 1.3×, P0 at 3×, P1 at 2.4×; and P2 at 2.3×). FIG. 3D shows yet another way of formulating the probe through the mixing of two sub-probes individually formed through annealing or mixing (C0 at 1×; C1 at 1.1×; C2 at 1.1×, P0 at 2.1×, P1 at 2.1×; and P2 at 2.1×).

FIG. 4 shows experimental results on a modular probe targeting a DNA sequence including the first 143 nucleotides of the KRAS cDNA on the sense strand and the 17 intron nucleotides directly to the 5' of the KRAS cDNA. The probe was formulated based on the protocol shown in FIG. 3B. The probe, designed against a 99 nt sequence including the first 82 nt of the KRAS cDNA, was at concentration of 10 nM, and the reaction proceeded at 37° C. in 1×PBS buffer. A 179 nt ssDNA amplicon bearing target sequence was generated by asymmetric PCR from human genomic DNA and purified via size exclusion filtration; this matched target elicited a strong fluorescence response within 30 minutes, indicating efficiently hybridization. In contrast, a 136 nt ssDNA amplicon bearing an unrelated target sequence (also generated by asymmetric PCR) did not elicit any fluorescent signal. The probe was formed using sequences 1-6, and the target was sequence 41, prepared by PCR amplification using sequences 42 and 43 as primers. The unrelated target was sequence 44, prepared by PCR amplification using sequence 45 and 46 as primers. Addition of the target at time t=0 resulted in a rapid increase in fluorescence, indicating successful binding of the target. In contrast, the addition of an unrelated sequence at time t=0 resulted in no significant increase in fluorescence.

Figure 5A:
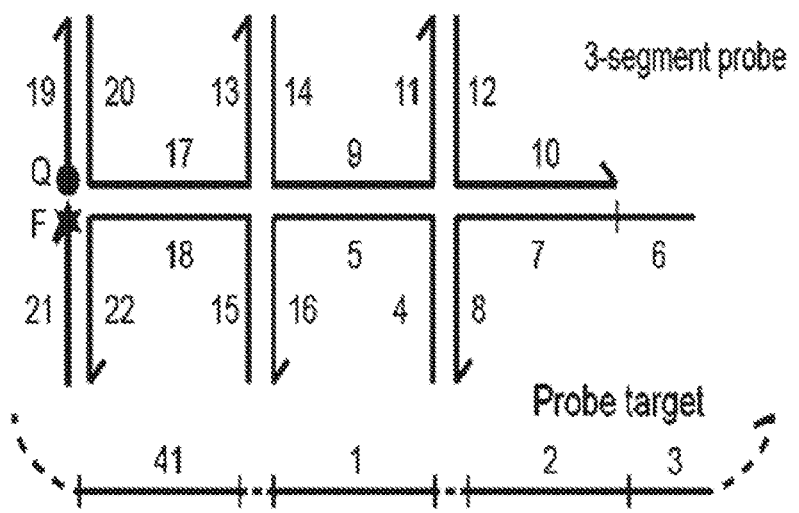
FIG. 5A depicts a schematic of a three-Segment probe consisting of 3 Complement Oligonucleotides and 3 Protector Oligonucleotides, in addition to the universal fluorophore oligonucleotide and the universal quencher oligonucleotide. All three Complement Oligonucleotides comprise a middle region that is complementary to a region in the target sequence.
Figure 5B:
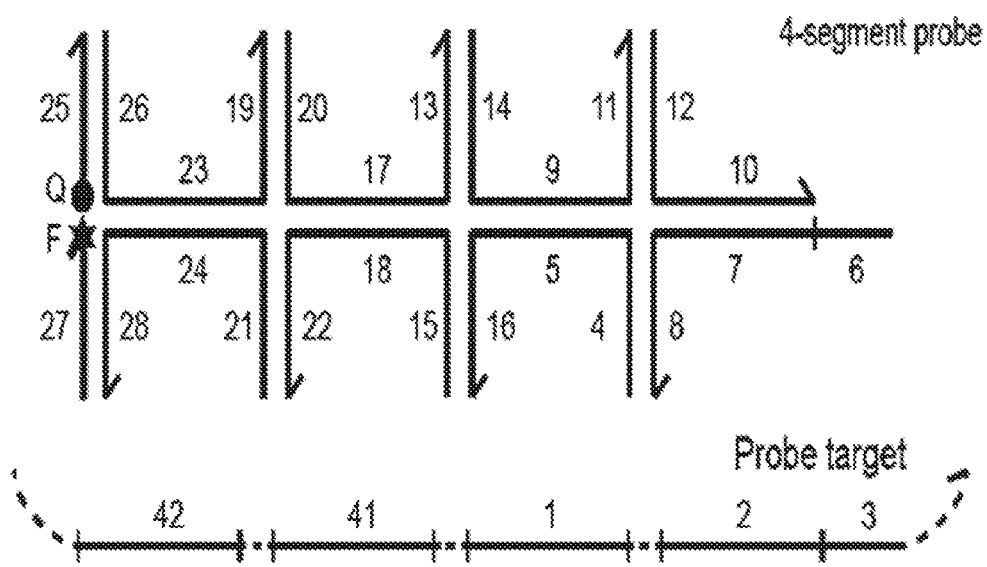
FIG. 5B depicts a schematic of a four-Segment probe.

Modular Probes with Additional Segments. The modular probes, as embodied thus far in FIGS. 2A-4, contain two Complement Oligonucleotides and two Protector Oligonucleotides. Hereafter, we refer to the combination of a Complement Oligonucleotide and the Protector Oligonucleotide bearing a complementary region to be a Segment. Thus, the probe as embodied in FIGS. 2A-2B is a two-Segment probe; FIGS. 5A-5B show schematics of a three-Segment probe and a four-Segment probe. As depicted in FIGS. 5A-5B the Complement Oligonucleotides can include regions 22, 18, 15, 16, 5, 4, 8, 7 and 6 (FIGS. 5A-5B) as well as 28, 24 and 21 (FIG. 5B). The Protector Oligonucleotides can include regions 20, 17, 13, 14, 9, 11, 12, and 10 (FIGS. 5A-5B) as well as 26, 23 and 19 (FIG. 5B). In FIG. 5A, two Universal Oligonucleotides (19 and 21) can be included which include a fluorophore (F) on 21 and a quencher (Q) on 19. In FIG. 5B, two Universal Oligonucleotides (27 and 25) can be included which include a fluorophore (F) on 27 and a quencher (Q) on 25. In FIGS. 5A-5B, regions 24, 18, 5, 7 and 6 are complementary to regions 23, 17, 9, 10, and 3 respectively. Regions 24, 18, 5 and 7 are also complementary to regions 42, 41, 1 and 2 of the target. Regions 19 and 20, 13 and 14, 11 and 12, 21 and 22, 15 and 16, 4 and 8, 25 and 26, and 27 and 28 are complementary to one another, respectively.

In some embodiments, the nucleic acid hybridization probe or M-probe, can include two or more segments. In some embodiments, the nucleic acid hybridization probe or M-probe, can include three segments. In some embodiments, the nucleic acid hybridization probe or M-probe, can include four segments. In some embodiments, the nucleic acid hybridization probe or M-probe can include 5, 6, 7, 8, 9, 10 or more than 10 segments.

The probe in FIGS. 2A-2B consists of two Complement Oligonucleotides and two Protector Oligonucleotides, but the number of complement and Protector Oligonucleotides can, in principle, be extended arbitrarily. Advantages of building modular probes with more Segments include (1) capability to probe longer target sequences, (2) easier synthesis of component oligonucleotides due to shorter lengths, (3) additional combinatorial diversity in probe formulation, and (4) additional positions and molecules upon which to functionalize chemical moieties.

Figure 6:
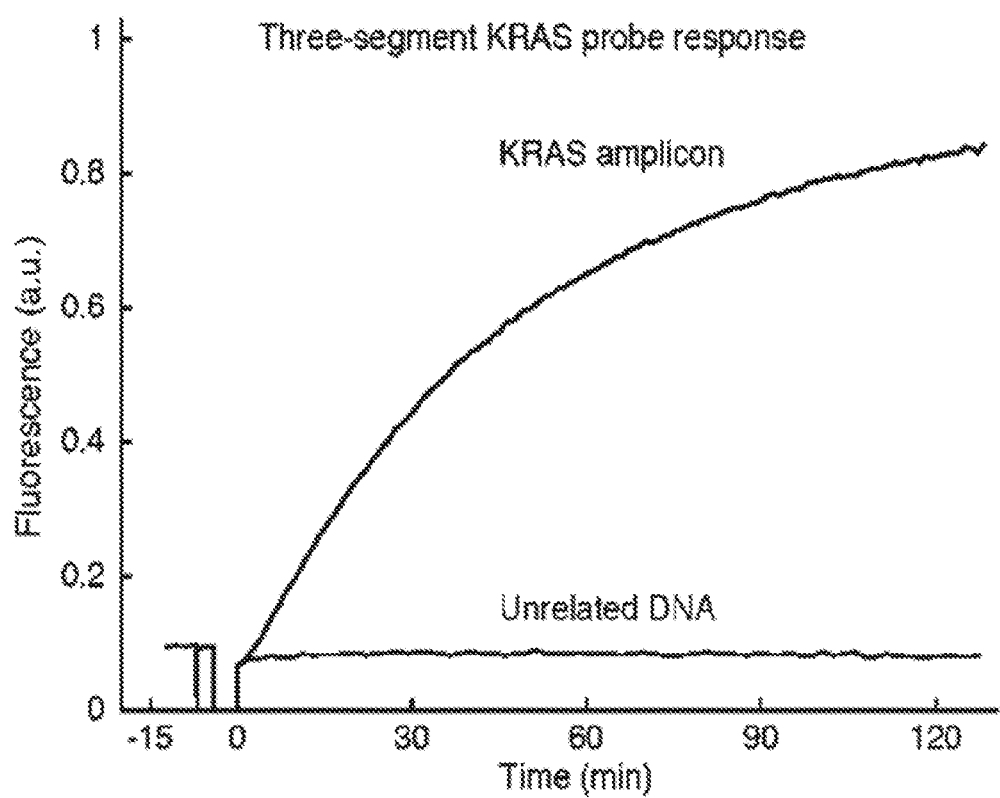
FIG. 6 shows the experimental results of modular probe targeting a sequence including the first 143 nucleotides of the KRAS cDNA on the sense strand and the 17 intron nucleotides directly to the 5' of the KRAS cDNA.

FIG. 6 shows the experimental results of modular probe targeting a sequence including the first 143 nucleotides of the KRAS cDNA on the sense strand and the 17 intron nucleotides directly to the 5' of the KRAS cDNA. The probe was formulated based on the protocol shown in FIG. 3B. The probe, designed against a 160 nt sequence including the first 143 nt of the KRAS cDNA, was at concentration of 10 nM, and the reaction proceeded at 37° C. in 1×PBS buffer. A 179 nt ssDNA amplicon bearing target sequence was generated by asymmetric PCR from human genomic DNA and purified via size exclusion filtration; this matched target elicited a strong fluorescence response within 60 minutes, indicating efficiently hybridization. In contrast, a 150 nt ssDNA amplicon bearing an unrelated target sequence (also generated by asymmetric PCR) did not elicit any fluorescent signal. The probe was formed using sequences 1, 2, 3, 4, 7, 8, 9, and 10, and the target was sequence 41 prepared by PCR amplification using sequences 42 and 43 as primers. The unrelated target was sequence 44 prepared by PCR amplification using sequences 45 and 46 as primers. As with the two-segment probe, the intended target quickly induces an increase in fluorescence signal, whereas the unrelated sequence does not result in any fluorescence change.

Quantitating Triplet Repeats. Several diseases are caused or characterized by an abnormal number of triplet repeats; examples include Huntington's Disease (excessive number of CAG repeats), Friedreich's Ataxia (GAA repeats), Myotonic dystrophy (CTG repeats), and the Fragile X syndrome (CGG repeats). Biologically, these repeats induce slipped strand mispairing during DNA replication; slipped strand mispairing likewise complicate or preclude many conventional DNA analysis techniques, such as Sanger Sequencing, quantitative PCR, and next-generation sequencing.

Figure 7:
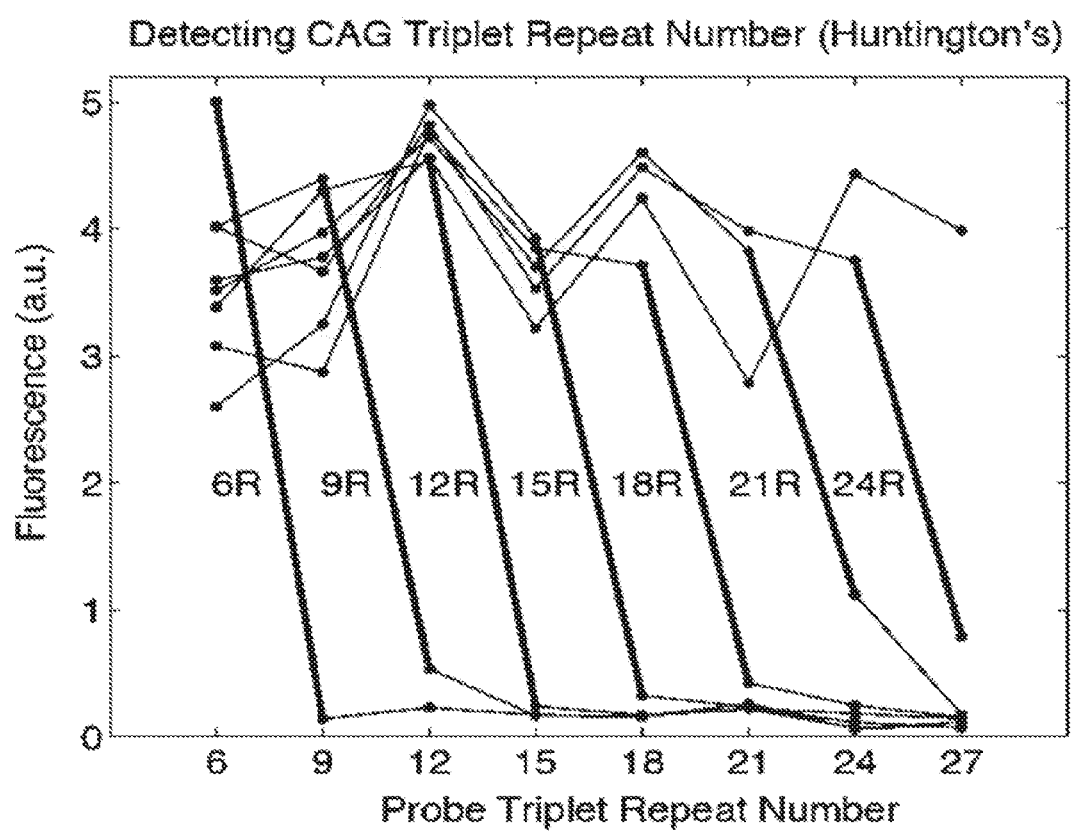
FIG. 7 depicts the observed fluorescence after 30 minutes of hybridization reaction.

Here, we designed several modular probes to the Huntington's gene sequence, each designed to target a threshold number of repeats (6, 9, 12, 15, 18, 21, 24, and 27), as well as the 3' neighboring sequence. For example, a 12 repeat probe is designed to hybridize to any target sequences bearing 12 or more CAG repeats, in addition to the 8 nt downstream of the CAG repeats. FIG. 7 summarizes the observed fluorescence after 30 minutes of hybridization reaction. The 6 repeat probe (6 on the X-axis) was formed using sequences 1, 2, 19, and 20. The 9 repeat probe (9 on the X-axis) was formed using sequences 1, 2, 21, and 22. The 12 repeat probe (12 on the X-axis) was formed using sequences 1, 2, 23, 24, 25, and 26. The 15 repeat probe (15 on the X-axis) was formed using sequences 1, 2, 23, 24, 27, and 28. The 18 repeat probe (18 on the X-axis) was formed using sequences 1, 2, 23, 24, 29, 30, 31, and 32. The 21 repeat probe (21 on the X-axis) was formed using sequences 1, 2, 23, 24, 29, 30, 33, and 34. The 24 repeat probe (24 on the X-axis) was formed using sequences 1, 2, 23, 24, 29, 30, 35, 36, 37, and 38. The 27 repeat probe (27 on the X-axis) was formed using sequences 1, 2, 23, 24, 29, 30, 35, 36, 39, and 40. The 6 repeat (6R) target is sequence 11. The 9 repeat (9R) target is sequence 12. The 12 repeat (12R) target is sequence 13. The 15 repeat (15R) target is sequence 14. The 18 repeat (18R) target is sequence 15. The 21 repeat (21R) target is sequence 16. The 24 repeat (24R) target is sequence 17. The 27 repeat (27R) target is sequence 18. Targets used were synthetic oligonucleotides bearing 6, 9, 12, 15, 18, 21, 24, and 27 copies of the CAG triplet, and the 8 nt downstream sequence. As predicted, the fluorescence is high when the target's number of triplet repeats is greater than or equal to the number of repeats tested by the modular probe, and low otherwise.

Figure 8B:
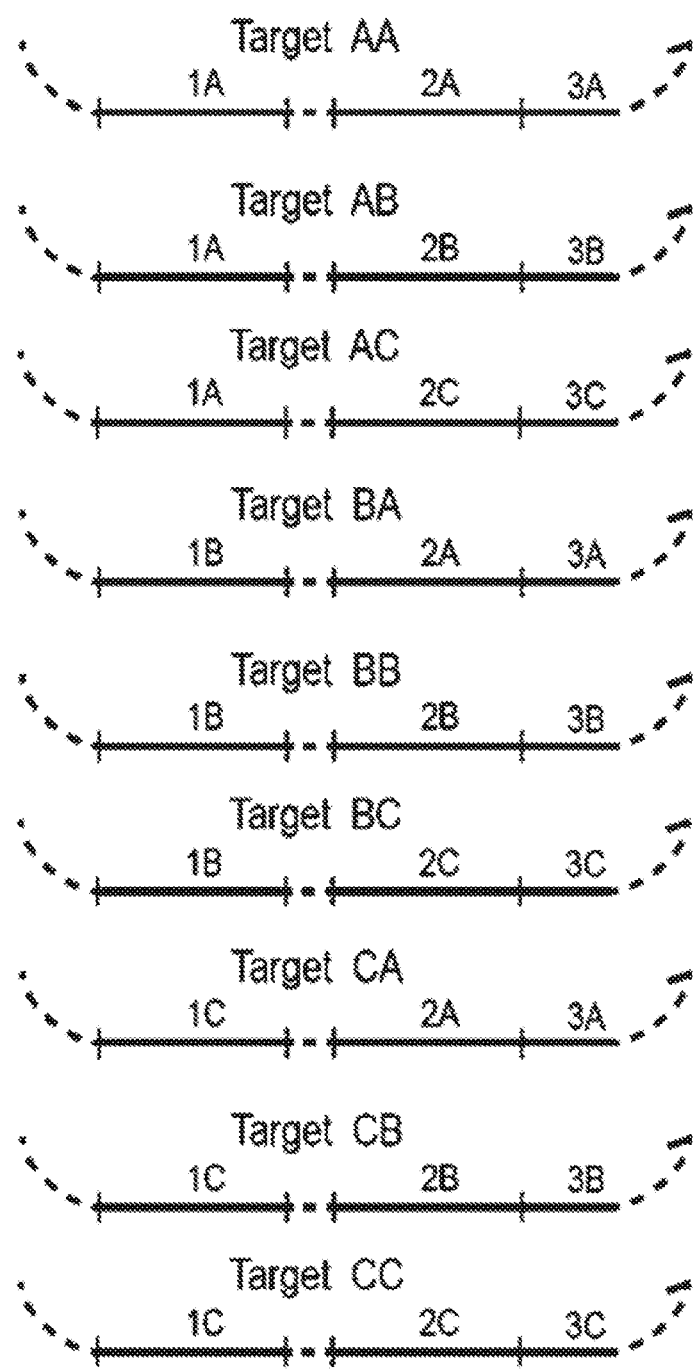
FIG. 8B depicts different target sequences for the versions of each segment of a modular probe depicted in FIG. 8A. The two-letter code for each target corresponds to Segment 1 (first letter) and Segment 2 (second letter) of the segments in FIG. 8A.
Figure 9:
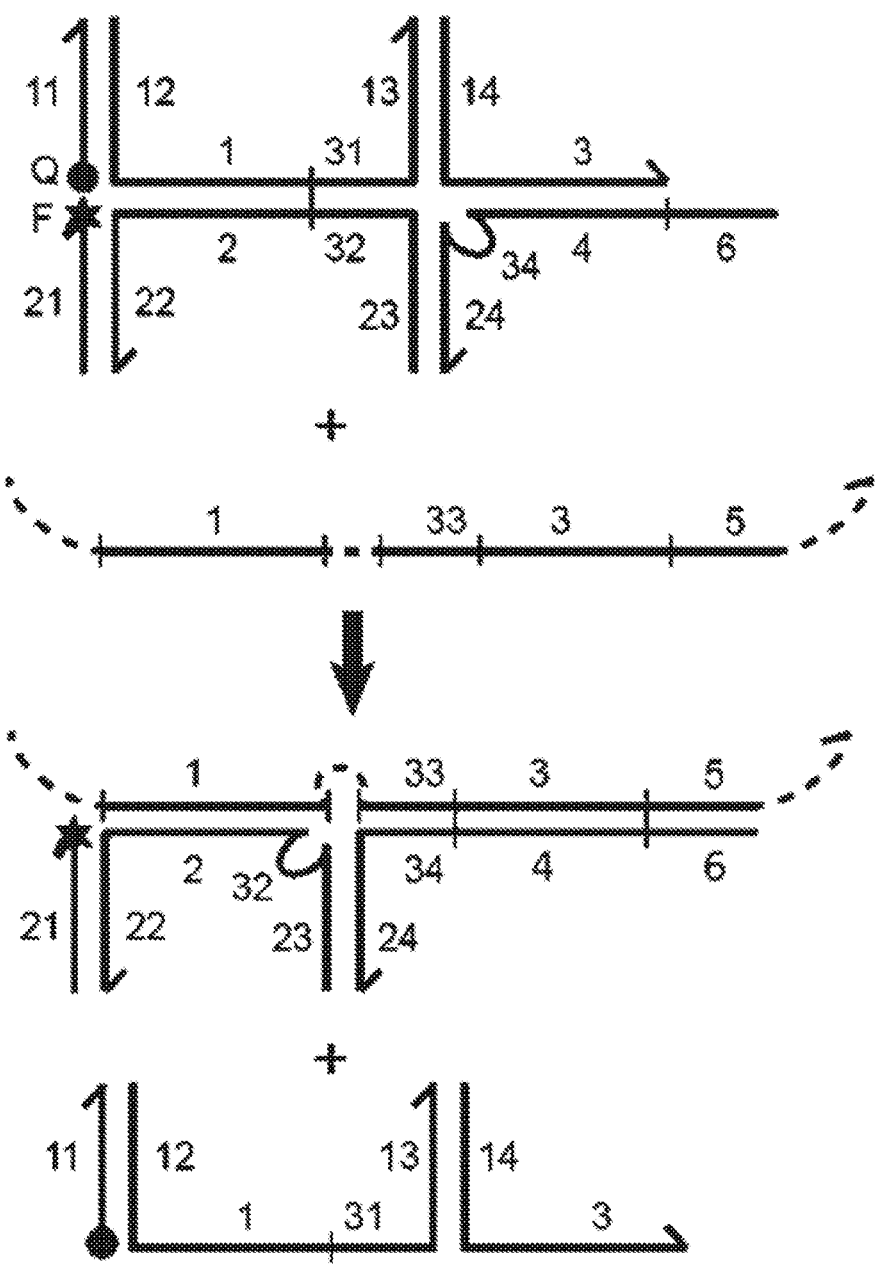
FIG. 9 depicts an additional example of the modular probe.

Combinatorial Probe Formulation. Different versions of each Segment of the modular probe can be synthesized and constructed that bind different target subsequences (FIGS. 8A-8B). These different versions of each Segment can be modularly combined to form combinatorially many different modular probes. In FIGS. 8A-8B region 5A is complementary to region 9A and to region 1A of the target, region 5B is complementary to region 9B and to region 1B of the target, and region 5C is complementary to region 9C and to region 1C of the target. In FIGS. 8A-8B region 7A is complementary to region 10A and to region 2A of the target, region 7B is complementary to region 10B and to region 2B of the target, and region 7C is complementary to region 10C and to region 2C of the target. In FIGS. 8A-8B region 6A is complementary to region 3A of the target, region 6B is complementary to region 3B of the target, and region 3C is complementary to region 6C of the target. Regions 11 and 12 and 4 and 8 are also complementary to one another, respectively.

For a 2-Segment probe with 3 versions for each Segment, probes can be formulated to target 9 different sequences, as depicted in FIGS. 8A-8B. For a 3-Segment probe with 20 versions for each Segment, 8000 different probes can be formulated to as many target sequences, even though only 120 oligonucleotides were synthesized. We envision that this combinatorial formulation feature of our modular probes renders it uniquely suitable for immune profiling applications, where T-cell and B-cells undergo genetic rearrangement (i.e. VDJ recombination) and exhibit high sequence diversity. Combinatorial formulation of modular probes may also be well-suited for detection of gene fusions from cDNA.

Modular Probe Structure Variations. In addition to the embodiments shown previously in FIGS. 1A-1B, 2A-2B and 5A-5B, many other variations can be imagined that feature different advantages for specific applications. FIGS. 9 and 10A-10C show additional embodiments of the modular probe. In the example depicted in FIG. 9, region 32 on the first Complement Oligonucleotide is not complementary to any region of the target sequence, but complementary to region 31 on the first Protector Oligonucleotide. Region 34 on the second Complement Oligonucleotide is complementary to region 33 of the target sequence, but not complementary to any region of the second Protector Oligonucleotide. These additional types of regions may be added to confer improve sensitivity or specificity to the probe, or alternatively to help relax steric hindrance effects on hybridizations. Further, in FIG. 9, regions 11 and 12, 13 and 14, 21 and 22, 1 and 2, 31 and 32, 23 and 24, 3 and 4, 5 and 6, 33 and 34 are complementary to one another, respectively.

Figure 10A:
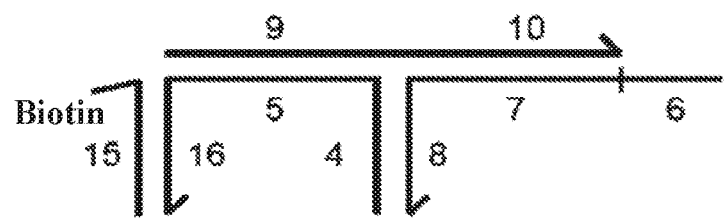
FIG. 10A depicts an additional example of the modular probe with a universal biotinylated oligonucleotide hybridized to the first Complement Oligonucleotide, for surface-based capture of the target sequence.
Figure 10B:
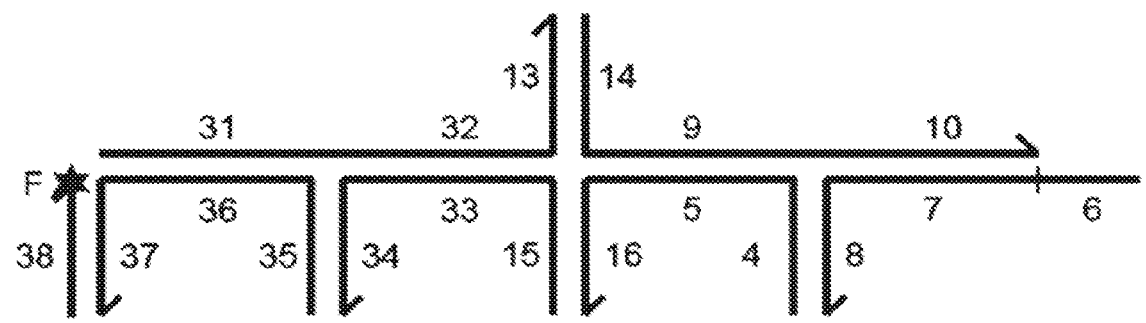
FIG. 10B depicts an additional example of the modular probe with a universal fluorophores oligonucleotide hybridized to the first Complement Oligonucleotide, but not a universal quencher oligonucleotide.
Figure 10C:
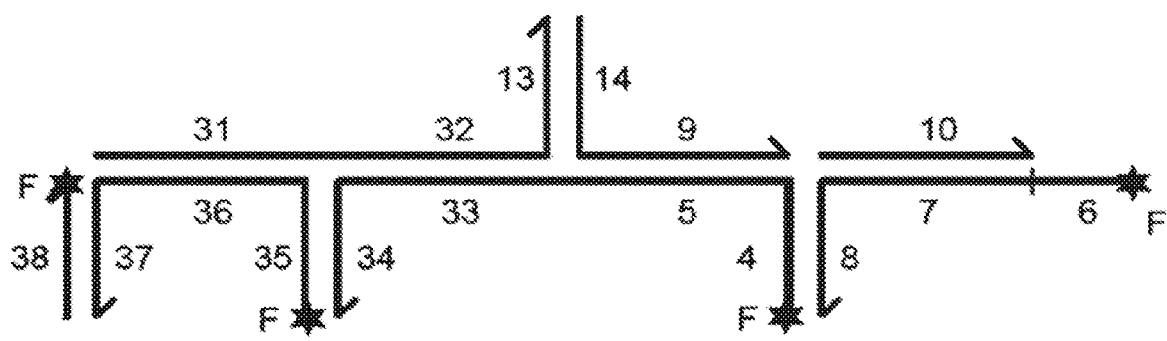
FIG. 10C depicts another exemplary modular probe.

The probe depicted in FIG. 10B may be more suitable for assays in which unbound probe molecules can be washed away, such as in fluorescence in situ hybridization (FISH) assays. The probe depicted in FIG. 10C is functionalized on several Complement Oligonucleotides with fluorophores, and could yield brighter fluorescent signal per target molecule, resulting in improved molecular sensitivity. Additionally, one of the Protector Oligonucleotides (bearing region 10) is not hybridized to any of the other Protector Oligonucleotides, and can be more easily displaced without requiring cooperative displacement of other Protector Oligonucleotides. This probe may be more suitable for assays against targets with significant secondary structures. In FIGS. 10A-10C, regions 5 and 9, 15 and 16, 4 and 8, 7 and 10, 37 and 38, 31 and 36, 35 and 34, 32 and 33, and 13 and 14 are complementary to one another respectively. These probe designs are meant to serve as examples and not to limit the scope of the claims or invention to the specific embodiments presented here.

Language Exactness. Unless explicitly stated otherwise, "complementary" in this document refers to "partially or fully complementary". Two sequences are defined to be "partially complementary" when over 80% of the aligned nucleotides of one sequence is complementary to corresponding nucleotides of the other sequence.

EXAMPLES

The present invention is demonstrated in the following examples, it being understood that the following methods apply and that the examples are for illustrative purposes only, and the invention is not intended to be limited thereto.

Methods

Oligo synthesis and storage conditions. Oligonucleotide molecules used in this study were purchased from Integrated DNA Technologies (IDT). Depending on oligo length, modifications, and sequence, each oligo was ordered either with standard desalting or with post-synthesis PAGE or HPLC purification. All oligos were sequence verified by IDT via mass spectrometry; purified oligos and gBlock gene fragments were also subject to size verification by capillary electrophoresis. The sequence and purification method of each oligo can be found in Tables 8-21. Except ultramer oligos and gBlock gene fragments, all other oligos were originally pre-suspended by IDT in Tris.EDTA (pH=8.0) buffer at roughly 100 µM; stock solutions were stored at 4° C. until use.

VDJ recombination sequence selection and hybridization target design. Sequences of human T-cell receptor β variable (V), diversity (D), and joining (J) germline-encoded genes were downloaded from the IMGT/Gene-DB database (http://www.imgt.org/genedb/). There are 48 functional TRBV genes (ORF and pseudogene excluded), 2 functional TRBD genes, and 13 functional TRBJ genes in total. As proof of concept, we designed 48 VDJ recombination targets composed of the last 35 nt bases of 8 TRBV genes, 48 biologically occurring sequences of regions between V and J, and the first 35 nt base of 6 TRBJ genes. Then, based on the distribution of number of deletion being observed in biology, the 3' end of each V sequence is deleted by 0 to 7 nucleotides, and the 5' end of each J sequence was deleted by 0 to 10 nucleotides. A detailed description of VDJ recombination targets design is provided in text accompanying FIGS. 24-26.

M-Probe formulation and strand stoichiometry. For all the probes targeting non-repetitive sequences, 1 µM M-Probe stock solutions were formulated by mixing together all the component strands in a specified ratio to minimize the formation of multi-stranded complexes that poisons the reaction (FIGS. 16-23D and accompanying text). For example, to formulate the M-Probe showed in FIG. 11C, we mixed its component strands in 1:1.1:1.1:2.1:2.1:2.1 ratio in 1× Phosphate Buffered Saline (PBS, diluted from 10×PBS purchased from Sigma-Aldrich). Starting from the lower universal strand and ending at the upper universal strand, the ratio counterclockwise corresponds to each component strand. The stoichiometric ratios of M-Probes used are listed Table 1. Then, we performed thermal annealing to the M-Probe solution using one of the three Eppendorf Master-Cycler Personal Thermocyclers in our lab, following a program of initial denaturing at 95° C. for 5 min and subsequent uniform cooling down to 20° C. over 75 minutes. Annealed probes were stored at 4° C. until use.

For all the probes targeting repetitive sequences, 1 µM M-Probe stock solutions were formulated by two-step formation: individual segments were formulated separately and then combined to avoid probe malformation. To formulate n=1 probes (e.g. the MP-12 showed in FIGS. 15A-15G) 4 component strands of u and s1 were annealed to form u: s1, 2 component strands of t were annealed to form t, and the two solutions were mixed to form the full probe. To formulate n=2 probes (e.g. the MP-18 showed in FIGS. 15A-15G) 4 component strands of u and s1 were annealed to form u: s1, 4 component strands of s2 and t were annealed to form s2 t, and the two solutions were mixed to form the full probe. To formulate n=3 probes (e.g. the MP-24 showed in FIGS. 15A-15G) 4 component strands of u and s1 were annealed to form u: s1, 4 component strands of s2 and s3 were annealed to form s2: s3, 2 component strands of t were annealed to form t, and the three solutions were mixed to form the full probe.

Figure 14A:
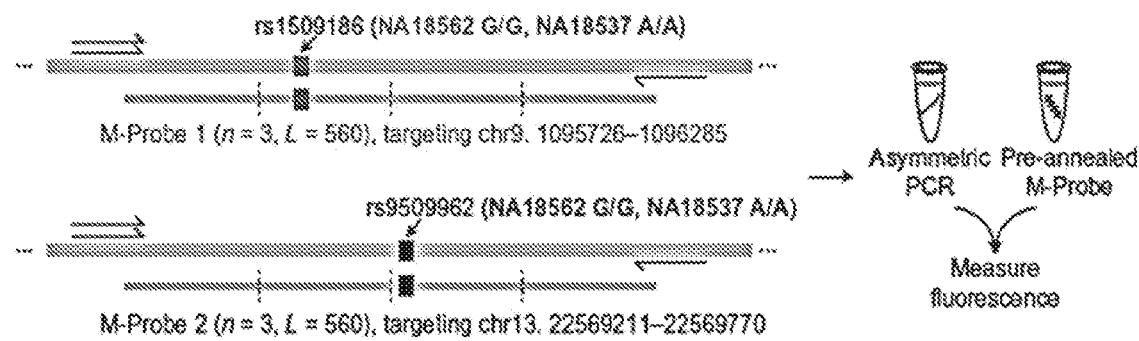
FIG. 14A depicts the M-Probe detection of single nucleotide variants within 560 nt targeting regions. The rs1509186 single nucleotide polymorphism (SNP) is homozygous G/G in the NA18562 genomic DNA (gDNA) sample, and homozygous A/A in NA18537.
Figure 14B:
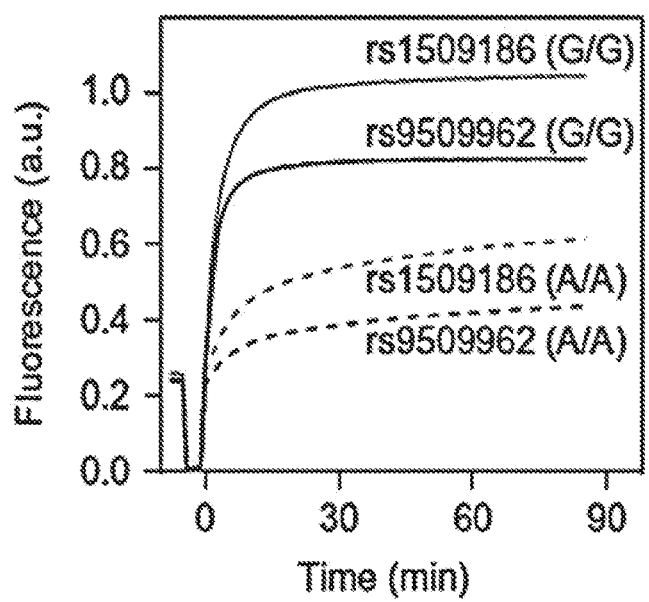
FIG. 14B shows the fluorescence responses of the M-Probes (10 nM final concentration) to respective amplicon targets from FIG. 14A.

Protocol for time-based fluorescence measurement. Time-based fluorescence traces shown in FIGS. 11C, 12D and 15B were measured using one of two Horiba Fluoromax-4 fluorimeters in 1×PBS, at 37° C. Time-based fluorescence traces showed in FIG. 14B were measured using one of two Horiba Fluoromax-4 fluorimeters in 1×PBS, at 45° C. M-Probe concentrations in experiments were set at 10 nM, synthetic target concentrations were 30 nM (FIG. 12D, FIG. 15B), PCR amplicon concentrations were not quantified (FIG. 14B). To achieve these final concentration, we pipetted 12 µL 1 µM (FIGS. 11C, 12D and 15B) or 40 µL 0.3 µM (FIG. 14B) M-Probe solution into Hellma Semi-Micro 114F spectrofluorimeter cuvettes filled with 1200 µL 1×PBS buffer. Then, we incubated cuvettes in the machine at desired temperature for 20 min to 1 hour to allow temperature equilibration after data acquisition started. Subsequently, cuvettes are removed from the machine; target or post-PCR solutions were added to the cuvettes. After proper mixing, cuvettes were placed back to the machine. For experiments showed in FIG. 11C, mutated targets (12G>T, 31G>A) were allowed to react with the M-Probe for 2 hours. Afterwards, cuvettes were removed from the machine again, and solutions with correct target were added to the cuvettes to generate a final mixture of 10 nM M-Probe, 30 nM mismatched target, and 30 nM perfect-matched target.

For data acquisition, excitation and emission wavelengths were set at 582 nm and 600 nm to generate optimal fluorescence signal for ROX fluorophore in our current buffer. Slit sizes were set at 4 nm for both excitation and emission, and integration time was 10 seconds (per cuvette) with a 60 seconds integration interval. Reaction temperature during fluorescence measurement was controlled by an external water bath purchased from Thermo Fisher Scientific. Experimental data was exported to a text file, which was subsequently imported and plotted using MATLAB scripts. Time t=0 corresponds to the first data point acquired after addition of target solutions.

TABLE 1

Component strand stoichiometric ratio of M-Probes used in each experiment. Stoichiometric ratios were ordered counterclockwise from the lower universal strand to the upper universal strand.

| FIG. | Experiment | n Internal Segments | Stoichiometric ratio |
|---|---|---|---|
| 1 | Basic Validation | 1 | 1:1.1:1.1:2.1:2.1:2.1 |
| 2 | Programmed Sequence Variation Tolerance | 1 | 1:1.1:1.1:6.1:6.1:6.1 |
| 3 | Combinatorial Construction | 1 | 1:1.1:1.1:2.1:2.1:2.1 |
| 4 | Long M-Probe 1 | 3 | 1:1.2:1.2:1.2:1.2: 2.2:2.2:2.2:2.2:2.2 |
| 4 | Long M-Probe 2 | 3 | 1:1.2:1.2:1.2:1.2: 2.2:2.2:2.2:2.2:2.2 |

TABLE 1-continued

Component strand stoichiometric ratio of M-Probes used in each experiment. Stoichiometric ratios were ordered counterclockwise from the lower universal strand to the upper universal strand.

| FIG. | Experiment | n Internal Segments | Stoichiometric ratio |
|---|---|---|---|
| 5 | CAG Repeat Detection | 0 | 1:1.1: |
| 5 | MP-6, MP-9 | 1 | 2.1:2.1 |
| 5 | CAG Repeat Detection MP-12, MP-15 | 2 | 1:1.1:1.1: 2.1:2.1:2.1 |
| 5 | CAG Repeat Detection MP-18, MP-21 | 3 | 1:1.1:1.1:1.1: 2.1:2.1:2.1:2.1 |
| 5 | CAG Repeat Detection MP-24, MP-27 |  | 1:1.1:1.1:1.1:1.1: 2.1:2.1:2.1:2.1:2.1 |
| 5 | CAG Repeat Capture MP-9 | 0 | 1:1.2: |
| 5 | CAG Repeat Capture MP-27 | 3 | 2.2:2.5 |
| 5 | CAG Repeat Capture MP-33 | 1 | 1:1.2:1.4:1.5:1.6: 2.6:2.7:2.8:3.0:3.4 |
| 5 | CAG Repeat Capture MP-35 | 1 | 1:1.2:1.4: 2.4:2.6:3.0 |
| 5 | CAG Repeat Capture | 1 | 1:1.2:1.4: 2.4:2.6:3.0 |
| | CAG Repeat Capture MP-36 | | 1:1.2:1.4: 2.4:2.6:3.0 |
| | CAG Repeat Capture MP-37 | | 1:1.2:1.4: 2.4:2.6:3.0 |
| | CAG Repeat Capture MP-39 | | 1:1.2:1.4: 2.4:2.6:3.0 |

Protocol for equilibrium fluorescence measurement. Equilibrium fluorescence signal showed in FIG. 13D, and FIG. 15C were measured using Applied Biosystems QuantStudio 7 Flex Real-Time PCR System as a plate reader. Final M-Probe concentrations in these experiments were 100 nM, synthetic target concentrations were 300 nM. M-Probes and targets were first mixed together to reach desired concentrations in 1×PBS, then reaction mixture were incubated at 37° C. overnight (12-18 hours) in an Eppendorf MasterCycler Personal Thermocyclers or a MULTI-THERM Temperature Controlled Vortexers (Benchmark Scientific).

After incubation, 10 µL the M-Probe and target mixtures were pipetted into 96-well PCR plates (Thermo Fisher Scientific) which were subsequently sealed. 30 continuous data points were collected (30 seconds per data point) in each well following a 30 min incubation step in a PCR machine at 37° C.

Experimental data were collected and exported as Excel files, and subsequently analyzed and plotted using MATLAB scripts. The analysis included a fluorescence signal correction for position biases. Detailed description of the data analysis procedure can be found in FIGS. 31A-32B and accompanying text.

Protocol for asymmetric PCR. Asymmetric PCR was applied to generate hybridization targets used in FIG. 14B. For experiments shown in FIGS. 14A-14B, human genomic DNA samples (NA18537 and NA18562) were purchased from Coriell and used as amplification template. The gDNA sample was first quantitated using a Nanodrop 2000c spectrophotometer (Thermo Fisher Scientific), and then diluted to reach 100 ng/µL in 1× Tris-EDTA 0.1% Tween20 solution. Diluted template stocks were stored at 4° C. until use. As shown in FIG. 14A, PCR primers were designed to amplify a 590 nt amplicon containing the rs1509186 SNP, and an n=3 M-Probe was designed to bind to 560 nt of the amplicon with sequence matching NA18562. No other sequence differences between NA18537 and NA18562 are expected in the 560 nt targeting region, based on the 1000 Genomes genotype database. The SNP is located 196 nt from the 5' end of the M-Probe target region. Similarly, a separate 590 nt amplicon is generated around the rs9509962

SNP; this second M-Probe is also 560 nt long, and the SNP lies 285 nt from the 5' end of the target region. The vertical dashed lines denote the junctions separating M-Probe segments. See text accompanying FIGS. 33A-37C for probe and target preparation details. In FIG. 14B, hybridization experiments were performed at 45° C. in 1×PBS. Amplicons from the NA18562 gDNA sample (solid lines) induced significantly higher fluorescence than amplicons from NA18537 sample (dashed lines), indicating that the M-Probes are selective for even single nucleotide variants across a 560 nt target sequence.

We prepared our PCR reaction mix by combining 10×PCR buffer (with $Mg^{2+}$, Sigma-Aldrich), dNTP mix (prepared from dATP, dTTP, dCTP, and dGTP stocks, Sigma-Aldrich), forward primer, reverse primer, Taq polymerase (Sigma-Aldrich), template solution, and Milli-Q $H_2O$. The total reaction volume was 50 μL in a 0.7 mL Eppendorf PCR tube as shown in Table S0-2. The centrifuge tubes containing the reaction mixtures were placed into one of the three Eppendorf MasterCycler Personal Thermocycler, amplified following the PCR protocol listed in Table 3.

Protocol for selective capture of long triplet repeats. CAG repeats in the HTT gene of 7 genomic DNA samples (NA18537, NA18524, NA20245, NA20248, NA20208, NA20209, and NA20210) were first amplified using a 5-cycle PCR procedure (TABLE 4, TABLE 5). All genomic were purchased from Coriell as reference templates for validating our technology. NA20245, NA20248, NA20208, NA20209, and NA20210 have known CAG repeat lengths, while NA18537 and NA18524 have unknown CAG repeat lengths. gDNA samples were first quantitated by Nanodrop 2000c spectrophotometer (Thermo Fisher Scientific). Then various amount of template solutions were used to prepare the PCR mixtures.

TABLE 2

Asymmetric PCR reaction mixture formulation

| Reagent | Working Stock Concentration | Final Concentration | Add in Volume (μL) |
|---|---|---|---|
| 10 × PCR buffer | 10 × 2.5 mM | 1 × 200 μM | 5 |
| dNTP (each) | fP 5 μM, rP 500 nM | fP 1 μM, rP 100 nM | 4 |
| Primer mix | 0.5 Unit/μL | 0.1 Unit/μL | 10 |
| Taq Polymerase | | | 10 |
| Template | 100 ng/μL | 10 ng/μL | 5 |
| $H_2O$ | — | — | 16 |
| Total volume | | 50 | |

TABLE 3

Thermocycler asymmetric PCR program.

| Step | Temperature | Duration |
|---|---|---|
| 1. Initial Denaturation | 95° C. | 3 min |
| 2. Denaturation | 95° C. | 15 s |
| 3. Annealing | 60° C. | 2 min |
| Repeat Steps 2 to 3 for 70 times | | |
| 6. Hold | 10° C. | |

TABLE 4

5-cycle PCR reaction mix formulation.

| Reagent | Working Stock Concentration | Final Concentration | Add in Volume (μL) |
|---|---|---|---|
| 10 × PCR buffer | 10 × 2 mM fP 0.5 μM, rP | 1 × 200 μM fP 0.2 μM, rP | 10 10 |
| dNTP (each) | 0.5 μM | 0.2 μM | 40 |
| Primer mix | 0.5 Unit/μL | 0.1 Unit/μL | 20 |
| Taq Polymerase | | | |
| gDNA samples | Varies | 7.5 ng/μL | Varies |
| 1 × TE | — | — | Varies |
| Total volume | | 100 | |

TABLE 5

5-cycle PCR program.

| Step | Temperature | Duration |
|---|---|---|
| 1. Initial Denaturation | 95° C. | 4 min |
| 2. Denaturation | 95° C. | 30 s |
| 3. Annealing | 60° C. | 2 min |
| Repeat Steps 2 to 3 for 5 times | | |
| 4. Final extension | 72° C. | 2 min |
| 5. Hold | 10° C. | |

After PCR, 100 μL reaction product samples were column purified, and each eluted in 90 μL MilliQ water. 15 μL elution product was denatured at 95° C. for 10 min, and then mixed with 15 μL 2×PBS, and 15 μL pre-annealed 600 μM probe solution, containing one of the following capture probe, MP-9, MP-27, MP-33, MP-35, MP-36, MP-37, or MP-39 in 1×PBS, to form a 45 μL hybridization reaction mixture (probe final concentration 200 μM). Here, the universal strands of the M-Probes are not fluorophore and quencher functionalized. Instead, the $5^1$ end the lower universal strand is functionalized with a biotin moiety, so that DNA molecules bound to the probe can be subsequently separated by streptavidin-functionalized magnetic beads. The mixtures were allowed to react overnight (12 to 18 hours) at 37° C.

Before using beads to capture bound DNA, 10 μL of Dynabeads MyOne Streptavidin T1 magnetic beads solution was aliquoted, washed three times in 1×PBS, and resuspended in 65 μL 1×PBS for each reaction. Then, 45 μL of the incubated samples were transferred into tubes containing prepared beads. After thorough mixing, the tubes were incubated at 37° C. for 1 hour with constant shaking (rpm=450). Supernatant containing unbound DNA was washed away, and strands that were captured on the bead surface were subsequently released by incubating beads in 25 μL MilliQ water at 95° C. for 10 minutes. The eluted solutions were then quantified by qPCR using protocol shown in Tables 6. qPCR were performed in triplicate in a Bio-Rad CFX96 machine.

TABLE 6 qPCR program.

| Step | Temperature | Duration |
|---|---|---|
| 1. Initial Denaturation | 95° C. | 3 min |
| 2. Denaturation | 95° C. | 5 s |
| 3. Annealing | 60° C. | 1 min |
| Repeat Steps 2 to 3 for 40 times | | |

M-Probe Design Principle

M-Probe reaction mechanism. Conceptually, the M-Probe can be thought of as a multi-stranded equivalent of the toehold probe, in which the probe and protector sequences are distributed across multiple oligonucleotides connected by arms. The upper strands collectively form the protector, and the bottom strands collectively form the probe. Upon hybridization with the target, the protector complex (the upper strands) will dissociate from the probe complex (the bottom strands) through strand displacement.

Figure 16:
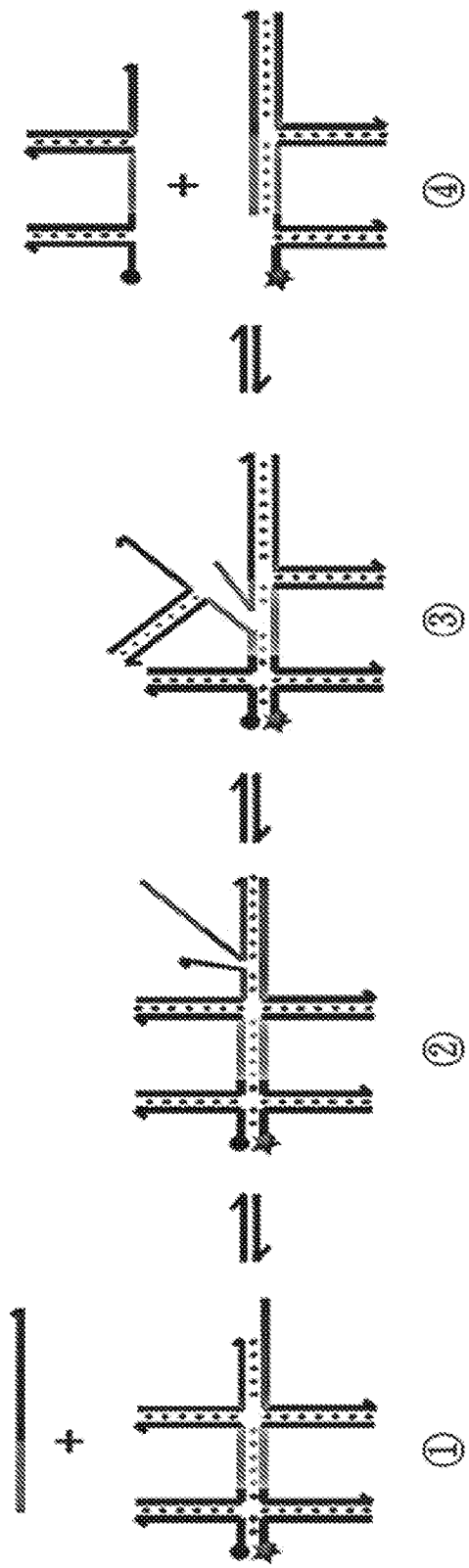
FIG. 16 depicts the reaction mechanism of M-Probe with example n=1. Step 1: The single stranded part of the probe, known as a toehold, serves as the initiation region for the strand displacement process. Step 2: The multi-stranded intermediate progresses in a random-walk fashion from the termination segment t through internal segments si Step 3: ending at internal segments s1. Step 4: Finally, the protector complex comprising all top strands is released.

The mechanism of the hybridization reaction between an M-Probe and its target is illustrated in FIG. 16. The single stranded portion of the t segment of the M-probe is known as a toehold, and serves as an initiation region of the strand displacement process. Then, the multi-stranded intermediate progresses in a random-walk fashion from termination segment/to the left-most segment s1, passing through internal segments $s_i$. Following the hybridization reaction with the target sequence, the upper M-Probe oligos are released as a multi-stranded protector complex.

Figure 11A:
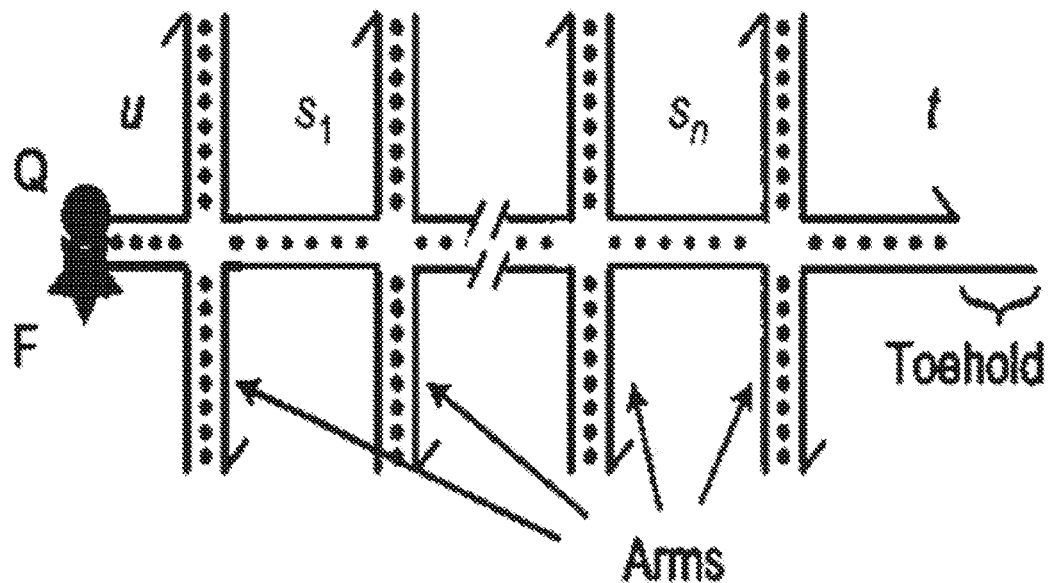
FIG. 11A depicts a design of a conditionally fluorescent M-probe bearing n internal segments.
Figure 11B:
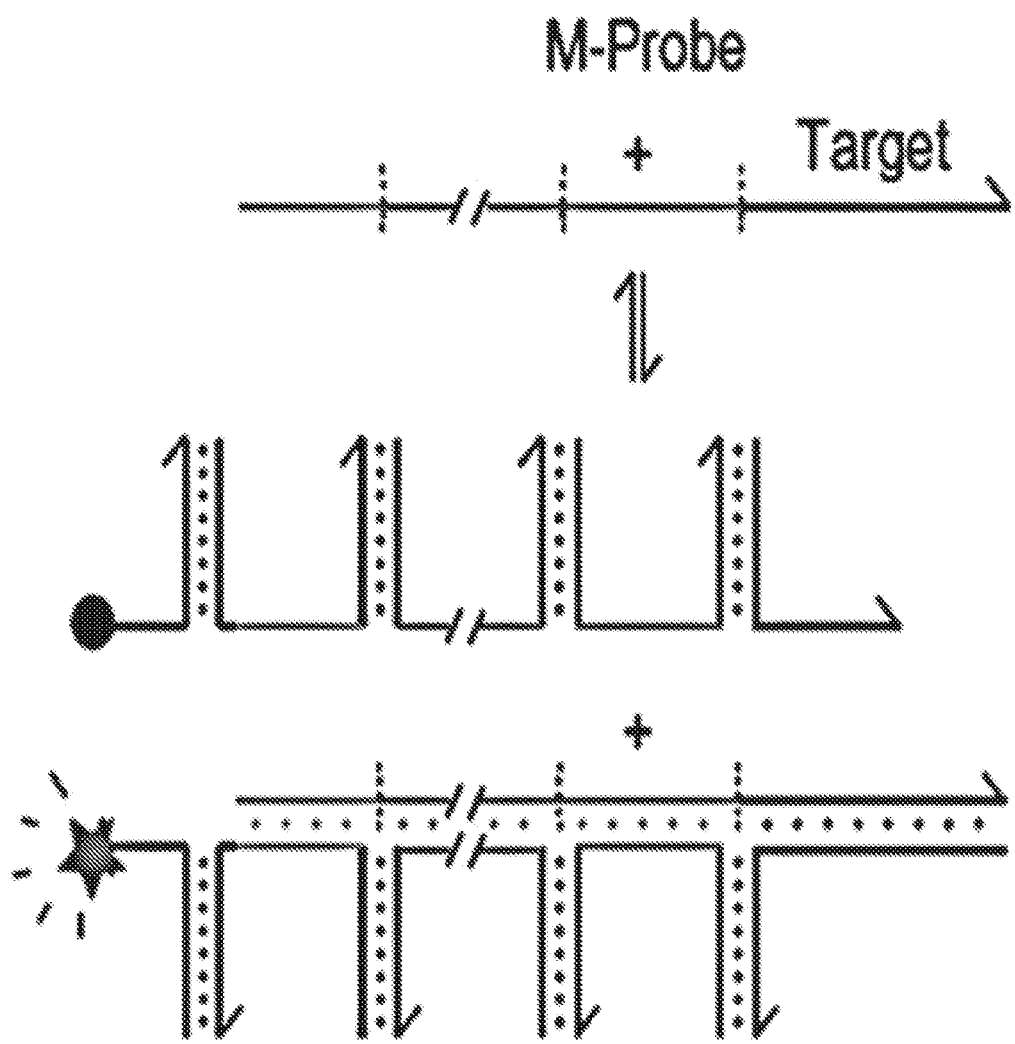
FIG. 11B shows hybridization of the M-probe of FIG. 11A to the target results in displacement of the upper oligos as a multi-stranded complex.

As depicted in FIG. 11A, the lower oligonucleotides have sequence complementary to subsequences of the target, and the upper oligonucleotides have sequence identical to subsequences of the target. The single-stranded nucleotides of the right-most lower oligo initiate the hybridization reaction, and is referred to as the toehold. In the universal segment u, the upper and lower oligos are functionalized with a quencher (Q) and fluorophore (F), respectively. As depicted in FIG. 11B, fluorescence increases through the hybridization of the M-Probe to the target process, due to delocalization of the fluorophore and quencher. The hybridization reaction is designed to be both reversible and sequence-specific. FIG. 11C depicts experimental results for an n=1 M-probe (10 nM) to a 43 nt synthetic target oligonucleotide (30 nM) at 37° C. in 1×PBS. Single-nucleotide variants of the target (12G>T and 31G>A, respectively in the $s_i$ and t segments, highlighted) elicit significantly lower fluorescence signal than the intended target T. FIG. 11C shows that addition of the matched target to a solution of M-Probes that was pre-reacted to targets bearing a single-nucleotide variant still generates immediate and strong fluorescence response. This indicates that variants 12G>T and 31G>A do not trap the M-Probe at 1 and 2 intermediate states (FIG. 16). Thus, the M-Probe is not easily "poisoned" by variants, and reliably hybridizes to its intended target sequence.

Figure 17:
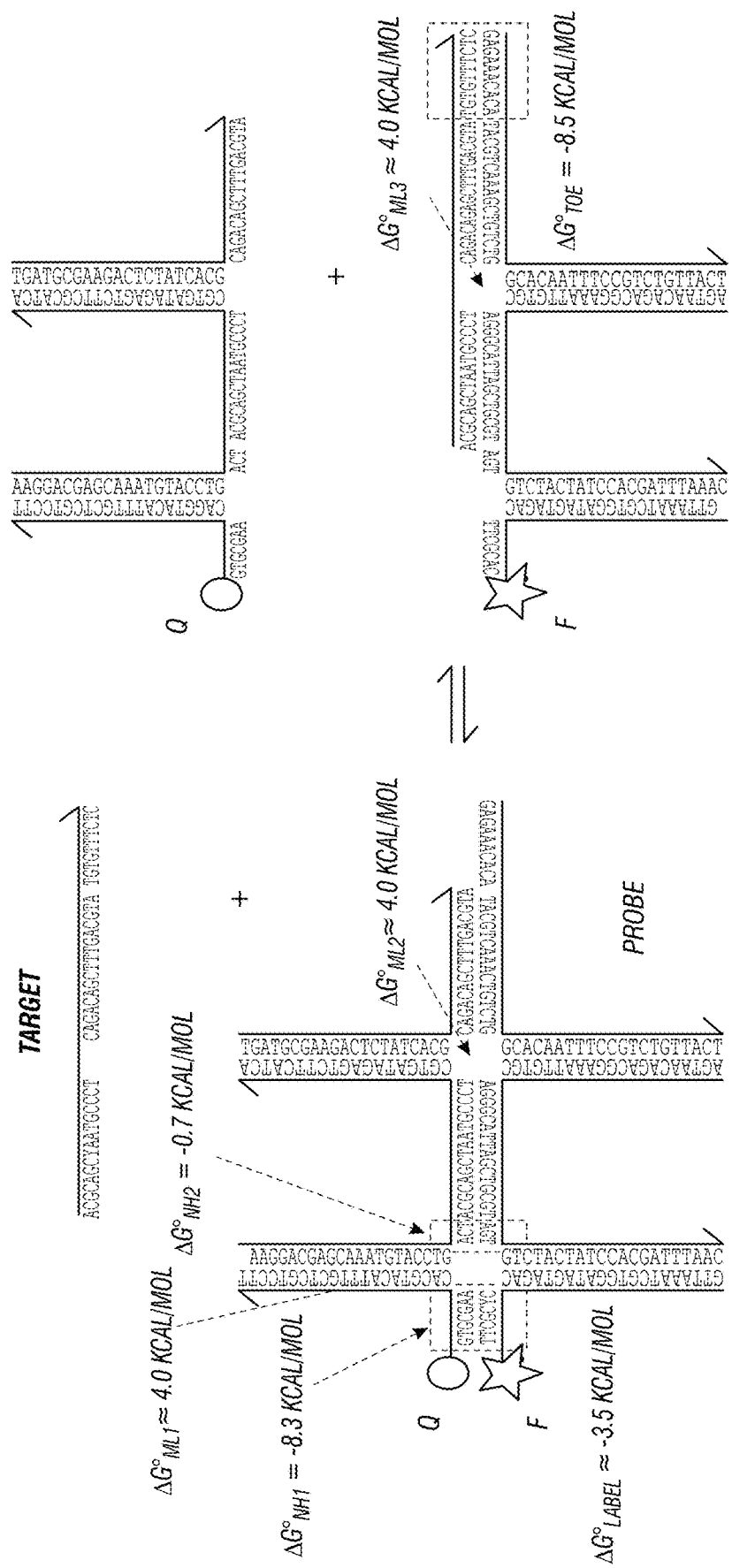
FIG. 17 illustrates of calculation of the standard free energy of hybridization (ΔG°) between an M-Probe and its intended target. For single nucleotide specificity, ΔG° should be roughly 0. The ΔG° terms of individual motifs are based on literature measurements or estimates in Santa Lucia, J. & Hicks, D. The Thermodynamics of DNA Structural Motifs. Ann. Rev. Biochem. 33, 415-440 (2004). Figure discloses the Target sequence as SEQ ID NO: 47; left structure sequences as SEQ ID NOS 2, 50, 52, 1, 51, and 53, respectively, in order of appearance; top right structure sequences as SEQ ID NOS 2, 50, and 52, respectively, in order of appearance; bottom right structure sequences as SEQ ID NOS 262, 263, 1, 51, and 53, respectively, in order of appearance.
Figure 18:
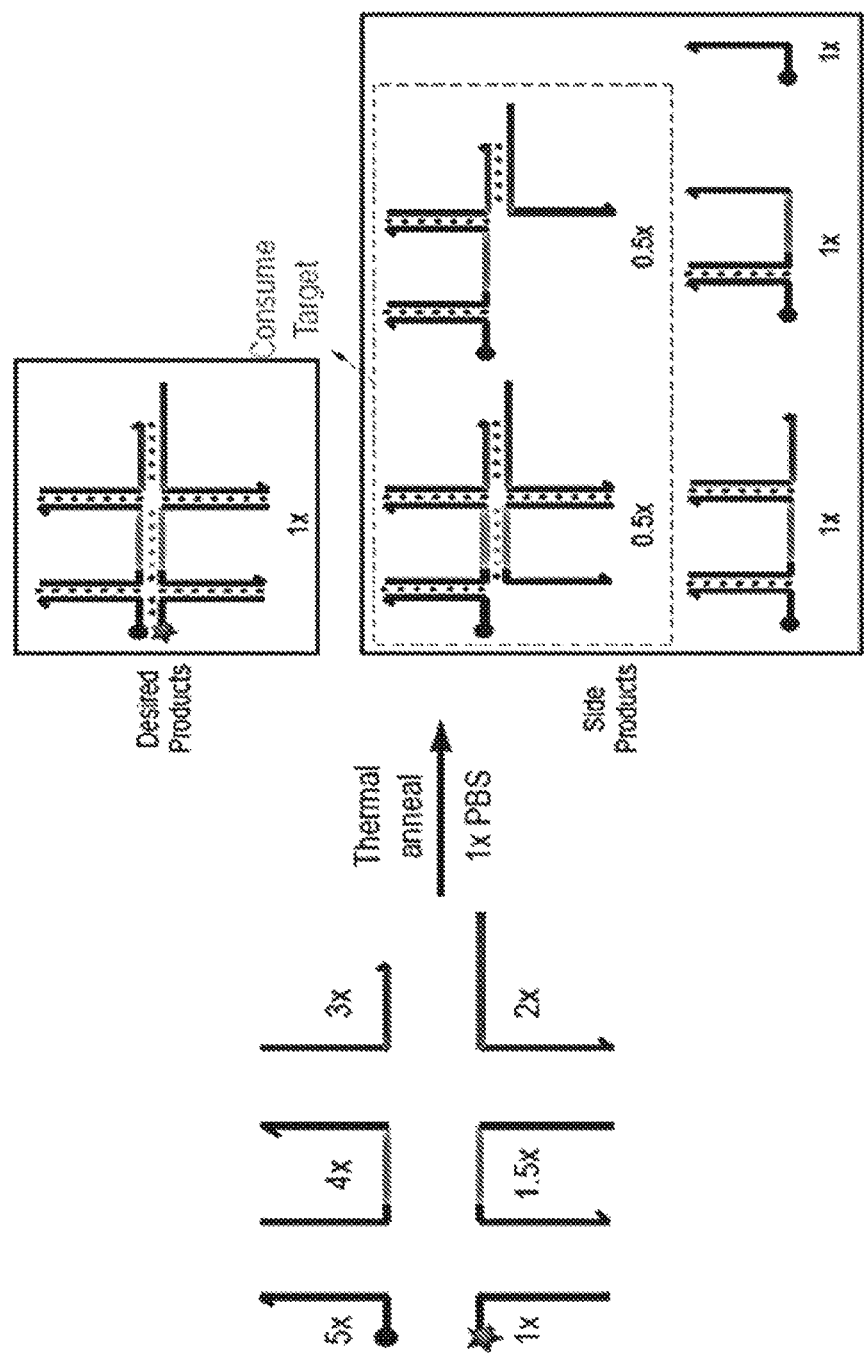
FIG. 18 depicts a M-Probe formulation using counterclockwise-increasing stoichiometries. There is up to 1× of side products that may consume target sequence, but no side products that are high fluorescence in absence of target.
Figure 19:
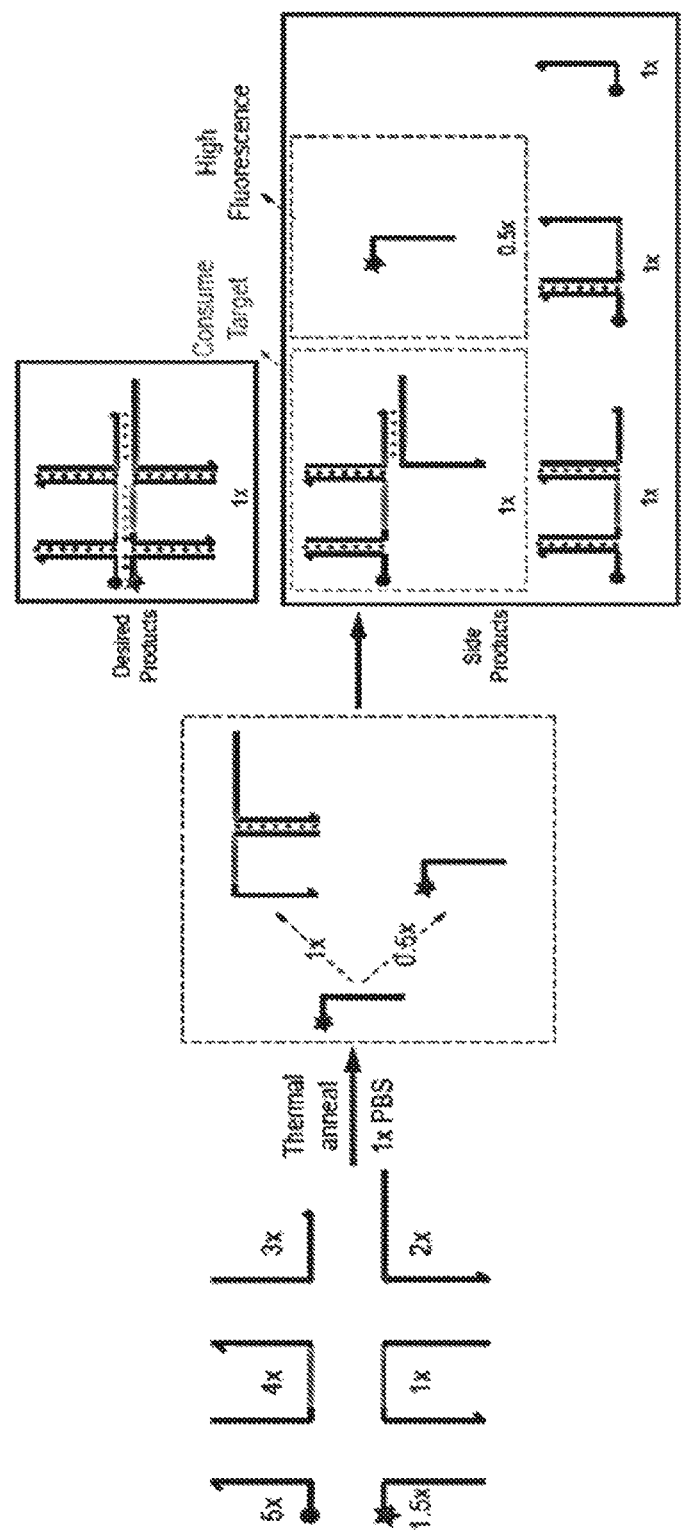
FIG. 19 depts a hypothetical formulation using a different stoichiometry. In this case, 0.5× excess universal fluorescence species exhibits high fluorescence, resulting in lowered signal/background ratio and a worse limit of detection.

Design of M-Probe thermodynamics. The standard free energy of the hybridization reaction between the M-Probe and its intended target can be calculated based on literature parameters, and is illustrated in FIG. 17.

$$\Delta G°_{rxn} = \Delta G°_{Toe} + \Delta G°_{ML3} - \Delta G°_{NH1} - \Delta G°_{NH2} - \Delta G°_{ML1} - \Delta G°_{ML2} - \Delta G°_{label}$$

The ΔG° Toe term denotes the standard free energy of binding of the toehold, ΔG° NH1,2 are the standard free energies of the non-homologous regions, ΔG° ML1,2,3 are the estimated standard free energies of the multi-loops formed at the junction of different hybridized regions, and ΔG° label is the estimated standard free energy difference between the thermodynamic contribution of fluorophore in close proximity to the quencher and the thermodynamic of free fluorophore in solution. The standard free energies of hybridization between regions are calculated based on the nearest neighbor model.

The vertical arm sequences are designed to be orthogonal to each other, and unlikely to bind to the human genome because they are selected from a sequence library with low homology to human DNA (e.g. ERCC external RNA controls). The vertical arms remain hybridized through the course of the reaction with a target, so the calculation of ΔG° rxn does not explicitly consider these regions.

M-Probe formulation stoichiometry. We typically formulate the M-probe using a stoichiometric ratio of component strands such that the quantity of each individual strand increases in a counterclockwise fashion from the lower-left corner (the fluorophore-labeled uC strand, see FIG. 18). Using an n=1 M-Probe as an example, we formulate it with uC:s1C:tC:tP:s1P:uP=1:1.5:2:3:4:5 ratio. After thermal anneal, we should get 1× desired product and several undesired products. This stoichiometry was designed to prevent the formulation of undesirable side products (e.g., see FIG. 19), given the inaccuracies in strand quantification. However, as long as the universal fluorescence strand is the limiting subcomponent, an arbitrary stoichiometry should work for most applications.

Figure 20A:
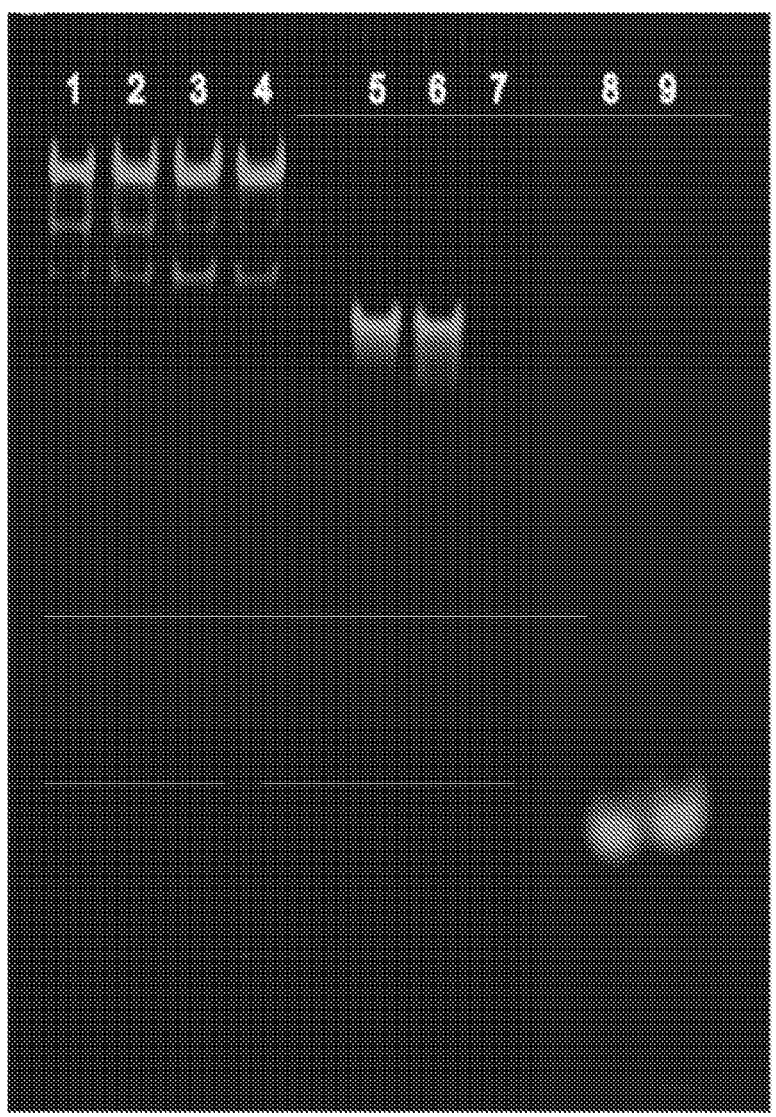
FIG. 20A shows the yield of M-Probe preparation from 8% polyacrylamide gel electrophoresis results.
Figure 20B:
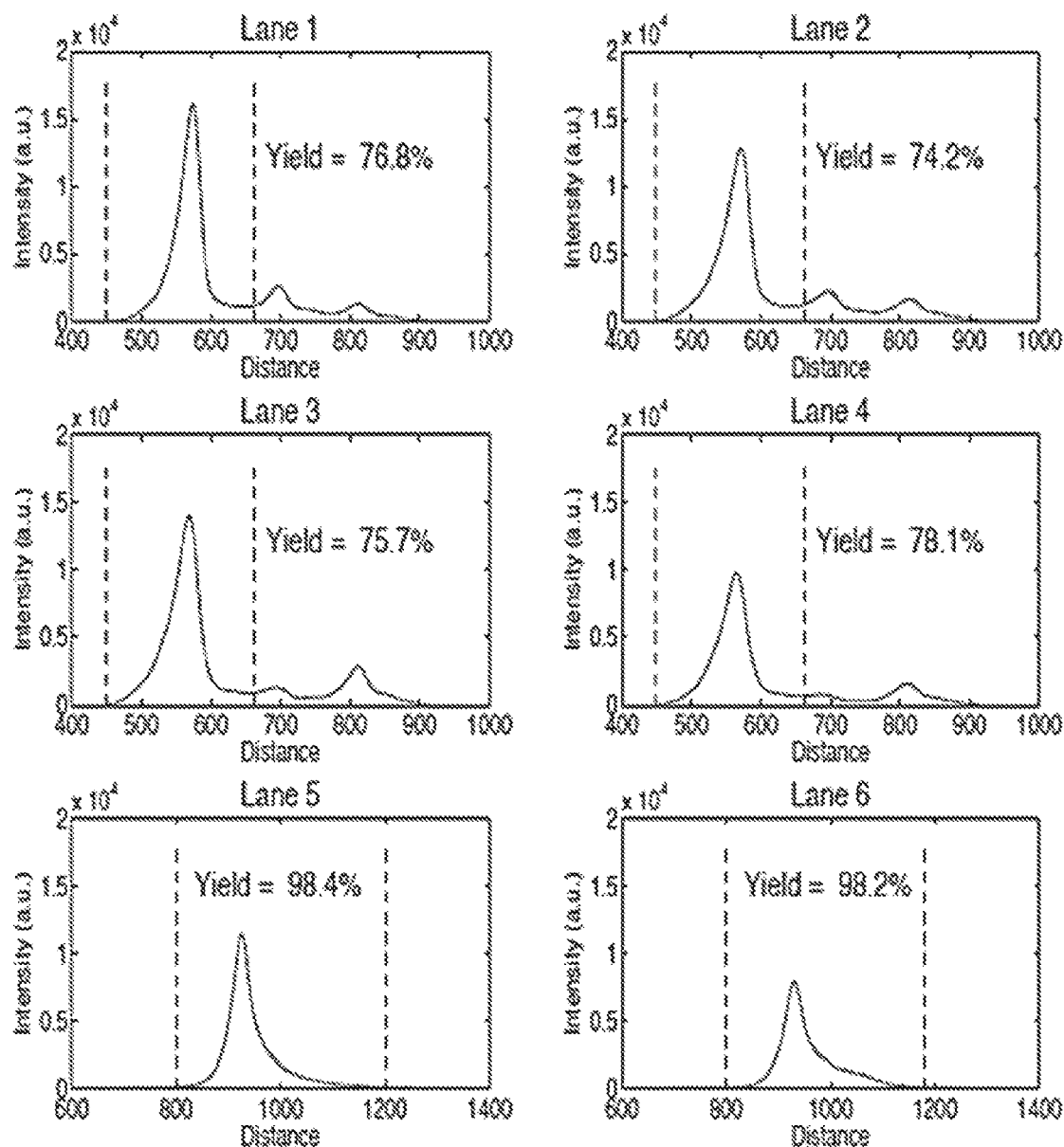
FIG. 20B shows the yield of M-probe preparation based on the gel band spectra of lanes 1-6.

M-Probe formulation yield. To show the efficiency and yield of M-Probe preparation, we prepared basic validation probe (used in FIG. 11C) and repetitive CAG repeat probe MP-18 (used in FIG. 15B) with different annealing protocols and different stoichiometry ratios. Then 8% native polyacrylamide gel electrophoresis (PAGE) was used to evaluate the yield of each M-Probe preparation method. 5 uL of 500 nM DNA was pipetted into each lane and the gel was run at 100 volt. The gel was scanned at the excitation/emission wavelengths of the ROX fluorophore (582 nm/600 nm). In general, different preparation protocols produce little variation in M-Probe formulation yield, with a variations within 2% (FIG. 20B). In FIG. 20A, each lane was loaded with 5 uL 500 nM DNA. Lane 1 to Lane 4 were loaded with CAG repeat probe MP-18. Lane 1: MP-18 prepared with stoichiometric ratio of 1:1.1:1.1:1.1:2.1:2.1:2.1:2.1, one-step formation. Lane 2: 1:1.1:1.1:1.1:2.1:2.1:2.1:2.1, two-step formation. Lane 3: 1:1.2:2.8:3.2:1.4:1.5:2.5:2.6, one-step formation. Lane 4: 1 :1.2:2.8:3.2:1.4:1.5:2.5:2.6, two-step formation. Lane 5 to Lane 7 were loaded with a non-repetitive probe (probe used in FIG. 11C). Lane 5: 1:1.1:1.1:2.1:2.1:2.1, one-step formation. Lane 6: 1:1.1:1.1:2.1:2.1:2.1, two-step formation. Lane 7: 1:1.1:1.1:2.1:2.1:2.1, with a uC strand without ROX fluorophore. Lane 8 to lane 9 are single-stranded ROX fluorophore strand. In FIG. 20B, Gel image was analyzed with Image Quant TL software. Bands were automatically detected, and fluorescence background of the gel was subtracted using a "rolling ball" algorithm packaged with the Image Quant TL software. The band intensities were plotted. Ratio of the AUC between the 2 dashed lines and total AUC was taken as the yield of M-Probe preparation.

Figure 21A:
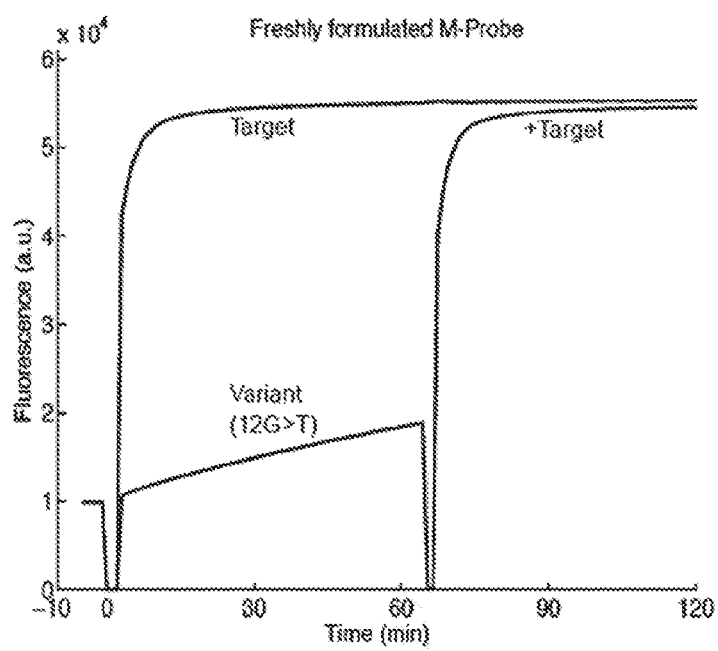
FIG. 21A shows the stability of the M-probes by basic validation of freshly prepared M-Probe. Experimental protocol was the same as that of FIG. 11C.
Figure 21B:
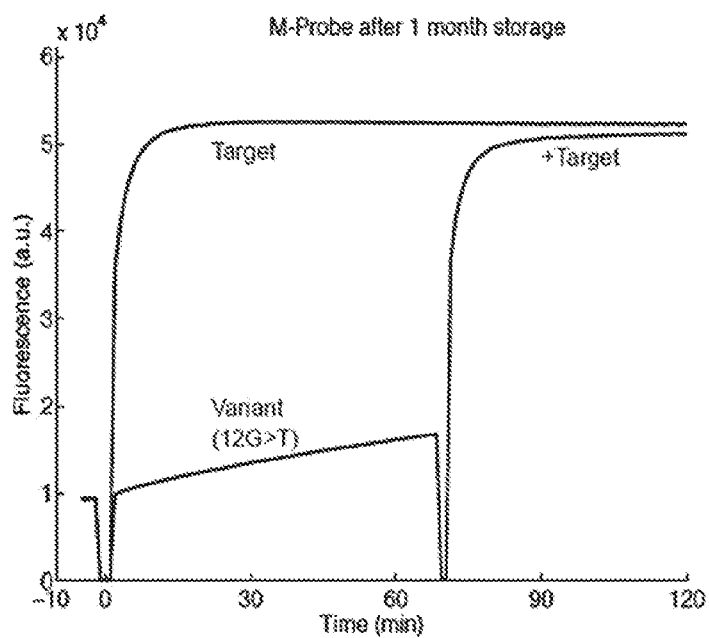
FIG. 21B shows the stability of M-probes by basic validation of M-Probe after 1 month storage at 4-C in 1×PBS.

Stability of the M-probes. To evaluate the stability of M-probe, we performed basic probe validation experiment (same as that shown in FIG. 11C) on Day 1 and Day 33. The kinetics and selectivity of the M-Probe stay the same (FIGS. 21A-21B). The results show that the annealed M-Probe can be stored for more than one month and a fresh preparation is not required for each analysis.

Figure 22A:
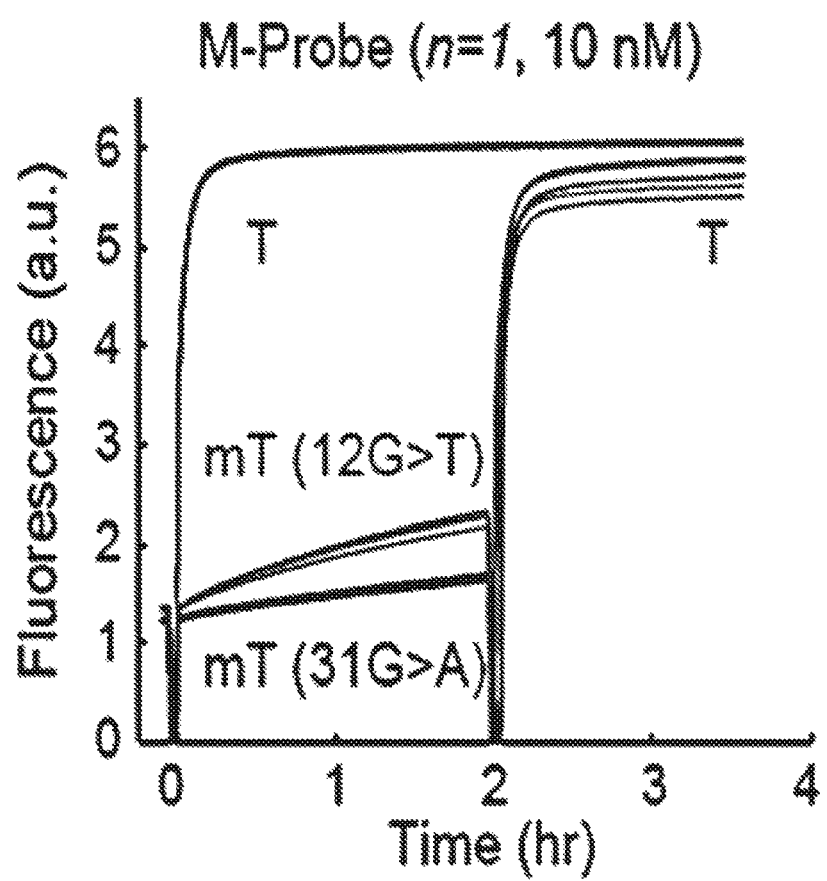
FIG. 22A shows the performance of an M-probe for comparison to that of a toehold probe in FIG. 22B and an X-probe in FIG. 22C.
Figure 22C:
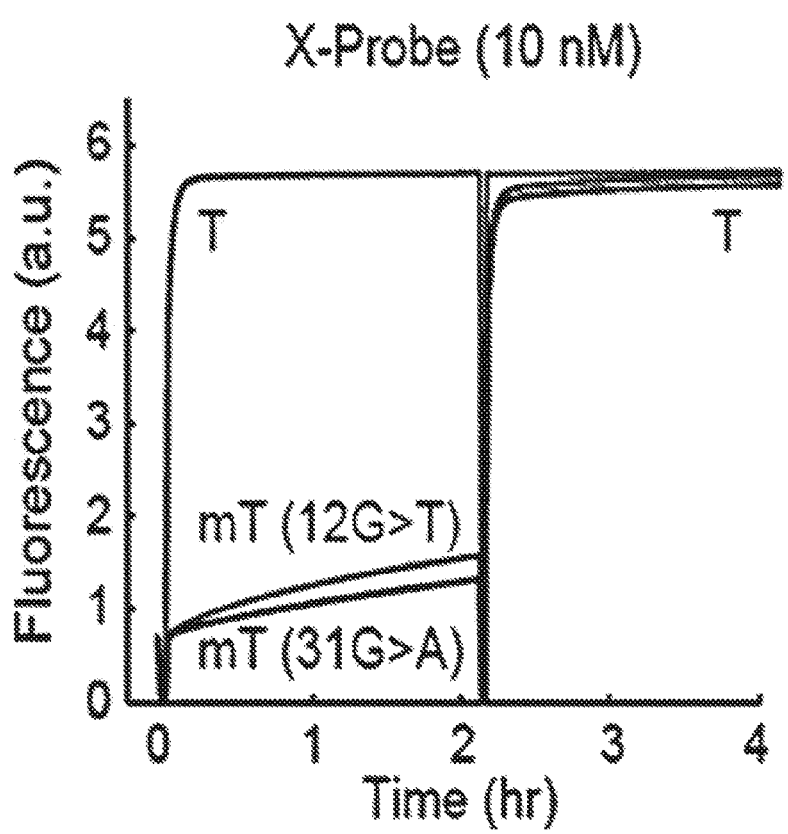
FIG. 22C shows the performance of an X-probe for comparison to that of the M-probe in FIG. 22A and the toehold probe in FIG. 22B.

Comparison of M-Probe to toehold probe and X-Probe. Toehold probes, X-Probes (an n=0 M-Probe), and M-Probes all follow the same design principles and exhibit high sequence specificity when reaction ΔG° is approximately 0. To study whether there are systematic differences between these three implementations, we tested one of each design against the same synthetic target DNA sequence (FIGS. 22A-22C).

The three designs qualitative produced similar results, but the M-Probe and X-Probe exhibited higher back-ground signal in the absence of addition of target. The higher background is likely because the multiloop near the fluorophore and quencher increases the probability that the fluorophore and quencher are separated by a distance greater than the Forster radius of the fluorophore. Additionally, the toehold probe exhibited lower fluorescence from the single nucleotide variant targets than the M-Probe and X-Probe; this is likely because of an underestimate in the ΔG° m term for the M-Probe and the X-Probe, resulting in a reaction ΔG° that is significantly more negative than expected from calculation, leading to lower specificity. We believe that optimization of the M-Probe and X-Probe sequences to shorten the length of the toehold would correct this difference from the toehold probe.

M-Probe universal segment design. The universal segment u of the M-Probe is typically functionalized with one or more chemical moieties to facilitate detection or enrichment of the targets of interest. The two oligonucleotides that comprise the universal segment may optionally possess a horizontal region of complementarity, in addition to the required arm sequences that connect them to segment s1. The X-Probe, a special case of M-Probe with n=0, is used to study the effects of the length of the complementary region in the universal segment.

Figure 23B:
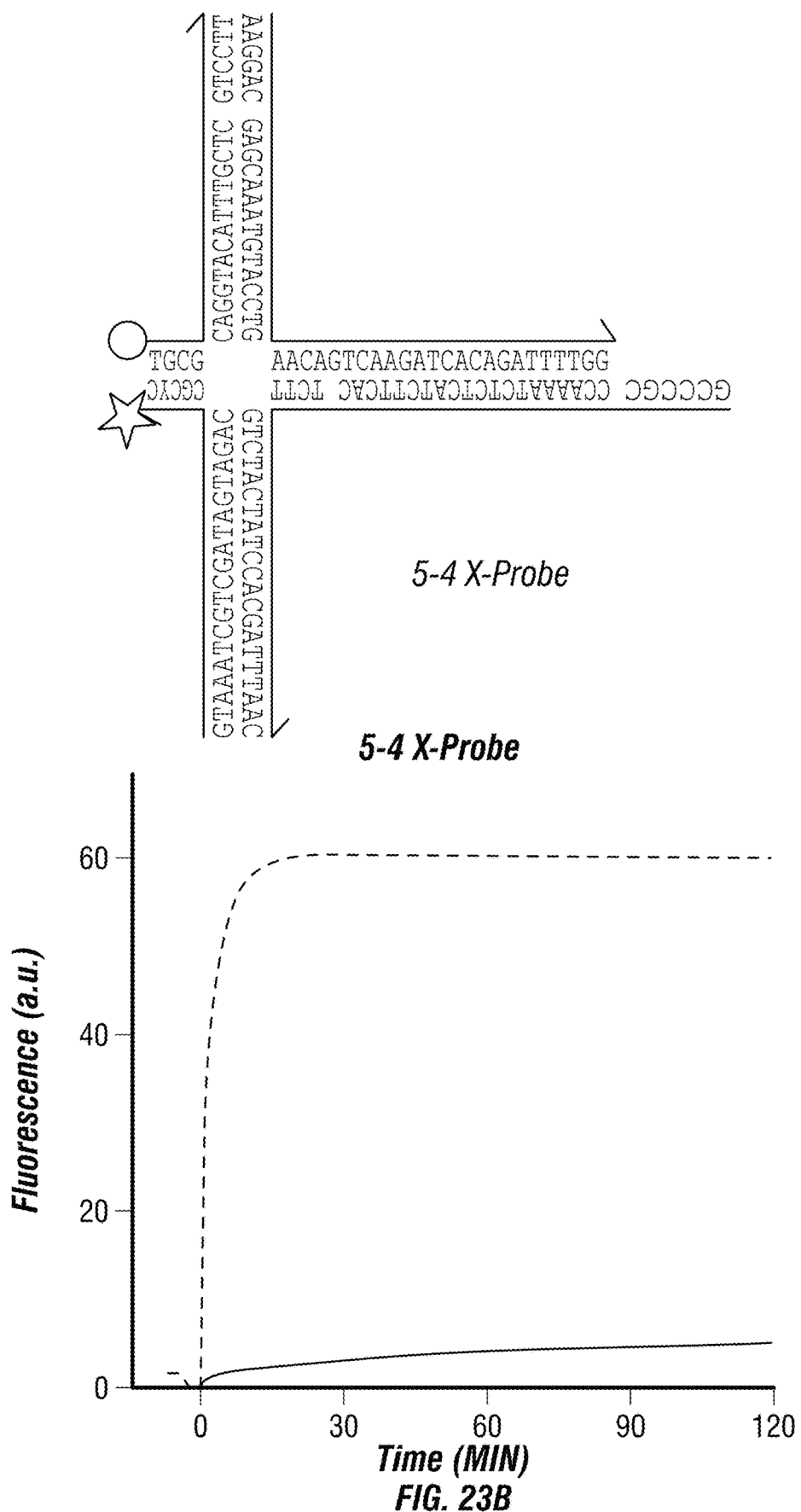

FIGS. 23A-23D shows the sequence design of 4 different X-Probe designs with varying lengths of complementarity in u. To maintain sequence selectivity against single nucleotide variants, additional nucleotides not complementary to the target are introduced upstream to target-specific segments to maintain an overall reaction standard free energy of ΔG°≈0. We denote these additional nucleotides as left and right non-homologous regions. The strength of the complementary region in u (left non-homologous region) affects reaction kinetics and fluorescence signal-to-noise ratio. In the limit of very long left non-homologous region, the dissociation of the fluorophore- and quencher-labeled strands can be very slow. In the limit of a very short left non-homologous region, where the strength of the base stacks is not strong enough to overcome the entropic penalty of closing a multi-loop, the fluorophore and quencher are not colocalized and the M-probes exhibits high background fluorescence. The quenching efficiency of probes with short left non-homologous region is often worse than that of probes without left non-homologous region (FIG. 23D).

Example 2

VDJ Target Design.

We designed synthetic VDJ hybridization targets based on published VDJ combinations sequences of T lymphocytes from peripheral blood. 33664 sequences of CDR3 clonotypes assembled from sequencing data of pooled peripheral T cells mRNA from 380 males and 170 females were analyzed, and 22704 sequences with unambiguous assignments of both V and J were used in further analysis.

To determine number of deletions present near the 3' end of the V and the 5' end of the J regions, V and J sequences observed in CDR3 clonodypes were compared with corresponding germline-encoded V and J gene sequences downloaded from IMGT/Gene-DB (http://www.imgt.org/genedb/). For this dataset, deletions at the 3' of the V segment can be up to 13 bases, and deletions at the 5' end of the J segment can be up to 25 bases (FIG. 24B).

According to IMGT/Gene-DB, the 2 germ-line encoded functional TRBD genes are very short, 12 and 16 nt, respectively. Thus, after substantial base deletions and insertions, origin of the D segment is often unidentifiable. In our analysis, we considered the non-templated bases and remaining D gene sequence as 'sequence between V-J', and did not specifically distinguish the two. The results show that the length of sequence between V and J ranges between 0 and 44 bases (FIG. 24B).

Figure 25:
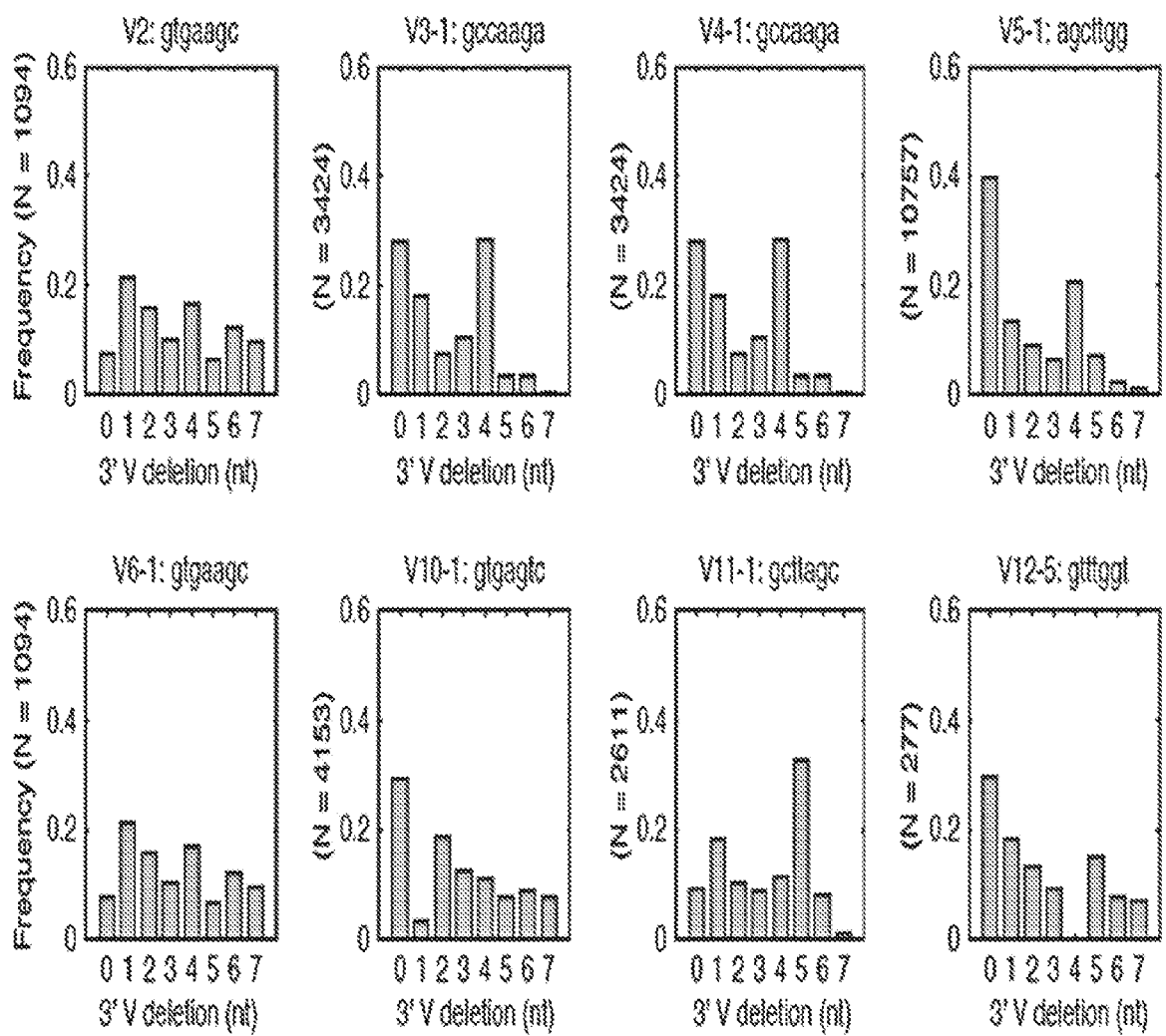
FIG. 25 shows the distribution of deletion lengths for the 8 selected V segments. Frequencies of deletions that are over 7 bases are not represented as they only correspond to less than 3% of the clonotypes. Sequence of the 7 bases that are closest to the 3' end of each V segment is displayed above each subplot.
Figure 26:
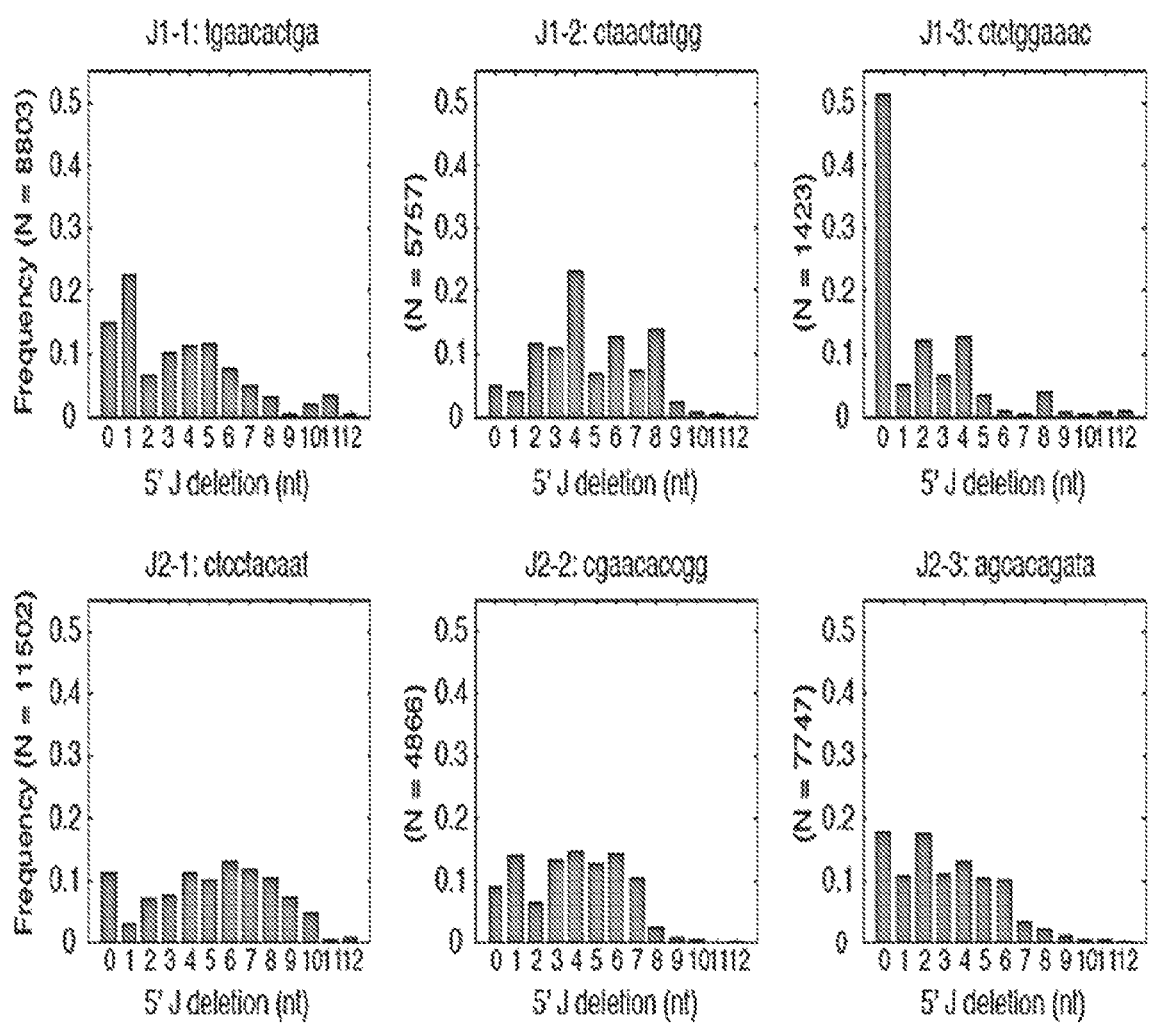
FIG. 26 shows deletion d Distribution of deletion lengths for the 6 selected J segments. Frequencies of deletions that are over 12 bases are not represented as they only correspond to about 3% of the clonotypes. Sequence of the 10 bases that are closest to the 5' end of each J segment is displayed above each subplot (SEQ ID NOS 265-270, respectively, in order of appearance).

We designed 48 VDJ recombination targets based on 8 arbitrarily chosen TRBV genes, 48 biologically occurring sequences between V-J, and 6 arbitrarily chosen TRBJ genes. Therefore, 6 targets were assigned to each V segment, and 8 targets were assigned to each J segment. The distribution of deletions within the chosen V and J segments in biology are shown in FIG. 25 and FIG. 26, and is roughly conserved in our designs. For example, for the 6 targets bearing V5-1 as V segment, 2 of them do not have any deletions in V region, another 2 of them have 4 nt deletions, 1 has an 1 nt deletion, and the last one has a 2 nt deletion. For the 8 target bearing J1-3 as J segment, 4 of them do not have any deletions in J region, 2 of them have 4 nt deletions, 1 has a 2 nt deletion, and the last one has a 3 nt deletion. 48 distinct sequences between V-J were arbitrarily chosen from corresponding sequence list extracted from the 22704 CDR3 clonotypes, following the length distribution shown in FIG. 24B. These V segments, sequence between V-J, and J segments were then randomly assembled to form the full length hybridization targets.

Example 3

VDJ Probe Design

Germ-line encoded D genes are very short and D gene usage in mature T cells is often unidentifiable due to substantial base deletion and random insertions. Consequently, we designed n=1 M-Probes with s1 and t segments only targeting V and J germ-line gene subsequences that are unlikely to be deleted during the VDJ recombination process. When the matching target DNA sequence binds to the M-Probe, a bulge will be formed at the junction between s1 and t segments. The bulge includes all the bases in the remaining D region, as well as random deletions and non-templated insertions at the V-D and D-J junctions. The targeting region of VDJ probes was designed to only cover sequences from the 3' most 35th base of V to the 5' most 35th base of J, because sequences upstream and downstream of CDR3 (5' of V, and 3' of J) are usually conserved and so are not informative in this context.

Figure 27:
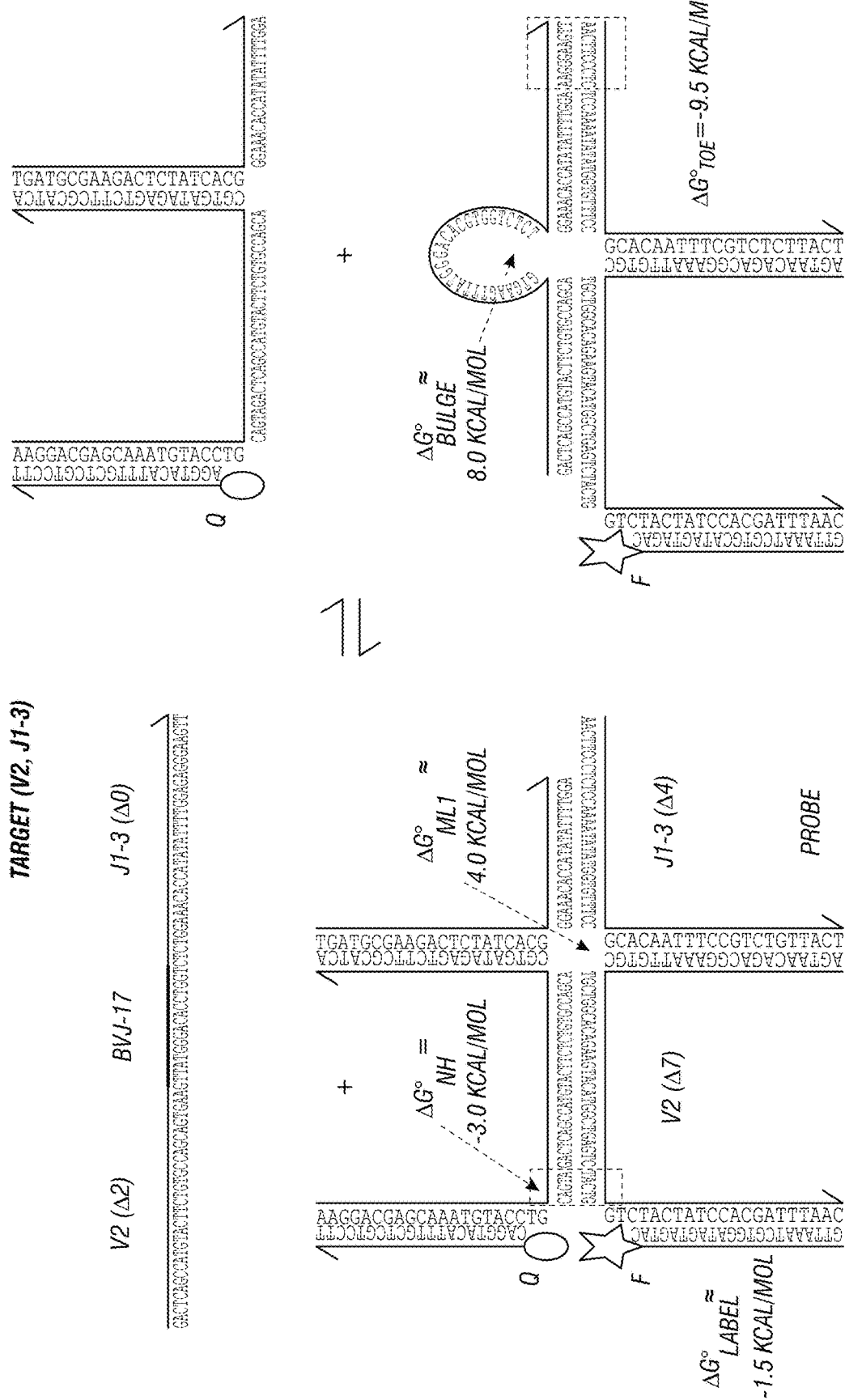
FIG. 27 depicts an example M-Probe design for VDJ targets. V region, sequence between V-J, and J region are color-coded as blue, green, and yellow. Number following the symbol Δ indicates the length of the deletion. Figure discloses the Target sequence as SEQ ID NO: 132; left structure sequences as SEQ ID NOS 64, 104, 76, 65, 112, and 77, respectively, in order of appearance; upper right structure sequences as SEQ ID NOS 64, 104, and 76, respectively, in order of appearance; and lower right structure sequences as SEQ ID NOS 132, 65, 112, and 77, respectively, in order of appearance.
Figure 28:
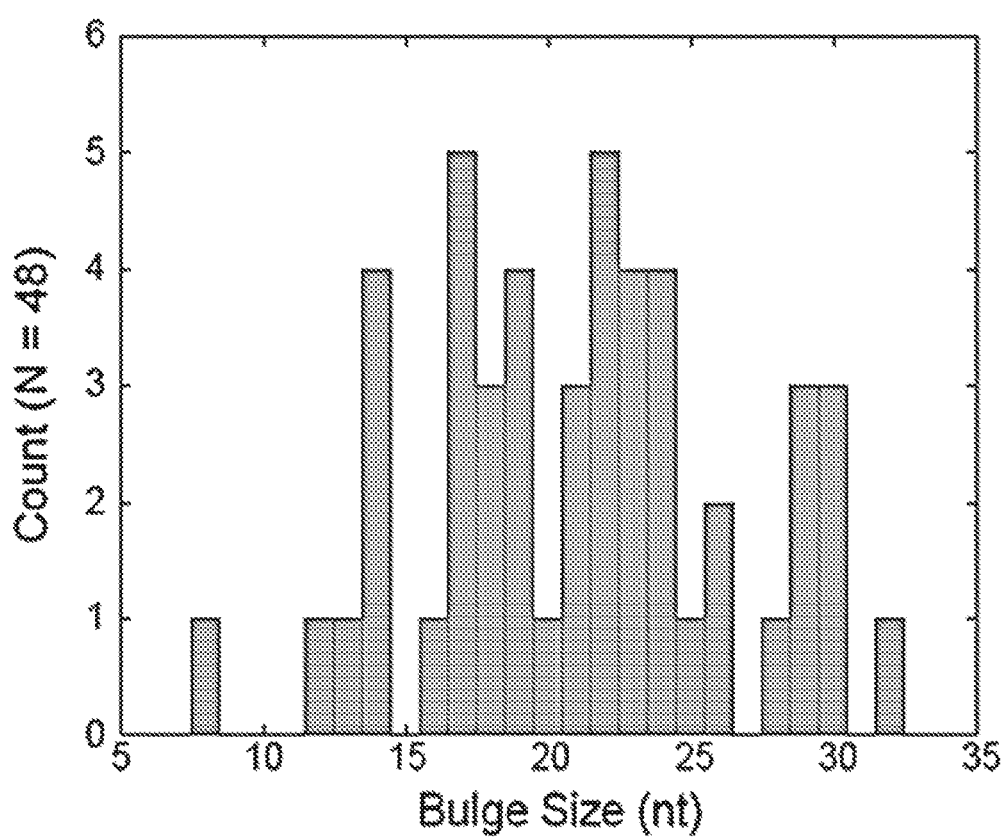
FIG. 28 depicts the bulge size distribution of 48 perfectly matched M-Probe reactions.

FIG. 27 shows the values used in the thermodynamics calculation for the reaction between an M-Probe targeting the V2 and J1-3, and its corresponding target with a 2 nt deletion in V, 0 nt deletion in J, and a 17 nt sequence between V and J. Upon target hybridization with the probe, a 26 nt bulge will form at the junction between V and J. The distribution of the bulge sizes of the 48 perfectly matched M-Probe and Target reactions is shown in FIG. 28. The free energy calculated for the reaction in FIG. 27 is as follows:

$$\Delta G°_{rxn} = \Delta G°_{Toe} + \Delta G°_{Bulge} - \Delta G°_{NH} - \Delta G°_{ML1} - \Delta G°_{label} \approx -9.5 + (+8.0) - (-3.0) - (+4.0) - (-1.5) \approx -1.0 \text{ kcal/mol}$$

Figure 29A:
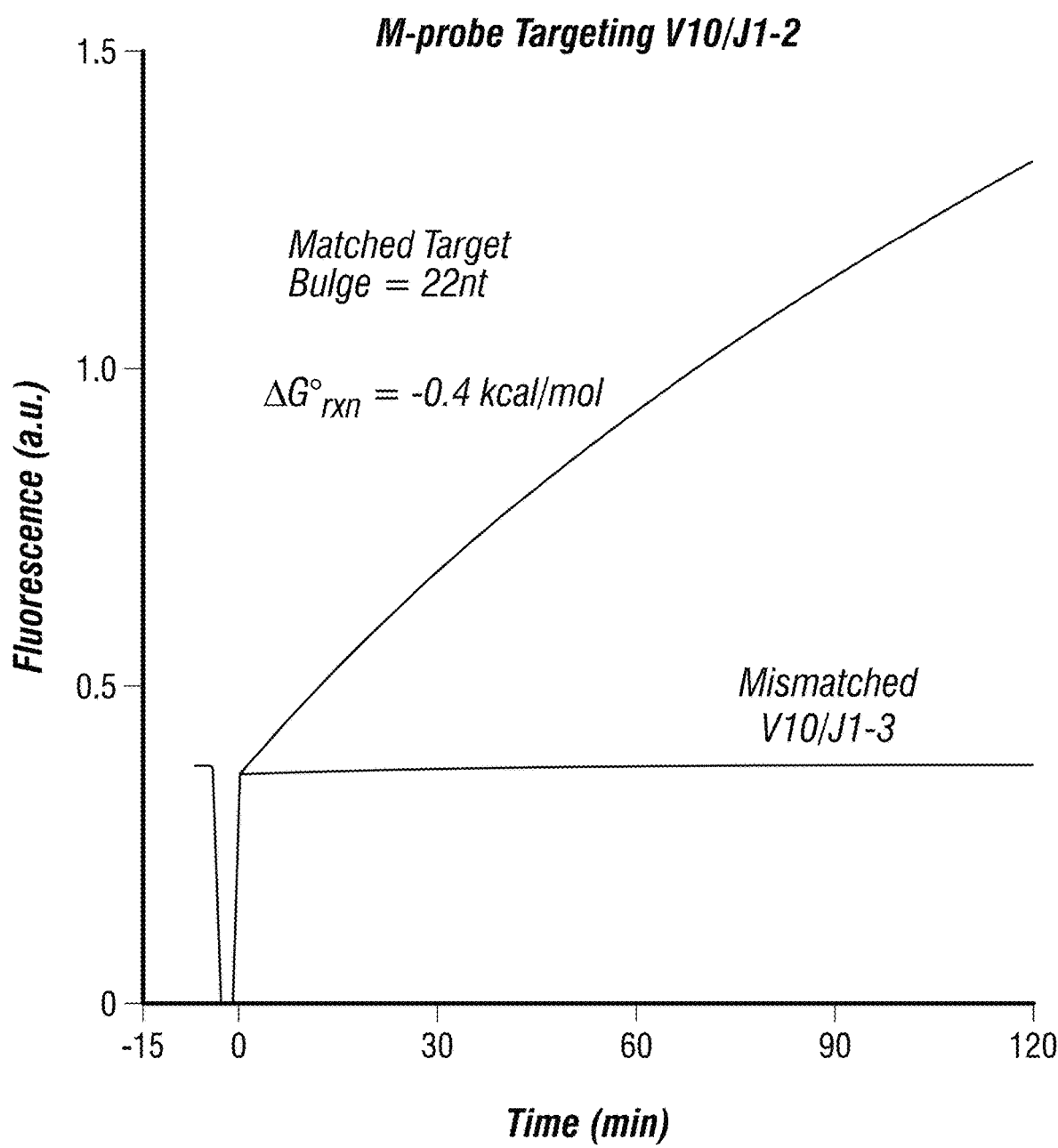
FIG. 29A-29C depict the binding kinetics of 3 M-Probes to their respective targets bearing V10/J1-2, V11/J1-2, and V12/J1-3.
Figure 29B:
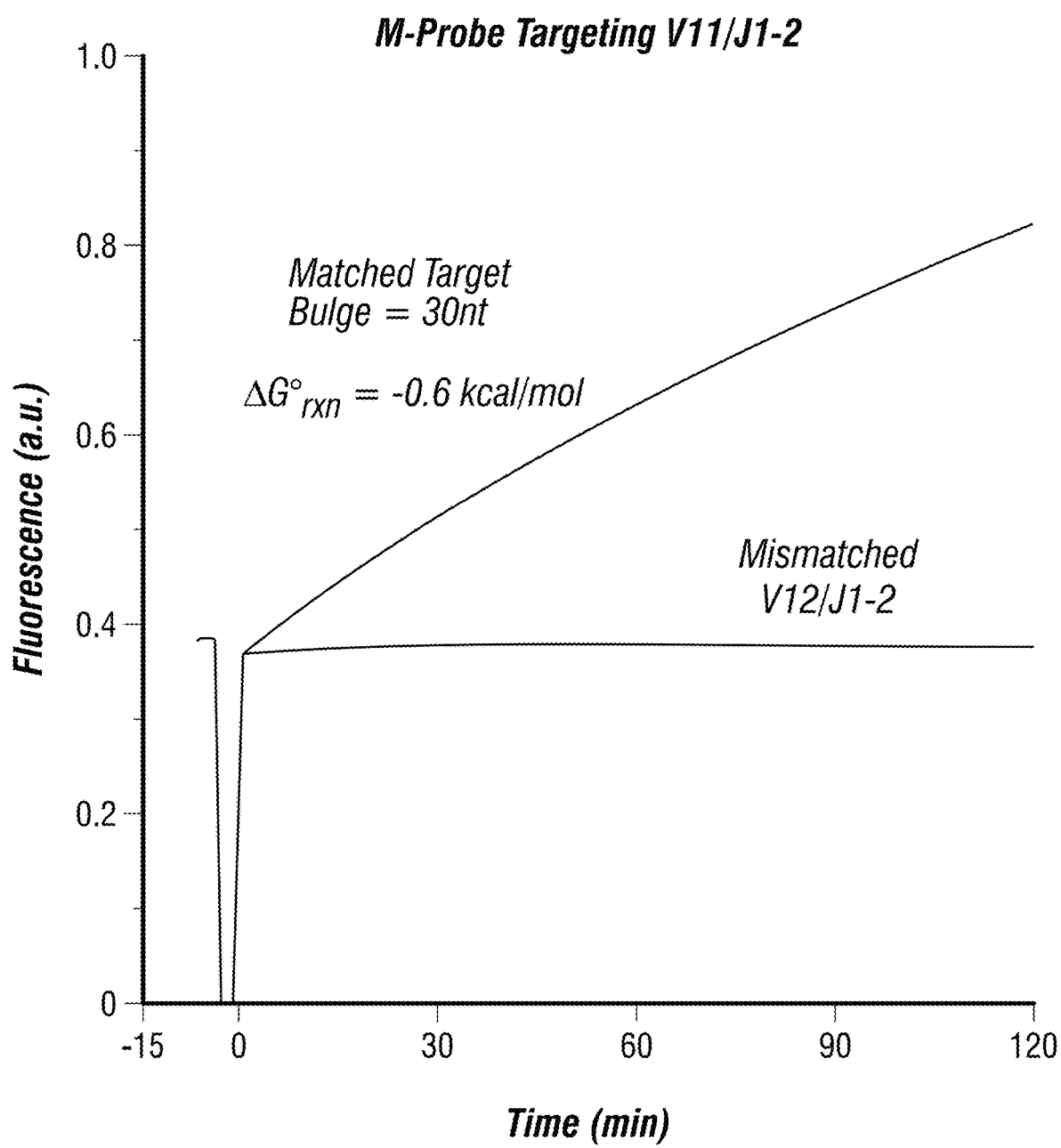
Figure 29C:
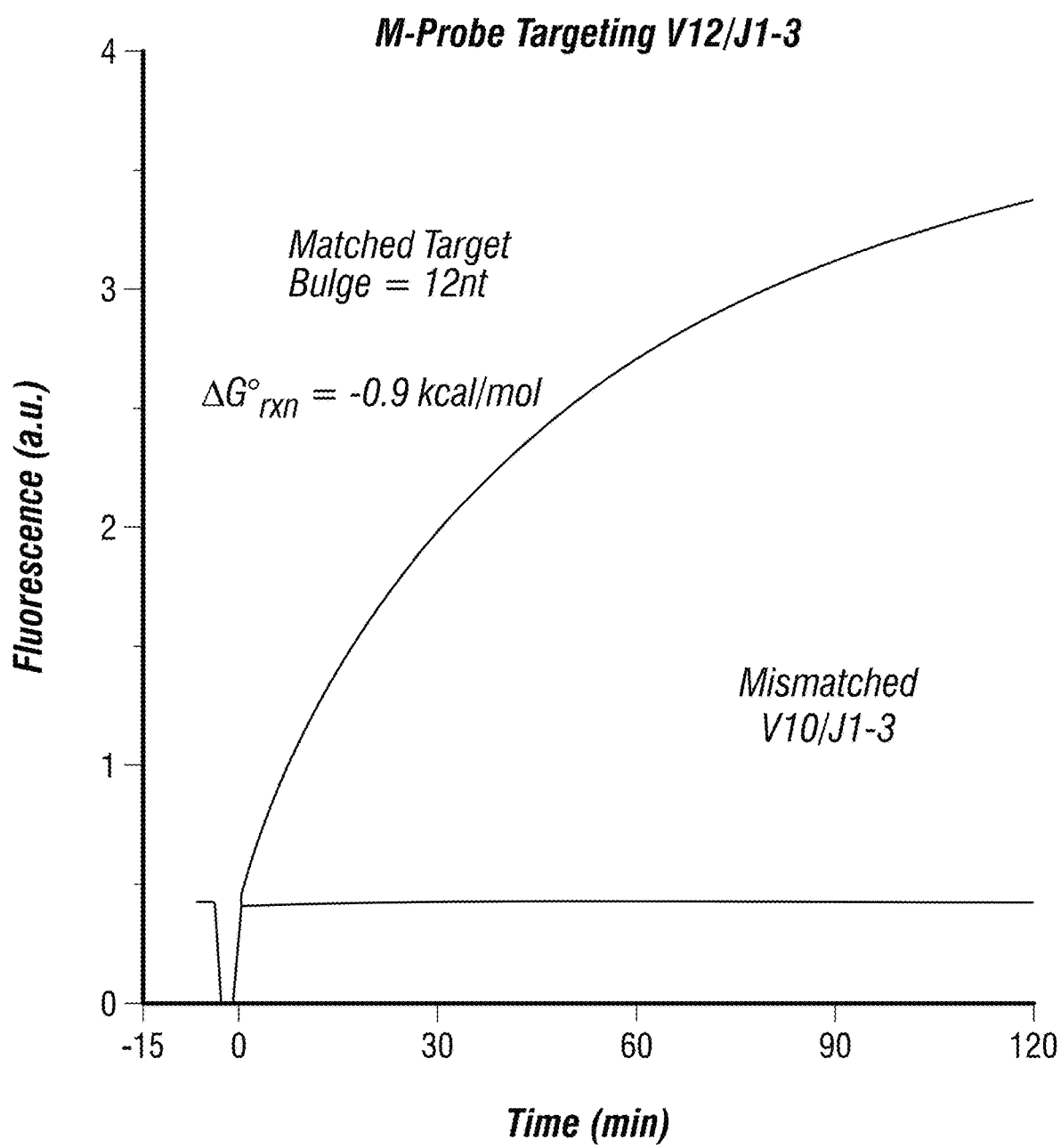

We estimated the free energy values of the bulge (including multiloop penalty) in the product to be roughly +8.0 kcal/mol, and fluorophore-quencher interaction to be −1.5 kcal/mol. The standard model of DNA hybridization indicates a logarithmic dependence of energy on the length of bulges, so there should not be large deviations of $\Delta G°$ values for different target sequences to the same M-Probe, except in the case of significant target secondary structure. We then designed the toehold and non-homologous regions to make the overall reaction energy to be slightly negative than 0 kcal/mol. So that probes will maintain good specificity against mutations in V and J segments, but also provide tolerance to larger bulge domains formed at the junction. As a result, despite the fact that some bulge sequences can be over 30 nt long, fluorescence response curves showed that these targets can still react with M-Probes in a reasonably fast manner (FIGS. 29A-29C).

Figure 30A:
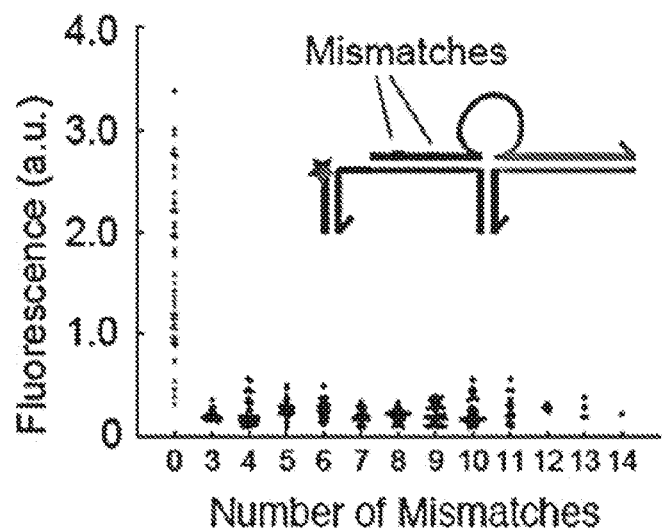
FIGS. 30A-30B depict beeswarm plots of fluorescence signals vs number of mismatches in V segments and J segments, respectively. V sequences are more conserve than J sequences, so numbers of mismatches are fewer.
Figure 30B:
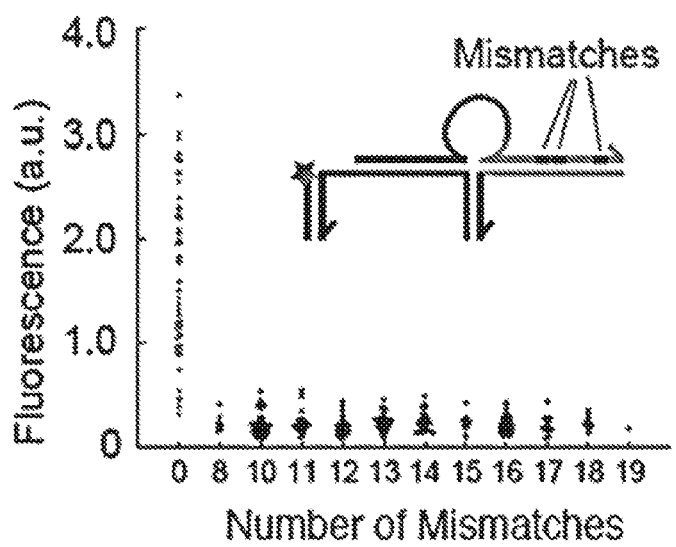

FIGS. 30A-30B shows beeswarm plot of fluorescence signal vs number of mismatches between probe and target. The same data set we used to generate FIG. 13D was used in the analysis. 0 mismatches represent perfect-matched probe and target pairs. Purple dots in the left panel represent 336 probe and target pairs with mismatches in V segment, while purple dots in the right panel represent 240 probe and target pairs with mismatches in J segment. High specificity is observed regardless of the number and positions of mismatches.

Example 4

End-Point Fluorescence Measurement for VDJ M-Probe Reactions.

In Example 3, we showed kinetics traces of the VDJ M-Probes hybridization to their targets. To enable higher throughput collection of end-point data for a large number of target-probe combinations, we used the Applied Biosystems QuantStudio 7 Flex Real-Time PCR System to measure the fluorescence of products after hybridization. Note that no polymerase enzyme was added; the instrument was used solely for temperature control and fluorescence measurement. The 96 different well positions each exhibit slight biases in fluorescence levels. We performed calibration experiments to correct for these systematic position biases before experimental analysis.

Figure 31A:
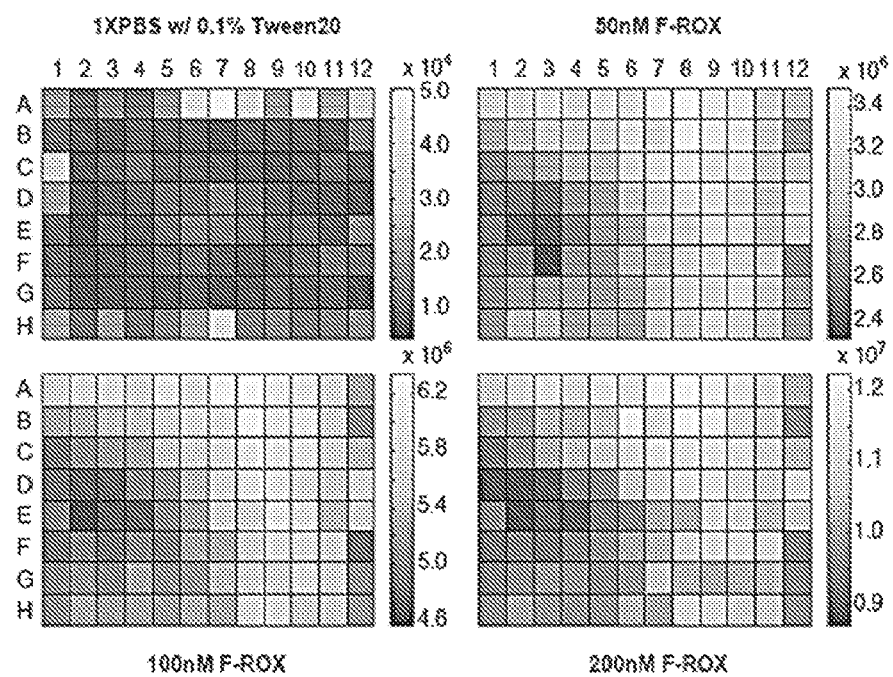
FIGS. 31A-31B show position correction of 96-well plate in the Applied Biosystems QuantStudio 7 instrument used for end-point fluorescence measurement.
Figure 31B:
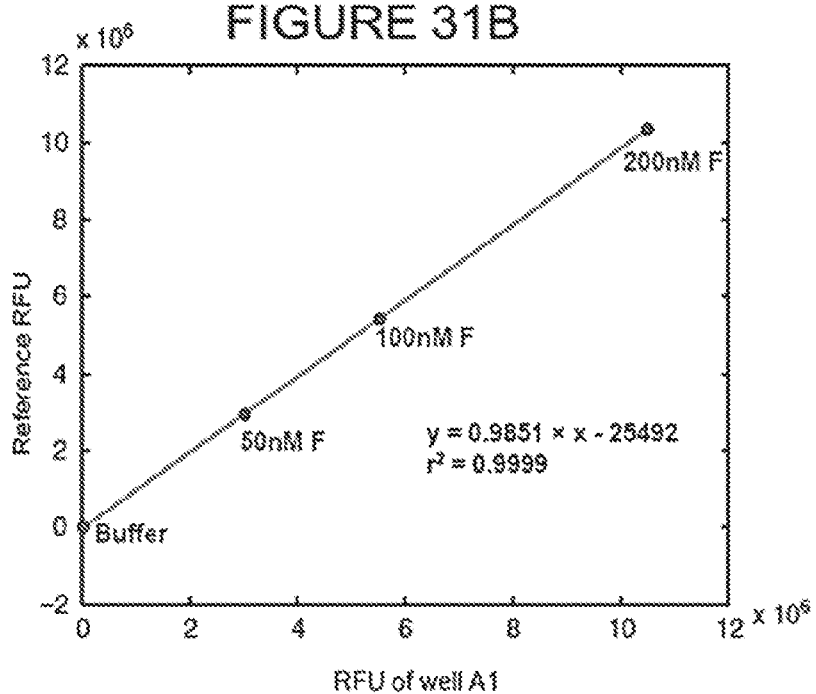

FIG. 31A shows the averaged Relative Fluorescence Unit (RFU) levels of 4 plates before position correction. We pipetted 10 μL of a 0 nM, 50 nM, 100 nM, and 200 nM ROX-labeled oligo solution into each well of each plate. The x and y axes indicate well position, and the color of each well represents the mean value of 20 continuous measurements of fluorescence, collected after a 20 min incubation at 37° C. For all concentrations, the average fluorescence value varies in different well position; wells in the middle-left of the plate tend to have up to 30% lower fluorescence than other wells.

To correct for position dependence, the average fluorescence of the entire plate is used as a reference. We performed linear regression between the reference fluorescences and the raw fluorescences of the four concentrations, and then applied the best-fit slope and intercept values to linearly transform the fluorescence of each well into the equivalent reference fluorescence. Position correction of well A1 is shown as an example in FIG. 31B.

Initial Experiments. Before conducting experiments of all 48 VDJ M-Probes, we first conducted a smaller-scale test on 8 M-Probes and their corresponding 8 target sequences. Every pairwise interaction between probe and target was studied, for a total of 64 reactions (FIG. 32A). Reactions in which the M-Probe is paired with its corresponding target showed high end-point fluorescence (red and pink traces), and all others showed significantly lower fluorescence (green and light green traces). The results are summarized in FIG. 32B. Due to different secondary structures and effective $\Delta G°$ rxn among targets and probes, there is some variation in the observed fluorescence values for perfect match hybridization reactions (main diagonal in FIG. 32B).

Example 5

Long Targets

Longer target DNA sequences are more prone to formation of significant secondary structure, which may interfere with intended hybridization to M-Probe for both thermodynamics and kinetics reasons. For this reason, when working with genomic DNA samples we first perform PCR amplification to generate shorter amplicons, which are then hybridized to the M-Probes. Even just considering amplicons, however, significant secondary structure may exist for some target sequences.

To demonstrate M-Probe's capability to probe long sequences, we designed respective M-Probes targeting 99, 160, 218, 430, and 560 nt (FIGS. 14A-14B) target sequences.

Figure 33A:
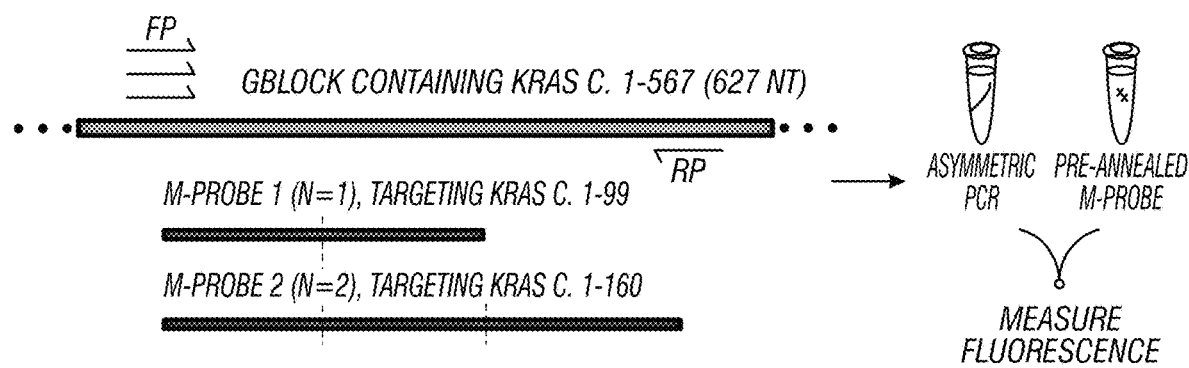
FIG. 33A depicts two M-Probes designed for targeting the first 99 and 160 nt of the KRAS cDNA, respectively. Vertical dashed lines denote the junctions separating M-Probe segments. Here, both M-Probes each bind to only a subsequence of the entire target.
Figure 33B:
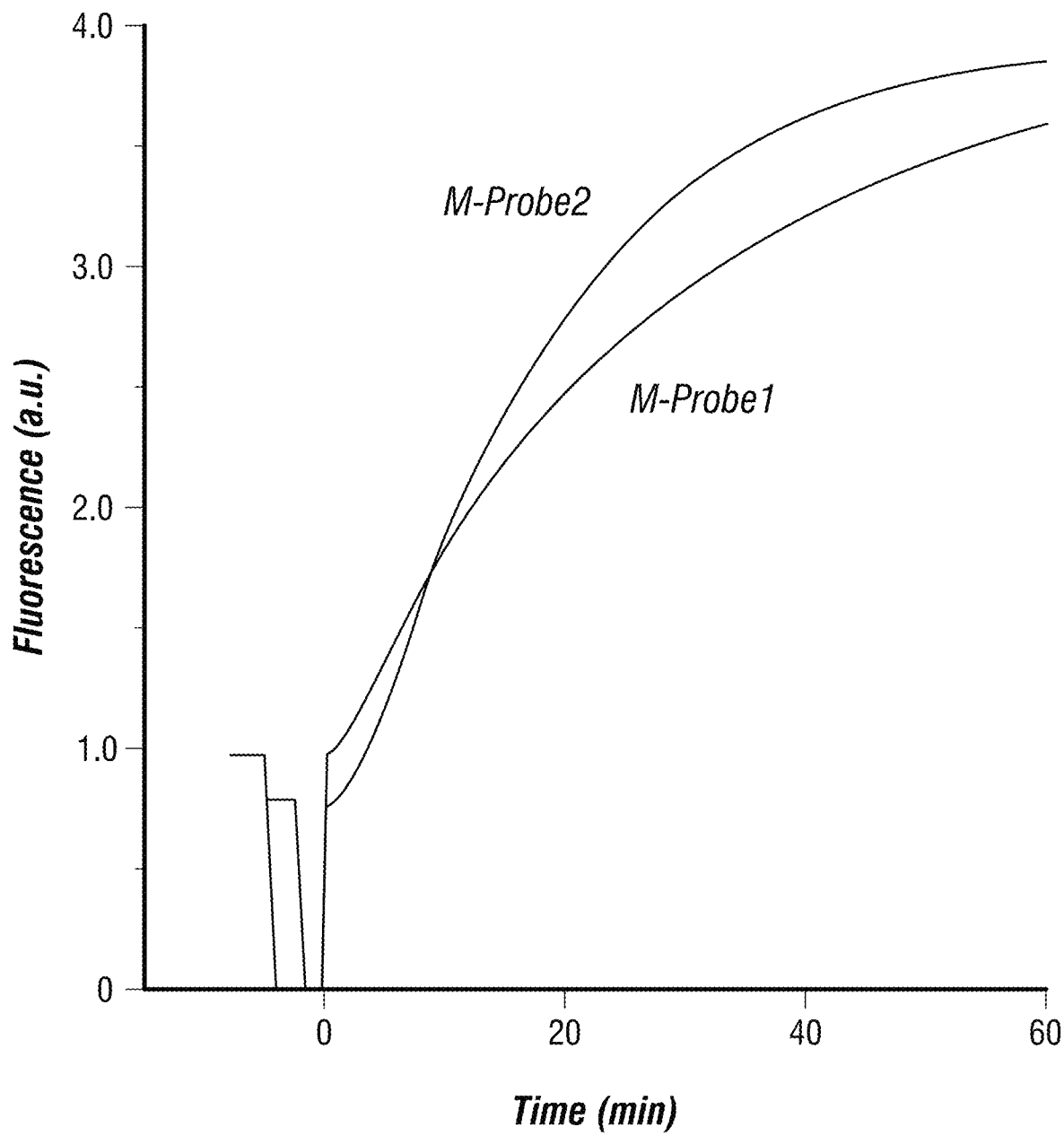
FIG. 33B shows the fluorescence response of the M-Probes (10 nM final concentration) to the amplicon target. Hybridization experiments were performed at 37° C. in 1×PBS.
Figure 33C:
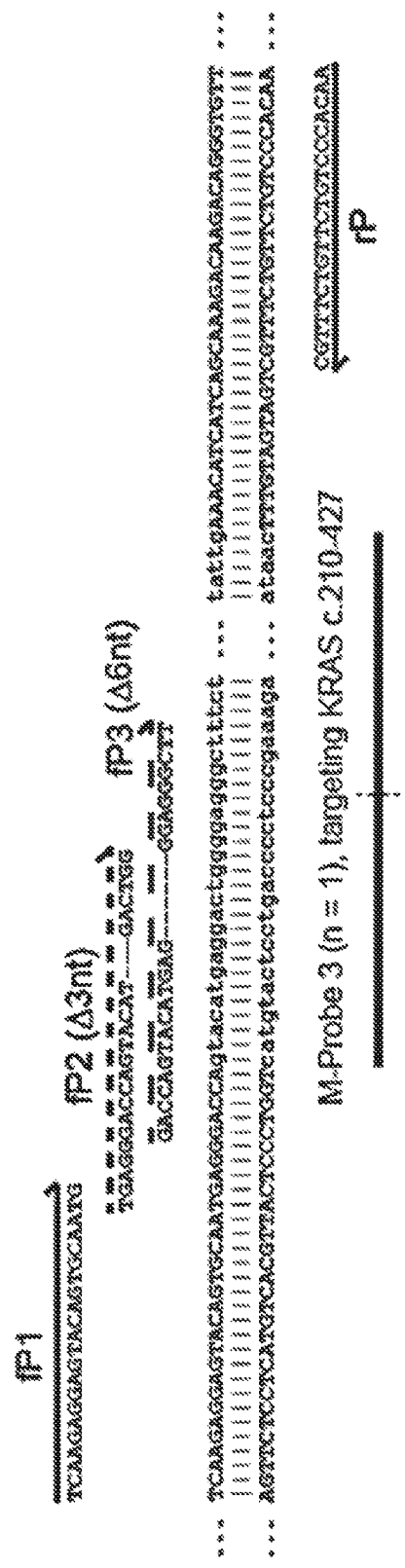
FIG. 33C shows the sequence selectivity of M-Probes to deletions in target sequence over 200 nt. Three different forward primers (fP) are used with the reverse primer (rP): fP1 generates an amplicon bearing the full target sequence of M-Probe 3, fP2 generates an amplicon with a 3 nucleotide deletion (Δ3nt), and the fP3 amplicon has a 6 nt deletion (Δ6nt). The length of the target-specific regions of s and t are 115 nt and 103 nt, respectively. Figure discloses SEQ ID NOS 182-184, 271-272, and 185, respectively, in order of appearance.
Figure 33D:
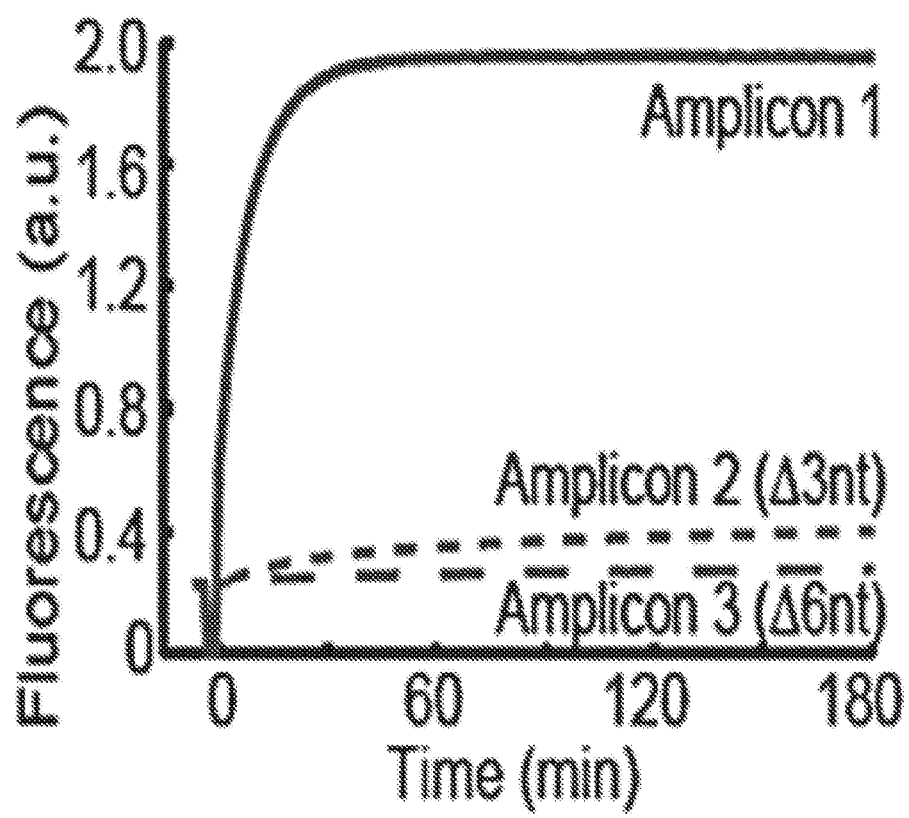
FIG. 33D shows the fluorescence response of M-Probe 3 (10 nM final concentration) to the amplicon targets.

FIGS. 33A-33B shows the design and performance of two M-Probes targeting 99 nt and 160 nt subsequences of the KRAS gene cDNA target, and FIGS. 33C-33D further show the sequence selectivity of an M-Probe targeting a 218 nt subsequence of the KRAS cDNA. All hybridization reactions between the M-Probes and their respective targets generated expected fluorescence within 20 minutes of reaction at 10 nM M-Probe concentration. Here, the target is the single-stranded amplicon sequence generated using asymmetric PCR from a synthetic IDT gBlock gene fragment.

Figure 34A:
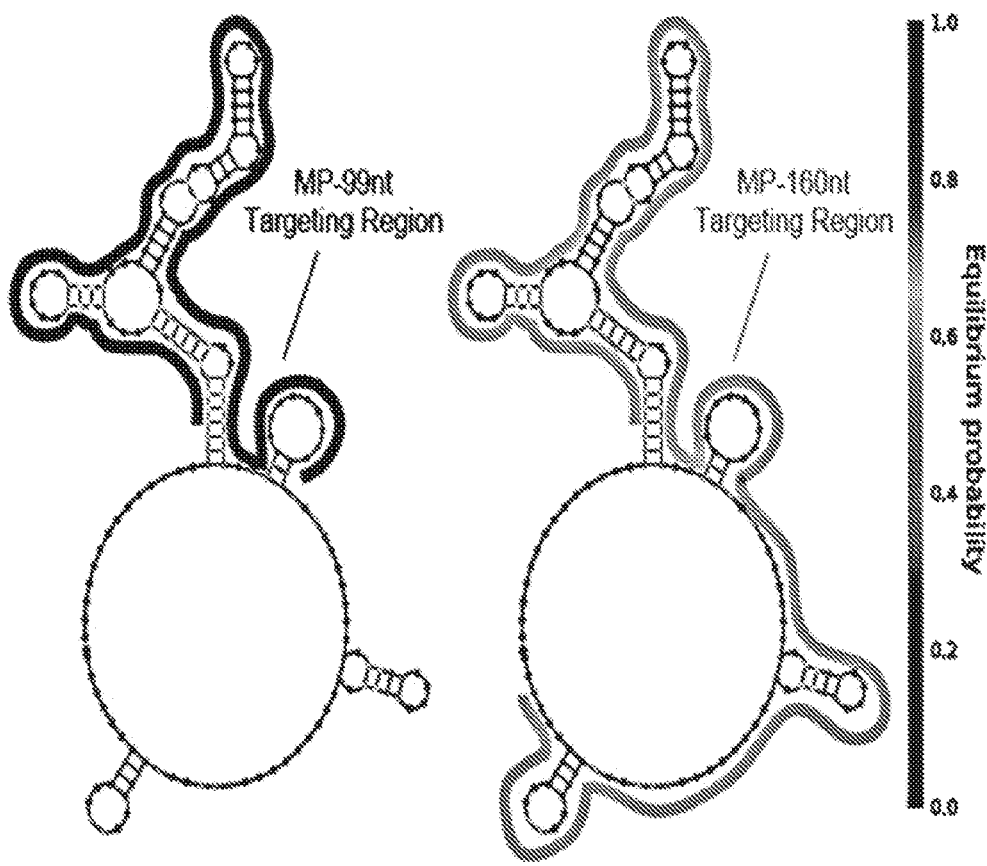
FIGS. 34A-34B depict KRAS amplicon minimum free energy (mfe) secondary structure, as predicted by NUPACK. Nucleotides are colored by probability of adopting the shown state.
Figure 34B:
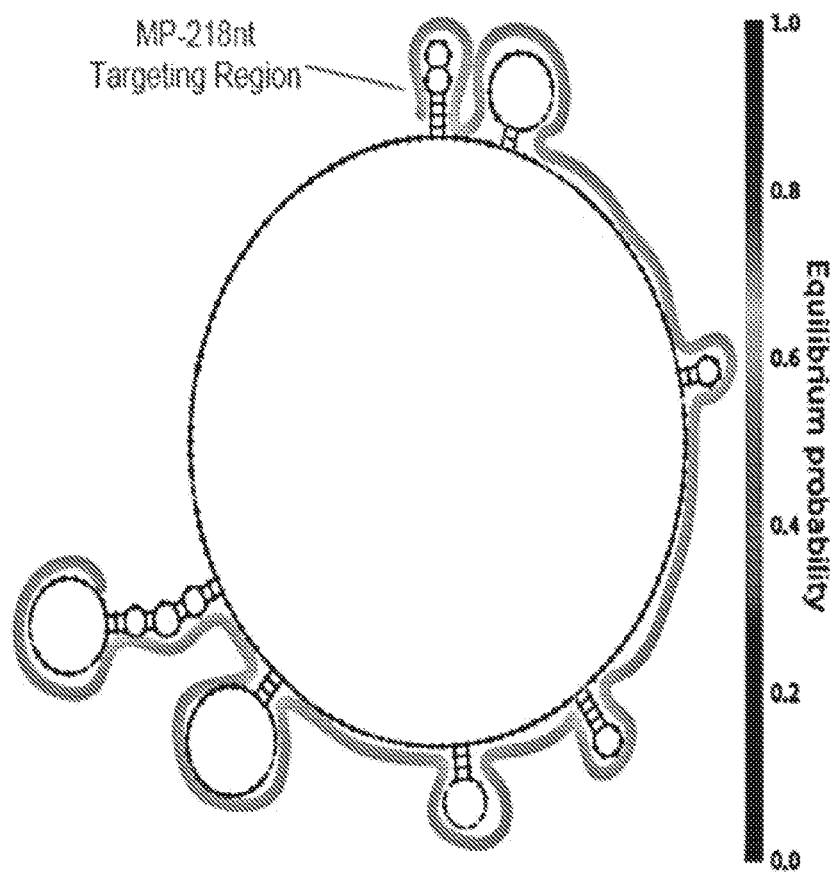

Shown in FIGS. 34A-34B are predicted minimum free energy (mfe) structures for targets used in the above experiments, as predicted by NUPACK for experimental conditions of 1×PBS (equivalent salinity to 0.15M Na+) and 37° C. The structures are presented by probability shading, in which each base in the target structure is shaded by the probability that each nucleotide base adopts the pairing depicted state in the figure. FIG. 34A shows the targeting regions on the 179 nt KRAS amplicon, including a 17 nt intron region to the 5' region of the KRAS target sequence. FIG. 34B shows the targeting regions on the 277 nt KRAS amplicon, spanning KRAS cDNA positions 180 through 456.

Figures 35A, 35B:
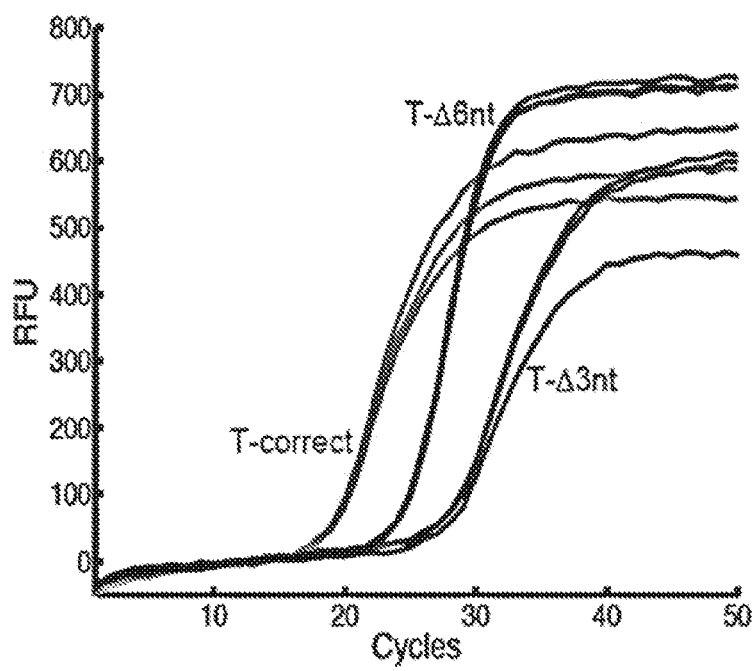
FIGS. 35A-35B show qPCR verification of target amplicon generation by asymmetric PCR using the Applied Biosystems PowerUp SYBR Green Master Mix.

FIGS. 35A-35B show the qPCR analysis of the amplification of the three target sequences. Some delay in the amplification is observed for primers used to generate amplicons with 3 nt and 6 nt deletion (fP2 and fP3), because fP2 and fP3 bind less favorably to the template as compared to fP1. Because asymmetric PCR was run for 70 cycles, the quantity of the three Amplicon targets should be nearly the same despite the difference in their Ct values. No template control Ct values indicate that primer dimer formation is not significant compared to amplicon.

Figure 36A:
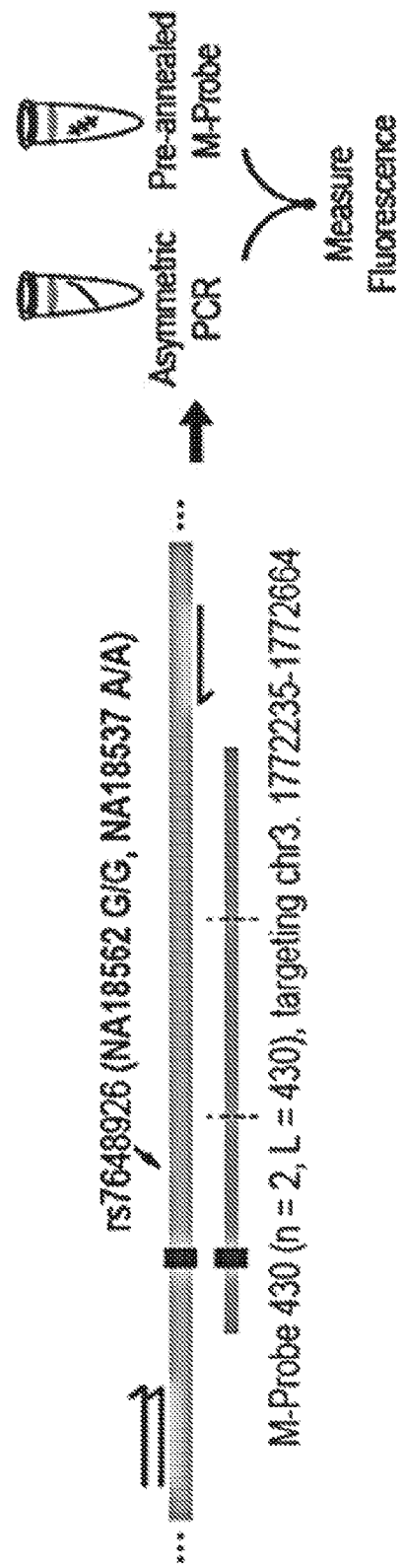
FIGS. 36A-36B depict the design and performance of M-Probe targeting 430 nt flanking sequence around SNP rs7648926.
Figure 36B:
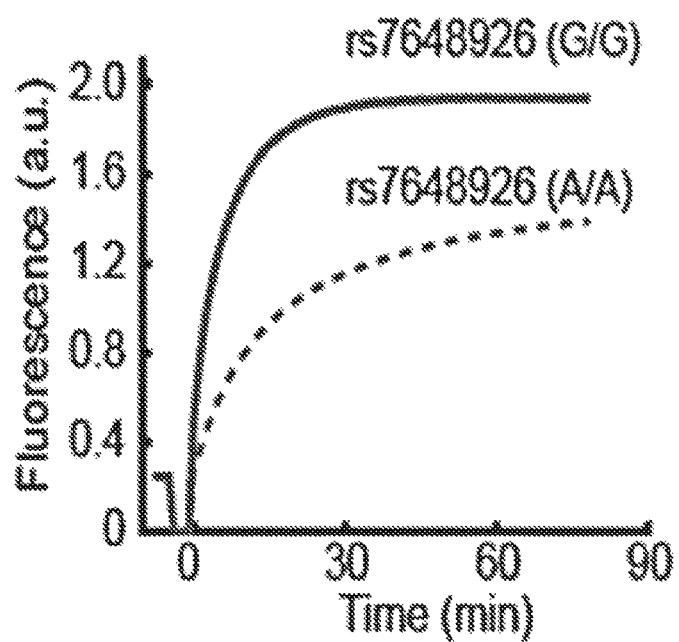
Figure 37A:
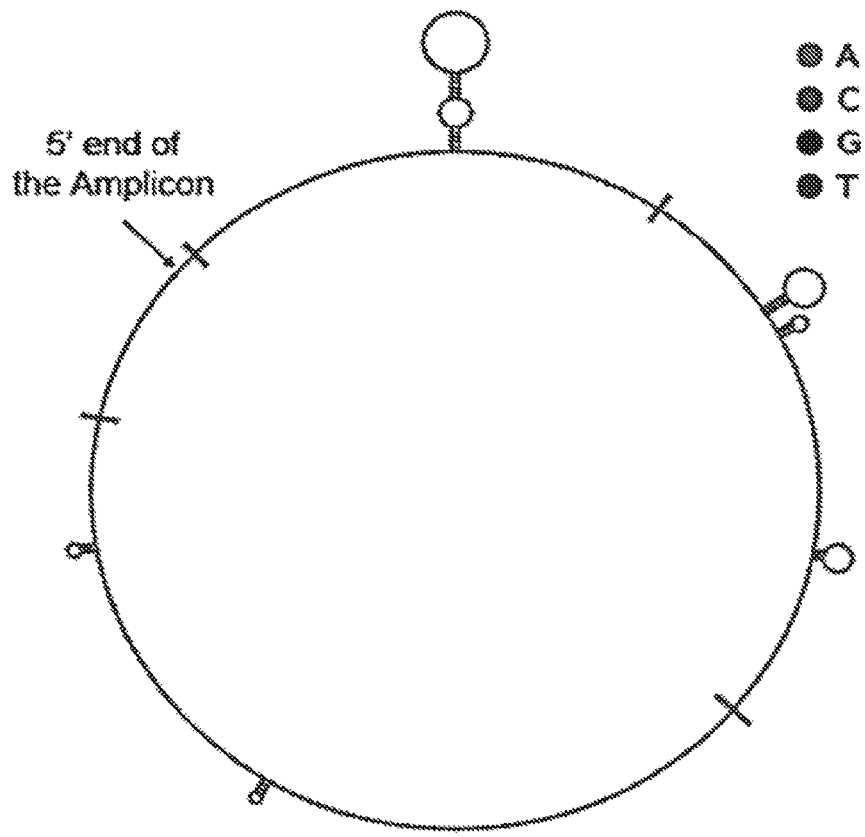
FIGS. 37A-37C depict long amplicons minimum free energy (mfe) secondary structure, as predicted by NUPACK. Colored lines indicate junction position of corresponding M-Probes.
Figure 37B:
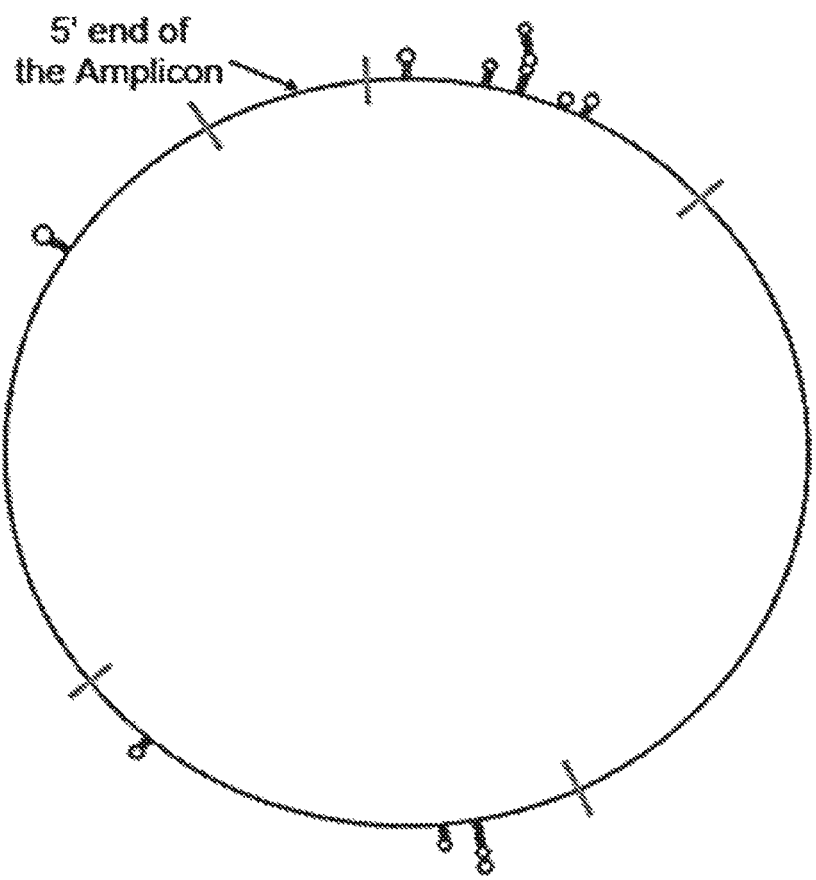
Figure 37C:
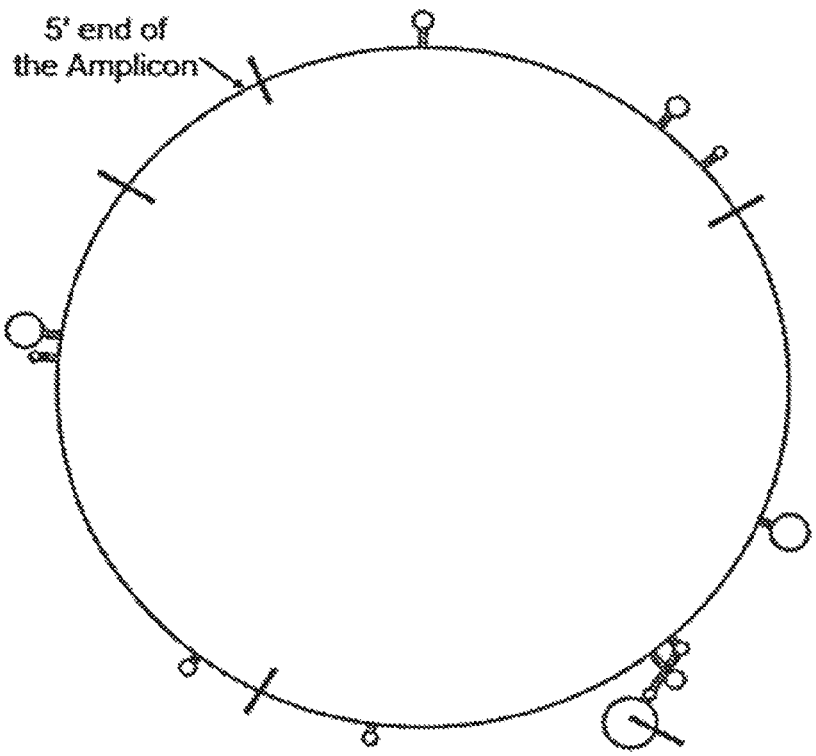

Design and performance of M-Probe targeting a 430 nt sequence flanking around SNP rs7648926 were shown in FIGS. 36A-36B. Similar to 560 nt M-Probes, M-Probe 430 has the same genotype as sample NA18562, while has a different genotype with sample NA18537. Single base discrimination was shown immediately after hybridization. A better separation between the perfect matched and the mismatched reaction curves could be achieved by optimizing probe thermodynamics. To minimize potential effect of target secondary structure on probe reaction kinetics, reactions of M-Probes with over 400 nt targeting region were performed at 45° C. instead of 37° C. Minimum free energy of secondary structures of amplicons over 400 nt and corresponding M-Probes' segment distribution are shown in FIGS. 37A-37C.

M-Probes with $n \geq 1$ have multiple target-specific segments (including t), and can circumvent oligonucleotide synthesis limitations to probe longer continuous target sequences. For example, given an oligonucleotide synthesis limitation of L nucleotides (L=100 for standard oligo, L=200 for IDT Ultramer oligo), each of the n internal s segments can probe (L−2A) nucleotides (where A is the length of the arm sequence), and the terminal t segment can probe (L−A) nucleotides. An n internal segment M-Probe can thus probe a maximum length LM of $$LM = (n+1) \cdot L - (2n+1) \cdot A$$

continuous nucleotides. From the above equation, it's clear that the M-Probe benefits shorter arm lengths A. The minimum length of A for stable formation of the M-Probe depends on arm sequence, temperature, and buffer salinity; at 37-45° C. and 1×PBS, A=22 is sufficient for stability for most arm sequences. For L=180 and A=22, an n=2 M-Probe can probe up to 430 nt, and an n=3 M-Probe can probe up to 564 nt.

M-Probes retain their high sequence selectivity even when binding long DNA targets. FIGS. 14A-14B show the detection of two single nucleotide polymorphisms (SNPs) within two different 560 nt targeting regions. The targets for these experiments are amplicons from the NA18562 and NA18537 cell line genomic DNA, that differ by only a single nucleotide in the middle of the M-Probe targeting region. There has been no previous demonstrations of single-nucleotide selectivity in DNA hybridization probes for probe lengths of longer than about 50 nt. Consequently, M-Probes increased the effective length range of allele-specific detection and enrichment by more than 10-fold, and could potentially be used as a novel method for confirming sequence. We also designed and tested M-Probes with targeting sequences 99, 160, 218, and 430 nt long and obtained expected results; see FIGS. 33A-37C and accompanying text for details.

Example 6

Trinucleotide Repeat Profiling.

Figure 38:
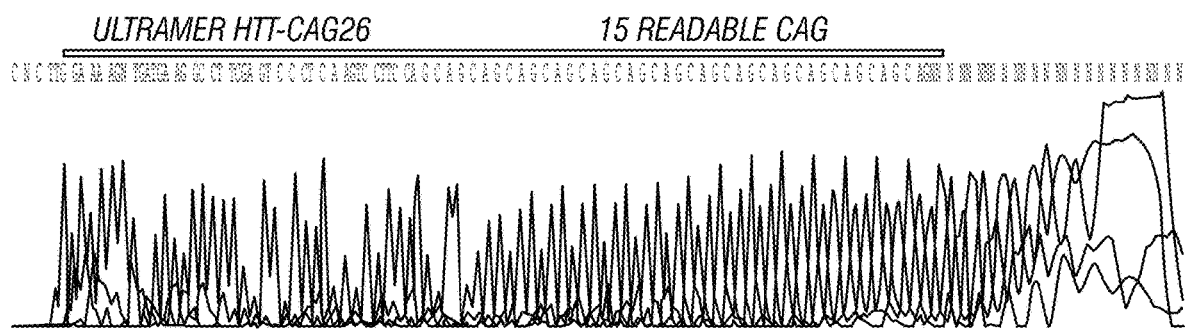
FIG. 38 depicts Sanger sequencing of synthetic DNA oligonucleotide with 26 CAG repeats (SEQ ID NO: 273).

DNA trinucleotide repeat expansion profiling is difficult for standard molecular analysis technologies. FIG. 38 shows the results of Sanger sequencing a synthetic (Ultramer) DNA oligonucleotide with 26 CAG repeats. Only the first 15 CAG repeats can be unambiguously profiled; this is insufficient for diagnostic analysis of Huntington's disease and other triplet repeat disorders.

Figure 39:
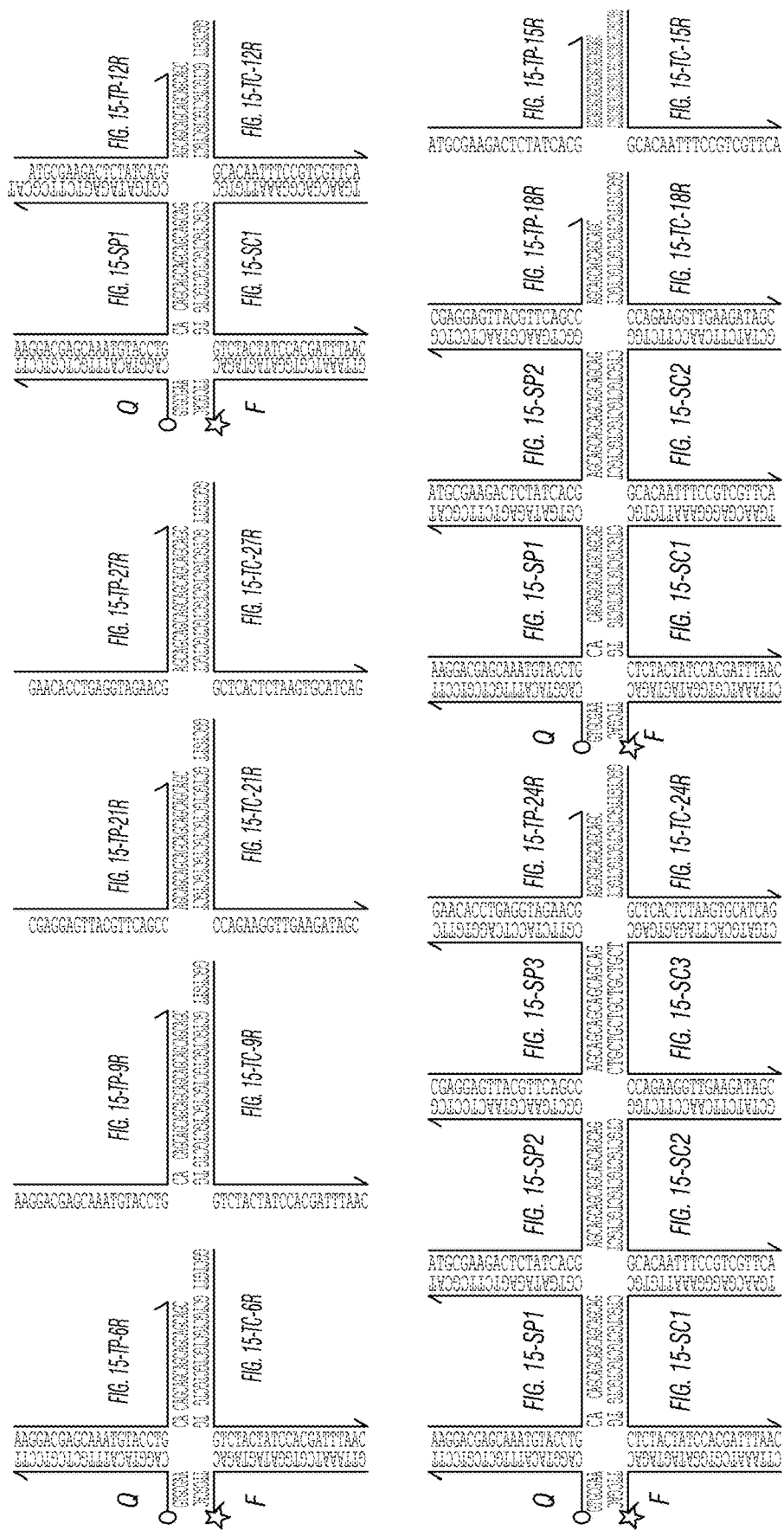
FIG. 39 depicts schematics and sequences of conditionally fluorescent M-Probes designed for HTT triplet repeat profiling. M-Probes for 6 and 9 repeats have n=0, and use their own t segments. M-probes for 12 and 15 repeats have n=1, and use s1. M-probes for 18 and 21 repeats have n=2, and use s1 and s2. M-probes for 24 and 27 repeats have n=3, and use s1, s2, and s3. Figure discloses sequences within the top row of structures as SEQ ID NOS 2, 19, 1, and 20, SEQ ID NOS 21 and 22, SEQ ID NOS 33 and 34, SEQ ID NOS 222 and 40, respectively, in order of appearance. Figure discloses sequences within the middle row of structures as SEQ ID NOS 2, 23, 25, 1, 24, and 26, and SEQ ID NOS 2, 23, 29, 31, 1, 24, 30, and 32, respectively, in order of appearance. Figure discloses sequences within the bottom row of structures as SEQ ID NOS 2, 23, 29, 35, 221, 1, 24, 30, 36, and 38, and SEQ ID NOS 27-28, respectively, in order of appearance.

Conditionally fluorescent M-Probes design and formulation. Each M-Probe provides information on whether a DNA sample contains the HTT gene with triplet repeats equal to or exceeding the designed number. A series of different M-Probes with different triplet repeat thresholds thus is able to provide precise information on triplet repeat number. FIG. 39 shows the components of the M-Probes with thresholds between 3 and 27 repeats.

Figure 40A:
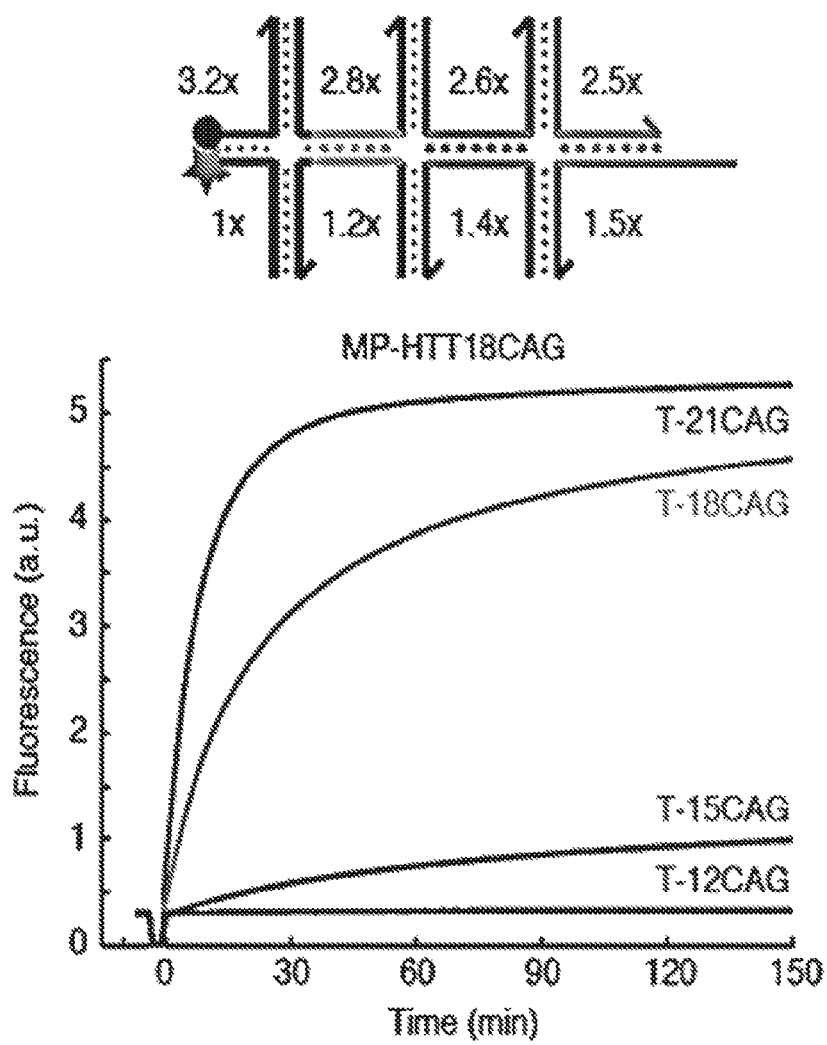

We studied whether the stoichiometric ratio of component strands has significant effect on M-Probe performance (FIGS. 40A-40B). The concern we addressed is that because DNA oligonucleotide quantitation by absorbance at 260 nm (A260) is inaccurate due to both errors in extinction coefficient estimation and in contributions to A260 from buffers and other impurities, that some oligo species will be at higher or lower concentrations than expected, by up to 20%. In adversarial circumstances this could result in a significant fraction of the M-Probes being mal-formed, that either do not react with the intended target, or reacts nonspecifically even with variants. One way to prevent this is to use intentional excesses of some strands over others, so that all possible side products are non-fluorescent species that do not result in false positive signals. Our comparison experiments again show that this potential problem is not significant in practice.

M-Probes for profiling CGG and GAA triplet repeats. We also designed M-Probes targeting FMR1 gene CGG repeats region (FIG. 41A) and FXN gene GAA repeats region (FIG. 41B). Trinucleotide repeat expansion of the former is associated with Fragile X syndrome and that of the latter is associated with Friedreich's Ataxis. For CGG repeat detection, we designed M-Probes to target the reverse strand to avoid strong secondary structures formed by G-rich sequence.

Figure 42:
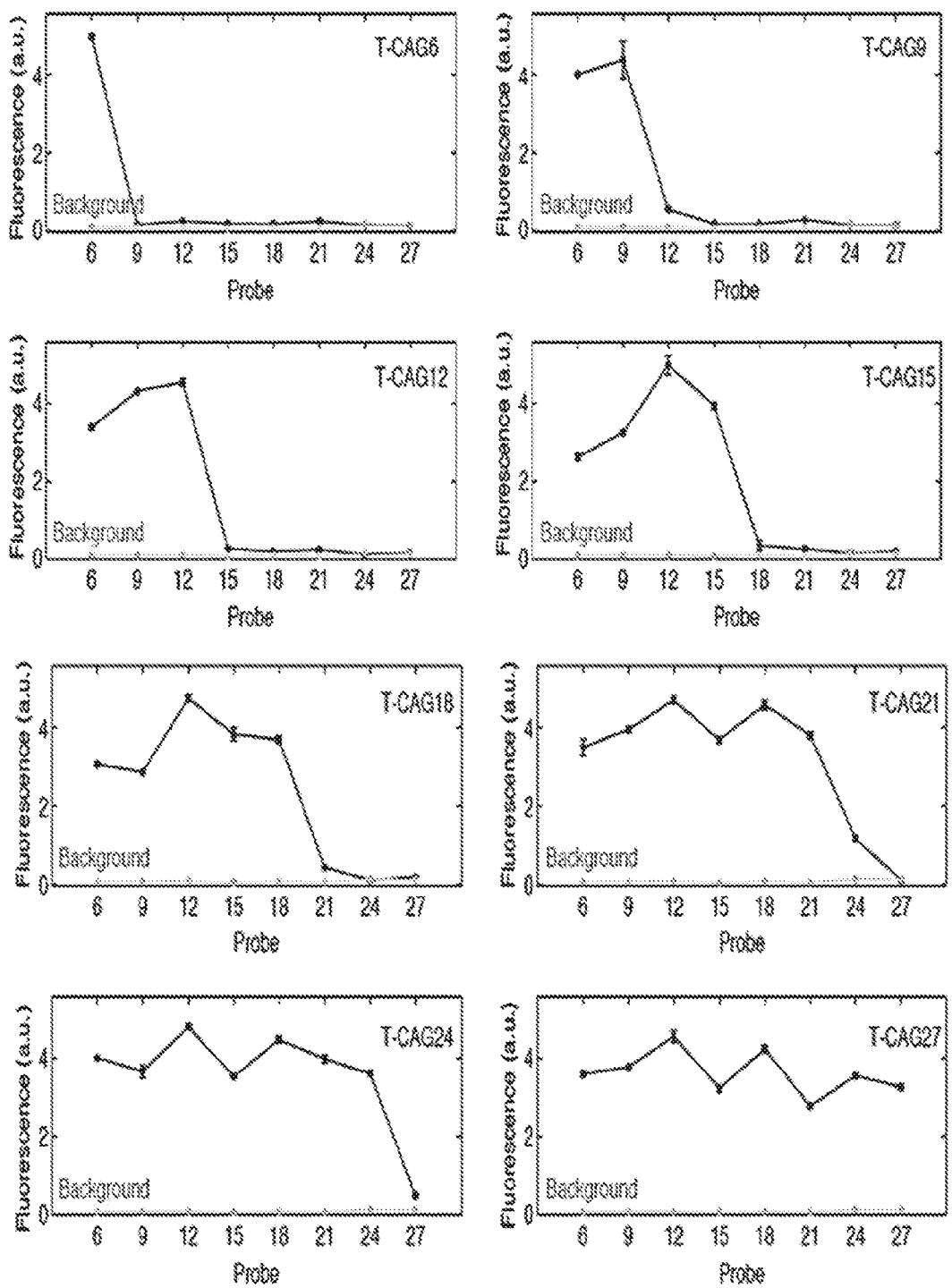
FIG. 42 shows individual plots of M-Probe responses to 8 synthetic targets (see FIG. 5C for combined version). Error bars represent ±s.d. of triplicate experiments. The final concentrations of probe and target in each reaction were 100 nM and 300 nM, respectively.
Figure 43A:
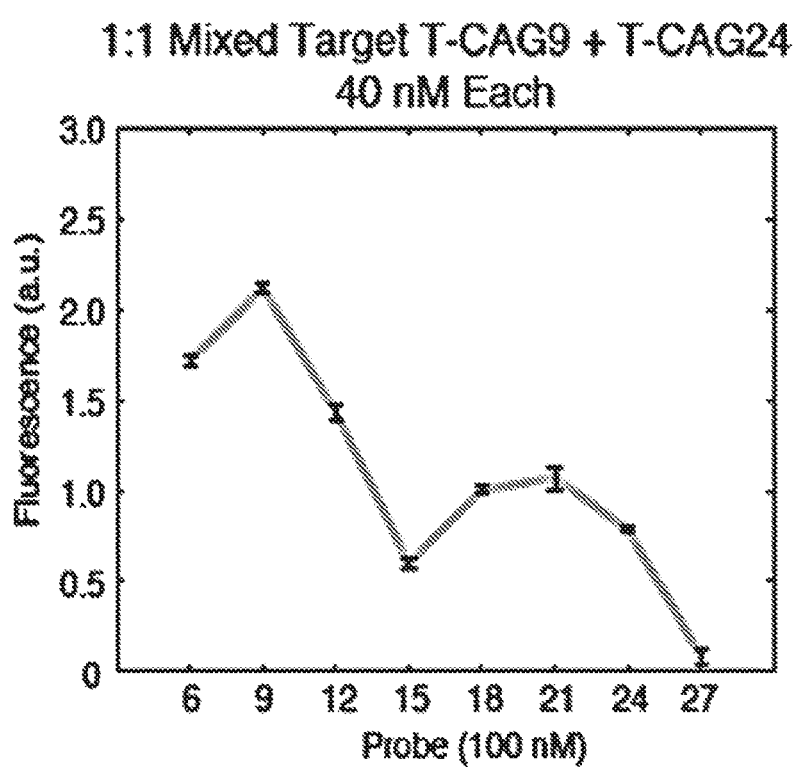
Figure 43B:
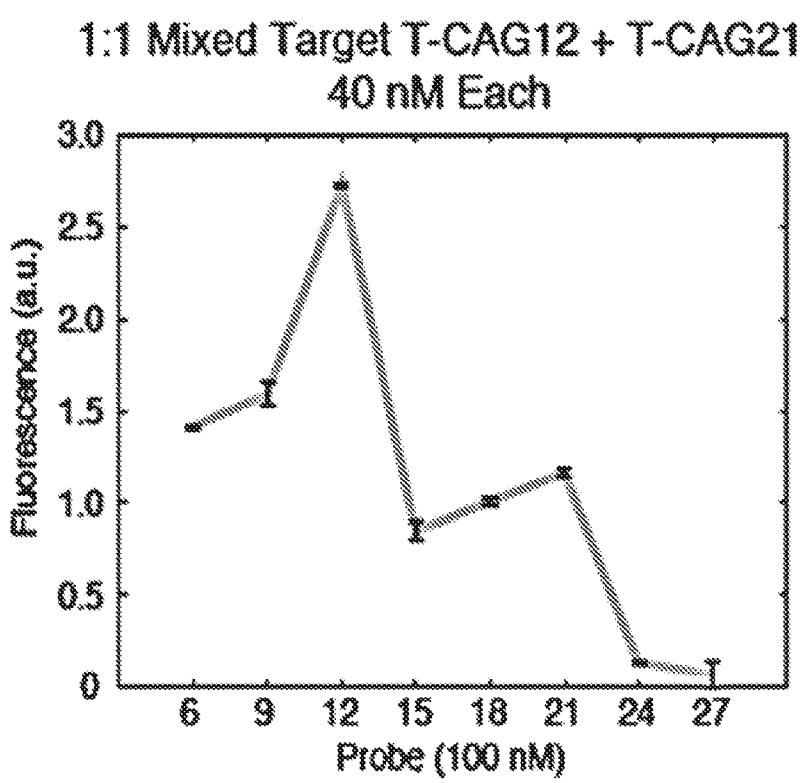
Figure 43C:
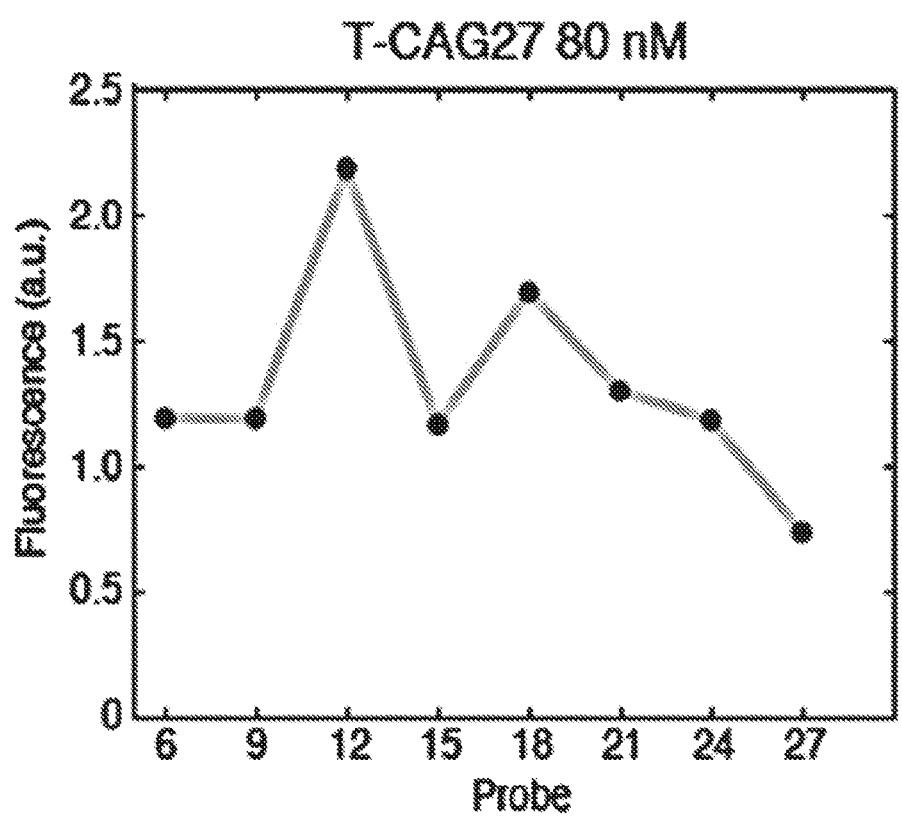

Control fluorescence experiments on synthetic triplet repeat samples. FIG. 42 shows the individual plots of M-Probe responses to 8 synthetic targets, background levels, and standard deviation of each data point. In contrast to synthetic oligonucleotide targets, genomic DNA samples are usually heterozygous in HTT gene locus—CAG repeat number are different for the two haploid copies. To demonstrate our approach can also profile heterozygous samples, we tested our probes with 1:1 mixture of targets with 9 and 24 CAG repeats (FIG. 43A), and 1:1 mixture of targets with 12 and 21 repeats (FIG. 43B). The transition point is less obvious as compared to homozygous samples (FIG. 42). After data normalization by using signals between probes and T-CAG27, we observed 2 significant (about 50% of the maximum fluorescence) signal drops when probe repeat number exceeds the repeat number of each allele. These results show that with minor modification to experimental protocol, M-Probe has the potential to profile heterozygous samples.

Figure 44A:
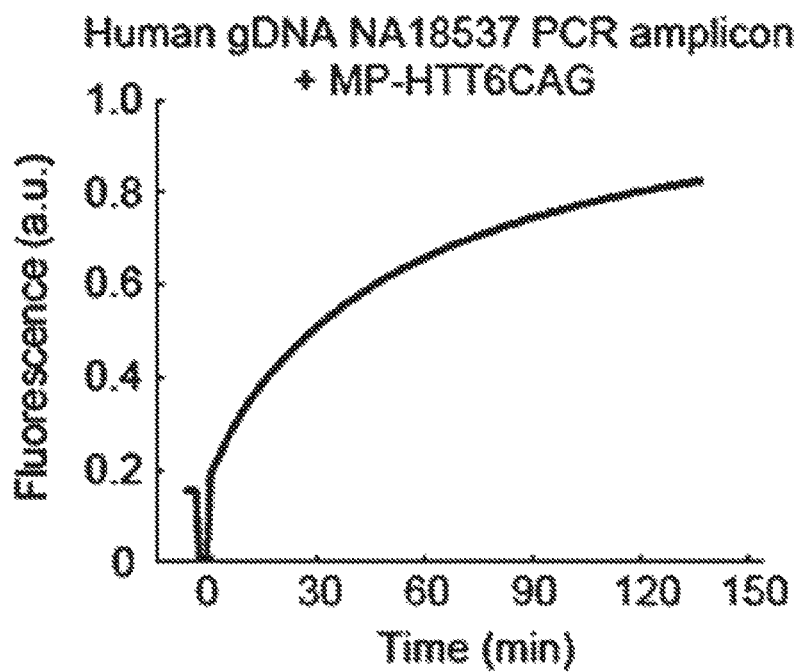
FIGS. 44A-44C show HTT triplet repeat profiling of genomic DNA samples using conditionally fluorescent M-Probes. a Fluorescence response of M-Probe targeting 6 repeats in amplicon target. The target was produced by asymmetric PCR (see Methods) amplification of genomic DNA sample NA18537. b HTT triplet repeat profiling of human genomic DNA sample NA18537. c HTT triplet repeat profiling 6 other human genomic DNA samples. Error bars represent ±s.d. of triplicate experiment.

To analyze HTT triplet repeats from human genomic DNA samples, the HTT repeat region was PCR amplified and the amplicons are used as hybridization targets. FIG. 44A shows fluorescence response of an M-Probe target 6 CAG repeats to the PCR amplicon generated from human genomic DNA sample NA18537.

Figure 44B:
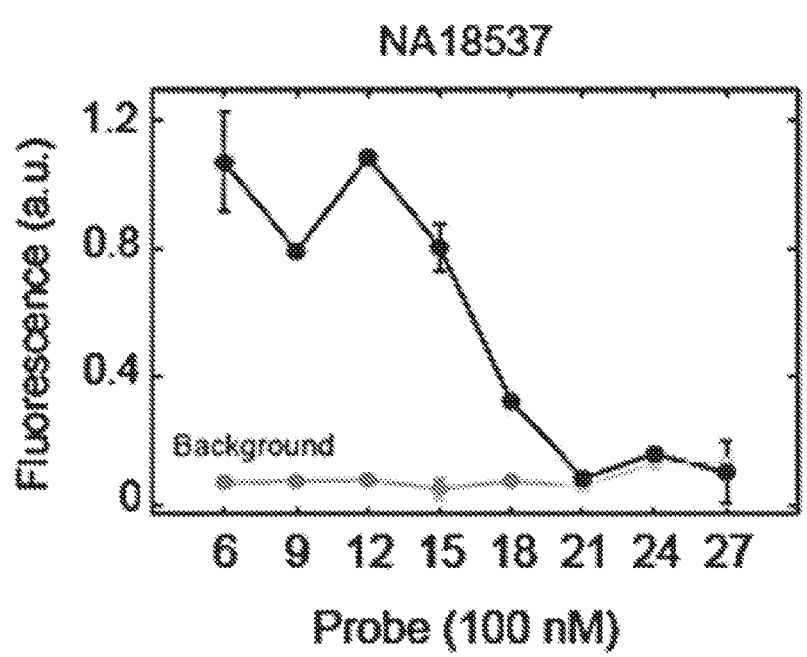
Figure 44C:
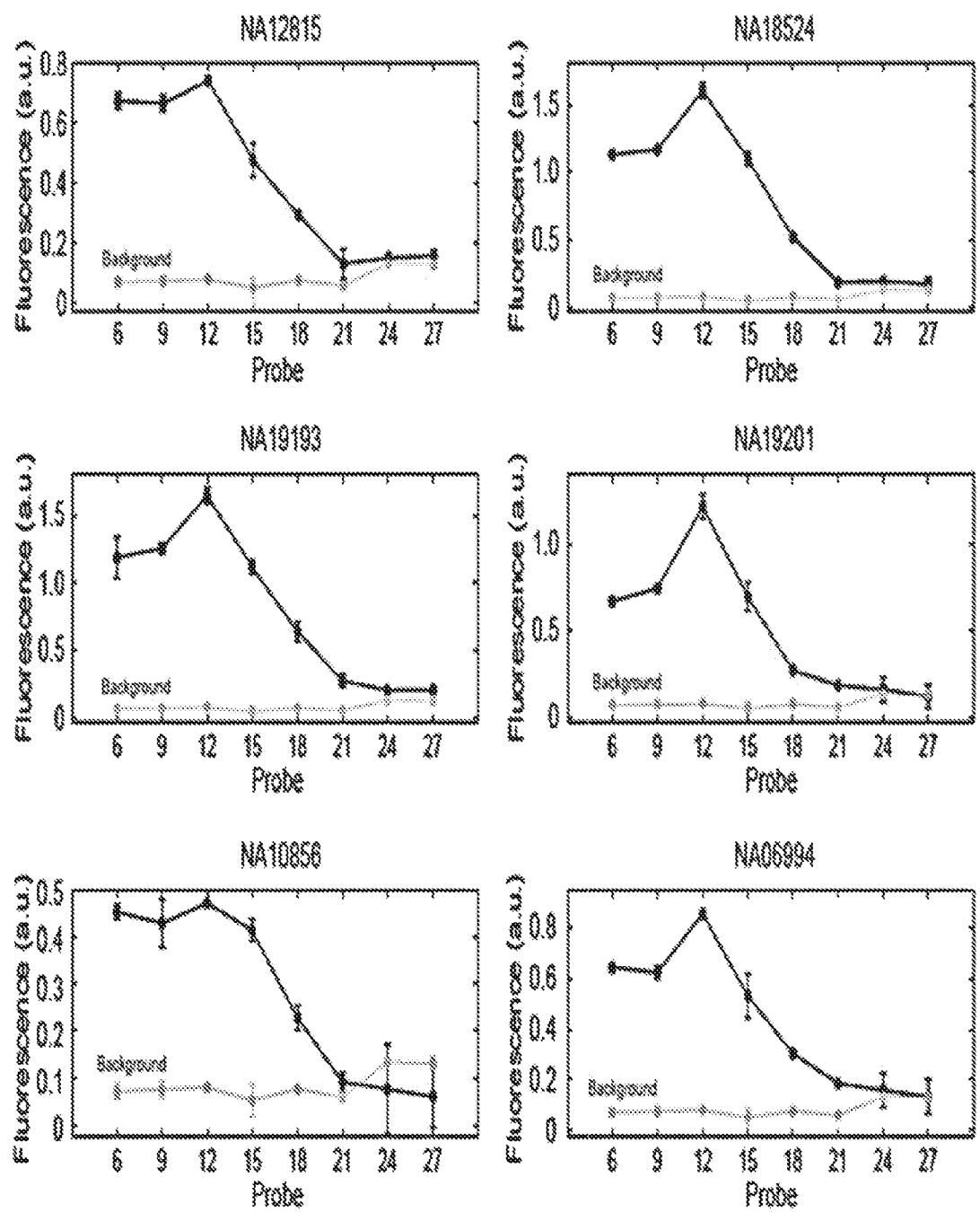
Figure 45:
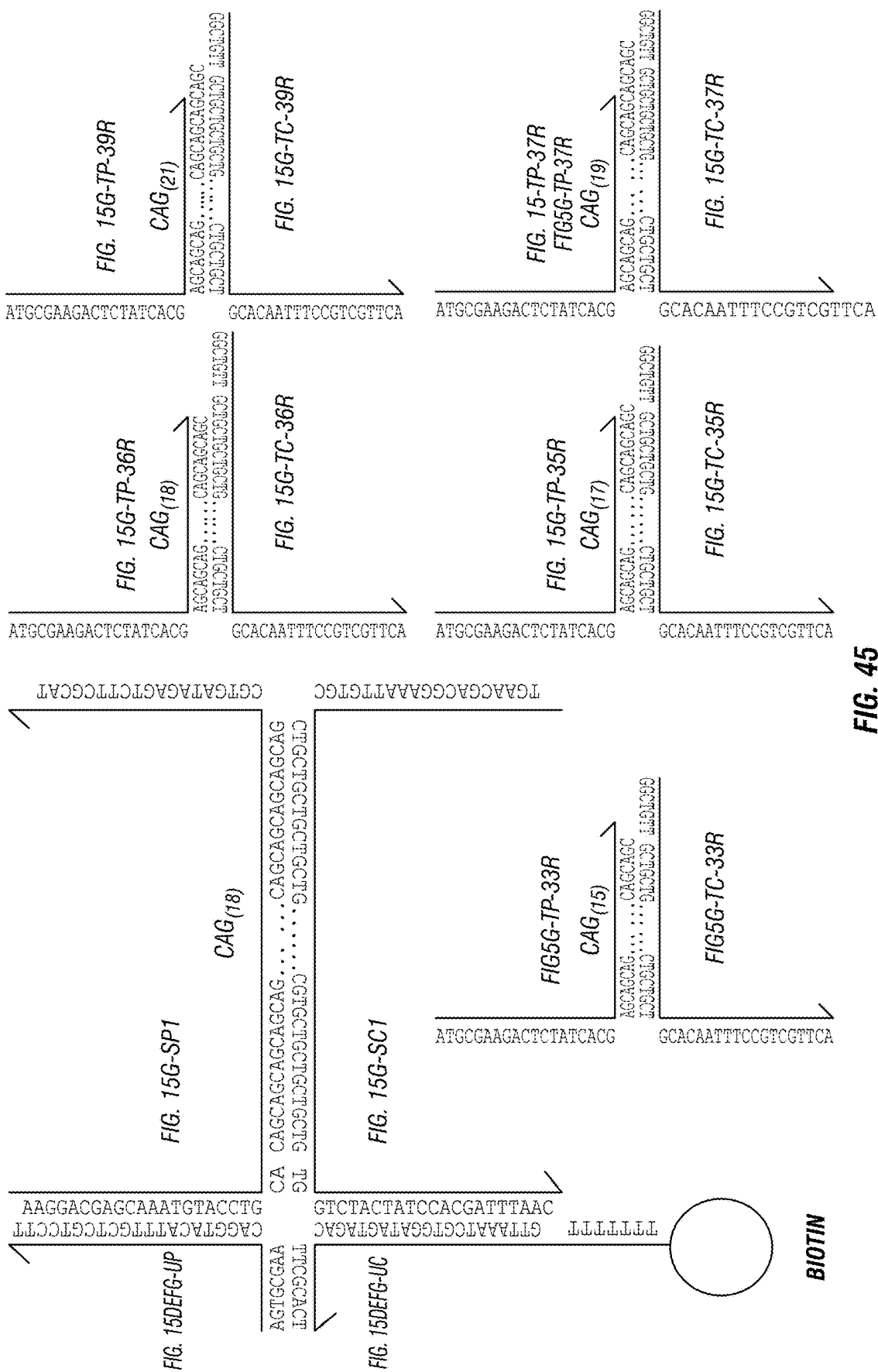
FIG. 45 depicts schematics and sequences of capture M-Probes designed for NA20248 (CAG repeat 17/36) HTT triplet repeat profiling. M-Probes for 33, 35, 36, 37 and 39 repeats have n=1, and use their own t segments. They share the same S1 segment probing 18 CAG repeats. Their own t segments probe 15, 17, 18, 19, 21 CAG repeats, respectively. Figure discloses the sequences within the top structures as SEQ ID NOS 223, 276, 277, 224, 279, and 278, SEQ ID NOS 280, 281, 283, and 282, and SEQ ID NOS 280, 281, 283, and 282, respectively, in order of appearance. Figure discloses the sequences within the bottom structures as SEQ ID NOS 280, 283, and 284, SEQ ID NOS 280, 285, 283, and 286, and SEQ ID NOS 280, 281, 283, and 282, respectively, in order of appearance.

FIG. 44B summarizes the observed response of a serials of M-Probes to the NA18537 amplicon, in which CAG repeats in the HTT gene is not characterized in the 1000 Genomes database. Because human genomic DNA is diploid, two copies are HTT are present, presumably with different triplet repeat numbers. Based on the data in FIG. 44B, we believe that both HTT gene copies have fewer than 21 repeats, and one of them may have fewer than 18 repeats. HTT gene repeat numbers of 6 other genomic samples with unknown HTT repeat status were also profiled by the same approach (FIG. 44C).

Selective capture of high repeat HTT gene from genomic DNA using biotin-functionalized M-Probes. To apply M-Probes to profiling triplet repeat number in HTT in genomic DNA samples, biotin-functionalized M-Probes are used to selectively bind DNA with HTT exceeding the threshold number of triplet repeats. To demonstrate that our approach can precisely determine the repeat number in genomic DNA sample, we designed HTT probes with 33, 35, 36, 37, and 39 CAG repeats (schematic shown in FIG.

Figure 46:
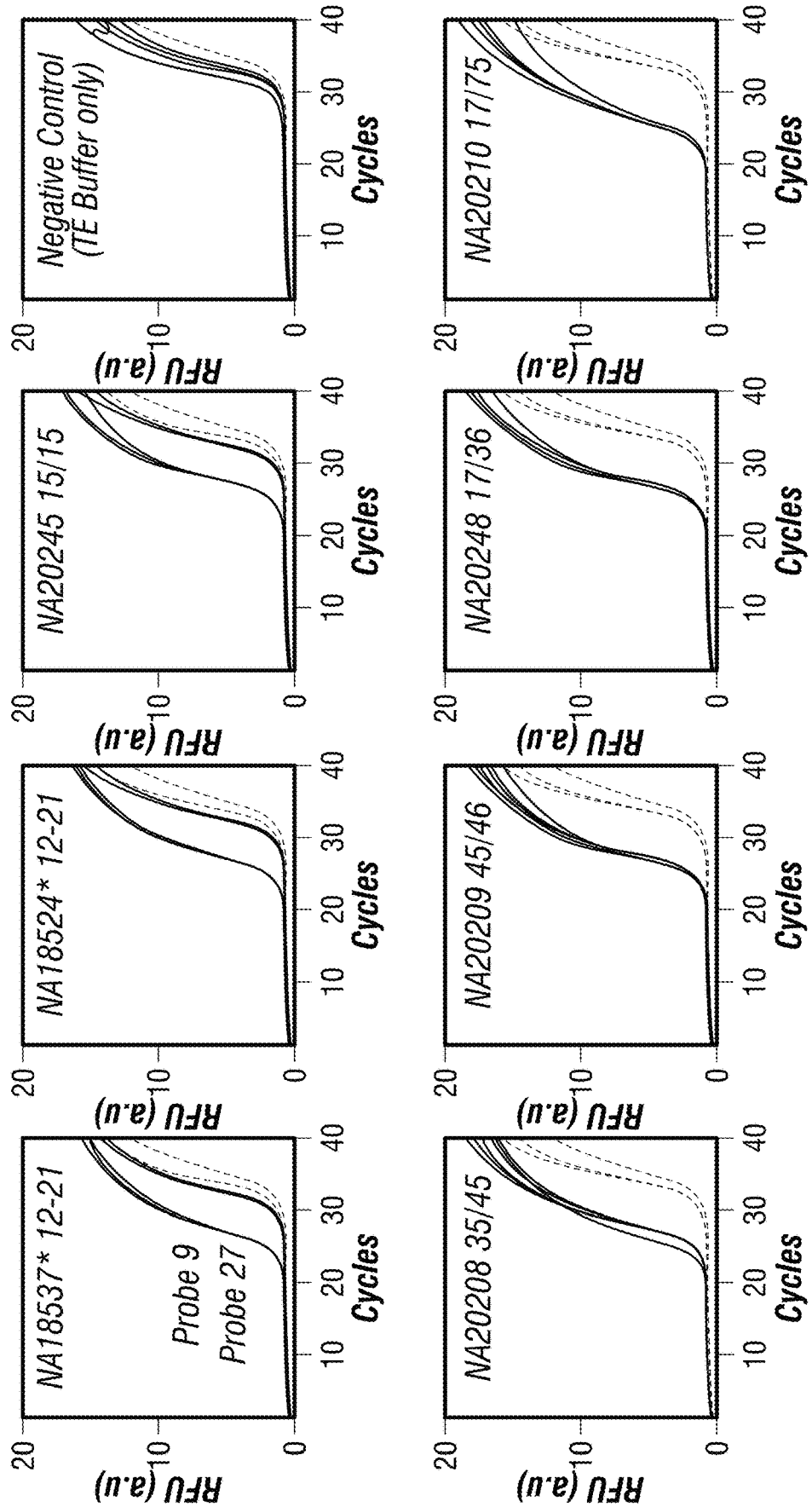
FIG. 46 depicts raw qPCR traces of captured HTT gene from the 7 genomic DNA samples.

45) and used them to capture the HTT region in sample NA20248 with a dominant allele of 36 CAG repeats. As a minimal approach to determine the disease likelihood in genomic DNA sample, we used probes HTT9 and HTT27 to capture the HTT region of 8 genomic samples. Individual qPCR traces are showed in FIG. 46. All Ct values are listed in Table 7.

TABLE 7

Summary of qPCR results for biotin-funtionalized M-Probe hybrid-capture products. NA18537 and NA18524 samples' triplet repeats numbers are not reported in publicly available databases. 1 × TE denotes the negative control experiment in which M-Probes are hybridized to a blank sample with no gDNA sample. 'Bare Beads' denotes the negative control experiment in which M-Probes are not used, to characterize the amount of non-specific capture of genomic DNA by magnetic beads. The last row shows the negative control using only the primers but no sample (primer dimer Ct).

| Sample | Repeat | Probe | Ct1 | Ct2 | Ct3 | Ct Mean | Ct S.D. | ΔCt |
|---|---|---|---|---|---|---|---|---|
| NA18537* | 12-21 | HTT9 | 25.23 | 25.34 | 25.13 | 25.2 | 0.1 | 5.7 |
| | 12-21 | HTT27 | 30.61 | 31.14 | 31.06 | 30.9 | 0.3 | |
| NA18524* | 12-21 | HTT9 | 25.22 | 25.13 | 25.23 | 25.2 | 0.1 | 5.4 |
| | 12-21 | HTT27 | 30.39 | 30.88 | 30.49 | 30.6 | 0.3 | |
| NA20245 | 15/15 | HTT9 | 25.52 | 25.38 | 25.46 | 25.5 | 0.1 | 5.5 |
| | 15/15 | HTT27 | 31.10 | 31.17 | 30.60 | 31.0 | 0.3 | |
| NA20248 | 17/36 | HTT9 | 25.18 | 25.01 | 25.08 | 25.1 | 0.1 | 0.5 |
| | 17/36 | HTT27 | 25.70 | 25.66 | 25.40 | 25.6 | 0.2 | |
| | 17/36 | HTT33 | 26.62 | 26.39 | 26.36 | 26.5 | 0.1 | 5.3 |
| NA20248 | 17/36 | HTT35 | 26.58 | 26.17 | 26.18 | 26.3 | 0.2 | |
| | 17/36 | HTT36 | 26.33 | 26.34 | 26.25 | 26.3 | 0.0 | |
| | 17/36 | HTT37 | 31.52 | 31.80 | 31.61 | 31.6 | 0.1 | |
| | 17/36 | HTT39 | 31.33 | 32.31 | 31.63 | 31.8 | 0.5 | |
| NA20208 | 35/45 | HTT9 | 24.21 | 24.21 | 24.18 | 24.2 | 0.0 | 1.5 |
| | 35/45 | HTT27 | 25.81 | 25.65 | 25.54 | 25.7 | 0.1 | |
| NA20209 | 45/46 | HTT9 | 25.28 | 25.13 | 25.11 | 25.2 | 0.1 | 0.1 |
| | 45/46 | HTT27 | 25.41 | 25.28 | 25.25 | 25.3 | 0.1 | |
| NA20210 | 17/75 | HTT9 | 23.73 | 23.52 | 23.38 | 23.5 | 0.2 | 0.6 |
| | 17/75 | HTT27 | 24.19 | 24.05 | 24.08 | 24.1 | 0.1 | |
| 1 × TE | N/A | HTT9 | 31.40 | 31.26 | 31.95 | 31.5 | 0.4 | — |
| | N/A | HTT27 | 31.76 | 30.34 | 32.23 | 31.4 | 1.0 | |
| | N/A | HTT39 | 32.35 | 32.03 | 32.07 | 32.2 | 0.2 | |
| NA20210 | 17/75 | Bare Beads | 32.81 | 32.24 | 30.21 | 31.8 | 1.4 | — |
| — | — | — | 33.18 | 31.99 | 32.10 | 32.4 | 0.7 | — | different number of CAG repeats; any HTT gene sequence with repeat number equal to or exceeding an M-Probe's repeat number will elicit a positive signal. Thus, when aliquots of an HTT gene or amplicon are reacted with the series of M-Probes, the longest M-Probe that still generates a positive signal indicates the number of triplet repeats. T18, T21, and T24 show significant binding to the M-Probe, but not to T12 and T15, confirming that this M-Probe functions as designed in acting as a programmable high-pass filter on trinucleotide repeat number. FIG. 15C shows a summary of the response between different M-Probes and synthetic oligonucleotide targets; significant hybridization is observed only when the target repeats equals or exceeds the M-Probe repeat number. Similar M-Probes are also verified to profile triplet repeat number for CGG repeats (associated with Fragile X syndrome) and GAA repeats (associated with Friedriech's Ataxia); see discussion of FIGS. 38-46 for details and results.

Figure 15A:
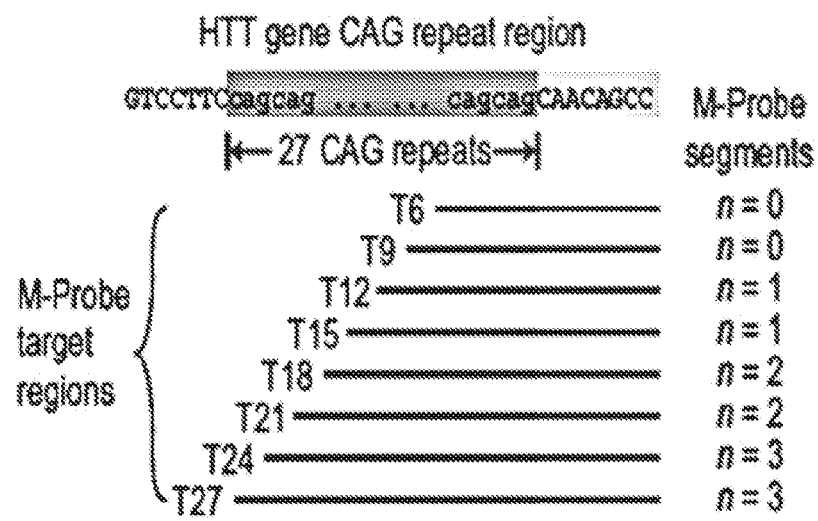
FIG. 15A depicts profiling of triplet repeat number using M-probes using a series of M-probes. Figure discloses SEQ ID NO: 261.

FIG. 15A shows the schematic of M-Probes designed for profiling GAG triplet repeats in Huntington's gene HTT. In FIG. 15A, a series of M-Probes are designed, each targeting a threshold number of triplet repeats (GAG in the case of Huntington's gene HTT). Only target sequences meeting or exceeding its threshold repeat number will hybridize significantly to an M-Probe. In addition to the repeat region (yellow), the M-Probe also binds to an 8 nt downstream sequence (green) to ensure specific hybridization to the HTT gene.

Figure 15B:
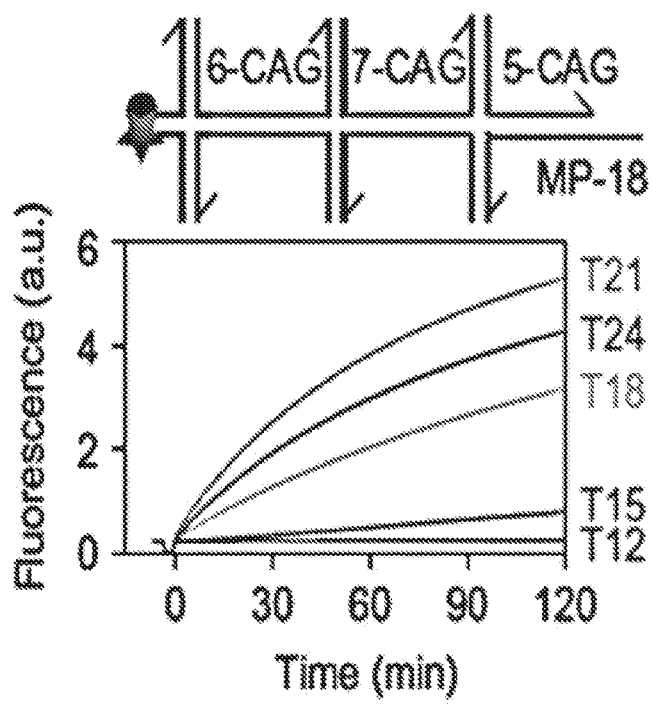
FIG. 15B shows the experimental fluorescence response of synthetic oligonucleotide targets bearing different numbers of triplet repeats to an M-probe designed to detect targets with ≥18 CAG repeats.
Figure 15C:
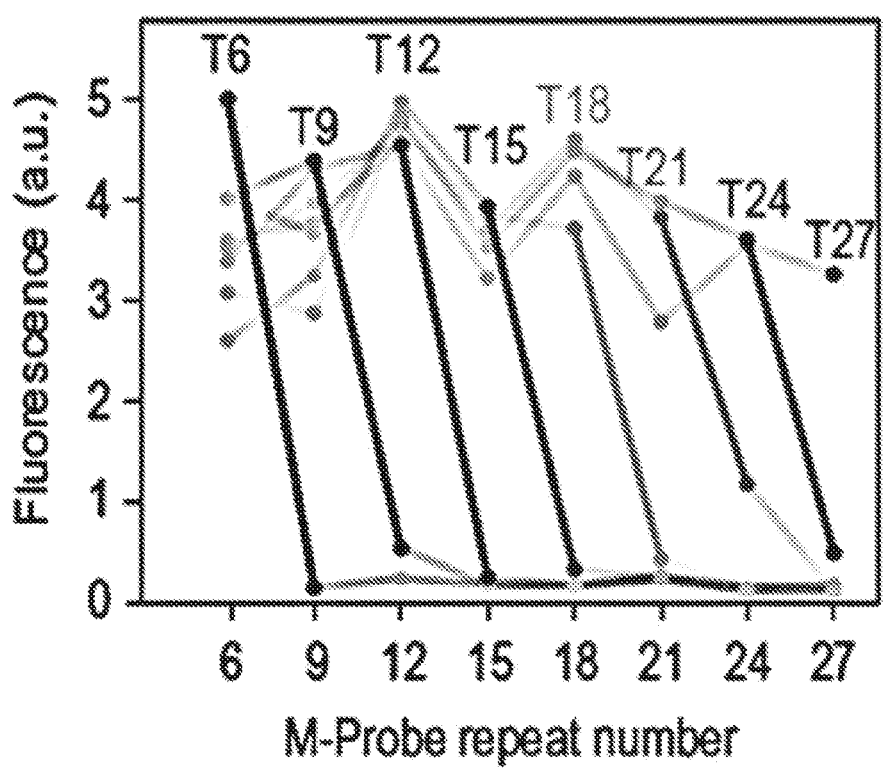
FIG. 15C shows a summary of M-Probe responses to 8 synthetic targets; minimal hybridization was observed when target repeat number is fewer than the M-Probe repeat number.
Figure 15D:
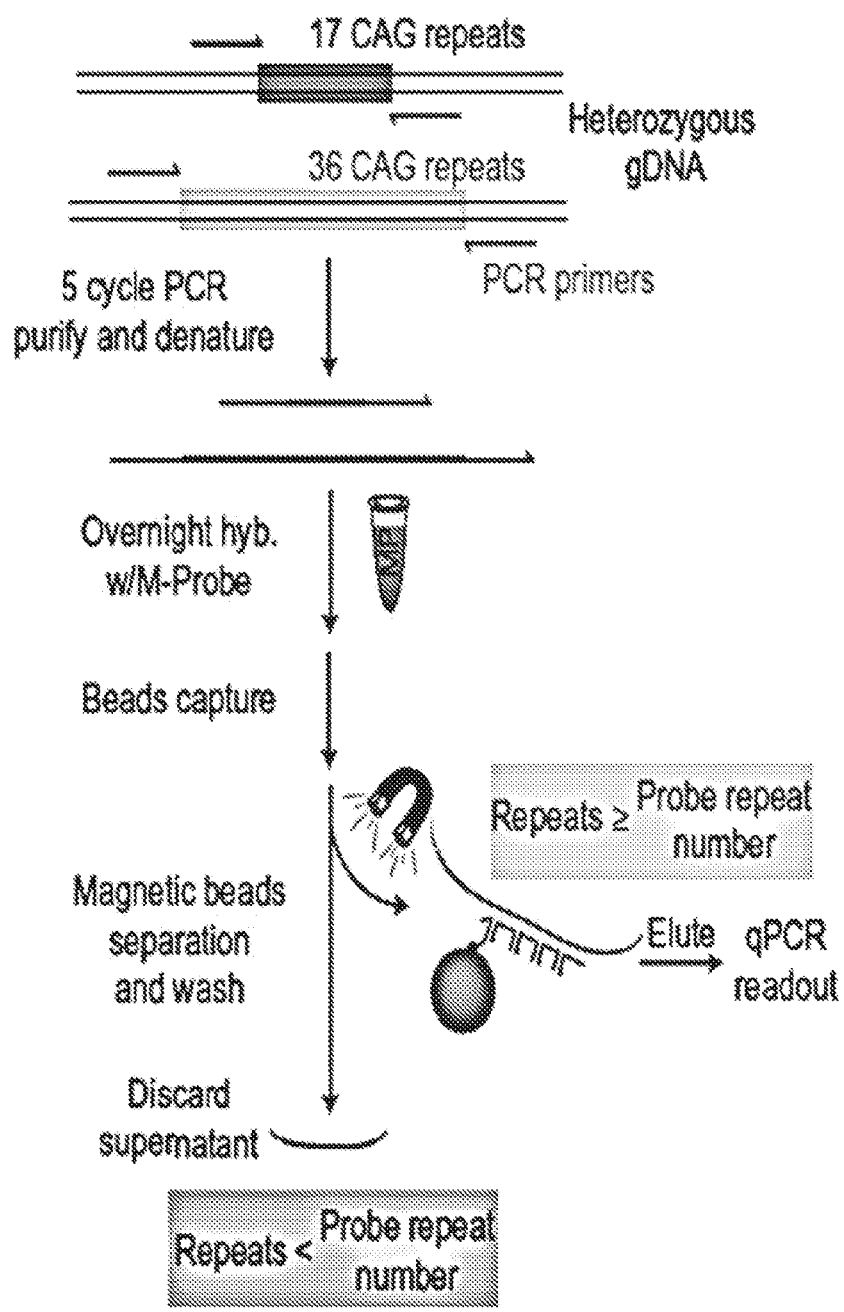
FIG. 15D depicts a workflow for selective capture of high repeat HTT gene from genomic DNA using biotin-functionalized M-Probes (FIG. 45).
Figure 15E:
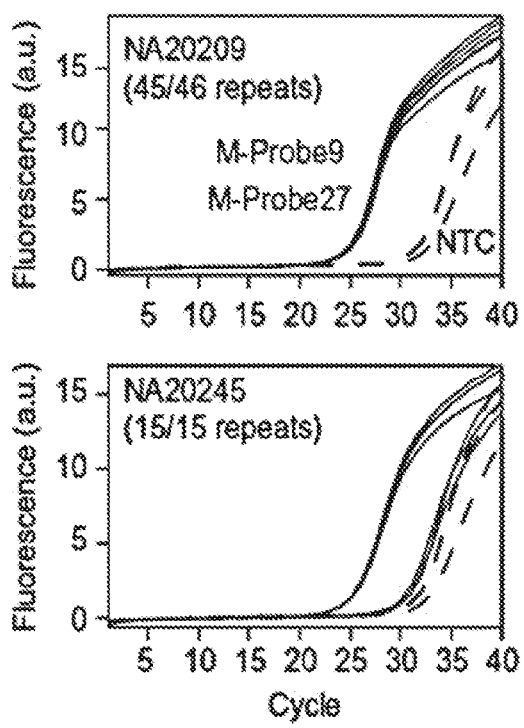
FIG. 15E depicts qPCR amplification traces of captured HTT gene from the NA20209 and NA20245 genomic DNA samples (125 ng gDNA initial input per reaction).

FIG. 15B shows the fluorescence response of a conditionally fluorescent M-Probe targeting 18 CAG repeats to 5 different DNA oligonucleotide targets bearing 12, 15, 18, 21, and 24 repeats (labeled as T12, T15, T18, T21, and T24, respectively). In FIG. 15B, [M-Probe]=10 nM and [Target] =30 nM; hybridization proceeded at 37° C. in 1×PBS. A nonrepetitive HTT-specific sequence in the t segment of each M-Probe ensures that M-Probe binding is specific to the HTT gene, and not other genomic regions bearing CAG triplet repeats. Although various M-Probe formulation protocols generally produce similar formation yields (FIGS. 20A-20B), for the repeat sequence M-Probes in this section, segments were individually annealed and subsequently combined. A series of M-Probes are designed, each targeting a To apply M-Probes to profiling triplet repeat number in HTT in genomic DNA samples, biotin-functionalized M-Probes are used to selectively bind DNA with HTT exceeding the threshold number of triplet repeats (FIG. 15D). In FIG. 15D, streptavidin-functionalized magnetic beads are used to separate bound from unbound DNA. Captured DNA molecules are subsequently amplified and quantitated by qPCR. Genomic DNA sample was first pre-amplified with a 5-cycle PCR protocol in order to generate amplicons bearing the HTT triplet repeats as well as a minimal 20 nt upstream and 14 nt downstream from the repeats. Amplicons generated in this fashion do not have long 5' and 3' overhangs that may interfere with hybridization to M-Probes (due to secondary structure, etc.) These amplicons are subsequently incubated with the appropriate M-Probe and captured by streptavidin-coated magnetic beads; unbound DNA molecules are removed through a wash step. The captured DNA is eluted and quantitated using qPCR (FIG. 15E). In FIG. 15E, M-Probes targeting 9 repeats (M-Probe9) and 27 repeats (M-Probe27) were used to classify gDNA samples. The 5 cycle threshold difference (ΔCt) observed for NA20245 indicates that capture of HTT genes with above the threshold number of repeats was roughly 30-fold more efficient as compared to those below the threshold.

Amplification of HTT genes with fewer than the threshold repeat number (number of triplets in the M-Probe) shows significantly higher cycle threshold (Ct) than the HTT genes exceeding the threshold repeat number. By designing two different M-Probes, one targeting 9 repeats and one targeting 27 repeats, we can control for sample variability, and determine potential disease status through the difference in the observed Ct values (ΔCt). Small (<2) ΔCt values indicate that at least one of the two HTT gene copies exceeds 27 repeats, and large (>5) ΔCt values indicate the opposite. Residual amplification of the low-repeat number HTT genes is likely due to nonspecific binding of genomic DNA to the magnetic beads (data not shown).

Figure 15F:
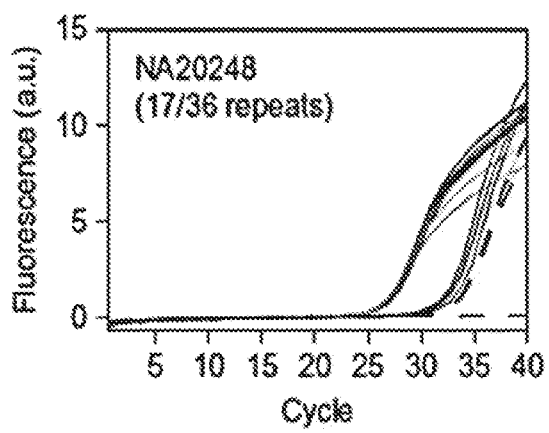
FIG. 15F depicts a summary of experimentally observed Ct values for 7 genomic DNA samples (mean values for triplicate runs).

FIG. 15F summarizes the observed results for 7 genomic DNA samples, 5 with known HTT genotypes and 2 unknown. In FIG. 15F, samples with fewer than 27 repeats show more than 5 cycle ΔCt; and samples with expanded triplet repeats (at risk for Huntington's disease) exhibit less than 2 cycle ΔCt. Our method correctly identifies the length status of the 5 known samples, and determined the NA18537 and NA18524 samples to both only possess HTT genes with below 27 CAG repeats. The 2 M-Probe systems (here targeting 9 and 27 repeats) represent the minimal protocol needed for determining disease likelihood in an unknown genomic DNA sample.

More precise quantitation of the HTT triplet repeat number can be achieved by extending the method to include more M-Probes with varying triplet repeat thresholds. To demonstrate this point, we designed 5 different M-Probes targeting 33, 35, 36, 37, and 39 CAG repeats, and applied it to the NA20248 genomic DNA sample. The experimental Ct values for the M-Probes targeting 37 and 39 repeats were more than 5 cycles higher than for M-Probes targeting 33, 35, and 36 repeats, suggesting correctly that the sample has one HTT gene copy with exactly 36 CAG repeats (FIG. 15G). In FIG. 15G, 5 different M-Probes targeting 33, 35, 36, 37, and 39 repeats were constructed and applied to the NA20248 genomic DNA sample. NA20248 is determined correctly to possess a HTT gene with 36 repeats based on the observed Ct values.

In addition to the hybrid-capture workflow we presented here, an alternative approach to profiling triplet repeats using M-Probes is to amplify the HTT gene to above nanomolar concentrations, and then directly react the amplicons with conditionally fluorescent M-Probes. The relative advantage of this second approach is that the solid-phase separation steps are avoided, reducing total hands-on time. The relative disadvantage is that open-tube steps on high concentration amplicons are likely to lead to laboratory contamination, and undesirable in diagnostic settings. Both approaches can reliable detect repeat expansion with single repeat resolution in a small range of expansion (e.g. 27-40 for Huntington's disease) that it is difficult to achieve by previously reported methods. Budworth, H., & McMurray, C. T. Problems and solutions for the analysis of somatic CAG repeat expansion and their relationship to Huntington's disease toxicity. *Rare Dis*, 4: e1131885 (2016); Jama, M., Millson, A., Miller, C. E., & Lyon E. Triplet repeat primed PCR simplifies testing for Huntington disease. *J Mol Diagn*, 15: 255-262 (2016); Bonifazi, E., et al. Use of RNA fluorescence in situ hybridization in the prenatal molecular diagnosis of myotonic dystrophy type I. *Clin Chem*, 52: 319-322 (2006); Kern, A., & Seitz, O. Template-directed ligation on repetitive DNA sequences: a chemical method to probe the length of Huntington DNA. *Chem Sci*, 6: 724-728 (2015). Larger range of expansion can also be profiled by using M-Probes with more and/or longer segments.

Example 7

List of Oligonucleotide Sequences.

Oligonucleotide sequences used for all experiments are listed here. For each M-Probe, the top oligos with sequence homologous to the target sequence are referred to as P (protector) sequences, and the bottom oligos with sequence complementary to the target sequence are referred to as C (complement) sequences. Each strand includes in its name/label: the figure in which it is used, the segment to which it belongs, and additional descriptors as necessary. For example, FIG. 11-uP refers to the Quencher-labeled oligonucleotide in FIGS. 11A-11C (u corresponding to universal segment, P corresponding to upper strand).

M-Probe Proof-of-Concept Experiments (FIGS. 11A-11C). Oligonucleotide sequences of synthetic DNA targets and probes used in FIG. 11C and FIGS. 16-23D are shown in Table 8. All the sequences were ordered from Integrate DNA Technologies (IIDT). /5IAbRQ/denotes an Iowa Black RQ quencher moiety functionalized at the 5' end of the oligo, and /3Rox_N/ denotes the IDT entry code for the ROX fluorophore functionalized by NHS ester chemistry at the 3' end of the oligo. The fluorophore-labeled uC and quencher-labeled uP strands were post-synthesis H-PLC purified by IDT; all other strands were ordered with standard desalting and not purified.

TABLE 8

| Species | Sequence |
|---|---|
| | Oligonucleotide sequences used for FIGS. 11A-11C and FIGS. 16-22C. |
| FIG. 11-uP | /5IAbRQ/ GTGCGAACAGGTACATTTGCT (SEQ ID NO: 2) |
| FIG. 11-uC | CGTCCTTGTTAAATCGTGGATAGTAGAC TTCGCAC /3Rox_N/ (SEQ ID NO: 1) |
| FIG. 11-Target | ACGCAGCTAATGCCCTCAGACAGCTTTG |
| FIG. 11-Variant | ACGTATGTGTTTCTC (SEQ ID NO: 47) |

TABLE 8-continued

Oligonucleotide sequences used for
FIGS. 11A-11C and FIGS. 16-22C.

| Species | Sequence |
| --- | --- |
| (12G > t) | ACGCAGCTAATtCCCTCAGACAGCTTTGA CGTATGTGTTTCTC (SEQ ID NO: 48) |
| FIG. 11-Variant (31G > a) | ACGCAGCTAATGCCCTCAGACAGCTTTG ACaTATGTGTTTCTC (SEQ ID NO: 49) |
| FIG. 11-s1P | AAGGACGAGCAAATGTACCTGACT ACGCAGCTAATGCCCT CGTGATAGAGTCTTCGCATCA (SEQ ID NO: 50) |
| FIG. 11-s1C | AGTAACAGACGGAAATTGTGC AGGGCATTAGCTGCGT AGTGTCTACTATCCACGATTTAAC (SEQ ID NO: 51) |
| FIG. 11-tP | TGATGCGAAGACTCTATCACG CAGACAGCTTTGACGTA (SEQ ID NO: 52) |
| FIG. 11-tC | GAGAAACACATACGTCAAAGCTGTCTG GCACAATTTCCGTCTGTTACT (SEQ ID NO: 53) |
| FIG. 22b-P | /5IAbRQ/ GTGCG ACGCAGCTAATGCCCTCAGACAGCTTTGACG (SEQ ID NO: 54) |
| FIG. 22b-C | GAGAAACACATACGTCAAAGCTGTCTGAGGGCAT TAGCTGCGT CGCAC /3ROX N/ (SEQ ID NO: 55) |
| FIG. 22c-XP | AAGGACGAGCAAATGTACCTGACT ACGCAGCTAATGCCCTCAGACAGCTTTGACGTA (SEQ ID NO: 56) |
| FIG. 22c-XC | GAGAAACACATACGTCAAAGCTGTCTGAGGGCAT TAGCTGCGT AGTGTCTACTATCCACGATTTAAC (SEQ ID NO: 57) |

TABLE 9

Sequences for non-homologous distribution
experiments as shown in FIGS. 23A-23D.

| Species | Sequence |
| --- | --- |
| FIG. 23-Target | ATGTCAAGATCACAGATTTTGGGCGGGCCA (SEQ ID NO: 58) |
| FIG. 23-Variant | ATGTCAAGATCACAGATTTTGGGCtGGCCA (SEQ ID NO: 59) |
| FIG. 23a-uP | /5IAbRQ/ GTGCGAA CAGGTACATTTGCTCGT (SEQ ID NO: 2) |
| FIG. 23a-uC | CCTTGTTAAATCGTGGATAGTAGAC TTCGCA C /3Rox N/ (SEQ ID NO: 1) |
| FIG. 23b-uP | /5IAbRQ/ GTGCG CAGGTACATTTGCTCGTCC (SEQ ID NO: 60) |
| FIG. 23b-uC | TTGTTAAATCGTGGATAGTAGAC CGCAC / 3Rox N/ (SEQ ID NO: 61) |
| FIG. 23c-uP | /5IAbRQ/ GTG CAGGTACATTTGCTCGTCCTT (SEQ ID NO: 62) |
| FIG. 23c-uC | GTTAAATCGTGGATAGTAGAC CAC /3Rox N/ (SEQ ID NO: 63) |
| FIG. 23d-uP | /5IAbRQ/ CAGGTACATTTGCTCGTCCTT (SEQ ID NO: 64) |
| FIG. 23d-uC | GTTAAATCGTGGATAGTAGAC /3Rox N/ (SEQ ID NO: 65) |
| FIG. 23a-tP | AAGGACGAGCAAATGTACCTG CA GTCAAGATCACAGATTTTGG (SEQ ID NO: 66) |
| FIG. 23a-tC | GCCCGCCCAAAATCTGTGATCTTGAC TG GTCTACTATCCACGATTTAAC (SEQ ID NO: 67) |
| FIG. 23b-tP | AAGGACGAGCAAATGTACCTG AACA GTCAAGATCACAGATTTTGG (SEQ ID NO: 68) |
| FIG. 23b-tC | GCCCGCCCAAAATCTGTGATCTTGAC TGTT GTCTACTATCCACGATTTAAC (SEQ ID NO: 69) |
| FIG. 23c-tP | AAGGACGAGCAAATGTACCTG GCAACA GTCAAGATCACAGATTTTGG (SEQ ID NO: 70) |
| FIG. 23c-tC | GCCCGCCCAAAATCTGTGATCTTGAC TGTTGC GTCTACTATCCACGATTTAAC (SEQ ID NO: 71) |
| FIG. 23d-tP | AAGGACGAGCAAATGTACCTG GTGCGAA GTCAAGATCACAGATTTTGG (SEQ ID NO: 72) |
| FIG. 23d-tC | GCCCGCCCAAAATCTGTGATCTTGAC TTCGCAC GTCTACTATCCACGATTTAAC (SEQ ID NO: 73) |

Sequence variation tolerance at M-Probe junctions (FIGS. 12A-12D). Sequences of targets and probes used for sequence variance tolerance experiments as shown in FIGS. 12A-12D are listed in the following tables. All oligos were HPLC-purified except for FIG. 12-tP and FIG. 12-tC.

TABLE 10

Oligonucleotide sequences used for constructing M-Probe used in FIGS. 12A-12D. /5IABkFQ/ represents an Iowa Black FQ quencher modification at 5' end of the oligo. Arm regions are shown in uppercase.

| Species | Sequence |
|---|---|
| FIG. 12-uC | GTTAAATCGTGGATAGTAGAC /3Rox N/ (SEQ ID NO: 65) |
| FIG. 12-uP | /5IABkFQ/ CAGGTACATTTGCTCGTCCTT (SEQ ID NO: 64) |

TABLE 10-continued

Oligonucleotide sequences used for constructing M-Probe used in FIGS. 12A-12D. /5IABkFQ/ represents an Iowa Black FQ quencher modification at 5' end of the oligo. Arm regions are shown in uppercase.

| Species | Sequence |
|---|---|
| FIG. 12-s1P | AAGGACGAGCAAATGTACCTGCAGTA cacgactcagctgtgtattttttgtgctagtggCGTGATAG AGTCTTCGCATCA (SEQ ID NO: 74) |
| FIG. 12-s1C | AGTAACAGACGGAAATTGTGCccactagcaca aaaatacacagctgagtcgtgTACTGGTCTACT ATCCACGATTTAAC (SEQ ID NO: 75) |
| FIG. 12-tP | TGATGCGAAGACTCTATCACGggaaacaccatatattttgga (SEQ ID NO: 76) |
| FIG. 12-tC | aacttccctctccaaaatatatggtgtttcc GCACAATTTC CGTCTGTTACT (SEQ ID NO: 77) |

TABLE 11

Oligonucleotide sequences used as targets and variants for FIGS. 12A-12D experiments. Underscore ( ) indicates deletion, and elipsis ( . . . ) indicates that the sequence is continued on the following line.

| Species | Type | Sequence |
|---|---|---|
| FIG. 12-Target | Perfect Match | GACTCAGCTGTGTATTTTTGTGCTAGTG G aac . . . GGAAACACCATATATTTTGGAGAGGG AAGTT (SEQ ID NO: 78) |
| FIG. 12-Variant-s1-G > c | 1 nt mutation | GACTCAcCTGTGTATTTTTGTGCTAGTGG aac . . . |
| FIG. 12-Variant-s1-GC > ct | 2 nt mutation | GGAAACACCATATATTTTGGAGA |
| FIG. 12-Variant-t-G > t | 1 nt mutation | GGGAAGTT (SEQ ID NO: 79) |
| FIG. 12-Variant-t-GG > ac | 2 nt mutation | GACTCActTGTGTATTTTTGTGCTAG |
| FIG. 12-Variant-s1-GC > GaC | 1 nt insertion | TGG aac . . . |
| FIG. 12-Variant-s1-GC > GgatC | 3 nt insertion | GGAAACACCATATATTTTGGAGA |
| FIG. 12-Variant-t-CC > CtC | 1 nt insertion | GGGAAGTT (SEQ ID NO: 80) |
| FIG. 12-Variant-t-CC > CagtC | 3 nt insertion | GACTCAGCTGTGTATTTTTGTGCTA |
| FIG. 12-Variant-s1-TGC > TC | 1 nt deletion | GTGG aac . . . |
| FIG. 12-Variant-s1-GTGCT > GT | 3 nt deletion | GGAAACACCATATATTTTGGAGA |
| FIG. 12-Variant-t-GGA > GA | 1 nt deletion | GtGAAGTT (SEQ ID NO: 81) |
| FIG. 12-Variant-t-TGGAG > TG | 3 nt deletion | GACTCAGCTGTGTATTTTTGTGCTA GTGG aac . . . GGAAACACCATATATTTTGGAGA GacAAGTT (SEQ ID NO: 82) GACTCAGCTGTGTATTTTTGTGaCTA GTGG aac . . . GGAAACACCATATATTTTGGAGAG GGAAGTT (SEQ ID NO: 83) GACTCAGCTGTGTATTTTTGTgatCT AGTGG aac . . . GGAAACACCATATATTTTGGAGA GGGAAGTT (SEQ ID NO: 84) GACTCAGCTGTGTATTTTTGTGCTA GTGG aac . . . GGAAACACtCATATATTTTGGAGA GGGAAGTT (SEQ ID NO: 85) GACTCAGCTGTGTATTTTTGTGCTA GTGG aac . . . GGAAACACagtCATATATTTTGGAGA GGGAAGTT (SEQ ID NO: 86) GACTCAGCTGTGTATTTTTGT CTAGTGG aac . . . GGAAACACCATATATTTTGGAGA GGGAAGTT (SEQ ID NO: 87) GACTCAGCTGTGTATTTTTG TAGTGG aac . . . GGAAACACCATATATTTTGGAGA GGGAAGTT (SEQ ID NO: 88) GACTCAGCTGTGTATTTTTGTGCTA GTGG aac . . . GGAAACACCATATATTTTG AGAGGGAAGTT (SEQ ID NO: 89) |

TABLE 11-continued

Oligonucleotide sequences used as targets and variants for FIGS. 12A-12D experiments. Underscore ( ) indicates deletion, and elipsis ( . . . ) indicates that the sequence is continued on the following line.

| Species | Type | Sequence |
|---|---|---|
| | | GACTCAGCTGTGTATTTTTGTGCTA GTGG aac . . . GGAAACACCATATATTTT GAGGGAAGTT (SEQ ID NO: 90) |
| FIG. 12-Tolerated-s1t-GAACG > GG | 3 nt deletion | GACTCAGCTGTGTATTTTTGTGCTAGTG G . . . GGAAACACCATATATTTTGGAGA GGGAAGTT (SEQ ID NO: 91) |
| FIG. 12-Tolerated-s1t-AACG > AG | 2 nt deletion | |
| FIG. 12-Tolerated-s1t-ACG > AG | 1 nt deletion | GACTCAGCTGTGTATTTTTGTGCTA GTGG a . . . GGAAACACCATATATTTTGGAGA GGGAAGTT (SEQ ID NO: 92) |
| FIG. 12-Tolerated-s1t-GaacG > GgtataG | 2 nt ins. + 3 nt mut. | |
| FIG. 12-Tolerated-s1t-GaacG > GaatgtaacG | 5 nt ins. | GACTCAGCTGTGTATTTTTGTGCTA GTGG aa . . . GGAAACACCATATATTTTGGAGAG GGAAGTT (SEQ ID NO: 93) |
| FIG. 12-Tolerated-s1t-GaacG > GatattaaacG | 6 nt ins. | |
| FIG. 12-Tolerated-s1t-GaacG > GaatatgtaacG | 7 nt ins. | GACTCAGCTGTGTATTTTTGTGCTA GTGG gtata . . . GGAAACACCATATATTTTGGAGAGGGAA GTT (SEQ ID NO: 94) |
| FIG. 12-Tolerated-s1t-GaacG > GgaaG | 3 nt mutation | |
| FIG. 12-Tolerated-s1t-GaacG > GgtcG | 3 nt mutation | GACTCAGCTGTGTATTTTTGTGCTAGT GG aatgt aac . . . GGAAACACCATATATTTTGGAGAGGGAA GTT (SEQ ID NO: 95) |
| FIG. 12-Tolerated-s1t-GaacG > GacgG | 3 nt mutation | GACTCAGCTGTGTATTTTTGTGCTAGT GG atatta aac . . . GGAAACACCATATATTTTGGAGAGGG AAGTT (SEQ ID NO: 96) |
| | | GACTCAGCTGTGTATTTTTGTGCTAGTG G aatatgt aac . . . GGAAACACCATATATTTTGGAGA GGGAAGTT (SEQ ID NO: 97) |
| | | GACTCAGCTGTGTATTTTTGTGCTA GTGG gaa . . . GGAAACACCATATATTTTGGAGA GGGAAGTT (SEQ ID NO: 98) |
| | | GACTCAGCTGTGTATTTTTGTGCTA GTGG gtc . . . GGAAACACCATATATTTTGGAGA GGGAAGTT (SEQ ID NO: 99) |
| | | GACTCAGCTGTGTATTTTTGTGCTA GTGG acg . . . GGAAACACCATATATTTTGGAGA GGGAAGTT (SEQ ID NO: 100) |

VDJ Recombination Detection via M-Probes Constructed by Combinatorial Modules (FIGS. 13A-13D). This section shows oligonucleotide sequences of targets and probes used for T-cell receptor β VDJ recombination experiments in FIGS. 13A-13D and FIGS. 24-32B. All target strands were ordered with HPLC purification, while M-Probe related strands (e.g. s1P) were ordered as standard desalted oligos.

TABLE 12

Oligonucleotide sequences used to construct M-Probes for experiments in FIGS. 13A-13D and FIGS. 24-32B.

| Species | Sequence |
|---|---|
| FIG. 13-uP | GTTAAATCGTGGATAGTAGAC /3Rox N/ (SEQ ID NO: 65) |
| FIG. 13-uC | /5IABkFQ/ CAGGTACATTTGCTCGTCCTT (SEQ ID NO: 64) |
| FIG. 13-s1P-V2 | AAGGACGAGCAAATGTACCTGCAGTA gactcagccatgtacttctgtgccagca CGTGATAGAGTCTTCGCATCA (SEQ ID NO: 104) |
| FIG. 13-s1P-V3-1 | AAGGACGAGCAAATGTACCTGCAGTA gactctgctgtgtatttctgtgccagcagcc CGTGATAGAGTCTTCGCATCA (SEQ ID NO: 105) |
| FIG. 13-s1P-V4-1 | AAGGACGAGCAAATGTACCTGCAGTA gactcagccctgtatctctgcgccagcagcc CGTGATAGAGTCTTCGCATCA (SEQ ID NO: 106) |

TABLE 12-continued

Oligonucleotide sequences used to construct M-Probes for
experiments in FIGS. 13A-13D and FIGS. 24-32B.

| Species | Sequence |
|---|---|
| FIG. 13-s1P-V5-1 | AAGGACGAGCAAATGTACCTGCAGTA ggactcggccctttatctttgcgccagcag CGTGATAGAGTCTTCGCATCA (SEQ ID NO: 107) |
| FIG. 13-s1P-V6-1 | AAGGACGAGCAAATGTACCTGCAGTA cagacatctgtgtacttctgtgccagca CGTGATAGAGTCTTCGCATCA (SEQ ID NO: 108) |
| FIG. 13-s1P-V10-1 | AAGGACGAGCAAATGTACCTGCAGTA cagacatctgtatatttctgcgccagcag CGTGATAGAGTCTTCGCATCA (SEQ ID NO: 109) |
| FIG. 13-s1P-V11-1 | AAGGACGAGCAAATGTACCTGCAGTA gactcggccatgtatctctgtgccagcagc CGTGATAGAGTCTTCGCATCA (SEQ ID NO: 110) |
| FIG. 13-s1P-V12-5 | AAGGACGAGCAAATGTACCTGCAGTA gactcagctgtgtattttgtgctagtgg CGTGATAGAGTCTTCGCATCA (SEQ ID NO: 111) |
| FIG. 13-s1C-V2 | AGTAACAGACGGAAATTGTGC tgctggcacagaagtacatggctgagtc TACTGGTCTACTATCCACGATTTAAC (SEQ ID NO: 112) |
| FIG. 13-s1C-V3-1 | AGTAACAGACGGAAATTGTGC ggctgctggcacagaaatacacagcagagtc TACTGGTCTACTATCCACGATTTAAC (SEQ ID NO: 113) |
| FIG. 13-s1C-V4-1 | AGTAACAGACGGAAATTGTGC ggctgctggcgcagagatacagggctgagtc TACTGGTCTACTATCCACGATTTAAC (SEQ ID NO: 114) |
| FIG. 13-s1C-V5-1 | AGTAACAGACGGAAATTGTGC ctgctggcgcaaagataaagggccgagtcc TACTGGTCTACTATCCACGATTTAAC (SEQ ID NO: 115) |
| FIG. 13-s1C-V6-1 | AGTAACAGACGGAAATTGTGC tgctggcacagaagtacacagatgtctg TACTGGTCTACTATCCACGATTTAAC (SEQ ID NO: 116) |
| FIG. 13-s1C-V10-1 | AGTAACAGACGGAAATTGTGC ctgctggcgcagaaatatacagatgtctg TACTGGTCTACTATCCACGATTTAAC (SEQ ID NO: 117) |
| FIG. 13-s1C-V11-1 | AGTAACAGACGGAAATTGTGC gctgctggcacagagatacatggccgagtc TACTGGTCTACTATCCACGATTTAAC (SEQ ID NO: 118) |
| FIG. 13-s1C-V12-5 | AGTAACAGACGGAAATTGTGC ccactagcacaaaaatacacagctgagtc TACTGGTCTACTATCCACGATTTAAC (SEQ ID NO: 119) |
| FIG. 13-tP-J1-1 | TGATGCGAAGACTCTATCACG tgaagctttctttggacaag (SEQ ID NO: 120) TGATGCGAAGACTCTATCAC |
| FIG. 13-tP-J1-2 | G ggctacaccttcggttcgg (SEQ ID NO: 121) TGATGCGAAGACTCTATCAC |
| FIG. 13-tP-J1-3 | G ggaaacaccatatattttgga (SEQ ID NO: 76) TGATGCGAAGACTCTATCAC |
| FIG. 13-tP-J2-1 | G gagcagttatcgggc (SEQ ID NO: 122) TGATGCGAAGACTCTATCAC |
| FIG. 13-tP-J2-2 | G cggggagctgttttttgg (SEQ ID NO: 123) TGATGCGAAGACTCTATCAC |
| FIG. 13-tP-J2-3 | G gatacgcagtattttggcccag (SEQ ID NO: 124) |
| FIG. 13-tC-J1-1 | tctggtgccttgtccaaagaaagcttca GCACAATTTCCGTCTGTTACT (SEQ ID NO: 125) cctggtccccgaaccgaaggtgtagcc |
| FIG. 13-tC-J1-2 | GCACAATTTCCGTCTGTTACT (SEQ ID NO: 126) aacttccctctccaaaatatatggtgtttcc |
| FIG. 13-tC-J1-3 | GCACAATTTCCGTCTGTTACT (SEQ ID NO: 77) gtgtccctggcccgaagaactgctc |
| FIG. 13-tC-J2-1 | GCACAATTTCCGTCTGTTACT (SEQ ID NO: 127) agagccttctccaaaaaacagctccccg |
| FIG. 13-tC-J2-2 | GCACAATTTCCGTCTGTTACT (SEQ ID NO: 128) cgggtgcctgggccaaaatactgcgtatc |
| FIG. 13-tC-J2-3 | GCACAATTTCCGTCTGTTACT (SEQ ID NO: 129) |

TABLE 13

Oligonucleotide sequences used as targets for
experiments in FIGS. 13A-13D and FIGS. 24-32B.

| Species | Sequence |
|---|---|
| FIG. 13-Target-V2/J1-1 | GACTCAGCCATGTACTTCTGTGCCAGCAgat aggctccaatgagcagttca . . . TGAAGCTTTCTTTGGACAAGGCACCAGA (SEQ ID NO: 130) |
| FIG. 13-Target-V2/J1-2 | GACTCAGCCATGTACTTCTGTGCCAGCAGTGA ttgcgggaggttggagatacgcagtc. . . GGCTACACCTTCGGTTCGGGGACCAGG (SEQ ID NO: 131) |

TABLE 13-continued

Oligonucleotide sequences used as targets for
experiments in FIGS. 13A-13D and FIGS. 24-32B.

| Species | Sequence |
|---|---|
| FIG. 13-Target-V2/J1-3 | GACTCAGCCATGTACTTCTGTGCCAGCAGTGA Agttatgggacacctggt . . . CTCTGGAAACACCATATATTTTGGAGAGGGAA GTT (SEQ ID NO: 132) |
| FIG. 13-Target-V2/J2-1 | GACTCAGCCATGTACTTCTGTGCCAGCAGTGA AGCacagggatcg . . . CAATGAGCAGTTCTTCGGGCCAGGGACAC (SEQ |
| FIG. 13-Target-V2/J2-2 | GACTCAGCCATGTACTTCTGTGCCAGCAGTGA AGgctacttagcgtc . . . ACCGGGGAGCTGTTTTTTGGAGAAGGCTCT (SEQ ID NO: 134) |
| FIG. 13-Target-V2J/2-3 | GACTCAGCCATGTACTTCTGTGCCA GCAGtgtgggacag . . . ACAGATACGCAGTATTTTGGC CCAGGCACCCG (SEQ ID NO: 135) |
| FIG. 13-Target-V3 1/J1-1 | GACTCTGCTGTGTATTTCTGTGCCAGCAGCCA AGggactagcggtta . . . ACACTGAAGCTTTCTTTGGACAAGGCACCAGA (SEQ ID NO: 136) |
| FIG. 13-Target-V3 1/J1-2 | GACTCTGCTGTGTATTTCTGTGCCAGCAGCCA cacgggacagggtc . . . CTATGGCTACACCTTCGGTTCGGGGACCAGG (SEQ ID NO: 137) |
| FIG. 13-Target-V3 1/J1-3 | GACTCTGCTGTGTATTTCTGTGCCAGCAGCCA AGAgggagggctagcgaggg . . . CTCTGGAAACACCATATATTTTGGAGAGGGAA GTT (SEQ ID NO: 138) |
| FIG. 13-Target-V3 1/J2-1 | GACTCTGCTGTGTATTTCTGTGCCAGCAGCCA AGAggga . . . GAGCAGTTCTTCGGGCCAGGGACAC (SEQ ID NO: 139) |
| FIG. 13-Target-V3 1/J2-2 | GACTCTGCTGTGTATTTCTGTGCCAGCAGCCA AGtcgtatcaa . . . ACCGGGGAGCTGTTTTTTGGAGAAGGCTCT (SEQ ID NO: 140) |
| FIG. 13-Target-V3 1/J2-3 | GACTCTGCTGTGTATTTCTGTGCCAGCC AAtttggtctagcgggata . . . CACAGATACGCAGTATTTTGGCCCAGGCACC CG (SEQ ID NO: 141) |
| FIG. 13-Target-V4 1/J1-1 | GACTCAGCCCTGTATCTCTGCGCCAG CAGCCaggacagttg . . . GAACACTGAAGCTTTCTTTGGA CAAGGCACCAGA (SEQ ID NO: 142) |
| FIG. 13-Target-V4 1/J1-2 | GACTCAGCCCTGTATCTCTGCGCCAGCAGCCA AGAcgaggacagtaa . . . TGGCTACACCTTCGGTTCGGGGACCAGG (SEQ ID NO: 143) |
| FIG. 13-Target-V4 1/J1-3 | GACTCAGCCCTGTATCTCTGCGCCAGCAGCCA AGAgactagcgggaata . . . TGGAAACACCATATATTTTGGAGAGGGAAGTT (SEQ ID NO: 144) |
| FIG. 13-Target-V4 1/J2-1 | GACTCAGCCCTGTATCTCTGCGCCAGCAGCCA AGgcccgggaaagaggt . . . CAATGAGCAGTTCTTCGGGCCAGGGACAC (SEQ ID NO: 145) |
| FIG. 13-Target-V4 1/J2-2 | GACTCAGCCCTGTATCTCTGCGCCAGCAGCCA Attacggtgg . . . CACCGGGGAGCTGTTTTTTGGAGAAGGCTCT (SEQ ID NO: 146) |
| FIG. 13-Target-V4 1/J2-3 | GACTCAGCCCTGTATCTCTGCGCCAG CAGCCgggactacgtc . . . AGCACAGATACGCAGTATTTTGG CCCAGGCACCCG (SEQ ID NO: 147) |
| FIG. 13-Target-V5 1/J1-1 | GGACTCGGCCCTTTATCTTTGCGCCAGCAGCT TGGacgggacaggta . . . |

TABLE 13-continued

Oligonucleotide sequences used as targets for experiments in FIGS. 13A-13D and FIGS. 24-32B.

| Species | Sequence |
| --- | --- |
| | GAACACTGAAGCTTTCTTTGGACAAGGCACCA GA (SEQ ID NO: 148) |
| FIG. 13-Target-V5- 1/J1-2 | GGACTCGGCCCTTTATCTTTGCGCCAGCAGC TTgcagggtgg . . . ACTATGGCTACACCTTCGGTTCGGGGACCAGG (SEQ ID NO: 149) |
| FIG. 13-Target-V5- 1/J1-3 | GGACTCGGCCCTTTATCTTTGCGCCAGCAGC ccgtacaggcttcctaagata . . . CTGGAAACACCATATATTTTGGAGAGGGAAG TT (SEQ ID NO: 150) |
| FIG. 13-Target-V5- 1/J2-1 | GGACTCGGCCCTTTATCTTTGCGCCA GCAGCTTGGcctttt . . . CCTACAATGAGCAGTTCTTCG GGCCAGGGACAC (SEQ ID NO: 151) |
| FIG. 13-Target-V5- 1/J2-2 | GGACTCGGCCCTTTATCTTTGCGCCAGCAGC TTGtggacagggaggtatcc . . . CACCGGGGAGCTGTTTTTTGGAGAAGGCTCT (SEQ ID NO: 152) |
| FIG. 13-Target-V5- 1/J2-3 | GGACTCGGCCCTTTATCTTTGCGCC AGCAGCtccatcta . . . CACAGATACGCAGTATTTTGG CCCAGGCACCCG (SEQ ID NO: 153) |
| FIG. 13-Target-V6- 1/J1-1 | CAGACATCTGTGTACTTCTGTGCCAGC AGTGaccatcagactgg . . . GAACACTGAAGCTTTCTTTGGA CAAGGCACCAGA (SEQ ID NO: 154) |
| FIG. 13-Target-V6- 1/J1-2 | CAGACATCTGTGTACTTCTGTGCCA GCAccaagggacagg . . . AACTATGGCTACACCTTCGGTT CGGGGACCAGG (SEQ ID NO: 155) |
| FIG. 13-Target-V6- 1/J1-3 | CAGACATCTGTGTACTTCTGTGCCAGC AGtctcataacgaattgg . . . CTCTGGAAACACCATATATTTTG GAGAGGGAAGTT (SEQ ID NO: 156) |
| FIG. 13-Target-V6- 1/J2-1 | CAGACATCTGTGTACTTCTGTGCCAGCAGTGA AGacagggaatcagccccagcc . . . AATGAGCAGTTCTTCGGGCCAGGGACAC (SEQ ID NO: 157) |
| FIG. 13-Target-V6- 1/J2-2 | CAGACATCTGTGTACTTCTGTGCCAGCAGTGA AGCggtcggacagggct . . . CCGGGGAGCTGTTTTTTGGAGAAGGCTCT (SEQ ID NO: 158) |
| FIG. 13-Target-V6- 1/J2-3 | CAGACATCTGTGTACTTCTGTGCCAGCAGTGA AGagacagcgaaa . . . CAGATACGCAGTATTTTGGCCCAGGCACCCG (SEQ ID NO: 159) |

TABLE 14

Oligonucleotide sequences used as targets for experiments in FIGS. 13A-13D and FIGS. 24-32B.

| Species | Sequence |
| --- | --- |
| FIG. 13-Target-V10- 1/J1-1 | CAGACATCTGTATATTTCTGCGCCAGCAGT GAGgaatacccgggaa . . . AACACTGAAGCTTTCTTTGGACAAGGCACCA GA (SEQ ID NO: 160) |
| FIG. 13-Target-V10- 1/J1-2 | CAGACATCTGTATATTTCTGCGCCAGCAGT GAgactcggacagtctg . . . CTATGGCTACACCTTCGGTTCGGGGACCAGG (SEQ ID NO: 161) |
| FIG. 13-Target-V10- 1/J1-3 | CAGACATCTGTATATTTCTGCGCCAGCAGT GAGTCgtcgacagttccaa . . . |

TABLE 14-continued

Oligonucleotide sequences used as
targets for experiments in FIGS. 13A-13D
and FIGS. 24-32B.

| Species | Sequence |
|---|---|
| | CTCTGGAAACACCATATATTTTGGAGAGGG AAGTT (SEQ ID NO: 162) |
| FIG. 13-Target-V10-1/J2-1 | CAGACATCTGTATATTTCTGCGCCAGCAGg agggacagggatttgtgg ... CTCCTACAATGAGCAGTTCTTCGGGCCAGG GACAC (SEQ ID NO: 163) |
| FIG. 13-Target-V10-1/J2-2 | CAGACATCTGTATATTTCTGCGCCAG CAGTGAGcggcaat ... GAACACCGGGGAGCTGTTTTTT GGAGAAGGCTCT (SEQ ID NO: 164) |
| FIG. 13-Target-V10-1/J2-3 | CAGACATCTGTATATTTCTGCGCCAGCAGT gggagggaaac ... CAGATACGCAGTATTTTGGCCCAGGCACCCG (SEQ ID NO: 165) |
| FIG. 13-Target-V11-1/J1-1 | GACTCGGCCATGTATCTCTGTGCCAGC AGCTTccgggaccg ... TGAACACTGAAGCTTTCTTTGGA CAAGGCACCAGA (SEQ ID NO: 166) |
| FIG. 13-Target-V11-1/J1-2 | GACTCGGCCATGTATCTCTGTGCCAGCAGC tccggacagggccccctatggctacc ... TATGGCTACACCTTCGGTTCGGGGACCAGG (SEQ ID NO: 167) |
| FIG. 13-Target-V11-1/J1-3 | GACTCGGCCATGTATCTCTGTGCCAGCAGC ttcctgtaagcgggagtta ... GGAAACACCATATATTTTGGAGAGGGAAGTT (SEQ ID NO: 168) |
| FIG. 13-Target-V11-1/J2-1 | GACTCGGCCATGTATCTCTGTGCCAGCAGC tcgcaggccgggagggcccag ... CTACAATGAGCAGTTCTTCGGGCCAGGGA CAC (SEQ ID NO: 169) |
| FIG. 13-Target-V11-1/J2-2 | GACTCGGCCATGTATCTCTGTGCCAGCAGC TTAGacctaaaaacagggaccgacgg ... GAACACCGGGGAGCTGTTTTTTGGAGAAGGC TCT (SEQ ID NO: 170) |
| FIG. 13-Target-V11-1/J2-3 | GACTCGGCCATGTATCTCTGTGCCAGCAGC TTAGatctgggcggactcttgga ... GATACGCAGTATTTTGGCCCAGGCACCCG (SEQ ID NO: 171) |
| FIG. 13-Target-V12-5/J1-1 | GACTCAGCTGTGTATTTTTGTGCTAGTGGT TTgggctccgtctatggctacaa ... ACTGAAGCTTTCTTTGGACAAGGCACCAGA (SEQ ID NO: 172) |
| FIG. 13-Target-V12-5/J1-2 | GACTCAGCTGTGTATTTTTGTGCTAGTGGT TTGcacaccgcaaccggcggtctag ... CTATGGCTACACCTTCGGTTCGGGGACCAGG (SEQ ID NO: 173) |
| FIG. 13-Target-V12-5/J1-3 | GACTCAGCTGTGTATTTTTGTGCTAGTGGT gtgattcttga ... GGAAACACCATATATTTTGGAGAGGGAAGTT (SEQ ID NO: 174) |
| FIG. 13-Target-V12-5/J2-1 | GACTCAGCTGTGTATTTTTGTGCTAGTGGT TTGGTtcctcgacagggacggga ... ACAATGAGCAGTTCTTCGGGCCAGGGACAC (SEQ ID NO: 175) |
| FIG. 13-Target-V12-5/J2-2 | GACTCAGCTGTGTATTTTTGTGCTAGTGGT TTGGgagactagcgggtct ... ACACCGGGGAGCTGTTTTTTGGAGAAGGC TCT (SEQ ID NO: 176) |
| FIG. 13-Target-V12-5/J2-3 | GACTCAGCTGTGTATTTTTGTGCTAG TGGTTTGGagggtc ... AGCACAGATACGCAGTATTTTGG CCCAGGCACCCG (SEQ ID NO: 177) |

Probing and Detection of Long Targets with M-Probes (FIGS. 14A-14B). This section shows oligonucleotide sequences of targets and probes used for experiments with M-Probes binding long continuous target sequences (FIG. 14A-14B). Other than the primers, all oligos in this section were post-synthesis purified using PAGE.

TABLE 15

Oligonucleotide sequences used for constructing M-Probes used in FIGS. 33A-33D.

| Probe | Species | Sequence |
|---|---|---|
| FIG. 33ab-99nt | s1P | AAGGACGAGCAAATGTACCTGCA . . . atgactgaatataaacttgtggtagttggagctggtggc gtaggcaag . . . CGTGATAGAGTCTTCGCAT (SEQ ID NO: 3) |
| | s1C | TGAACGACGGAAATTGTGC . . . cttgcctacgccaccagctccaactaccacaagtttat attcagtcat . . . TGGTCTACTATCCACGATTTAAC (SEQ ID NO: 4) |
| | tP | ATGCGAAGACTCTATCACG . . . gtgccttgacgatacagctaattcagaatcattttgtg (SEQ ID NO: 5) |
| | tC | atcatattcgtccacaaaatgattctgaattagctgtatcgtcaagg cac . . . GCACAATTTCCGTCGTTCA (SEQ ID NO: 6) |
| FIG. 33ab-160nt | s1P | AAGGACGAGCAAATGTACCTGCA . . . atgactgaatataaacttgtggtagttggagctggtggc gtaggcaag . . . CGTGATAGAGTCTTCGCAT (SEQ ID NO: 3) |
| | s1C | TGAACGACGGAAATTGTGC . . . cttgcctacgccaccagctccaactaccacaagtttat attcagtcat . . . TGGTCTACTATCCACGATTTAAC (SEQ ID NO: 4) |
| | s2P | ATGCGAAGACTCTATCACG . . . gtgccttgacgatacagctaattcagaatcattttgtgga cgaatatgat . . . GGCTGAACGTAACTCCTCG (SEQ ID NO: 7) |
| | s2C | GCTATCTTCAACCTTCTGG . . . atcatattcgtccacaaaatgattctgaattagctgtatcg tcaaggcac . . . GCACAATTTCCGTCGTTCA (SEQ ID NO: 8) |
| | tP | CGAGGAGTTACGTTCAGCC . . . caacaatagaggattcctacaggaagcaagtagtaattgatggag (SEQ ID NO: 9) |
| | tC | ccaagagacaggtttctccatcaattactacttgcttcctgtagga atcctctattgttg . . . CCAGAAGGTTGAAGATAGC (SEQ ID NO: 10) |
| FIG. 33cd-218nt | s1P | AAGGACGAGCAAATGTACCTGCA . . . gtacatgaggactggggagggctttctttgtgtatttgccataaa taatactaaat . . . catttgaagatattcaccattatagagaacaaattaaaagagtta aggactctgaagat CGTGATAGAGTCTTCGCATCA (SEQ ID NO: 178) |
| | s1C | AGTAACAGACGGAAATTGTGC . . . atcttcagagtccttaactcttttaatttgttctctataatggtgaa tatcttcaaa . . . tgatttagtattatttatggcaaatacacaaagaaagccctcccca gtcctcatgtac . . . TGGTCTACTATCCACGATTTAAC (SEQ ID NO: 179) |
| | tP | TGATGCGAAGACTCTATCACG . . . gtacctatggtcctagtaggaaataaatgtgatttgc cttctagaa . . . cagtagacacaaaacaggctcaggacttagcaaga agttatg (SEQ ID NO: 180) |
| | tC | caataaaaggaattccataacttcttgctaagtcctgagcctgtttt gtgtc . . . tactgttctagaaggcaaatcacatttatttcctactagga ccataggtac . . . GCACAATTTCCGTCTGTTACT (SEQ ID NO: 181) |

TABLE 16

Primer used to generate amplicons as targets
for reaction with M-Probes in FIGS. 33A-33D.

| Amplicon | Type | Sequence |
| --- | --- | --- |
| FIG. 33ab Primers | forward Primer (fP) | TATAAGGCCTGCTGAAAATGACT (SEQ ID NO: 42) |
| | reverse Primer (rP) | ATCCAAGAGACAGGTTTCTCCA (SEQ ID NO: 43) |
| FIG. 33cd Primers | fP1 | TCAAGAGGAGTACAGTGCAATG (SEQ ID NO: 182) |
| | fP2 | TGAGGGACCAGTACATGACTGG (SEQ ID NO: 183) |
| | fP3 | GACCAGTACATGAGGGAGGGCTT (SEQ ID NO: 184) |
| | rP | AACACCCTGTCTTGTCTTTGC (SEQ ID NO: 185) |

TABLE 17 gBlock sequence serving as template for PCR amplification.
Sequences in uppercase are the flanking intron sequences

| FIG. 33 template (KRAS cDNA gBlock) | TATAAGGCCTGCTGAAA . . . atgactgaatataaacttgtggtagttggagctggtggcgtaggcaagagtgccttgacg . . . atacagctaattcagaatcattttgtggacgaatatgatccaacaatagaggattcctac . . . aggaagcaagtagtaattgatggagaaacctgtctcttggatattctcgacacagcaggt . . . caagaggagtacagtgcaatgagggaccagtacatgaggactggggagggctttctttgt . . . gtatttgccataaataatactaaatcatttgaagatattcaccattatagagaacaaatt . . . aaaagagttaaggactctgaagatgtacctatggtcctagtaggaaataaatgtgatttg . . . ccttctagaacagtagacacaaaacaggctcaggacttagcaagaagttatggaattcct . . . tttattgaaacatcagcaaagacaagacagggtgttgatgatgccttctatacattagtt . . . cgagaaattcgaaaacataaagaaaagatgagcaaagatggtaaaaagaagaaaaagaag . . . tcaaagacaaagtgtgtaattatgtaa . . . ATACAATTTGTACTTTTTTCTTAAGGCATACTAGTACAAGTGG (SEQ ID NO: 41) |
| --- | --- |

TABLE 18

Universal P and C sequences used for
FIGS. 14A-14B and FIGS. 36A-36B

| Species | Sequence |
| --- | --- |
| FIG. 14-uP | /5IAbRQ/ GTGCGAACAGGTACATTTGCTCGTCCTT (SEQ ID NO: 2) |
| FIG. 14-uC | GTTGACAATCGTGGATAGTAGACTTCGCAC /3Rox N/ (SEQ ID NO: 186) |

TABLE 19

Primer used to generate amplicons as
targets for reaction with M-Probes in
FIGS. 14A-14B and FIGS. 36A-36B.

| Amplicon | Type | Sequence |
| --- | --- | --- |
| FIG. 36 Primers | fP | CCTATTTCTCCTCAGCTCAAAACC (SEQ ID NO: 187) |
| | rP | ATAGTCAACTTAAGGACTAAATAAATGATCTAATG (SEQ ID NO: 188) |
| FIG. 14 Primers | fP1 | AAGGTCAGGGTCTCTGTTAGG (SEQ ID NO: 189) |
| | rP1 | AGTGGTTAGAGACAATATGACATCG (SEQ ID NO: 190) |
| | fP2 | CTTCACCTATCCTGCAACCTTT (SEQ ID NO: 191) |
| | rP2 | TTCTAATCTGTCTAAATTACCTAACGCT (SEQ ID NO: 192) |

TABLE 20

Oligonucleotide sequences used for constructing M-Probes used in
FIGS. 36A-36B.

| Probe | Species | Sequence |
|---|---|---|
| FIG. 36-430nt | s1P | AAGGACGAGCAAATGTACCTGCA ... tttctcctcagctcaaaaccttcagtggcactccgttttattggtgtcaaagccaaag tcctttcaatggtctac ... aaaacactgtttggccaggccaccaaataccttgctagtttcttctagttctattc ... CGTGATAGAGTCTTCGCATCAG (SEQ ID NO: 193) |
| | s1C | ACTGAACGACGGAAATTGTGC ... gaatagaactagaagaaactagcaaggtatttggtggcctggccaaacagtgttttgta gaccattgaaaggactt ... tggctttgacaccaataaaacggagtgccactgaagggttttgagctgaggagaaa ... TGGTCTACTATCCACGATTGTCAAC (SEQ ID NO: 194) |
| | s2P | CTGATGCAAGACTCTATCACG ... tctctcacttggctccagtcacactgacctccccgccattccttcagtgcatgggaata tcccaccttcagaccat ... tgctccaattcttctcatttttgggaatgttctttacccagataatagcttgactaactcc ttct ... GGCTGAACGTAACTCCTCTTTG (SEQ ID NO: 195) |
| | s2C | GTGCTACTCTTCAACCTTCTGG ... agaaggagttagtcaagctattatctgggtaaagaacattcccaaaatgagaagaattgg agcaatggtctgaagg ... tgggatattcccatgcactgaaggaatggcggggaggtcagtgtgactggagccaagtg agaga ... GCACAATTTCCGTCGTTCAGT (SEQ ID NO: 196) |
| | tP | CAAAGAGGAGTTACGTTCAGCC... tttatgtctgacttggctcaacagtttaatctcaatgagacttaccctgaccaccct atttca ... tagttccaacctggattccagcattcctaatcccttactctgcacgacttcttttttt tcccatggtactcaccac (SEQ ID NO: 197) |
| | tC | tgatctaatgagttagaggtggtgagtaccatgggaaaaaaaagaagtcgtgcagagtaaggg gattaggaatgct... ggaatccaggttggaactatgaaatagggtggtcagggtaagtctcattgagattaaactgttg agccaagtcagacataaa ... CCAGAAGGTTGAAGAGTAGCAC (SEQ ID NO: 198) |

TABLE 21

Oligonucleotide sequences used for constructing M-Probes used in
FIGS. 14A-14B.

| Probe | Species | Sequence |
|---|---|---|
| FIG. 14-560nt-1 | s1P | AAGGACGAGCAAATGTACCTGCA ... ctgttaggaaagcaaaatttccccagatattctcagcagttttctgcttgtgcttccatgtct agagctgtctctagttcc ... tggaagttcctagcttcaagcatgtctaagaaagacttcatttgagtaccttgctacctta ... CGTGATAGAGTCTTCGCATCAG (SEQ ID NO: 199) |
| | s1C | ACTGAACGACGGAAATTGTGC ... taaggtagcaaggtactcaaatgaagtctttcttagacatgcttgaagctaggaacttc caggaactagagaca ... gctctagacatggaagcacaagcagaaaactgctgagaatatctggggaaattttgc tttcctaacag ... TGGTCTACTATCCACGATTGTCAAC (SEQ ID NO: 200) |
| | s2P | CTGATGCAAGACTCTATCACG ... tagtcttccctagcttaataatttttctgtacctaatgatttcagagtgagatg gtgaggtgatcatg ... ggcaaaattattagtctttctgagttctcttattccttttatatcattgaatgtt cttttttgtg ... GGCTGAACGTAACTCCTCTTTG (SEQ ID NO: 201) |
| | s2C | GTGCTACTCTTCAACCTTCTGG ... cacaaaaagaacattcaatgatataaaaggaataagagaactcagaaagacta ataattttgcccatgat ... cacctcaccatctcactctgaaatcattaggtacagaaaaaattattaagctaggg aagacta ... GCACAATTTCCGTCGTTCAGT (SEQ ID NO: 202) |
| | s3P | CAAAGAGGAGTTACGTTCAGCC ... gctattgttaggattagtgtttcaatgtgaatggcagattgaagcttcagagtgctttca ctcatcttcagttgtttct ... ccgagttgccttgagagagagaaagaggtagttttagccctattttgtaggtatagtaat agtga... CGTTCTACCTCAGGTGTTCGT (SEQ ID NO: 203) |
| | s3C | TTTCTGATGCACTTAGAGTGAGC ... tcactattactataacctacaaaatagggctaaaactacctcttttctctctcaaggcaact cggagaaacaactgaa ... gatgagtgaaagcactctgaagcttcaatctgccattcacattgaaacactaatcctaaca atagc ... CCAGAAGGTTGAAGAGTAGCAC (SEQ ID NO: 204) |
| | tP | ACGAACACCTGAGGTAGAACG... ttcccttttcctttgtgtctattcgaatcctaccattttattccctatgtttc tgttgcctgtcctc... acatttggtccttctcaggatatggcatgctttccatatttcccagtaaaa atcccag (SEQ ID NO: 205) |

TABLE 21-continued

Oligonucleotide sequences used for constructing M-Probes used in FIGS. 14A-14B.

| Probe | Species | Sequence |
|---|---|---|
| | tC | tgacatcggaaaggctgggattttttactgggaaatatggaaagcatgccatatcctgagaagga<br>ccaaatgtgaggacaggc...<br>aacagaaacatagggaataaaatggtaggattcgaaagagacacaa<br>aggaaaagggaa ...<br>GCTCACTCTAAGTGCATCAGAAA (SEQ ID NO: 206) |
| FIG. 14-<br>560nt-2 | s1P | AAGGACGAGCAAATGTACCTGCA ...<br>acctatcctgcaacctttccacatactcttccctcaacctggaagactcctcctgt<br>tctttacctggataatt...<br>cttacatagccttccattctcaactcaaatggtgttacttcaaagatgcctttgct<br>cattacc... CGTGATAGAGTCTTCGCATCAG (SEQ ID NO: 207) |
| | s1C | ACTGAACGACGGAAATTGTGC ...<br>ggtaatgagcaaaggcatctttgaagtaacaccatttgagttgagaatggaagg<br>ctatgtaagaattatcc...<br>aggtaaagaacaggaggagtcttccaggttgagggaagagtatgtggaaaggtt<br>gcaggataggt... TGGTCTACTATCCACGATTGTCAAC (SEQ ID NO: 208) |
| | s2P | CTGATGCGAAGACTCTATCACG ...<br>aaacgtatattaggcccctctcttacttatttatacttcctttgtaagcagcgacatgg<br>ctcttttgctcaccctg ...<br>gtaagcctagtgcccagtatatcatctgacacacaattggtggtcaactgttgatt ...<br>GGCTGAACGTAACTCCTCTTTG (SEQ ID NO: 209) |
| | s2C | GTGCTACTCTTCAACCTTCTGG ...<br>aatcaacagttgaccaccaattgtgtgtcagatgatatactgggcactaggcttac<br>cagggtgagcaaaag ...<br>agccatgtcgctgcttacaaaggaagtataaataagtaagagaggggcctaatat<br>acgttt ... GCACAATTTCCGTCGTTCAGT (SEQ ID NO: 210) |
| | s3P | CAAAGAGGAGTTACGTTCAGCC ...<br>catgagtgaattttattggttactgttgatcgccagtgaaataagtgcttagaaaca<br>cttataggctgaatag ...<br>gaagaattaaacaaatgaatgactagataataggtacgtgggagtcacagggatt<br>gacatcttattt ... CGTTCTACCTCAGGTGTTCGT (SEQ ID NO: 211) |
| | s3C | TTTCTGATGCACTTAGAGTGAGC ...<br>aaaataagatgtcaatccctgtgactcccacgtacctattatctagtcattcatttgtt<br>taattcttcctattcag ...<br>cctataagtgtttctaagcacttatttcactggcgatcaacagtaaccaataaaattc<br>actcatg ... CCAGAAGGTTGAAGAGTAGCAC (SEQ ID NO: 212) |
| | tP | ACGAACACCTGAGGTAGAACG...<br>tattcagttttgcctacattggctcttttcttacaaatgtcctgatgcctattga<br>gtatatatccataag...<br>gtttctttgagttttctggaagaaatggctgttgttgatgttgttttttagcagc<br>tcttttgactcgac (SEQ ID NO: 213) |
| | tC | ctggtgtgaggatggtcgagtcaaaagagctgctaaaaacaacatcaacaacagccatttcttc<br>cagaaaactcaaagaa ...<br>accttatggatatatactcaataggcatcaggacatttgtaagaaaagagccaatgt<br>aggcaaaactgaata ... GCTCACTCTAAGTGCATCAGAAA (SEQ ID NO: 214) |

TABLE 22

Amplicon sequence serving as target for 430nt M-Probe (chr3. 1772231-1772689, GRCh37.p13 Primary Assembly). Sequences in uppercase are probing sequences.

MP-     cctaTTTCTCCTCAGCTCAAAACCCTTCAGTGGCACTCCATTTTATT
430    GGTGTCAAAGCCAAAGTCCTTTC ...
       AATGGTCTACAAAACACTGTTTGGCCAGGCCACCAAATACCTTGCTA
       GTTTCTTCTAGTTCTATTCTCTC...
       TCACTTGGCTCCAGTCACACTGACCTCCCCGCCATTCCTTCAGTGCA
       TGGGAATATCCCACCTTCAGACC...
       ATTGCTCCAATTCTTCTCATTTTGGGAATGTTCTTTACCCAGATAAT
       AGCTTGACTAACTCCTTCTTTTA ...
       TGTCTGACTTGGCTCAACAGTTTAATCTCAATGAGACTTACCCTGAC
       CACCCTATTTCATAGTTCCAACC ...
       TGGATTCCAGCATTCCTAATCCCCTTACTCTGCACGACTTCTTTTTT
       TTCCCATGGTACTCACCACCTCT ...
       AACTCATTAGATCAtttatttagtccttaagttgactat
       (SEQ ID NO: 215)

TABLE 23

Amplicon sequences serving as target for 560nt M-Probe-1
(chr9. 1095713-1096302, GRCh37.p13 Primary Assembly)
and M-Probe-2 (chr13.22569207-22569796, GRCh37.p13
Primary Assembly). Sequences in uppercase are probing
sequences.

```
MP-     aaggtcagggtctCTGTTAGGAAAGCAAAATTTCCCCAGATATTCTCAGCAG
560-1   TTTTCTGCTTGTGCTTCC ...
        ATGTCTAGAGCTGTCTCTAGTTCCTGGAAGTTCCTAGCTTCAAGCATG
        TCTAAGAAAGACTTCATTTGAG ...
        TACCTTGCTACCTTATAGTCTTCCCTAGCTTAATAATTTTTTCTGTACC
        TAATGATTTCAGAGTGAGATG ...
        GTGAGGTGATCATGGGCAAAATTATTAGTCTTTCTGAGTTCTCTTATT
        CCTTTTATATCATTGAATGTTC ...
        TTTTTTGTGGCTATTGTTAGGATTAGTGTTTCAATGTGAATGGCAGAT
        TGAAGCTTCAGAGTGCTTTCAC ...
        TCATCTTCAGTTGTTTCTCCGAGTTGCCTTGAGAGAGAGAAAGAGGT
        AGTTTTAGCCCTATTTTGTAGGT ...
        ATAGTAATAGTGATTCCCTTTTCCTTTGTGTCTCTTTCGAATCCTACC
        ATTTTATTCCCTATGTTTCTGT ...
        TGCCTGTCCTCACATTTGGTCCTTCTCAGGATATGGCATGCTTTCCAT
        ATTTCCCAGTAAAAATCCCAGC ... CTTTCCGATGTCAtattgtctctaaccact
        (SEQ ID NO: 216)

MP-     cttcACCTATCCTGCAACCTTTCCACATACTCTTCCCTCAACCTGGAAGA
560-2   CTCCTCCTGTTCTTTACCTG ...
        GATAATTCTTACATAGCCTTCCATTCTCAACTCAAATGGTGTTACTTC
        AAAGATGCCTTTGCTCATTACC ...
        AAACGTATATTAGGCCCCTCTCTTACTTATTTATACTTCCTTTGTAAGC
        AGCGACATGGCTCTTTTGCTC ...
        ACCCTGGTAAGCCTAGTGCCCAGTATATCATCTGACACACAATTGGTG
        GTCAACTGTTGATTCATGAGTG ...
        AATTTTATTGGTTACTGTTGATCGCCAGTGAAATAAGTGCTTAGAAAC
        ACTTATAGGCTGAATAGGAAGA ...
        ATTAAACAAATGAATGACTAGATAATAGGTACGTGGGAGTCACAGGG
        ATTGACATCTTATTTTATTCAGT ...
        TTTGCCTACATTGGCTCTTTTCTTACAAATGTCCTGATGCCTATTGAG
        TATATATCCATAAGGTTTCTTT ...
        GAGTTTTCTGGAAGAAATGGCTGTTGTTGATGTTGTTTTTAGCAGCTC
        TTTTGACTCGACCATCCTCACA ... CCAGcgttaggtaatttagacagattagaa
        (SEQ ID NO: 217)
```

Detection of Repetitive Sequences (FIGS. 15A-15G). This section shows oligonucleotide sequences of targets and probes used for experiments using M-Probes to analyze genomic DNA for triplet repeat number in Huntington's gene HTT (FIGS. 15A-15G, 38-40, 42-46), as well as other triplet repeats (FIG. 41). FIG. 15abc-Target-21r, FIG. 15abc-Target-24r, and FIG. 15abc-Target-27r were post-synthesis PAGE purified, and all other strands were HPLC purified.

TABLE 24

Oligonucleotide sequences used as synthetic
Targets for FIGS. 15A-15C.

| Species | Sequence |
| --- | --- |
| FIG. 15abc-Target-6r | CAGCAGCAGCAGCAGCAG CAACAGCC (SEQ ID NO: 11) |
| FIG. 15abc-Target-9r | CAGCAGCAGCAGCAGCAGCAGCAGCAG CAACAGCC (SEQ ID NO: 12) |
| FIG. 15abc-Target-12r | CAGCAGCAGCAGCAGCAGCAGCAGCAGCAGCAGCAG CAACAGCC (SEQ ID NO: 13) |
| FIG. 15abc-Target-15r | CAGCAGCAGCAGCAGCAGCAGCAGCAGCAGCAGCAGCAGCAGCAG CAACAGCC (SEQ ID NO: 14) |
| FIG. 15abc-Target-18r | CAGCAGCAGCAGCAGCAGCAGCAGCAGCAGCAGCAGCAGCAGCAGCAGCAGCAG CAACAGCC (SEQ ID NO: 15) |
| FIG. 15abc-Target-21r | CAGCAGCAGCAGCAGCAGCAGCAGCAGCAGCAGCAGCAGCAGCAGCAGCAGCAGCAGCAGCAG ... CAACAGCCg (SEQ ID NO: 18) |
| FIG. 15abc-Target-24r | CAGCAGCAGCAGCAGCAGCAGCAGCAGCAGCAGCAGCAGCAGCAGCAGCAGCAGCAGCAGCAG ... CAGCAGCAG CAACAGCCg (SEQ ID NO: 219) |

TABLE 24-continued

Oligonucleotide sequences used as synthetic Targets for FIGS. 15A-15C.

| Species | Sequence |
|---|---|
| FIG. 15abc-Target-27r | CAGCAGCAGCAGCAGCAGCAGCAGCAGCAGCAGCAGCAG CAGCAGCAGCAGCAGCAGCAG ... CAGCAGCAGCAGCAGCAG CAACAGCCg (SEQ ID NO: 220) |

TABLE 25

Oligonucleotide sequences used to construct M-Probes for FIGS. 15B-15F.

| Species | Sequence |
|---|---|
| FIG. 15-sP1 | AAGGACGAGCAAATGTACCTGCA cagcagcagcagcagcag |
| FIG. 15-sP2 | CGTGATAGAGTCTTCGCAT (SEQ ID NO: 23) |
| FIG. 15-sP3 | ATGCGAAGACTCTATCACG agcagcagcagcagcagcag GGCTGAACGTAACTCCTCG (SEQ ID NO: 29) CGAGGAGTTACGTTCAGCC agcagcagcagcagcag CGTTCTACCTCAGGTGTTC (SEQ ID NO: 35) |
| FIG. 15-sC1 | TGAACGACGGAAATTGTGC ctgctgctgctgctgctg |
| FIG. 15-sC2 | TGGTCTACTATCCACGATTTAAC (SEQ ID NO: 24) |
| FIG. 15-sC3 | GCTATCTTCAACCTTCTGG ctgctgctgctgctgctgct GCACAATTTCCGTCGTTCA (SEQ ID NO: 30) CTGATGCACTTAGAGTGAGC ctgctgctgctgctgct CCAGAAGGTTGAAGATAGC (SEQ ID NO: 36) |
| FIG. 15-tP-6r | AAGGACGAGCAAATGTACCTGCA cagcagcagcagcagcagc (SEQ ID NO: 19) AAGGACGAGCAAATGTACCTGCA |
| FIG. 15-tP-9r | cagcagcagcagcagcagcagcagcagc (SEQ ID NO: 21) ATGCGAAGACTCTATCACG |
| FIG. 15-tP-12r FIG. 15-tP-15r FIG. 15-tP-18r | agcagcagcagcagcagc (SEQ ID NO: 25) ATGCGAAGACTCTATCACG agcagcagcagcagcagcagcagc (SEQ ID NO: 27) CGAGGAGTTACGTTCAGCC |
| FIG. 15-tP-21r FIG. 15-tP-24r FIG. 15-tP-27r | agcagcagcagcagc (SEQ ID NO: 31) CGAGGAGTTACGTTCAGCC agcagcagcagcagcagcagc (SEQ ID NO: 33) GAACACCTGAGGTAGAACG agcagcagcagcagc (SEQ ID NO: 221) GAACACCTGAGGTAGAACG agcagcagcagcagcagcagc (SEQ ID NO: 222) |
| FIG. 15-tC-6r | ggctgttgctgctgctgctgctgtg TGGTCTACTATCCACGATTTAAC (SEQ ID NO: 20) ggctgttgctgctgctgctgctgctgctgtg |
| FIG. 15-tC-9r | TGGTCTACTATCCACGATTTAAC (SEQ ID NO: 22) ggctgttgctgctgctgctgctgct |
| FIG. 15-tC-12r FIG. 15-tC-15r FIG. 15-tC-18r | GCACAATTTCCGTCGTTCA (SEQ ID NO: 26) ggctgttgctgctgctgctgctgctgct GCACAATTTCCGTCGTTCA (SEQ ID NO: 28) ggctgttgctgctgctgctgct |
| FIG. 15-tC-21r FIG. 15-tC-24r FIG. 15-tC-27r | CCAGAAGGTTGAAGATAGC (SEQ ID NO: 32) ggctgttgctgctgctgctgctgctgct CCAGAAGGTTGAAGATAGC (SEQ ID NO: 34) ggctgttgctgctgctgctgct GCTCACTCTAAGTGCATCAG (SEQ ID NO: 38) ggctgttgctgctgctgctgctgctgctgct GCTCACTCTAAGTGCATCAG (SEQ ID NO: 40) |

TABLE 26

Universal segment oligos used for hybrid-capture experiments shown FIGS. 15D-15G.

| Species | Sequence |
|---|---|
| FIG. 15defg-uP | aGTGCGAA CAGGTACATTTGCTCGTCCTT (SEQ ID NO: 223) /5Biosg/ tttttttt GTTAAATCGTGGATAGTAGA |
| FIG. 15defg-uC | CTTCGCACt (SEQ ID NO: 224) |

TABLE 27

Oligonucleotide sequences used to construct M-Probes for FIG. 15G.

| Species | Sequence |
|---|---|
| FIG. 15g-sP1 | AAGGACGAGCAAATGTACCTGCA cagcagcagcagcagcagcagcagcagcagcagcagcagcagcagcagcagcag ... CGTGATAGAGTCTTCGCAT (SEQ ID NO: 225) |
| FIG. 15g-sC1 | TGAACGACGGAAATTGTGC ctgctgctgctgctgctgctgctgctgctgctgctgctgctgctgctgctg ... TGGTCTACTATCCACGATTTAAC (SEQ ID NO: 226) |
| FIG. 15g-tP-33r | ATGCGAAGACTCTATCACGAG cagcagcagcagcagcagcagcagcagcagcagcagcagcagcagc (SEQ ID NO: 227) |
| FIG. 15g-tP-35r | ATGCGAAGACTCTATCACGAG cagcagcagcagcagcagcagcagcagcagcagcagcagcagcagcagcagc (SEQ ID NO: 228) |
| FIG. 15g-tP-36r | ATGCGAAGACTCTATCACGAG cagcagcagcagcagcagcagcagcagcagcagcagcagcagcagcagcagcagc (SEQ ID NO: 229) |
| FIG. 15g-tP-37r | ATGCGAAGACTCTATCACGAG cagcagcagcagcagcagcagcagcagcagcagcagcagcagcagcagcagcagc (SEQ ID NO: 230) |
| FIG. 15g-tP-39r | ATGCGAAGACTCTATCACGAG cagcagcagcagcagcagcagcagcagcagcagcagcagcagcagcagcagcagcagcagc (SEQ ID NO: 231) |
| FIG. 15g-tC-33r | ggctgttgctgctgctgctgctgctgctgctgctgctgctgctgctgctgct GCACAATTTCCGTCGTTCA (SEQ ID NO: 232) |
| FIG. 15g-tC-35r | ggctgttgctgctgctgctgctgctgctgctgctgctgctgctgctgctgctgctgct GCACAATTTCCGTCGTTCA (SEQ ID NO: 233) |
| FIG. 15g-tC-36r | ggctgttgctgctgctgctgctgctgctgctgctgctgctgctgctgctgctgctgctgct GCACAATTTCCGTCGTTCA (SEQ ID NO: 234) |
| FIG. 15g-tC-37r | ggctgttgctgctgctgctgctgctgctgctgctgctgctgctgctgctgctgctgctgct GCACAATTTCCGTCGTTCA (SEQ ID NO: 235) |
| FIG. 15g-tC-39r | ggctgttgctgctgctgctgctgctgctgctgctgctgctgctgctgctgctgctgctgctgctgct GCACAATTTCCGTCGTTCA (SEQ ID NO: 236) |

TABLE 28

Ultramer synthetic sequence with 26 CAG repeats used for Sanger Sequencing experiment in FIG. 38.

| Species | Sequence |
|---|---|
| FIG. 38 Ultramer with 26 CAG repeats | TGGAAAAGCTGATGAAGGCCTTCGAGTCCCT CAAGTCCTTCCAGCAG ... CAGCAGCAGCAGCAGCAGCAGCAGCAGCAGCAGC AGCAGCAGCAGCAGCAGCAG ... CAGCAGCAGCAGCAGCAGCAGCAACAGCC ... GCCACCGCCGCCGCCGCCGCCGCCGCCTCCT CAGCTTCCTCAG (SEQ ID NO: 237) |
| Sequencing Primer (forward) | TCGAGTCCCTCAAGTCCTTC (SEQ ID NO: 45) |

TABLE 29

Oligonucleotide sequences used in FIGS. 40A-40B to test formulation protocol.

| Species | Sequence |
|---|---|
| FIG. 40-T-15r | CAGCAGCAGCAGCAGCAGCAGCAGCAGCAGCAGCAGCAGC |
| FIG. 40-T-18r | AGCAGCAG CAACAGCC (SEQ ID NO: 238) |
| FIG. 40-T-19r | CAGCAGCAGCAGCAGCAGCAGCAGCAGCAGCAGCAGCAGC |
| FIG. 40-T-20r | AGCAGCAGCAGCAG CAACAGCC (SEQ ID NO: 15) CAGCAGCAGCAGCAGCAGCAGCAGCAGCAGCAGCAGCAGC AGCAGCAGCAGCAGCAG CAACAGCC (SEQ ID NO: 239) CAGCAGCAGCAGCAGCAGCAGCAGCAGCAGCAGCAGCAGC AGCAGCAGCAGCAGCAGCAG CAACAGCC (SEQ ID NO: 240) |
| FIG. 40-s1P FIG. 40-s1C | AAGGACGAGCAAATGTACCTGCA cagcagcagcagcagcag CGTGATAGAGTCTTCGCAT (SEQ ID NO: 23) TGAACGACGGAAATTGTGC ctgctgctgctgctgctg TGGTCTACTATCCACGATTTAAC (SEQ ID NO: 24) |
| FIG. 40-s2P FIG. 40-s2C | ATGCGAAGACTCTATCACG cagcagcagcagcagcag GGCTGAACGTAACTCCTCG (SEQ ID NO: 241) GCTATCTTCAACCTTCTGG ctgctgctgctgctgctg GCACAATTTCCGTCGTTCA (SEQ ID NO: 242) |

TABLE 29-continued

Oligonucleotide sequences used in FIGS. 40A-40B to test formulation protocol.

| Species | Sequence |
|---|---|
| FIG. 40-tP | CGAGGAGTTACGTTCAGCC cagcagcagcagcagcag (SEQ ID NO: 243) |
| FIG. 40-tC | ggctgttgctgctgctgctgctg CCAGAAGGTTGAAGATAGC (SEQ ID NO: 244) |

TABLE 30

Figure 41A:
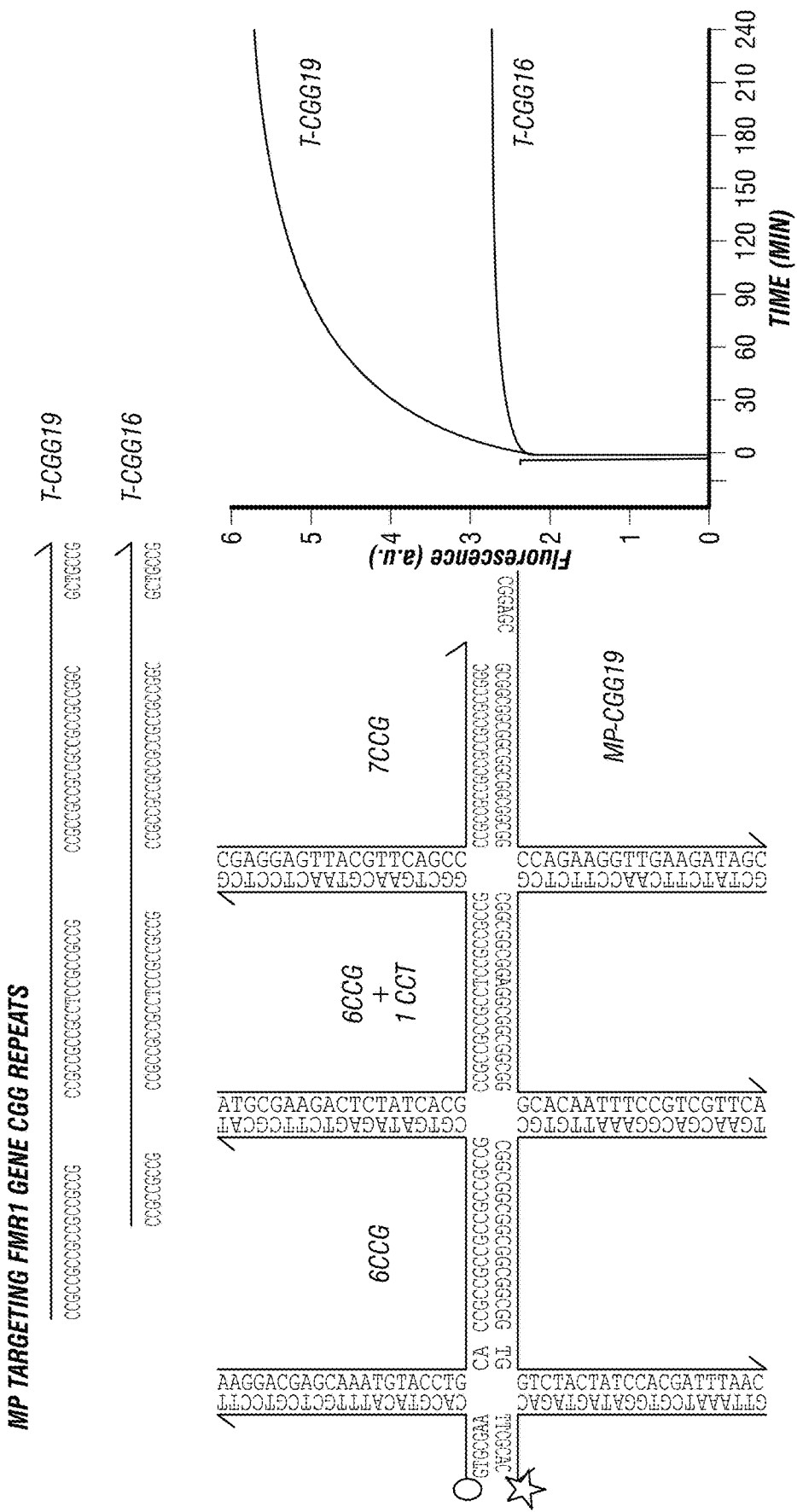
FIGS. 41A-41B depict M-Probes for detecting CGG and GAA triplet repeats for the FMR1 and FXN genes.
Figure 41B:
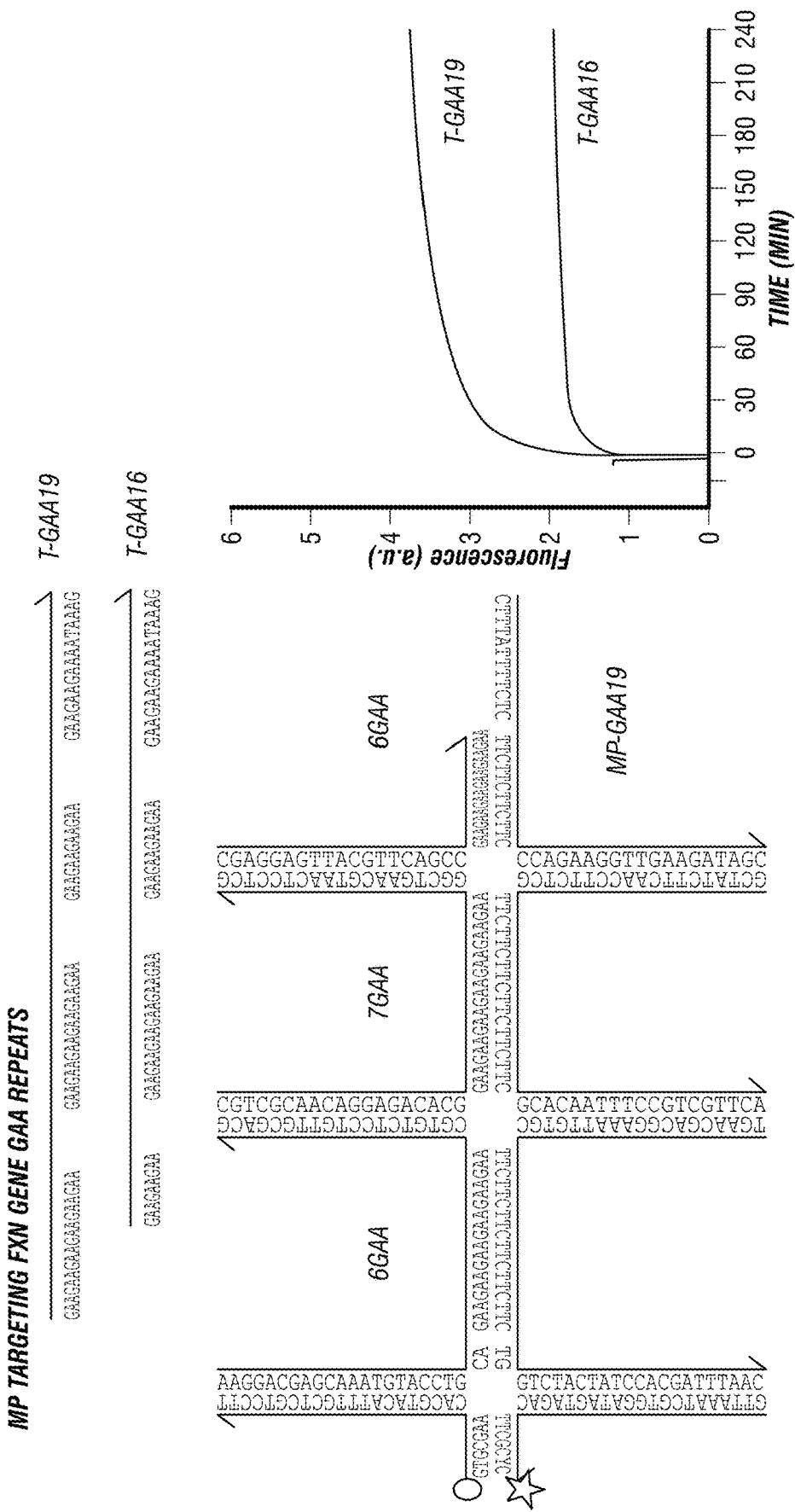

Oligonucleotide sequences used in FIG. 41A to examine CGG repeats in FMR1 gene.

| Species | Sequence |
|---|---|
| FIG. 41a-T-19r | CCGCCGCCGCCGCCGCCGCCGCCGCCGCCTCCGCCGCCGC |
| FIG. 41a-T-16r | CGCCGCCGCCGCCGCCGCCGC GCTGCCG (SEQ ID NO: 245) |
| | CCGCCGCCGCCGCCGCCGCCTCCGCCGCCGCCGCCGCCGC |
| | CGCCGCCGCCGC GCTGCCG (SEQ ID NO: 246) |
| FIG. 41a-sP1 | AAGGACGAGCAAATGTACCTGCA ccgccgccgccgccgccg |
| FIG. 41a-sC1 | CGTGATAGAGTCTTCGCAT (SEQ ID NO: 247) |
| | TGAACGACGGAAATTGTGC cggcggcggcggcggcgg |
| | TGGTCTACTATCCACGATTTAAC (SEQ ID NO: 248) |
| FIG. 41a-sP2 | ATGCGAAGACTCTATCACG ccgccgccgcctccgccgcc |
| FIG. 41a-sC2 | GGCTGAACGTAACTCCTCG (SEQ ID NO: 249) |
| | GCTATCTTCAACCTTCTGG cggcggcggaggcggcggcgg |
| | GCACAATTTCCGTCGTTCA (SEQ ID NO: 250) |
| FIG. 41a-tP | CGAGGAGTTACGTTCAGCC ccgccgccgccgccgccgccgc (SEQ ID NO: 251) |
| FIG. 41a-tC | cggcagcgcggcggcggcggcggcggcgg CCAGAAGGTTGAAGATAGC (SEQ ID NO: 252) |

TABLE 31

Oligonucleotide sequences used in FIG. 41B to examine GAA repeats in FXN gene.

| Species | Sequence |
|---|---|
| FIG. 41b-T-19r | GAAGAAGAAGAAGAAGAAGAAGAAGAAGAAGAAGAAGAAG |
| FIG. 41b-T-16r | AAGAAGAAGAAGAAGAAGAA AATAAAG (SEQ ID NO: 253) |
| | GAAGAAGAAGAAGAAGAAGAAGAAGAAGAAGAAGAAG |
| | AAGAAGAAGAA AATAAAG (SEQ ID NO: 254) |
| FIG. 41b-sP1 | AAGGACGAGCAAATGTACCTGCA gaagaagaagaagaagaa |
| FIG. 41b-sC1 | CGTGATAGAGTCTTCGCAT (SEQ ID NO: 255) |
| | TGAACGACGGAAATTGTGC ttcttcttcttcttcttc |
| | TGGTCTACTATCCACGATTTAAC (SEQ ID NO: 256) |
| FIG. 41b-sP2 | ATGCGAAGACTCTATCACG gaagaagaagaagaagaa |
| FIG. 41b-sC2 | GGCTGAACGTAACTCCTCG (SEQ ID NO: 257) |
| | GCTATCTTCAACCTTCTGG ttcttcttcttcttcttcttc |
| | GCACAATTTCCGTCGTTCA (SEQ ID NO: 258) |
| FIG. 41b-tP | CGAGGAGTTACGTTCAGCC gaagaagaagaa (SEQ ID NO: 259) |
| FIG. 41b-tC | ctttatttcttcttcttcttcttc CCAGAAGGTTGAAGATAGC (SEQ ID NO: 260) |

Example 8

M-Probe Design and Validation. FIG. 11A shows the general structure and construction of an M-Probe for direct detection of a target nucleic acid sequence. An M-Probe consists of a left universal segment u, n internal segments labeled $s_1$ through $s_n$, and a right termination segment t. In the termination segment t, the upper oligo is shorter than the lower oligo by a number of nucleotides; the single-stranded nucleotides on the right-most lower strand is referred to as the toehold. Zhang, D. Y. & Winfree, E. Control of DNA strand displacement kinetics using toehold exchange. *J Am Chem Soc,* 131, 17303-17314 (2009).

Each segment consists of two oligonucleotides hybridized to each other via a horizontal region; in the s and t segments, these horizontal regions' sequences are target-specific.

Throughout this paper, the lower oligonucleotides have sequence complementary to subsequences of the target, and the upper oligonucleotides have sequence identical to subsequences of the target. Different segments are hybridized to each other via two vertical "arms" with sequences independent of the target. For efficient formulation, every arm has a unique sequence that is in silico designed to be orthogonal to each other and also unlikely to bind to the human genome.

Following the hybridization reaction with the target sequence, the upper M-Probe oligos are released as a multi-stranded complex (FIG. 11B). Afterwards, the released multi-stranded complex can re-associate with the product and induce the reverse reaction. This reaction reversibility allows the hybridization between the target and M-Probe to be selective regardless of the length of the target, following principles described in ref. Zhang, D. Y., Chen, S. X. & Yin, P. Thermodynamic optimization of nucleic acid hybridization specificity. *Nat Chem*, 4, 208-214 (2012). (see FIGS. 16-23D and descriptions for design details). FIG. 11C shows the fluorescence response of a sequence-selective n=1 M-Probe to its target, a 43 nt sequence, as well as two single-nucleotide variants of the target. Simultaneously, the M-Probe is not poisoned by long-lived reaction intermediates with the variants, as addition of target at 2 hr results in an immediate and strong fluorescence response.

Example 9

Programmed Sequence Variation Tolerance. One technical challenge for many hybridization-based enrichment and detection methods is to tolerate potential single-nucleotide polymorphisms (SNPs) at known locations. Inherited SNPs are frequent in the human genome, with literature reporting SNP frequencies of roughly 1 per 1000 nt in the average human. International HapMap Consortium, et al. A second generation human haplotype map of over 3.1 million SNPs. *Nature*, 449, 851-861 (2007). Many SNPs are intronic or synonymous mutations with no effect on protein sequence, but may interfere with hybridization probe detection or enrichment due to their close proximity to clinically or scientifically important sequence variations. As one example, rs1050171 is a synonymous SNP in the EGFR gene (c.2361G>A) with a 43% allele frequency in the human population; it is 8 nucleotides away from the c.2369C>T (T790M) mutation that confers resistance to the cancer drug erlotinib. The 1000 Genomes and dbSNP databases provide sequence, position, and frequency information for SNPs with allele frequencies of 0.5% or higher in the human genome. 1000 Genomes Project Consortium, A global reference for human genetic variation. Nature, 526, 68-74 (2015); Sherry, S. T., et al. dbSNP: the NCBI database of genetic variation. *Nucleic Acids Res*, 29, 308-311 (2001).

Figure 12B:
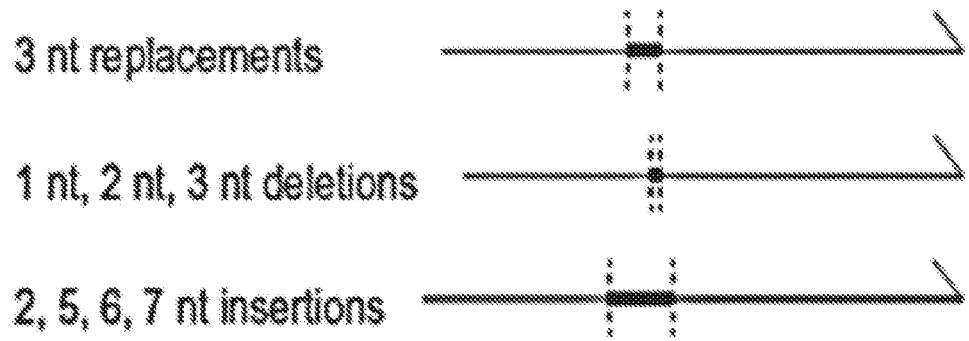
FIG. 12B depicts 10 tolerated variations.
Figure 12C:
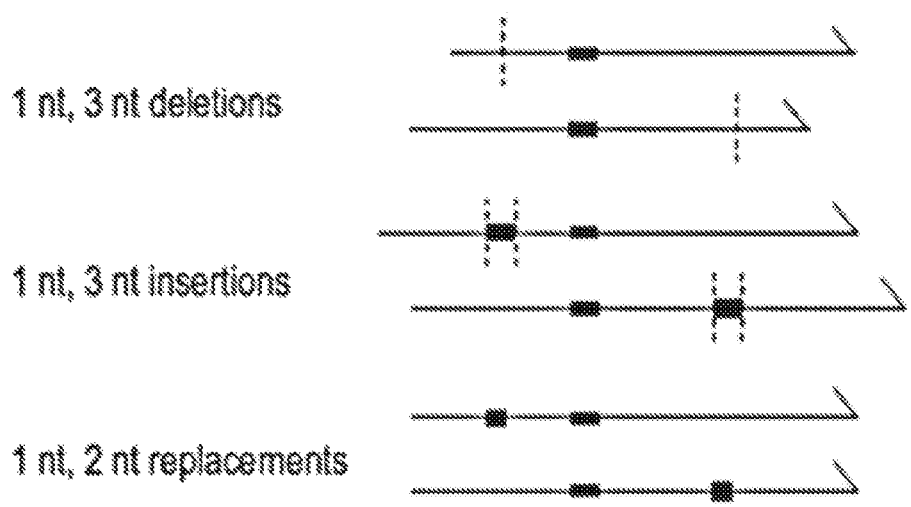
FIG. 12C depicts 12 non-tolerated variations.
Figure 12D:
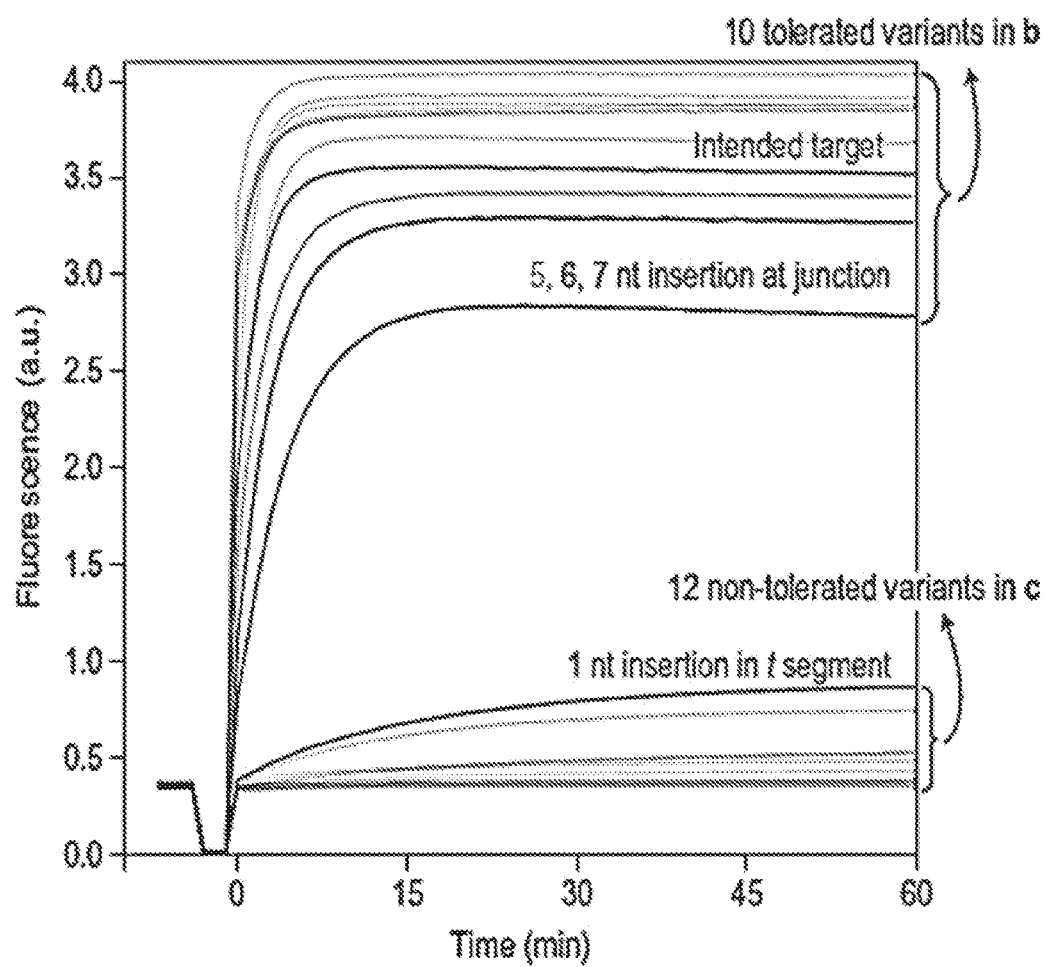
FIG. 12D shows the fluorescence response of targets with variations of up to 7 nucleotides.

FIG. 12A shows that the M-Probe may be designed such that a number of nucleotides in the intended target are at the segment junction and do not hybridize to any nucleotides in the M-Probe (green region). Sequence variations in this "tolerant" region have small effect on the $\Delta G°$ of hybridization reaction with the M-Probe. In contrast, even single nucleotide variants in other regions lead to large changes in reaction $\Delta G°$, resulting in significantly lower binding yield. FIG. 12D shows that using the same M-Probe, the fluorescence response of targets with tolerated variations of up to 7 nt are not significantly reduced below that of the intended target. Non-tolerated variants, on the other hand, show sharply reduced hybridization yield, even for 1 nt deletion, insertions, and replacements. The M-Probe uniquely offers tolerance to sequence variations at the segment junctions (FIG. 12A); sequence changes, insertions, and deletions at these positions have only a small to insignificant effect on the overall hybridization reaction standard free energy. In contrast, target sequence variations at positions that hybridize to the segments result in bulges or mismatch bubbles that destabilize the hybridization product and render $\Delta G°_{Hyb}$ significantly more positive as compared to the intended target sequence, resulting in lower hybridization yield and fluorescence. Experimentally, we observe that up to 7 nt variations at the segment junctions have little impact on M-Probe hybridization yield (FIGS. 12B and 12D), but even single nucleotide variants in the segments $s_i$ and t result in severe reduction of binding yield (FIGS. 12C and 12D). For targets with known potential variations at particular loci, the M-Probe can be designed so that these loci correspond to the segment junctions. In some embodiments, a segment junction can span at least 1, 2, 3, 4, 5, 6, 7, 8, 9, 10, 15, 20, 25, 30, 35, 40, 45, 50, 60, 70, 80, 90 or 100 nucleotides. In some embodiments, a segment junction can span from any one of 1, 2, 3, 4, 5, 6, 7, 8, 9, 10, 15, 20, 25, 30, 35, 40, 45, 50, 60, 70, 80, and 90 to any one of 100, 90, 80, 70, 60, 50, 45, 40, 35, 30, 25, 20, 15, 10, 9, 8, 7, 6, 5, 4, 3, 2, and 1 nucleotides. There is significant sequence variability in terms of number of nucleotides of insertion tolerated due to varying secondary structures. We believe, based on our experiments and published thermodynamic parameters, that a large majority of 7 nt insertions should be tolerated. However, there is no hard maximum on the number of insertion nucleotides tolerated—for example, a favorable target sequence bearing a 100 nt insertion that forms a perfect hairpin would likely still be tolerated.

Example 10

Figure 13A:
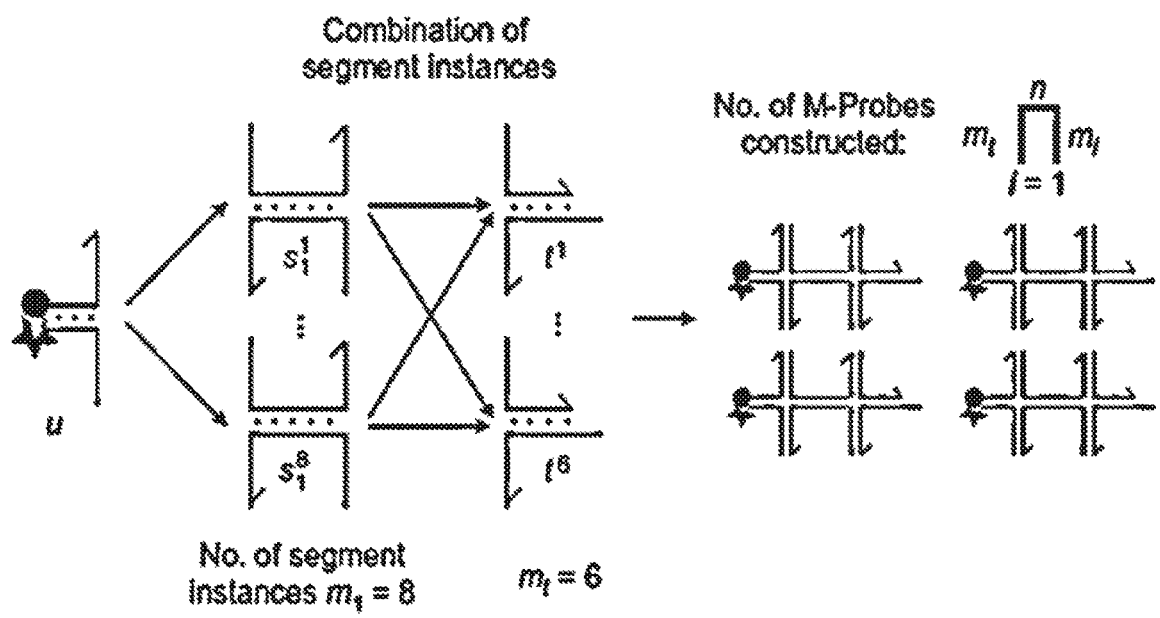
FIG. 13A depicts a combination of segment instances demonstrating combinatorial construction of M-probes for VDJ recombination detection.

Combinatorial M-Probe Formation. Another feature of the modular construction of the M-Probe is that multiple different internal segments can be combinatorially combined to generate many different M-Probes to different target sequences (FIG. 13A). FIG. 13A shows that each target-specific segment can be chosen from a number of modules ($m_i$). Pairwise combination of modules of adjacent segments allows construction of large number of probes targeting different targets by using limited number of component strands. Given $m_i$ instances for each segment $s_i$, the total number of M-Probes that can be constructed is:

$$\text{Num. unique } M\text{-Probes} = m_t \cdot \Pi_{i=1}^{n} m_i$$

where $m_t$ is the number of instances of the terminal segment t. The number of oligonucleotides used to construct these, in contrast, scales with the sum of $m_i$:

$$\text{Num. oligonucleotides} = 2 \cdot (1 + m_t + \Sigma_{i=1}^{n} m_i)$$

Figure 13B:
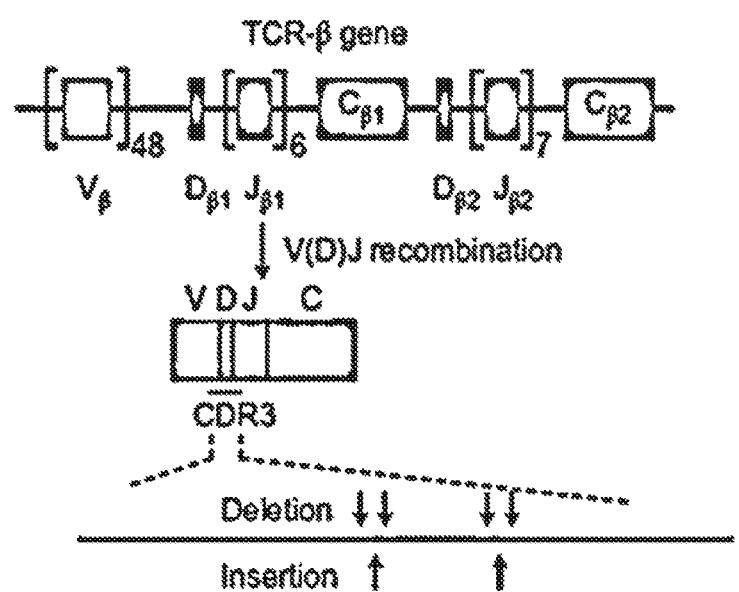
FIG. 13B depicts the Human TCR-β gene VDJ recombination process.

For large n and $m_i$ values, combinatorial formulation significantly reduces the number of oligonucleotides needed to detect or enrich sequences. In human T cells, the TCRβ gene undergoes VDJ recombination in which 1 V, 1 D, and 1 J gene region are selected from 48 V, 2 D, and 13 J genes segments, respectively (FIG. 13B). FIG. 13B shows that recombination occurs between 48 TRB V (blue), 2 TRB D (green), and 13 TRBJ genes (orange), followed by random deletions and non-templated insertions at the V-D and D-J junctions, resulting a hypervariable CDR3 that is important for antigen recognizing. Random deletions and non-templated insertions occur at the V-D and D-J junctions to provide further T-cell receptor diversity to facilitate recognition of diverse antigens. Combinatorially formulated M-Probes that tolerate sequence variation at the VDJ junction thus are well-suited for hybridization-based detection and enrichment of the recombined TCRβ gene.

Figure 13C:
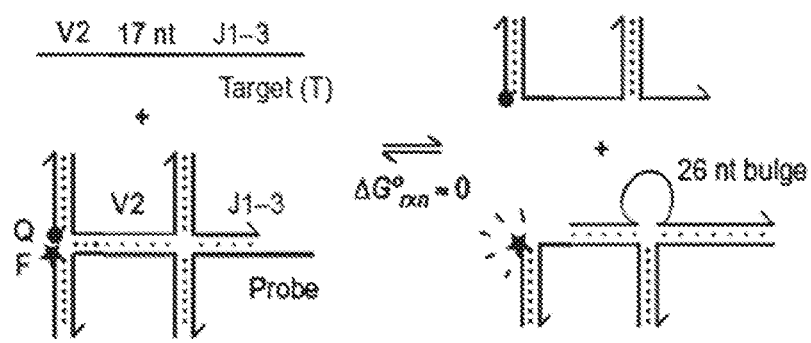
FIG. 13C depicts an exemplary hybridization reaction between an M-probe and a matched target sequence bearing the V2 and J1-3 regions.
Figure 13D:
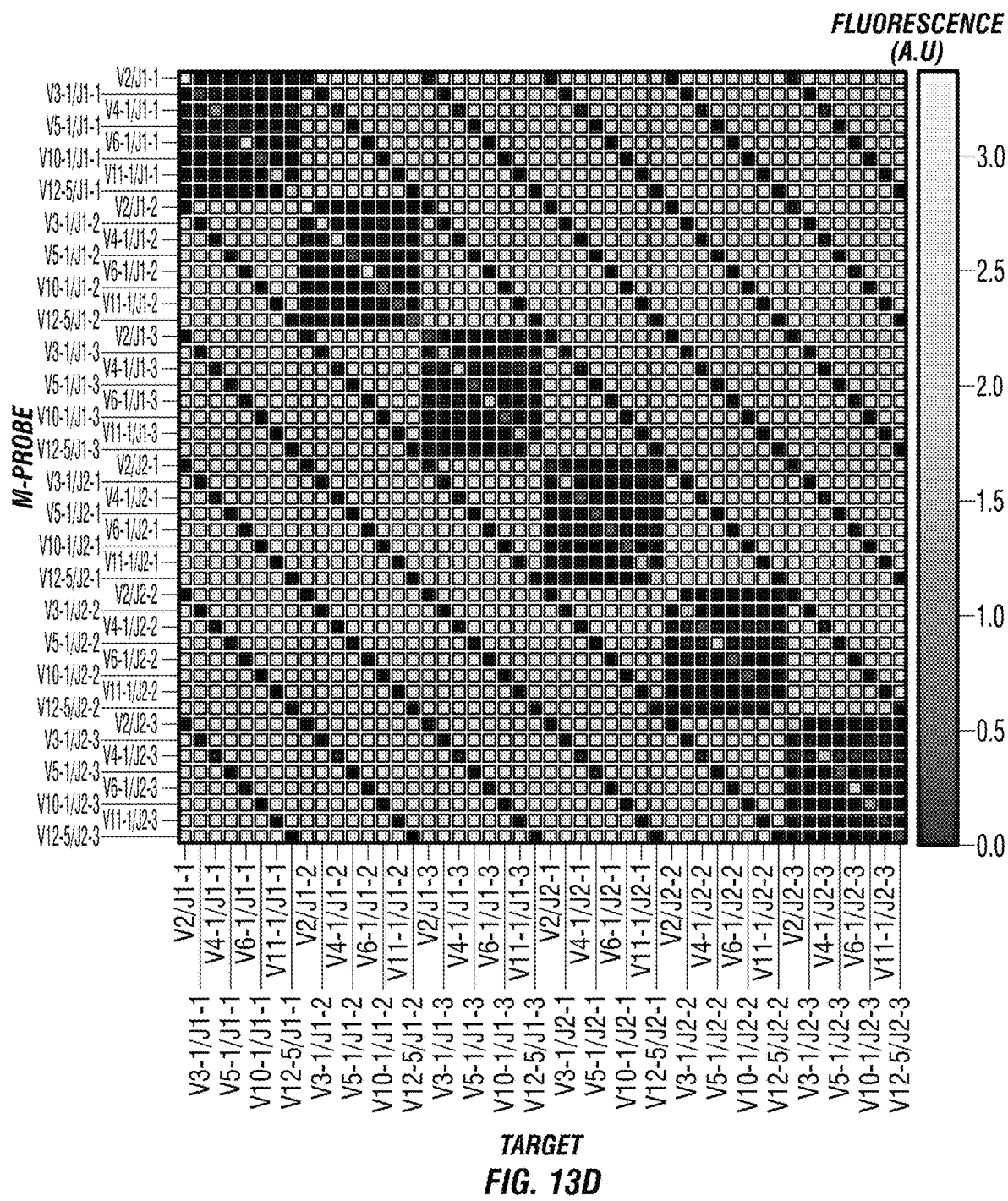
FIG. 13D shows the observed fluorescence for the M-probes after an overnight hybridization reaction.

Because of the short length and high sequence variability in the D gene region, we elected to consider the entire D region as variable, and designed the M-Probes to be n=1, with the $s_l$ segment corresponding to the V region and the t segment corresponding to the J region. The bulge formed upon binding an M-Probe to its intended target varies in length between 8 and 32 nt. $m_l=8$ and $m_t=6$ different instances of the $s_l$ and t segments were designed, allowing the detection of 48 combinatorially recombined VDJ sequences (FIG. 13C). FIG. 13C shows that the hypervariable sequence between V and J forms a bulge structure after hybridization with the M-Probe, with bulge size ranging between 8 and 32 nt. In FIG. 13D, the main diagonal corresponds to on-target hybridization in which the V and J regions of the target are matched to the M-Probe segments, and off-diagonal blue squares correspond to hybridization reactions in which one of the V and the J regions differs between the M-Probe and the target. Hybridization reactions in which the target and M-Probe differs in both the V and the J regions were not tested (grey squares). All experiments were performed in triplicate at 37° C. in 1×PBS, [M-Probe] =100 nM, [Target]=300 nM. See FIGS. 25-30B and accompanying text for M-Probe design details. FIG. 13D shows a summary of the hybridization between 48 TCRβ sequence targets and the 48 M-Probes. The main diagonal corresponds to endpoint fluorescence of the 48 on-target hybridization reactions in which the target perfectly matches the M-Probe in identity of the $s_l$ and t regions (see descriptions accompanying FIGS. 31A-32B for data acquisition details). The dark blue off-diagonal squares correspond to 576 off-target hybridization reactions in which the target matches the M-Probe in the identity of one of $s_l$ or t, but not both. Grayed square denote combinations in which both the $s_l$ and the t segments of the M-Probe are mismatched to the target, and were not tested as they were judged to be unlikely to yield a significant hybridization response.

Figure 13E:
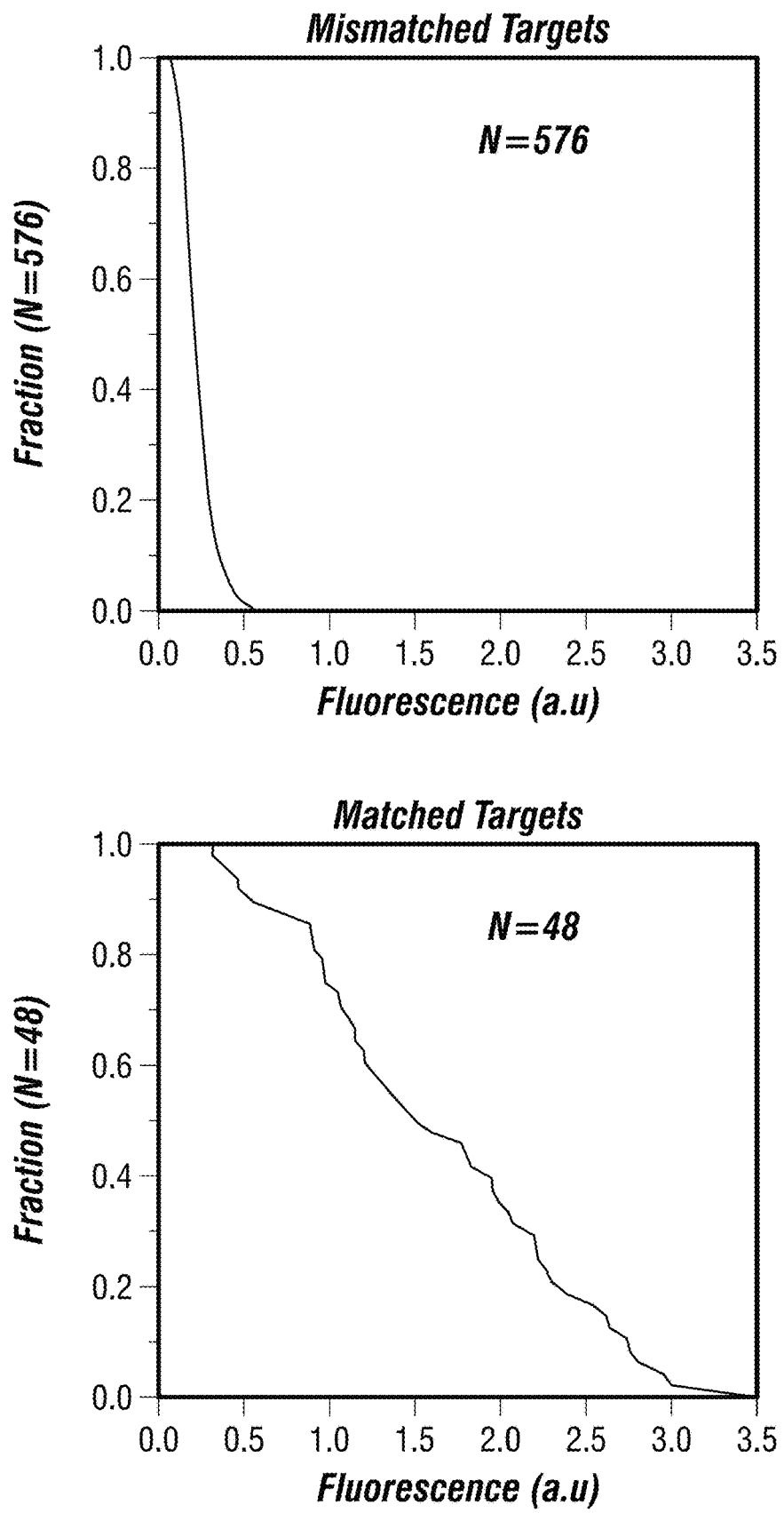
FIG. 13E depicts the distribution of observed off-target fluorescence (left) and on-target fluorescence (right).

Of the 624 hybridization reactions experimentally characterized, all off-target hybridization experiments generated less than 0.6 a.u. of fluorescence, while 43 (90%) of the on-target hybridization generated more than 0.6 a.u. of fluorescence, and 30 (63%) generated more than 1.2 a.u. of fluorescence (FIG. 13E). Thus, the predominant failure mode appears to be that a fraction of the M-Probes fail to hybridize significantly with their matched target sequences. Possible reasons for underperformance include unfavorable hybridization thermodynamics due to inaccurate estimates of the destabilizing effect of large bulges and slow hybridization kinetics due to secondary structure in the target sequence. Empirical optimization of M-Probe sequence design may overcome thermodynamics errors, and operation of M-Probes at higher temperatures may accelerate hybridization kinetics.

Therefore, the present invention is well adapted to attain the ends and advantages mentioned as well as those that are inherent therein. While numerous changes may be made by those skilled in the art, such changes are encompassed within the spirit of this invention as illustrated, in part, by the appended claims.

The foregoing description of specific embodiments of the present disclosure has been presented for purpose of illustration and description. The exemplary embodiments were chosen and described in order to best explain the principles of the disclosure and its practical application, to thereby enable others skilled in the art to best utilize the subject matter and various embodiments with various modifications are suited to the particular use contemplated. Different features and disclosures of the various embodiments within the present disclosure may be combined within the scope of the present disclosure.

| SEQUENCE LISTING | | |
|---|---|---|
| SEQ ID No. | Seq Name | Sequence |
| 1 | XP-F | GTTAAATCGTGGATAGTAGAC TTCGCAC /3Rox_N/ |
| 2 | XP-Q | /5IAbRQ/ GTGCGAA CAGGTACATTTGCTCGTCCTT |
| 3 | KRAS-1-Pss1 | AAG GAC GAG CAA ATG TAC CTG CAA TGA CTG AAT ATA AAC TTG TGG TAG TTG GAG CTG GTG GCG TAG GCA AGC GTG ATA GAG TCT TCG CAT |
| 4 | KRAS-1-Css1 | TGA ACG ACG GAA ATT GTG CCT TGC CTA CGC CAC CAG CTC CAA CTA CCA CAA GTT TAT ATT CAG TCA TTG GTC TAC TAT CCA CGA TTT AAC |
| 5 | KRAS-1-Pend-2AP | ATG CGA AGA CTC TAT CAC GGT GCC TTG ACG ATA CAG CTA ATT CAG AAT CAT TTT GTG |
| 6 | KRAS-1-Cend-2AP | ATC ATA TTC GTC CAC AAA ATG ATT CTG AAT TAG CTG TAT CGT CAA GGC ACG CAC AAT TTC CGT CGT TCA |
| 7 | KRAS-1-Pss2 | ATG CGA AGA CTC TAT CAC GGT GCC TTG ACG ATA CAG CTA ATT CAG AAT CAT TTT GTG GAC GAA TAT GAT GGC TGA ACG TAA CTC CTC G |
| 8 | KRAS-1-Css2 | GCT ATC TTC AAC CTT CTG GAT CAT ATT CGT CCA CAA AAT GAT TCT GAA TTA GCT GTA TCG TCA AGG CAC GCA CAA TTT CCG TCG TTC A |
| 9 | KRAS-1-Pend-AP3-t1 | CGA GGA GTT ACG TTC AGC CCA ACA ATA GAG GAT TCC TAC AGG AAG CAA GTA GTA ATT GAT GGA G |

SEQUENCE LISTING

| SEQ ID No. | Seq Name | Sequence |
|---|---|---|
| 10 | KRAS-1-Cend-AP3 | CCA AGA GAC AGG TTT CTC CAT CAA TTA CTA CTT GCT TCC TGT AGG AAT CCT CTA TTG TTG CCA GAA GGT TGA AGA TAG C |
| 11 | HTT-T6 | CAG CAG CAG CAG CAG CAG CAA CAG CC |
| 12 | HTT-T9 | CAG CAG CAG CAG CAG CAG CAG CAG CAG CAA CAG CC |
| 13 | HTT-T12 | CAG CAG CAG CAG CAG CAG CAG CAG CAG CAG CAG CAG CAA CAG CC |
| 14 | HTT-T15 | CAG CAG CAG CAG CAG CAG CAG CAG CAG CAG CAG CAG CAG CAG CAG CAA CAG CC |
| 15 | HTT-T18 | CAG CAG CAG CAG CAG CAG CAG CAG CAG CAG CAG CAG CAG CAG CAG CAG CAG CAA CAG CC |
| 16 | HTT-T21 | CAG CAG CAG CAG CAG CAG CAG CAG CAG CAG CAG CAG CAG CAG CAG CAG CAG CAG CAG CAA CAG CC |
| 17 | HTT-T24 | CAG CAG CAG CAG CAG CAG CAG CAG CAG CAG CAG CAG CAG CAG CAG CAG CAG CAG CAG CAG CAG CAG CAA CAG CC |
| 18 | HTT-T27 | CAG CAG CAG CAG CAG CAG CAG CAG CAG CAG CAG CAG CAG CAG CAG CAG CAG CAG CAG CAG CAG CAG CAG CAG CAG CAA CAG CC |
| 19 | HTT-6s-Pend-ex | AAG GAC GAG CAA ATG TAC CTG CAC AGC AGC AGC AGC AGC AGC |
| 20 | HTT-6s-Cend | GGC TGT TGC TGC TGC TGC TGC TGC TGT GGT CTA CTA TCC ACG ATT TAA C |
| 21 | HTT-9s-Pend-ex | AAG GAC GAG CAA ATG TAC CTG CAC AGC AGC AGC AGC AGC AGC AGC AGC AGC |
| 22 | HTT-9s-Cend | GGC TGT TGC TGC TGC TGC TGC TGC TGC TGC TGC TGT GGT CTA CTA TCC ACG ATT TAA C |
| 23 | HTT-s-Pss1 | AAG GAC GAG CAA ATG TAC CTG CAC AGC AGC AGC AGC AGC AGC GTG ATA GAG TCT TCG CAT |
| 24 | HTT-s-Css1 | TGA ACG ACG GAA ATT GTG CCT GCT GCT GCT GCT GCT GTG GTC TAC TAT CCA CGA TTT AAC |
| 25 | HTT-12s-Pend-ex | ATG CGA AGA CTC TAT CAC GAG CAG CAG CAG CAG CAG C |
| 26 | HTT-12s-Cend | GGC TGT TGC TGC TGC TGC TGC TGC TGC ACA ATT TCC GTC GTT CA |
| 27 | HTT-15s-Pend-ex | ATG CGA AGA CTC TAT CAC GAG CAG CAG CAG CAG CAG CAG CAG C |
| 28 | HTT-15s-Cend | GGC TGT TGC TGC TGC TGC TGC TGC TGC TGC TGC ACA ATT TCC GTC GTT CA |
| 29 | HTT-s-Pss2 | ATG CGA AGA CTC TAT CAC GAG CAG CAG CAG CAG CAG CAG GGC TGA ACG TAA CTC CTC G |
| 30 | HTT-s-Css2 | GCT ATC TTC AAC CTT CTG GCT GCT GCT GCT GCT GCT GCT GCA CAA TTT CCG TCG TTC A |
| 31 | HTT-18s-Pend-ex | CGA GGA GTT ACG TTC AGC CAG CAG CAG CAG CAG C |
| 32 | HTT-18s-Cend | GGC TGT TGC TGC TGC TGC TGC TGC TCC AGA AGG TTG AAG ATA GC |
| 33 | HTT-21s-Pend-ex | CGA GGA GTT ACG TTC AGC CAG CAG CAG CAG CAG CAG CAG CAG C |

SEQUENCE LISTING

| SEQ ID No. | Seq Name | Sequence |
|---|---|---|
| 34 | HTT-21s-Cend | GGC TGT TGC TGC TGC TGC TGC TGC TGC TGC TCC AGA AGG TTG AAG ATA GC |
| 35 | HTT-s-Pss3 | CGA GGA GTT ACG TTC AGC CAG CAG CAG CAG CAG CAG CGT TCT ACC TCA GGT GTT C |
| 36 | HTT-s-Css3 | CTG ATG CAC TTA GAG TGA GCC TGC TGC TGC TGC TGC TCC AGA AGG TTG AAG ATA GC |
| 37 | HTT-24s-Pend | GAA CAC CTG AGG TAG AAC GAG CAG CAG CAG CAG |
| 38 | HTT-24s-Cend | GGC TGT TGC TGC TGC TGC TGC TGC TCA CTC TAA GTG CAT CAG |
| 39 | HTT-27s-Pend | GAA CAC CTG AGG TAG AAC GAG CAG CAG CAG CAG CAG CAG CAG |
| 40 | HTT-27s-Cend | GGC TGT TGC TGC TGC TGC TGC TGC TGC TGC TGC TCA CTC TAA GTG CAT CAG |
| 41 | KRAScDNA-gBlock | TATAAGGCCTGCTGAAAATGACTGAATATAAACTTGTG GTAGTTGGAGCTGGTGGCGTAGGCAAGAGTGCCTTGAC GATACAGCTAATTCAGAATCATTTTGTGGACGAATATG ATCCAACAATAGAGGATTCCTACAGGAAGCAAGTAGTA ATTGATGGAGAAACCTGTCTCTTGGATATTCTCGACACA GCAGGTCAAGAGGAGTACAGTGCAATGAGGGACCAGT ACATGAGGACTGGGGAGGGCTTTCTTTGTGTATTTGCCA TAATAATACTAAATCATTTGAAGATATTCACCATTATA GAGAACAAATTAAAAGAGTTAAGGACTCTGAAGATGTA CCTATGGTCCTAGTAGGAAATAAATGTGATTTGCCTTCT AGAACAGTAGACACAAAACAGGCTCAGGACTTAGCAA GAAGTTATGGAATTCCTTTTATTGAAACATCAGCAAAG ACAAGACAGGGTGTTGATGATGCCTTCTATACATTAGTT CGAGAAATTCGAAAACATAAAGAAAAGATGAGCAAAG ATGGTAAAAAGAAGAAAAAGAAGTCAAAGACAAAGTG TGTAATTATGTAAATACAATTTGTACTTTTTTCTTAAGG CATACTAGTACAAGTGG |
| 42 | KRAS-full-fP1 | TATAAGGCCTGCTGAAAATGACT |
| 43 | KRAS-AP3-rP | ATCCAAGAGACAGGTTTCTCCA |
| 44 | HTTU27 | TGGAAAAGCTGATGAAGGCCTTCGAGTCCCTCAAGTCC TTCCAGCAGCAGCAGCAGCAGCAGCAGCAGCAGCAGCA GCAGCAGCAGCAGCAGCAGCAGCAGCAGCAGCAGCAG CAGCAGCAGCAACAGCCGCCACCGCCGCCGCCGCCGCC GCCGCCTCCTCAGCTTCCTCAG |
| 45 | HTT-FPnew1 | TCGAGTCCCTCAAGTCCTTC |
| 46 | HTT-rpn4 | GGTGGCGGCTGTTG |

What is claimed is:

1. A nucleic acid hybridization probe for sequence-selective binding of a target nucleic acid sequence, said target nucleic acid sequence comprising in 5' to 3' order a first region and a second region, said nucleic acid hybridization probe comprising
   a first Complement Oligonucleotide comprising
      in 5' to 3' order a fourth region and a fifth region, the fifth region being complementary in sequence to the first region,
   a second Complement Oligonucleotide comprising
      in 5' to 3' order a seventh region, and an eighth region, the seventh region being complementary to the second region, and the eighth region being complementary to the fourth region, and
   a first Protector Oligonucleotide comprising a ninth region, the ninth region being either (a) complementary to the fifth region and homologous to the first region or (b) complementary to the seventh region and homologous to the second region.

2. The nucleic acid hybridization probe of claim 1, wherein the target nucleic acid sequence further comprises a third region to the 5' end of the first region, and wherein the first Complement Oligonucleotide further comprises a sixth region to the 3' end of the fifth region, the sixth region being complementary to the third region.

3. The nucleic acid hybridization probe of claim 1, wherein the target nucleic acid sequence further comprises a third region to the 3' end of the second region, and wherein the second Complement Oligonucleotide further comprises a sixth region to the 5' end of the seventh region, the sixth region being complementary to the third region.

4. The nucleic acid hybridization probe of claim 1, wherein the ninth region is complementary to the fifth region and homologous to the first region, and wherein the nucleic acid hybridization probe further comprises a second Protector Oligonucleotide comprising a tenth region, the tenth region being complementary to the seventh region and homologous to the second region.

5. The nucleic acid hybridization probe of claim 4, wherein the first Protector Oligonucleotide further comprises an eleventh region, and wherein the second Protector Oligonucleotide further comprises a twelfth region, the twelfth region being complementary to the eleventh region.

6. The nucleic acid hybridization probe of claim 1, wherein the first Complement Oligonucleotide or second Complement Oligonucleotide is functionalized with a moiety for capture or detection.

7. The nucleic acid hybridization probe of claim 1, wherein the first Complement Oligonucleotide further comprises a sixteenth region, and wherein the nucleic acid hybridization probe further comprises a first Universal Oligonucleotide, the first Universal Oligonucleotide comprising a fifteenth region, the fifteenth region being complementary to the sixteenth region.

8. The nucleic acid hybridization probe of claim 7, wherein the first Universal Oligonucleotide is functionalized with a moiety for capture or detection.

9. The nucleic acid hybridization probe of claim 1, wherein the first Protector Oligonucleotide further comprises a fourteenth region, and wherein the nucleic acid hybridization probe further comprises a second Universal Oligonucleotide, the second Universal Oligonucleotide comprising a thirteenth region, the thirteenth region being complementary to the fourteenth region.

10. The nucleic acid hybridization probe of claim 9, wherein the second Universal Oligonucleotide is functionalized with a moiety for capture or detection.

11. The nucleic acid hybridization probe of claim 7, wherein the first Protector Oligonucleotide further comprises a fourteenth region, and wherein the nucleic acid hybridization probe further comprises a second Universal Oligonucleotide, the second Universal Oligonucleotide comprising a thirteenth region, the thirteenth region being complementary to the fourteenth region.

12. The nucleic acid hybridization probe of claim 11, wherein the first Universal Oligonucleotide and/or the second Universal Oligonucleotide are functionalized with a moiety for capture or detection.

13. The nucleic acid hybridization probe of claim 1, wherein the target nucleic acid sequence contains a trinucleotide repeat sequence, and wherein the first Complement Oligonucleotide and the second Complement Oligonucleotide collectively span a repeat threshold, wherein the target efficiently binds to the nucleic acid hybridization probe only when the target nucleic acid sequence's trinucleotide repeat number is equal to or in excess of the repeat threshold.

14. A solution comprising the nucleic acid hybridization probe of claim 1, wherein the concentration of the first Protector Oligonucleotide is between 1.01 times and 10,000 times the concentration of the first Complement Oligonucleotide.

15. A solution comprising the nucleic acid hybridization probe of claim 1, wherein the concentration of the second Complement Oligonucleotide is between 0.1 times and 10 times the concentration of the first Complement Oligonucleotide.

16. A process of formulating the nucleic acid hybridization probe of claim 1, comprising:
selecting a first Complement Oligonucleotide from a pool of first Complement Oligonucleotide candidates;
selecting a second Complement Oligonucleotide from a pool of second Complement Oligonucleotide candidates;
selecting a first Protector Oligonucleotide from a pool of first Protector Oligonucleotide candidates;
combining the first Complement Oligonucleotide, the second Complement Oligonucleotide, and the first Protector Oligonucleotide in aqueous solution;
reacting the solution in temperature and buffer conditions conducive to DNA hybridization.

17. A process of formulating multiple nucleic acid hybridization probes, comprising:
formulating a first nucleic acid hybridization probe through the process of claim 16 to yield a first nucleic acid hybridization probe solution;
formulating a second nucleic acid hybridization probe through the process of claim 16 to yield a second nucleic acid hybridization probe solution, wherein the fourth region of the second nucleic acid hybridization probe is identical in sequence to the fourth region of the first nucleic acid hybridization probe, and wherein the eighth region of the second nucleic acid hybridization probe is identical in sequence to the eighth region of the first nucleic acid hybridization probe; and
combining the first nucleic acid hybridization probe solution and the second nucleic acid hybridization probe solution in temperature and buffer conditions that are not conducive to dissociation of the hybridized duplex formed by the fourth and eighth regions of each of the first nucleic acid hybridization probe and the second nucleic acid hybridization probe.

18. A method for detecting a DNA or RNA target nucleic acid sequence from a sample, wherein the target nucleic acid sequence comprises in 5' to 3' order a first region and a second region, the method comprising:
contacting the sample with a nucleic acid hybridization probe, wherein the nucleic acid hybridization probe comprises:
a first Complement Oligonucleotide comprising:
in 5' to 3' order a fourth region and a fifth region, wherein the fifth region is complementary in sequence to the first region;
a second Complement Oligonucleotide comprising:
in 5' to 3' order a seventh region and an eighth region, wherein the seventh region is complementary in sequence to the second region, and wherein the eighth region is complementary to the fourth region; and
a first Protector Oligonucleotide comprising a ninth region, wherein the ninth region is either (a) complementary to the fifth region and homologous to the first region or (b) complementary to the seventh region and homologous to the second region.

19. A method for quantifying triplet repeat numbers in a DNA or RNA target nucleic acid sequence from a sample known to comprise a DNA or RNA target nucleic acid sequence, the method comprising:
dividing the sample into at least three aliquots;
contacting each aliquot with a nucleic acid hybridization probe of claim 13 wherein the nucleic acid hybridization probe for each aliquot has a different repeat threshold;
observing the binding yield for each aliquot;
determining or constraining target sequence numbers from relative binding yields of the aliquots to the different probes.

* * * * *

SEQUENCE LISTING

<160> NUMBER OF SEQ ID NOS: 286

<210> SEQ ID NO 1
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1
gttaaatcgt ggatagtaga cttcgcac         28

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gtgcgaacag gtacatttgc tcgtcctt                                         28

<210> SEQ ID NO 3
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
aaggacgagc aaatgtacct gcaatgactg aatataaact tgtggtagtt ggagctggtg      60
gcgtaggcaa gcgtgataga gtcttcgcat                                       90

<210> SEQ ID NO 4
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tgaacgacgg aaattgtgcc ttgcctacgc caccagctcc aactaccaca agtttatatt      60 cagtcattg tctactatcc acgatttaac                                        90

<210> SEQ ID NO 5
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
atgcgaagac tctatcacgg tgccttgacg atacagctaa ttcagaatca ttttgtg        57

<210> SEQ ID NO 6
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
atcatattcg tccacaaaat gattctgaat tagctgtatc gtcaaggcac gcacaatttc      60
cgtcgttca                                                              69

<210> SEQ ID NO 7
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
atgcgaagac tctatcacgg tgccttgacg atacagctaa ttcagaatca ttttgtggac    60
gaatatgatg gctgaacgta actcctcg                                      88

<210> SEQ ID NO 8
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gctatcttca accttctgga tcatattcgt ccacaaaatg attctgaatt agctgtatcg    60
tcaaggcacg cacaatttcc gtcgttca                                      88

<210> SEQ ID NO 9
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
cgaggagtta cgttcagccc aacaatagag gattcctaca ggaagcaagt agtaattgat    60
ggag                                                                64

<210> SEQ ID NO 10
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ccaagagaca ggtttctcca tcaattacta cttgcttcct gtaggaatcc tctattgttg    60
ccagaaggtt gaagatagc                                                79

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
cagcagcagc agcagcagca acagcc                                        26

<210> SEQ ID NO 12
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
cagcagcagc agcagcagca gcagcagcaa cagcc                              35

```
<210> SEQ ID NO 13
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
cagcagcagc agcagcagca gcagcagcag cagcagcaac agcc              44

<210> SEQ ID NO 14
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
cagcagcagc agcagcagca gcagcagcag cagcagcagc agcagcaaca gcc     53

<210> SEQ ID NO 15
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
cagcagcagc agcagcagca gcagcagcag cagcagcagc agcagcagca gcagcaacag    60
cc                                                                   62

<210> SEQ ID NO 16
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
cagcagcagc agcagcagca gcagcagcag cagcagcagc agcagcagca gcagcagcag    60
cagcaacagc c                                                         71

<210> SEQ ID NO 17
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
cagcagcagc agcagcagca gcagcagcag cagcagcagc agcagcagca gcagcagcag    60
cagcagcagc agcaacagcc                                                80

<210> SEQ ID NO 18
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 18
cagcagcagc agcagcagca gcagcagcag cagcagcagc agcagcagca gcagcagcag    60
cagcagcagc agcagcagca gcaacagcc                                     89

<210> SEQ ID NO 19
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
aaggacgagc aaatgtacct gcacagcagc agcagcagca gc                       42

<210> SEQ ID NO 20
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ggctgttgct gctgctgctg ctgctgtggt ctactatcca cgatttaac                49

<210> SEQ ID NO 21
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
aaggacgagc aaatgtacct gcacagcagc agcagcagca gcagcagcag c             51

<210> SEQ ID NO 22
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ggctgttgct gctgctgctg ctgctgctgc tgctgtggtc tactatccac gatttaac      58

<210> SEQ ID NO 23
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
aaggacgagc aaatgtacct gcacagcagc agcagcagca gcgtgataga gtcttcgcat    60

<210> SEQ ID NO 24
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 24
tgaacgacgg aaattgtgcc tgctgctgct gctgctgtgg tctactatcc acgatttaac    60

<210> SEQ ID NO 25
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
atgcgaagac tctatcacga gcagcagcag cagcagc    37

<210> SEQ ID NO 26
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
ggctgttgct gctgctgctg ctgctgcaca atttccgtcg ttca    44

<210> SEQ ID NO 27
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
atgcgaagac tctatcacga gcagcagcag cagcagcagc agcagc    46

<210> SEQ ID NO 28
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ggctgttgct gctgctgctg ctgctgctgc tgctgcacaa tttccgtcgt tca    53

<210> SEQ ID NO 29
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
atgcgaagac tctatcacga gcagcagcag cagcagcagg gctgaacgta actcctcg    58

<210> SEQ ID NO 30
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 30
gctatcttca accttctggc tgctgctgct gctgctgctg cacaatttcc gtcgttca        58

<210> SEQ ID NO 31
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
cgaggagtta cgttcagcca gcagcagcag cagc                                  34

<210> SEQ ID NO 32
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ggctgttgct gctgctgctg ctccagaagg ttgaagatag c                          41

<210> SEQ ID NO 33
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
cgaggagtta cgttcagcca gcagcagcag cagcagcagc agc                        43

<210> SEQ ID NO 34
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ggctgttgct gctgctgctg ctgctgctgc tccagaaggt tgaagatagc                 50

<210> SEQ ID NO 35
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
cgaggagtta cgttcagcca gcagcagcag cagcagcgtt ctacctcagg tgttc           55

<210> SEQ ID NO 36
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
```
ctgatgcact tagagtgagc ctgctgctgc tgctgctcca gaaggttgaa gatagc    56

<210> SEQ ID NO 37
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
gaacacctga ggtagaacga gcagcagcag cag    33

<210> SEQ ID NO 38
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
ggctgttgct gctgctgctg ctgctcactc taagtgcatc ag    42

<210> SEQ ID NO 39
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
gaacacctga ggtagaacga gcagcagcag cagcagcagc ag    42

<210> SEQ ID NO 40
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
ggctgttgct gctgctgctg ctgctgctgc tgctcactct aagtgcatca g    51

<210> SEQ ID NO 41
<211> LENGTH: 627
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
tataaggcct gctgaaaatg actgaatata aacttgtggt agttggagct ggtggcgtag    60
gcaagagtgc cttgacgata cagctaattc agaatcattt tgtggacgaa tatgatccaa    120
caatagagga ttcctacagg aagcaagtag taattgatgg agaaacctgt ctcttggata    180
ttctcgacac agcaggtcaa gaggagtaca gtgcaatgag ggaccagtac atgaggactg    240
gggagggctt tctttgtgta tttgccataa ataatactaa atcatttgaa gatattcacc    300
attatagaga acaaattaaa agagttaagg actctgaaga tgtacctatg gtcctagtag    360
gaaataaatg tgatttgcct tctagaacag tagacacaaa acaggctcag gacttagcaa    420

```
gaagttatgg aattcctttt attgaaacat cagcaaagac aagacagggt gttgatgatg    480
ccttctatac attagttcga gaaattcgaa aacataaaga aaagatgagc aaagatggta    540
aaaagaagaa aaagaagtca agacaaagt gtgtaattat gtaaatacaa tttgtacttt    600
tttcttaagg catactagta caagtgg                                         627
```

<210> SEQ ID NO 42
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42

```
tataaggcct gctgaaaatg act                                              23
```

<210> SEQ ID NO 43
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43

```
atccaagaga caggtttctc ca                                               22
```

<210> SEQ ID NO 44
<211> LENGTH: 173
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44

```
tggaaaagct gatgaaggcc ttcgagtccc tcaagtcctt ccagcagcag cagcagcagc     60
agcagcagca gcagcagcag cagcagcagc agcagcagca gcagcagcag cagcagcagc    120
agcaacagcc gccaccgccg ccgccgccgc cgccgcctcc tcagcttcct cag            173
```

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45

```
tcgagtccct caagtccttc                                                  20
```

<210> SEQ ID NO 46
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46

```
ggtggcggct gttg                                                        14
```

<210> SEQ ID NO 47
<211> LENGTH: 43
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 47
acgcagctaa tgccctcaga cagctttgac gtatgtgttt ctc        43

<210> SEQ ID NO 48
<211> LENGTH: 43
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 48
acgcagctaa ttccctcaga cagctttgac gtatgtgttt ctc        43

<210> SEQ ID NO 49
<211> LENGTH: 43
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 49
acgcagctaa tgccctcaga cagctttgac atatgtgttt ctc        43

<210> SEQ ID NO 50
<211> LENGTH: 61
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 50
aaggacgagc aaatgtacct gactacgcag ctaatgccct cgtgatagag tcttcgcatc        60
a        61

<210> SEQ ID NO 51
<211> LENGTH: 61
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 51
agtaacagac ggaaattgtg cagggcatta gctgcgtagt gtctactatc cacgatttaa        60
c        61

<210> SEQ ID NO 52
<211> LENGTH: 38
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 52

```
<210> SEQ ID NO 53
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
gagaaacaca tacgtcaaag ctgtctggca caatttccgt ctgttact                    48

<210> SEQ ID NO 54
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
gtgcgacgca gctaatgccc tcagacagct ttgacg                                 36

<210> SEQ ID NO 55
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
gagaaacaca tacgtcaaag ctgtctgagg gcattagctg cgtcgcac                    48

<210> SEQ ID NO 56
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
aaggacgagc aaatgtacct gactacgcag ctaatgccct cagacagctt tgacgta         57

<210> SEQ ID NO 57
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
gagaaacaca tacgtcaaag ctgtctgagg gcattagctg cgtagtgtct actatccacg      60
atttaac                                                                 67

<210> SEQ ID NO 58
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
```

```
atgtcaagat cacagatttt gggcgggcca                                              30
```

<210> SEQ ID NO 59
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59

```
atgtcaagat cacagatttt gggctggcca                                              30
```

<210> SEQ ID NO 60
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60

```
gtgcgcaggt acatttgctc gtcctt                                                  26
```

<210> SEQ ID NO 61
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61

```
gttaaatcgt ggatagtaga ccgcac                                                  26
```

<210> SEQ ID NO 62
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62

```
gtgcaggtac atttgctcgt cctt                                                    24
```

<210> SEQ ID NO 63
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63

```
gttaaatcgt ggatagtaga ccac                                                    24
```

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
caggtacatt tgctcgtcct t                                              21

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
gttaaatcgt ggatagtaga c                                              21

<210> SEQ ID NO 66
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
aaggacgagc aaatgtacct gcagtcaaga tcacagattt tgg                      43

<210> SEQ ID NO 67
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
gcccgcccaa aatctgtgat cttgactggt ctactatcca cgatttaac                49

<210> SEQ ID NO 68
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
aaggacgagc aaatgtacct gaacagtcaa gatcacagat tttgg                    45

<210> SEQ ID NO 69
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
gcccgcccaa aatctgtgat cttgactgtt gtctactatc cacgatttaa c             51

<210> SEQ ID NO 70
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
aaggacgagc aaatgtacct ggcaacagtc aagatcacag attttgg                  47

<210> SEQ ID NO 71
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
gcccgcccaa aatctgtgat cttgactgtt gcgtctacta tccacgattt aac          53

<210> SEQ ID NO 72
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
aaggacgagc aaatgtacct ggtgcgaagt caagatcaca gattttgg               48

<210> SEQ ID NO 73
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
gcccgcccaa aatctgtgat cttgacttcg cacgtctact atccacgatt taac         54

<210> SEQ ID NO 74
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
aaggacgagc aaatgtacct gcagtacacg actcagctgt gtattttgt gctagtggcg    60 tgatagagtc ttcgcatca                                                79

<210> SEQ ID NO 75
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
agtaacagac ggaaattgtg cccactagca caaaaataca cagctgagtc gtgtactggt   60
ctactatcca cgatttaac                                                79

<210> SEQ ID NO 76
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
tgatgcgaag actctatcac gggaaacacc atatattttg ga    42

<210> SEQ ID NO 77
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
aacttccctc tccaaaatat atggtgtttc cgcacaattt ccgtctgtta ct    52

<210> SEQ ID NO 78
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
gactcagctg tgtattttg tgctagtgga acggaaacac catatatttt ggagagggaa    60
gtt    63

<210> SEQ ID NO 79
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
gactcacctg tgtattttg tgctagtgga acggaaacac catatatttt ggagagggaa    60
gtt    63

<210> SEQ ID NO 80
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
gactcacttg tgtattttg tgctagtgga acggaaacac catatatttt ggagagggaa    60
gtt    63

<210> SEQ ID NO 81
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
gactcagctg tgtattttg tgctagtgga acggaaacac catatatttt ggagagtgaa    60
gtt    63

<210> SEQ ID NO 82

```
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
gactcagctg tgtatttttg tgctagtgga acggaaacac catatatttt ggagagacaa      60
gtt                                                                    63

<210> SEQ ID NO 83
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
gactcagctg tgtatttttg tgactagtgg aacggaaaca ccatatattt tggagaggga      60
agtt                                                                   64

<210> SEQ ID NO 84
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
gactcagctg tgtatttttg tggatctagt ggaacggaaa caccatatat tttggagagg      60
gaagtt                                                                 66

<210> SEQ ID NO 85
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
gactcagctg tgtatttttg tgctagtgga acggaaacac tcatatattt tggagaggga      60
agtt                                                                   64

<210> SEQ ID NO 86
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
gactcagctg tgtatttttg tgctagtgga acggaaacac agtcatatat tttggagagg      60
gaagtt                                                                 66

<210> SEQ ID NO 87
<211> LENGTH: 62
<212> TYPE: DNA
<213> ORGANISM: Artificial Sequence
<220> FEATURE:
```

<223> OTHER INFORMATION: Description of Artificial Sequence: Synthetic
     oligonucleotide

<400> SEQUENCE: 87
gactcagctg tgtattttg tctagtggaa cggaaacacc atatattttg gagagggaag    60
tt                                                                 62

<210> SEQ ID NO 88
<211> LENGTH: 60
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 88
gactcagctg tgtattttg tagtggaacg gaaacaccat atattttgga gagggaagtt    60

<210> SEQ ID NO 89
<211> LENGTH: 62
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 89
gactcagctg tgtattttg tgctagtgga acggaaacac catatatttt gagagggaag    60
tt                                                                 62

<210> SEQ ID NO 90
<211> LENGTH: 60
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 90
gactcagctg tgtattttg tgctagtgga acggaaacac catatatttt gagggaagtt    60

<210> SEQ ID NO 91
<211> LENGTH: 60
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 91
gactcagctg tgtattttg tgctagtggg gaaacaccat atattttgga gagggaagtt    60

<210> SEQ ID NO 92
<211> LENGTH: 61
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 92
gactcagctg tgtattttg tgctagtgga ggaaacacca tatattttgg agagggaagt    60
t                                                                  61

<210> SEQ ID NO 93
<211> LENGTH: 62
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 93
gactcagctg tgtattttg tgctagtgga aggaaacacc atatattttg gagagggaag    60
tt    62

<210> SEQ ID NO 94
<211> LENGTH: 65
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 94
gactcagctg tgtattttg tgctagtggg tataggaaac accatatatt ttggagaggg    60
aagtt    65

<210> SEQ ID NO 95
<211> LENGTH: 68
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 95
gactcagctg tgtattttg tgctagtgga atgtaacgga aacaccatat attttggaga    60
gggaagtt    68

<210> SEQ ID NO 96
<211> LENGTH: 69
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 96
gactcagctg tgtattttg tgctagtgga tattaaacgg aaacaccata tattttggag    60
agggaagtt    69

<210> SEQ ID NO 97
<211> LENGTH: 70
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 97
gactcagctg tgtattttg tgctagtgga atatgtaacg gaaacaccat atattttgga    60
gagggaagtt    70

<210> SEQ ID NO 98
<211> LENGTH: 63
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 98
gactcagctg tgtatttttg tgctagtggg aaggaaacac catatatttt ggagagggaa      60
gtt                                                                    63

<210> SEQ ID NO 99
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
gactcagctg tgtatttttg tgctagtggg tcggaaacac catatatttt ggagagggaa      60
gtt                                                                    63

<210> SEQ ID NO 100
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
gactcagctg tgtatttttg tgctagtgga cgggaaacac catatatttt ggagagggaa      60
gtt                                                                    63

<210> SEQ ID NO 101
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
gaatgtaacg                                                             10

<210> SEQ ID NO 102
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
gatattaaac g                                                           11

<210> SEQ ID NO 103
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
gaatatgtaa cg                                                          12
```

<210> SEQ ID NO 104
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
aaggacgagc aaatgtacct gcagtagact cagccatgta cttctgtgcc agcacgtgat      60
agagtcttcg catca                                                      75

<210> SEQ ID NO 105
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
aaggacgagc aaatgtacct gcagtagact ctgctgtgta tttctgtgcc agcagcccgt      60
gatagagtct tcgcatca                                                   78

<210> SEQ ID NO 106
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
aaggacgagc aaatgtacct gcagtagact cagccctgta tctctgcgcc agcagcccgt      60
gatagagtct tcgcatca                                                   78

<210> SEQ ID NO 107
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
aaggacgagc aaatgtacct gcagtaggac tcggcccttt atctttgcgc cagcagcgtg      60
atagagtctt cgcatca                                                    77

<210> SEQ ID NO 108
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
aaggacgagc aaatgtacct gcagtacaga catctgtgta cttctgtgcc agcacgtgat      60
agagtcttcg catca                                                      75

<210> SEQ ID NO 109
<211> LENGTH: 76
<212> TYPE: DNA

<213> ORGANISM: Artificial Sequence
<220> FEATURE:
<223> OTHER INFORMATION: Description of Artificial Sequence: Synthetic
     oligonucleotide

<400> SEQUENCE: 109
aaggacgagc aaatgtacct gcagtacaga catctgtata tttctgcgcc agcagcgtga    60
tagagtcttc gcatca                                                   76

<210> SEQ ID NO 110
<211> LENGTH: 77
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 110
aaggacgagc aaatgtacct gcagtagact cggccatgta tctctgtgcc agcagccgtg    60
atagagtctt cgcatca                                                  77

<210> SEQ ID NO 111
<211> LENGTH: 76
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 111
aaggacgagc aaatgtacct gcagtagact cagctgtgta tttttgtgct agtggcgtga    60
tagagtcttc gcatca                                                   76

<210> SEQ ID NO 112
<211> LENGTH: 75
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 112
agtaacagac ggaaattgtg ctgctggcac agaagtacat ggctgagtct actggtctac    60
tatccacgat ttaac                                                    75

<210> SEQ ID NO 113
<211> LENGTH: 78
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 113
agtaacagac ggaaattgtg cggctgctgg cacagaaata cacagcagag tctactggtc    60
tactatccac gatttaac                                                 78

<210> SEQ ID NO 114
<211> LENGTH: 78
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 114
agtaacagac ggaaattgtg cggctgctgg cgcagagata cagggctgag tctactggtc    60
tactatccac gatttaac                                                 78

<210> SEQ ID NO 115
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
agtaacagac ggaaattgtg cctgctggcg caaagataaa gggccgagtc ctactggtct    60
actatccacg atttaac                                                  77

<210> SEQ ID NO 116
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
agtaacagac ggaaattgtg ctgctggcac agaagtacac agatgtctgt actggtctac    60
tatccacgat ttaac                                                    75

<210> SEQ ID NO 117
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
agtaacagac ggaaattgtg cctgctggcg cagaaatata cagatgtctg tactggtcta    60
ctatccacga tttaac                                                   76

<210> SEQ ID NO 118
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
agtaacagac ggaaattgtg cgctgctggc acagagatac atggccgagt ctactggtct    60
actatccacg atttaac                                                  77

<210> SEQ ID NO 119
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
agtaacagac ggaaattgtg cccactagca caaaaataca cagctgagtc tactggtcta    60

-continued ctatccacga tttaac                                              76

<210> SEQ ID NO 120
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
tgatgcgaag actctatcac gtgaagcttt ctttggacaa g                  41

<210> SEQ ID NO 121
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
tgatgcgaag actctatcac gggctacacc ttcggttcgg                    40

<210> SEQ ID NO 122
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
tgatgcgaag actctatcac ggagcagttc ttcgggc                       37

<210> SEQ ID NO 123
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
tgatgcgaag actctatcac gcggggagct gtttttttgg                    39

<210> SEQ ID NO 124
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
tgatgcgaag actctatcac ggatacgcag tattttggcc cag                43

<210> SEQ ID NO 125
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
tctggtgcct tgtccaaaga aagcttcagc acaatttccg tctgttact        49

<210> SEQ ID NO 126
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
cctggtcccc gaaccgaagg tgtagccgca caatttccgt ctgttact         48

<210> SEQ ID NO 127
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
gtgtccctgg cccgaagaac tgctcgcaca atttccgtct gttact           46

<210> SEQ ID NO 128
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
agagccttct ccaaaaaaca gctccccggc acaatttccg tctgttact        49

<210> SEQ ID NO 129
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
cgggtgcctg ggccaaaata ctgcgtatcg cacaatttcc gtctgttact       50

<210> SEQ ID NO 130
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
gactcagcca tgtacttctg tgccagcaga taggctccaa tgagcagttc atgaagcttt    60
ctttggacaa ggcaccaga                                         79

<210> SEQ ID NO 131
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131

```
gactcagcca tgtacttctg tgccagcagt gattgcggga ggttggagat acgcagtcgg    60
ctacaccttc ggttcgggga ccagg                                         85

<210> SEQ ID NO 132
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
gactcagcca tgtacttctg tgccagcagt gaagttatgg gacacctggt ctctggaaac    60
accatatatt ttggagaggg aagtt                                         85

<210> SEQ ID NO 133
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
gactcagcca tgtacttctg tgccagcagt gaagcacagg gatcgcaatg agcagttctt    60
cgggccaggg acac                                                     74

<210> SEQ ID NO 134
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
gactcagcca tgtacttctg tgccagcagt gaaggctact tagcgtcacc ggggagctgt    60
tttttggaga aggctct                                                  77

<210> SEQ ID NO 135
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
gactcagcca tgtacttctg tgccagcagt gtgggacaga cagatacgca gtattttggc    60
ccaggcaccc g                                                        71

<210> SEQ ID NO 136
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
gactctgctg tgtatttctg tgccagcagc caagggacta gcggttaaca ctgaagcttt    60
ctttggacaa ggcaccaga                                                79
```

<210> SEQ ID NO 137
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
gactctgctg tgtatttctg tgccagcagc cacacgggac agggtcctat ggctacacct    60
tcggttcggg gaccagg                                                   77

<210> SEQ ID NO 138
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
gactctgctg tgtatttctg tgccagcagc caagagggag ggctagcgag ggctctggaa    60
acaccatata ttttggagag ggaagtt                                        87

<210> SEQ ID NO 139
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
gactctgctg tgtatttctg tgccagcagc caagagggag agcagttctt cgggccaggg    60
acac                                                                 64

<210> SEQ ID NO 140
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
gactctgctg tgtatttctg tgccagcagc caagtcgtat caaaccgggg agctgttttt    60
tggagaaggc tct                                                       73

<210> SEQ ID NO 141
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
gactctgctg tgtatttctg tgccagcagc caatttggtc tagcgggata cacagatacg    60
cagtattttg gcccaggcac ccg                                            83

<210> SEQ ID NO 142
<211> LENGTH: 75

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
gactcagccc tgtatctctg cgccagcagc caggacagtt ggaacactga agctttcttt      60
ggacaaggca ccaga                                                       75

<210> SEQ ID NO 143
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
gactcagccc tgtatctctg cgccagcagc caagacgagg acagtaatgg ctacaccttc      60
ggttcgggga ccagg                                                       75

<210> SEQ ID NO 144
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
gactcagccc tgtatctctg cgccagcagc caagagacta gcgggaatat ggaaacacca      60
tatattttgg agagggaagt t                                                81

<210> SEQ ID NO 145
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
gactcagccc tgtatctctg cgccagcagc caaggcccgg gaaagaggtc aatgagcagt      60
tcttcgggcc agggacac                                                    78

<210> SEQ ID NO 146
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
gactcagccc tgtatctctg cgccagcagc caattacggt ggcaccgggg agctgttttt      60
tggagaaggc tct                                                         73

<210> SEQ ID NO 147
<211> LENGTH: 76
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 147
gactcagccc tgtatctctg cgccagcagc cgggactacg tcagcacaga tacgcagtat    60
tttggcccag gcaccg                                                   76

<210> SEQ ID NO 148
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
ggactcggcc ctttatcttt gcgccagcag cttggacggg acaggtagaa cactgaagct    60
ttctttggac aaggcaccag a                                             81

<210> SEQ ID NO 149
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
ggactcggcc ctttatcttt gcgccagcag cttgcagggt ggactatggc tacaccttcg    60
gttcggggac cagg                                                     74

<210> SEQ ID NO 150
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
ggactcggcc ctttatcttt gcgccagcag cccgtacagg cttcctaaga tactggaaac    60
accatatatt ttggagaggg aagtt                                         85

<210> SEQ ID NO 151
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
ggactcggcc ctttatcttt gcgccagcag cttggccttt cctacaatga gcagttcttc    60
gggccaggga cac                                                      73

<210> SEQ ID NO 152
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152

```
ggactcggcc ctttatcttt gcgccagcag cttgtggaca gggaggtatc ccaccgggga    60 gctgttttt ggagaaggct ct                                              82

<210> SEQ ID NO 153
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
ggactcggcc ctttatcttt gcgccagcag ctccatctac acagatacgc agtattttgg    60
cccaggcacc cg                                                        72

<210> SEQ ID NO 154
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
cagacatctg tgtacttctg tgccagcagt gaccatcaga ctgggaacac tgaagctttc    60
tttggacaag gcaccaga                                                  78

<210> SEQ ID NO 155
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
cagacatctg tgtacttctg tgccagcacc aagggacagg aactatggct acaccttcgg    60
ttcggggacc agg                                                       73

<210> SEQ ID NO 156
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
cagacatctg tgtacttctg tgccagcagt ctcataacga attggctctg gaaacaccat    60
atattttgga gagggaagtt                                                80

<210> SEQ ID NO 157
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
cagacatctg tgtacttctg tgccagcagt gaagacaggg aatcagcccc agccaatgag    60
cagttcttcg ggccagggac ac                                             82
```

<210> SEQ ID NO 158
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
cagacatctg tgtacttctg tgccagcagt gaagcggtcg gacagggctc cggggagctg      60 tttttttggag aaggctct                                                   78

<210> SEQ ID NO 159
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
cagacatctg tgtacttctg tgccagcagt gaagagacag cgaaacagat acgcagtatt      60
ttggcccagg cacccg                                                      76

<210> SEQ ID NO 160
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
cagacatctg tatatttctg cgccagcagt gaggaatacc cgggaaaaca ctgaagcttt      60
ctttggacaa ggcaccaga                                                   79

<210> SEQ ID NO 161
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
cagacatctg tatatttctg cgccagcagt gagactcgga cagtctgcta tggctacacc      60
ttcggttcgg ggaccagg                                                    78

<210> SEQ ID NO 162
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
cagacatctg tatatttctg cgccagcagt gagtcgtcga cagttccaac tctggaaaca      60
ccatatattt tggagaggga agtt                                             84

<210> SEQ ID NO 163
<211> LENGTH: 83
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 163
cagacatctg tatatttctg cgccagcagg agggacaggg atttgtggct cctacaatga    60
gcagttcttc gggccaggga cac                                            83

<210> SEQ ID NO 164
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
cagacatctg tatatttctg cgccagcagt gagcggcaat gaacaccggg gagctgtttt    60
ttggagaagg ctct                                                      74

<210> SEQ ID NO 165
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
cagacatctg tatatttctg cgccagcagt gggagggaaa ccagatacgc agtattttgg    60
cccaggcacc cg                                                        72

<210> SEQ ID NO 166
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
gactcggcca tgtatctctg tgccagcagc ttccgggacc gtgaacactg aagctttctt    60
tggacaaggc accaga                                                    76

<210> SEQ ID NO 167
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
gactcggcca tgtatctctg tgccagcagc tccggacagg gccccctat ggctacctat     60 ggctacacct tcggttcggg gaccagg                                        87

<210> SEQ ID NO 168
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 168
gactcggcca tgtatctctg tgccagcagc ttcctgtaag cgggagttag gaaacaccat      60
atattttgga gagggaagtt                                                  80

<210> SEQ ID NO 169
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
gactcggcca tgtatctctg tgccagcagc tcgcaggccg ggagggccca gctacaatga      60
gcagttcttc gggccaggga cac                                              83

<210> SEQ ID NO 170
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
gactcggcca tgtatctctg tgccagcagc ttagacctaa aaacagggac cgacgggaac      60
accggggagc tgttttttgg agaaggctct                                       90

<210> SEQ ID NO 171
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
gactcggcca tgtatctctg tgccagcagc ttagatctgg gcggactctt ggagatacgc      60
agtattttgg cccaggcacc cg                                               82

<210> SEQ ID NO 172
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
gactcagctg tgtattttg tgctagtggt ttgggctccg tctatggcta caaactgaag       60
ctttctttgg acaaggcacc aga                                              83

<210> SEQ ID NO 173
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
gactcagctg tgtattttg tgctagtggt ttgcacaccg caaccggcgg tctagctatg       60
gctacacctt cggttcgggg accagg                                              86

<210> SEQ ID NO 174
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
gactcagctg tgtattttttg tgctagtggt gtgattcttg aggaaacacc atatattttg         60
gagagggaag tt                                                             72

<210> SEQ ID NO 175
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
gactcagctg tgtattttttg tgctagtggt ttggttcctc gacagggacg ggaacaatga        60
gcagttcttc gggccaggga cac                                                 83

<210> SEQ ID NO 176
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
gactcagctg tgtattttttg tgctagtggt ttgggagact agcgggtcta caccggggag        60
ctgttttttg gagaaggctc t                                                   81

<210> SEQ ID NO 177
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
gactcagctg tgtattttttg tgctagtggt ttggagggtc agcacagata cgcagtattt        60
tggcccaggc acccg                                                          75

<210> SEQ ID NO 178
<211> LENGTH: 159
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 178
aaggacgagc aaatgtacct gcagtacatg aggactgggg agggctttct ttgtgtattt         60
gccataaata atactaaatc atttgaagat attcaccatt atagagaaca aattaaaaga        120
gttaaggact ctgaagatcg tgatagagtc ttcgcatca                               159

<210> SEQ ID NO 179
<211> LENGTH: 159
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 179
agtaacagac ggaaattgtg catcttcaga gtccttaact cttttaattt gttctctata    60
atggtgaata tcttcaaatg atttagtatt atttatggca aatacacaaa gaaagccctc    120
cccagtcctc atgtactggt ctactatcca cgatttaac                           159

<210> SEQ ID NO 180
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 180
tgatgcgaag actctatcac ggtacctatg gtcctagtag gaaataaatg tgatttgcct    60
tctagaacag tagacacaaa acaggctcag gacttagcaa gaagttatg               109

<210> SEQ ID NO 181
<211> LENGTH: 124
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 181
caataaaagg aattccataa cttcttgcta agtcctgagc ctgttttgtg tctactgttc    60
tagaaggcaa atcacattta tttcctacta ggaccatagg tacgcacaat ttccgtctgt    120
tact                                                                 124

<210> SEQ ID NO 182
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
tcaagaggag tacagtgcaa tg                                             22

<210> SEQ ID NO 183
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
tgagggacca gtacatgact gg                                             22

<210> SEQ ID NO 184
<211> LENGTH: 23

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
gaccagtaca tgagggaggg ctt                                             23

<210> SEQ ID NO 185
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
aacaccctgt cttgtctttg c                                               21

<210> SEQ ID NO 186
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
gttgacaatc gtggatagta gacttcgcac                                      30

<210> SEQ ID NO 187
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
cctatttctc ctcagctcaa aacc                                            24

<210> SEQ ID NO 188
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
atagtcaact taaggactaa ataaatgatc taatg                                35

<210> SEQ ID NO 189
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
aaggtcaggg tctctgttag g                                               21

<210> SEQ ID NO 190
<211> LENGTH: 25
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 190
agtggttaga gacaatatga catcg                                          25

<210> SEQ ID NO 191
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
cttcacctat cctgcaacct tt                                             22

<210> SEQ ID NO 192
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
ttctaatctg tctaaattac ctaacgct                                       28

<210> SEQ ID NO 193
<211> LENGTH: 177
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 193
aaggacgagc aaatgtacct gcatttctcc tcagctcaaa acccttcagt ggcactccgt    60
tttattggtg tcaaagccaa agtcctttca atggtctaca aaacactgtt tggccaggcc   120
accaaatacc ttgctagttt cttctagttc tattccgtga tagagtcttc gcatcag      177

<210> SEQ ID NO 194
<211> LENGTH: 178
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 194
actgaacgac ggaaattgtg cgaatagaac tagaagaaac tagcaaggta tttggtggcc    60
tggccaaaca gtgttttgta gaccattgaa aggactttgg ctttgacacc aataaaacgg   120
agtgccactg aagggttttg agctgaggag aaatggtcta ctatccacga ttgtcaac     178

<210> SEQ ID NO 195
<211> LENGTH: 184
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 195
```

```
ctgatgcgaa gactctatca cgtctctcac ttggctccag tcacactgac ctccccgcca    60
ttccttcagt gcatgggaat atcccacctt cagaccattg ctccaattct tctcattttg   120
ggaatgttct ttacccagat aatagcttga ctaactcctt ctggctgaac gtaactcctc   180
tttg                                                                184
```

<210> SEQ ID NO 196
<211> LENGTH: 183
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 196

```
gtgctactct tcaaccttct ggagaaggag ttagtcaagc tattatctgg gtaaagaaca    60
ttcccaaaat gagaagaatt ggagcaatgg tctgaaggtg ggatattccc atgcactgaa   120
ggaatggcgg ggaggtcagt gtgactggag ccaagtgaga gagcacaatt tccgtcgttc   180
agt                                                                 183
```

<210> SEQ ID NO 197
<211> LENGTH: 162
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 197

```
caaagaggag ttacgttcag cctttatgtc tgacttggct caacagttta atctcaatga    60
gacttaccct gaccacccta tttcatagtt ccaacctgga ttccagcatt cctaatcccc   120
ttactctgca cgacttcttt ttttttcccat ggtactcacc ac                     162
```

<210> SEQ ID NO 198
<211> LENGTH: 180
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 198

```
tgatctaatg agttagaggt ggtgagtacc atgggaaaaa aaagaagtcg tgcagagtaa    60
ggggattagg aatgctggaa tccaggttgg aactatgaaa tagggtggtc agggtaagtc   120
tcattgagat taaactgttg agccaagtca gacataaacc agaaggttga agagtagcac   180
```

<210> SEQ ID NO 199
<211> LENGTH: 187
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 199

```
aaggacgagc aaatgtacct gcactgttag gaaagcaaaa tttccccaga tattctcagc    60
agttttctgc ttgtgcttcc atgtctagag ctgtctctag ttcctggaag ttcctagctt   120
caagcatgtc taagaaagac ttcatttgag taccttgcta ccttacgtga tagagtcttc   180
```

```
gcatcag                                                                    187

<210> SEQ ID NO 200
<211> LENGTH: 188
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 200
actgaacgac ggaaattgtg ctaaggtagc aaggtactca aatgaagtct ttcttagaca    60
tgcttgaagc taggaacttc caggaactag agacagctct agacatggaa gcacaagcag   120
aaaactgctg agaatatctg gggaaatttt gctttcctaa cagtggtcta ctatccacga   180
ttgtcaac                                                             188

<210> SEQ ID NO 201
<211> LENGTH: 178
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 201
ctgatgcgaa gactctatca cgtagtcttc cctagcttaa taatttttc tgtacctaat      60 gatttcagag tgagatggtg aggtgatcat gggcaaaatt attagtcttt ctgagttctc   120
ttattccttt tatatcattg aatgttcttt tttgtgggct gaacgtaact cctctttg    178

<210> SEQ ID NO 202
<211> LENGTH: 177
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 202
gtgctactct tcaaccttct ggcacaaaaa agaacattca atgatataaa aggaataaga    60
gaactcagaa agactaataa ttttgcccat gatcacctca ccatctcact ctgaaatcat   120
taggtacaga aaaaattatt aagctaggga agactagcac aatttccgtc gttcagt     177

<210> SEQ ID NO 203
<211> LENGTH: 187
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 203
caaagaggag ttacgttcag ccgctattgt taggattagt gtttcaatgt gaatggcaga    60
ttgaagcttc agagtgcttt cactcatctt cagttgtttc tccgagttgc cttgagagag   120
agaaagaggt agttttagcc ctattttgta ggtatagtaa tagtgacgtt ctacctcagg   180
tgttcgt                                                              187

<210> SEQ ID NO 204
<211> LENGTH: 189
<212> TYPE: DNA
<213> ORGANISM: Artificial Sequence
```

```
<220> FEATURE:
<223> OTHER INFORMATION: Description of Artificial Sequence: Synthetic
      polynucleotide

<400> SEQUENCE: 204
tttctgatgc acttagagtg agctcactat tactatacct acaaaatagg gctaaaacta      60
cctctttctc tctctcaagg caactcggag aaacaactga agatgagtga aagcactctg     120
aagcttcaat ctgccattca cattgaaaca ctaatcctaa caatagccca gaaggttgaa     180
gagtagcac                                                             189

<210> SEQ ID NO 205
<211> LENGTH: 147
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 205
acgaacacct gaggtagaac gttcccttt cctttgtgtc tctttcgaat cctaccattt       60
tattccctat gtttctgttg cctgtcctca catttggtcc ttctcaggat atggcatgct    120
ttccatattt cccagtaaaa atcccag                                         147

<210> SEQ ID NO 206
<211> LENGTH: 163
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 206
tgacatcgga aaggctggga tttttactgg gaaatatgga aagcatgcca tatcctgaga     60
aggaccaaat gtgaggacag gcaacagaaa catagggaat aaaatggtag gattcgaaag    120
agacacaaag gaaaagggaa gctcactcta agtgcatcag aaa                      163

<210> SEQ ID NO 207
<211> LENGTH: 181
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 207
aaggacgagc aaatgtacct gcaacctatc ctgcaacctt tccacatact cttccctcaa     60
cctggaagac tcctcctgtt ctttacctgg ataattctta catagccttc cattctcaac    120
tcaaatggtg ttacttcaaa gatgcctttg ctcattaccc gtgatagagt cttcgcatca    180
g                                                                    181

<210> SEQ ID NO 208
<211> LENGTH: 182
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 208
actgaacgac ggaaattgtg cggtaatgag caaaggcatc tttgaagtaa caccatttga     60
```

```
gttgagaatg gaaggctatg taagaattat ccaggtaaag aacaggagga gtcttccagg    120
ttgagggaag agtatgtgga aaggttgcag gataggttgg tctactatcc acgattgtca    180
ac                                                                   182

<210> SEQ ID NO 209
<211> LENGTH: 176
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 209
ctgatgcgaa gactctatca cgaaacgtat attaggcccc tctcttactt atttatactt    60
cctttgtaag cagcgacatg gctcttttgc tcaccctggt aagcctagtg cccagtatat    120
catctgacac acaattggtg gtcaactgtt gattggctga acgtaactcc tctttg        176

<210> SEQ ID NO 210
<211> LENGTH: 175
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 210
gtgctactct tcaaccttct ggaatcaaca gttgaccacc aattgtgtgt cagatgatat    60
actgggcact aggcttacca gggtgagcaa aagagccatg tcgctgctta caaaggaagt    120
ataaataagt aagagagggg cctaatatac gtttgcacaa tttccgtcgt tcagt         175

<210> SEQ ID NO 211
<211> LENGTH: 183
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 211
caaagaggag ttacgttcag cccatgagtg aattttattg gttactgttg atcgccagtg    60
aaataagtgc ttagaaacac ttataggctg aataggaaga attaaacaaa tgaatgacta    120
gataataggt acgtgggagt cacagggatt gacatcttat ttcgttctac ctcaggtgtt    180
cgt                                                                  183

<210> SEQ ID NO 212
<211> LENGTH: 185
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 212
tttctgatgc acttagagtg agcaaataag atgtcaatcc ctgtgactcc cacgtaccta    60
ttatctagtc attcatttgt ttaattcttc ctattcagcc tataagtgtt tctaagcact    120
tatttcactg gcgatcaaca gtaaccaata aaattcactc atgccagaag gttgaagagt    180
agcac                                                                185
```

<210> SEQ ID NO 213
<211> LENGTH: 159
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 213
acgaacacct gaggtagaac gtattcagtt ttgcctacat tggctctttt cttacaaatg      60
tcctgatgcc tattgagtat atatccataa ggtttctttg agttttctgg aagaaatggc    120
tgttgttgat gttgttttta gcagctcttt tgactcgac                            159

<210> SEQ ID NO 214
<211> LENGTH: 175
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 214
ctggtgtgag gatggtcgag tcaaaagagc tgctaaaaac aacatcaaca acagccattt      60
cttccagaaa actcaaagaa accttatgga tatatactca ataggcatca ggacatttgt    120
aagaaaagag ccaatgtagg caaaactgaa tagctcactc taagtgcatc agaaa          175

<210> SEQ ID NO 215
<211> LENGTH: 459
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 215
cctatttctc ctcagctcaa aacccttcag tggcactcca ttttattggt gtcaaagcca      60
aagtcctttc aatggtctac aaaacactgt ttggccaggc caccaaatac cttgctagtt    120
tcttctagtt ctattctctc tcacttggct ccagtcacac tgacctcccc gccattcctt    180
cagtgcatgg gaatatccca ccttcagacc attgctccaa ttcttctcat tttgggaatg    240
ttctttaccc agataatagc ttgactaact ccttctttta tgtctgactt ggctcaacag    300
tttaatctca atgagactta ccctgaccac cctatttcat agttccaacc tggattccag    360
cattcctaat ccccttactc tgcacgactt ctttttttc ccatggtact caccacctct     420
aactcattag atcatttatt tagtccttaa gttgactat                            459

<210> SEQ ID NO 216
<211> LENGTH: 590
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 216
aaggtcaggg tctctgttag gaaagcaaaa tttccccaga tattctcagc agttttctgc      60
ttgtgcttcc atgtctagag ctgtctctag ttcctggaag ttcctagctt caagcatgtc    120
taagaaagac ttcatttgag taccttgcta ccttatagtc ttccctagct taataatttt    180
ttctgtacct aatgatttca gagtgagatg gtgaggtgat catgggcaaa attattagtc    240

```
tttctgagtt ctcttattcc tttatatca ttgaatgttc tttttgtgg ctattgttag      300 gattagtgtt tcaatgtgaa tggcagattg aagcttcaga gtgctttcac tcatcttcag      360
ttgtttctcc gagttgcctt gagagagaga aagaggtagt tttagccta ttttgtaggt       420 atagtaatag tgattcccct ttcctttgtg tctctttcga atcctaccat tttattccct      480
atgtttctgt tgcctgtcct cacatttggt ccttctcagg atatggcatg ctttccatat      540
ttcccagtaa aaatcccagc ctttccgatg tcatattgtc tctaaccact               590
```

<210> SEQ ID NO 217
<211> LENGTH: 590
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 217

```
cttcacctat cctgcaacct ttccacatac tcttccctca acctggaaga ctcctcctgt      60
tctttacctg gataattctt acatagcctt ccattctcaa ctcaaatggt gttacttcaa      120
agatgccttt gctcattacc aaacgtatat taggcccctc tcttacttat ttatacttcc      180
tttgtaagca gcgacatggc tcttttgctc accctggtaa gcctagtgcc cagtatatca      240
tctgacacac aattggtggt caactgttga ttcatgagtg aatttttattg gttactgttg      300 atcgccagtg aaataagtgc ttagaaacac ttataggctg aataggaaga attaaacaaa      360
tgaatgacta gataataggt acgtgggagt cacaggatt gacatcttat tttattcagt       420
tttgcctaca ttggctcttt tcttacaaat gtcctgatgc ctattgagta tatatccata      480
aggtttcttt gagttttctg gaagaaatgg ctgttgttga tgttgttttt agcagctctt      540
ttgactcgac catcctcaca ccagcgttag gtaatttaga cagattagaa                590
```

<210> SEQ ID NO 218
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218

```
cagcagcagc agcagcagca gcagcagcag cagcagcagc agcagcagca gcagcagcag      60
cagcaacagc cg                                                         72
```

<210> SEQ ID NO 219
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219

```
cagcagcagc agcagcagca gcagcagcag cagcagcagc agcagcagca gcagcagcag      60
cagcagcagc agcaacagcc g                                              81
```

<210> SEQ ID NO 220
<211> LENGTH: 90
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 220
cagcagcagc agcagcagca gcagcagcag cagcagcagc agcagcagca gcagcagcag      60
cagcagcagc agcagcagca gcaacagccg                                       90

<210> SEQ ID NO 221
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
gaacacctga ggtagaacga gcagcagcag cagc                                  34

<210> SEQ ID NO 222
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222
gaacacctga ggtagaacga gcagcagcag cagcagcagc agc                        43

<210> SEQ ID NO 223
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
agtgcgaaca ggtacatttg ctcgtcctt                                        29

<210> SEQ ID NO 224
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
tttttttgtt aaatcgtgga tagtagactt cgcact                                36

<210> SEQ ID NO 225
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
aaggacgagc aaatgtacct gcacagcagc agcagcagca gcagcagcag cagcagcagc      60
agcagcagca gcagcagcgt gatagagtct tcgcat                                96

<210> SEQ ID NO 226
```

```
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226
tgaacgacgg aaattgtgcc tgctgctgct gctgctgctg ctgctgctgc tgctgctgct     60
gctgctgctg ctgtggtcta ctatccacga tttaac                              96

<210> SEQ ID NO 227
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
atgcgaagac tctatcacga gcagcagcag cagcagcagc agcagcagca gcagcagcag     60
cagc                                                                 64

<210> SEQ ID NO 228
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
atgcgaagac tctatcacga gcagcagcag cagcagcagc agcagcagca gcagcagcag     60
cagcagcagc                                                           70

<210> SEQ ID NO 229
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
atgcgaagac tctatcacga gcagcagcag cagcagcagc agcagcagca gcagcagcag     60
cagcagcagc agc                                                       73

<210> SEQ ID NO 230
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
atgcgaagac tctatcacga gcagcagcag cagcagcagc agcagcagca gcagcagcag     60
cagcagcagc agcagc                                                    76

<210> SEQ ID NO 231
<211> LENGTH: 82
<212> TYPE: DNA
<213> ORGANISM: Artificial Sequence
<220> FEATURE:
```

<223> OTHER INFORMATION: Description of Artificial Sequence: Synthetic
oligonucleotide

<400> SEQUENCE: 231
atgcgaagac tctatcacga gcagcagcag cagcagcagc agcagcagca gcagcagcag    60
cagcagcagc agcagcagca gc    82

<210> SEQ ID NO 232
<211> LENGTH: 71
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 232
ggctgttgct gctgctgctg ctgctgctgc tgctgctgct gctgctgctg ctgcacaatt    60
tccgtcgttc a    71

<210> SEQ ID NO 233
<211> LENGTH: 77
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 233
ggctgttgct gctgctgctg ctgctgctgc tgctgctgct gctgctgctg ctgctgctgc    60
acaatttccg tcgttca    77

<210> SEQ ID NO 234
<211> LENGTH: 80
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 234
ggctgttgct gctgctgctg ctgctgctgc tgctgctgct gctgctgctg ctgctgctgc    60
tgcacaattt ccgtcgttca    80

<210> SEQ ID NO 235
<211> LENGTH: 83
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 235
ggctgttgct gctgctgctg ctgctgctgc tgctgctgct gctgctgctg ctgctgctgc    60
tgctgcacaa tttccgtcgt tca    83

<210> SEQ ID NO 236
<211> LENGTH: 89
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 236

```
ggctgttgct gctgctgctg ctgctgctgc tgctgctgct gctgctgctg ctgctgctgc      60
tgctgctgct gcacaatttc cgtcgttca                                         89
```

<210> SEQ ID NO 237
<211> LENGTH: 170
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 237

```
tggaaaagct gatgaaggcc ttcgagtccc tcaagtcctt ccagcagcag cagcagcagc      60
agcagcagca gcagcagcag cagcagcagc agcagcagca gcagcagcag cagcagcagc     120
aacagccgcc accgccgccg ccgccgccgc cgcctcctca gcttcctcag                170
```

<210> SEQ ID NO 238
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238

```
cagcagcagc agcagcagca gcagcagcag cagcagcagc agcagcagca acagcc          56
```

<210> SEQ ID NO 239
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239

```
cagcagcagc agcagcagca gcagcagcag cagcagcagc agcagcagca gcagcagcaa      60
cagcc                                                                   65
```

<210> SEQ ID NO 240
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 240

```
cagcagcagc agcagcagca gcagcagcag cagcagcagc agcagcagca gcagcagcag      60
caacagcc                                                                68
```

<210> SEQ ID NO 241
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241

```
atgcgaagac tctatcacgc agcagcagca gcagcagcag ggctgaacgt aactcctcg       59
```

-continued

<210> SEQ ID NO 242
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 242
gctatcttca accttctggc tgctgctgct gctgctgctg gcacaatttc cgtcgttca        59

<210> SEQ ID NO 243
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243
cgaggagtta cgttcagccc agcagcagca gcagcag                               37

<210> SEQ ID NO 244
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
ggctgttgct gctgctgctg ctgctgccag aaggttgaag atagc                      45

<210> SEQ ID NO 245
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
ccgccgccgc cgccgccgcc gccgccgcct ccgccgccgc cgccgccgcc gccgccgccg       60
cgctgccg                                                               68

<210> SEQ ID NO 246
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 246
ccgccgccgc cgccgccgcc tccgccgccg ccgccgccgc cgccgccgcc gcgctgccg        59

<210> SEQ ID NO 247
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247
aaggacgagc aaatgtacct gcaccgccgc cgccgccgcc gcgtgataga gtcttcgcat       60

<210> SEQ ID NO 248
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
tgaacgacgg aaattgtgcc ggcggcggcg gcggcggtgg tctactatcc acgatttaac    60

<210> SEQ ID NO 249
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249
atgcgaagac tctatcacgc cgccgccgcc tccgccgccg ggctgaacgt aactcctcg     59

<210> SEQ ID NO 250
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250
gctatcttca accttctggc ggcggcggag gcggcggcgg gcacaatttc cgtcgttca     59

<210> SEQ ID NO 251
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251
cgaggagtta cgttcagccc cgccgccgcc gccgccgccg c                        41

<210> SEQ ID NO 252
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 252
cggcagcgcg gcggcggcgg cggcggcggc cagaaggttg aagatagc                 48

<210> SEQ ID NO 253
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253
gaagaagaag aagaagaaga agaagaagaa gaagaagaag aagaagaaga agaagaaaat    60
aaag                                                                 64

<210> SEQ ID NO 254
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 254
gaagaagaag aagaagaaga agaagaagaa gaagaagaag aagaagaaaa taaag        55

<210> SEQ ID NO 255
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255
aaggacgagc aaatgtacct gcagaagaag aagaagaaga acgtgataga gtcttcgcat   60

<210> SEQ ID NO 256
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256
tgaacgacgg aaattgtgct tcttcttctt cttcttctgg tctactatcc acgatttaac   60

<210> SEQ ID NO 257
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 257
atgcgaagac tctatcacgg aagaagaaga agaagaagaa ggctgaacgt aactcctcg    59

<210> SEQ ID NO 258
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 258
gctatcttca accttctggt tcttcttctt cttcttcttc gcacaatttc cgtcgttca    59

<210> SEQ ID NO 259
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
cgaggagtta cgttcagccg aagaagaaga a                                  31

```
<210> SEQ ID NO 260
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
ctttattttc ttcttcttct tcttcccaga aggttgaaga tagc                    44

<210> SEQ ID NO 261
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
gtccttccag cagcagcagc agcagcagca gcagcagcag cagcagcagc agcagcagca   60
gcagcagcag cagcagcagc agcagcagca acagcc                             96

<210> SEQ ID NO 262
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 262
acgcagctaa tgccct                                                    16

<210> SEQ ID NO 263
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263
cagacagctt tgacgtatgt gtttctc                                        27

<210> SEQ ID NO 264
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264
aaggacgagc aaatgtacct ggcaacagtg aagatcacag attttgg                  47

<210> SEQ ID NO 265
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265
tgaacactga                                                           10
```

<210> SEQ ID NO 266
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266
ctaactatgg                                                          10

<210> SEQ ID NO 267
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267
ctctggaaac                                                          10

<210> SEQ ID NO 268
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268
ctcctacaat                                                          10

<210> SEQ ID NO 269
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 269
cgaacaccgg                                                          10

<210> SEQ ID NO 270
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 270
agcacagata                                                          10

<210> SEQ ID NO 271
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
tcaagaggag tacagtgcaa tgagggacca gtacatgagg actggggagg gctttct     57

<210> SEQ ID NO 272
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272
tattgaaaca tcatcagcaa agacaagaca gggtgtt                              37

<210> SEQ ID NO 273
<211> LENGTH: 114
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other
<220> FEATURE:
<221> NAME/KEY: modified_base
<222> LOCATION: (91)..(114)
<223> OTHER INFORMATION: a, c, t, g, unknown or other

<400> SEQUENCE: 273
cncttggaaa agntgatgaa ggccttcgag tccctcaagt ccttccagca gcagcagcag      60
cagcagcagc agcagcagca gcagcagcag nnnnnnnnnn nnnnnnnnnn nnnn           114

<210> SEQ ID NO 274
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274
aaggacgagc aaatgtacct gcagaagaag aagaagaaga acgtgtctcc tgttgcgacg      60

<210> SEQ ID NO 275
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
cgtcgcaaca ggagacacgg aagaagaaga agaagaagaa ggctgaacgt aactcctcg       59

<210> SEQ ID NO 276
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 276
aaggacgagc aaatgtacct gcacagcagc agcagcag                             38

<210> SEQ ID NO 277
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
cagcagcagc agcagcgtga tagagtcttc gcat                              34

<210> SEQ ID NO 278
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 278
tgaacgacgg aaattgtgcc tgctgctgct gctg                              34

<210> SEQ ID NO 279
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 279
ctgctgctgc tgctgtggtc tactatccac gatttaac                          38

<210> SEQ ID NO 280
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 280
atgcgaagac tctatcacga gcagcag                                      27

<210> SEQ ID NO 281
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 281
cagcagcagc agc                                                     13

<210> SEQ ID NO 282
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 282
ggctgttgct gctgctgctg                                              20

```
<210> SEQ ID NO 283
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 283
ctgctgctgc acaatttccg tcgttca                                        27

<210> SEQ ID NO 284
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 284
ggctgttgct gctg                                                      14

<210> SEQ ID NO 285
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 285
cagcagcagc                                                           10

<210> SEQ ID NO 286
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 286
ggctgttgct gctgctg                                                   17
```